US009546215B2

(12) United States Patent
Bebbington et al.

(10) Patent No.: US 9,546,215 B2
(45) Date of Patent: Jan. 17, 2017

(54) ANTI-SIGLEC-8 ANTIBODIES AND METHODS OF USE THEREOF

(71) Applicant: Allakos Inc., San Carlos, CA (US)

(72) Inventors: Christopher R. Bebbington, San Mateo, CA (US); Rustom Falahati, Lafayette, CA (US); Carolina Rita Sousa Fernandes, London (GB); David John Matthews, Hitchin (GB); Nenad Tomasevic, Foster City, CA (US); Jason Williams, Redwood City, CA (US); John Leung, San Leandro, CA (US)

(73) Assignee: ALLAKOS INC., San Carlos, CA (US)

( * ) Notice: Subject to any disclaimer, the term of this patent is extended or adjusted under 35 U.S.C. 154(b) by 77 days.

(21) Appl. No.: 14/565,370

(22) Filed: Dec. 9, 2014

(65) Prior Publication Data
US 2015/0203578 A1    Jul. 23, 2015

Related U.S. Application Data

(60) Provisional application No. 61/913,891, filed on Dec. 9, 2013.

(51) Int. Cl.
C07K 16/28    (2006.01)

(52) U.S. Cl.
CPC ....... *C07K 16/2803* (2013.01); *C07K 2317/24* (2013.01); *C07K 2317/34* (2013.01); *C07K 2317/41* (2013.01); *C07K 2317/56* (2013.01); *C07K 2317/73* (2013.01); *C07K 2317/732* (2013.01); *C07K 2317/90* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| RE30,985 E | 6/1982 | Cartaya |
| 4,419,446 A | 12/1983 | Howley et al. |
| 4,560,655 A | 12/1985 | Baker |
| 4,601,978 A | 7/1986 | Karin |
| 4,657,866 A | 4/1987 | Kumar |
| 4,676,980 A | 6/1987 | Segal et al. |
| 4,767,704 A | 8/1988 | Cleveland et al. |
| 4,816,567 A | 3/1989 | Cabilly et al. |
| 4,927,762 A | 5/1990 | Darfler |
| 4,965,199 A | 10/1990 | Capon et al. |
| 5,122,464 A | 6/1992 | Wilson et al. |
| 5,122,469 A | 6/1992 | Mather et al. |
| 5,264,365 A | 11/1993 | Georgiou et al. |
| 5,500,362 A | 3/1996 | Robinson et al. |
| 5,508,192 A | 4/1996 | Georgiou et al. |
| 5,571,894 A | 11/1996 | Wels et al. |
| 5,587,458 A | 12/1996 | King et al. |
| 5,624,821 A | 4/1997 | Winter et al. |
| 5,639,635 A | 6/1997 | Joly et al. |
| 5,641,870 A | 6/1997 | Rinderknecht et al. |
| 5,648,237 A | 7/1997 | Carter et al. |
| 5,648,260 A | 7/1997 | Winter et al. |
| 5,677,425 A | 10/1997 | Bodmer et al. |
| 5,739,277 A | 4/1998 | Presta et al. |
| 5,821,337 A | 10/1998 | Carter et al. |
| 5,834,597 A | 11/1998 | Tso et al. |
| 5,840,523 A | 11/1998 | Simmons et al. |
| 5,869,046 A | 2/1999 | Presta et al. |
| 5,885,573 A | 3/1999 | Bluestone et al. |
| 5,891,693 A | 4/1999 | Bebbington et al. |
| 6,027,888 A | 2/2000 | Georgiou et al. |
| 6,083,715 A | 7/2000 | Georgiou et al. |
| 6,121,022 A | 9/2000 | Presta et al. |
| 6,165,745 A | 12/2000 | Ward et al. |
| 6,194,551 B1 | 2/2001 | Idusogie et al. |
| 6,248,516 B1 | 6/2001 | Winter et al. |
| 6,277,375 B1 | 8/2001 | Ward |
| 6,602,684 B1 | 8/2003 | Umaña et al. |
| 6,737,056 B1 | 5/2004 | Presta |
| 6,821,505 B2 | 11/2004 | Ward |
| 6,982,321 B2 | 1/2006 | Winter |
| 7,087,409 B2 | 8/2006 | Barbas et al. |
| 7,317,091 B2 | 1/2008 | Lazar et al. |
| 7,335,742 B2 | 2/2008 | Presta |
| 7,557,191 B2 | 7/2009 | Abrahamson et al. |
| 7,745,421 B2 | 6/2010 | Bochner et al. |
| 7,871,612 B2 | 1/2011 | Abrahamson et al. |
| 7,981,843 B2 | 7/2011 | Flynn et al. |

(Continued)

FOREIGN PATENT DOCUMENTS

| | | |
|---|---|---|
| EP | 2465873 A1 | 6/2012 |
| WO | 87/00195 A1 | 1/1987 |

(Continued)

OTHER PUBLICATIONS

Territo, http://www.merckmanuals.com/home/blood-disorders/white-blood-cell-disorders/eosinophilic-disorders, accessed Aug. 2, 2016.*
Rahimi-Rad et al. (2015, J. Clin. Med. 10(1):10-13).*
Hori et al. (2016, J. Stroke Cerebrovasc. Dis. 25(6):1307-1312).*
Alegre et al., "Prevention of the Humoral Response Induced by an Anti-cd3 Monoclonal Antibody by Deoxyspergualin in a Murine Model1", Transplantation, vol. 57, Issue 12, 1994, pp. 1537-1543.
Angal et al., "A Single Amino Acid Substitution Abolishes the Heterogeneity of Chimeric Mouse/human (igg4) Antibody", Molecular Immunology, vol. 30, Issue 1, Jan. 1993, pp. 105-108.
Arié et al., "Chaperone Function of FkpA, a Heat Shock Prolyl Isomerase, in the Periplasm of *Escherichia coli*", Molecular Microbiology, vol. 39, No. 1, 2001, pp. 199-210.

(Continued)

*Primary Examiner* — Elizabeth C Kemmerer
(74) *Attorney, Agent, or Firm* — Morrison & Foerster LLP

(57) ABSTRACT

The invention provides humanized anti-Siglec-8 antibodies and their use in treating and preventing eosinophil-mediated disorders and/or mast cell-mediated disorders, as well as compositions and kits comprising the humanized anti-Siglec-8 antibodies.

68 Claims, 10 Drawing Sheets

(56) References Cited

U.S. PATENT DOCUMENTS

| | | |
|---|---|---|
| 8,178,512 B2 | 5/2012 | Bochner et al. |
| 8,197,811 B2 | 6/2012 | Abrahamson et al. |
| 8,207,305 B2 | 6/2012 | Abrahamson et al. |
| 8,357,671 B2 | 1/2013 | Paulson et al. |
| 8,574,907 B2 | 11/2013 | Alley et al. |
| 2002/0164328 A1 | 11/2002 | Shinkawa et al. |
| 2003/0092091 A1 | 5/2003 | Abrahamson et al. |
| 2003/0115614 A1 | 6/2003 | Kanda et al. |
| 2003/0157108 A1 | 8/2003 | Presta |
| 2003/0190311 A1 | 10/2003 | Dall'Acqua et al. |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2005/0014934 A1 | 1/2005 | Hinton et al. |
| 2005/0123546 A1 | 6/2005 | Umana et al. |
| 2006/0134098 A1 | 6/2006 | Bebbington et al. |
| 2007/0134259 A1 | 6/2007 | Bundle et al. |
| 2007/0264258 A1 | 11/2007 | Abrahamson et al. |
| 2008/0139485 A1 | 6/2008 | Bochner et al. |
| 2008/0213212 A1 | 9/2008 | Abrahamson et al. |
| 2009/0238837 A1 | 9/2009 | Paulson et al. |
| 2010/0056760 A1 | 3/2010 | Abrahamson et al. |
| 2011/0046078 A1 | 2/2011 | Bochner et al. |
| 2011/0059107 A1* | 3/2011 | Allison ............... C07K 16/24 424/158.1 |
| 2011/0217319 A1 | 9/2011 | Abrahamson et al. |
| 2011/0293631 A1 | 12/2011 | Thumbikat et al. |
| 2012/0214975 A1 | 8/2012 | Sandig et al. |

FOREIGN PATENT DOCUMENTS

| | | |
|---|---|---|
| WO | 90/03430 A1 | 4/1990 |
| WO | 93/06213 A1 | 4/1993 |
| WO | 93/08829 A1 | 5/1993 |
| WO | 93/16185 A2 | 8/1993 |
| WO | 94/11026 A2 | 5/1994 |
| WO | 94/29351 A2 | 12/1994 |
| WO | 97/30087 A1 | 8/1997 |
| WO | 98/58964 A1 | 12/1998 |
| WO | 99/22764 A1 | 5/1999 |
| WO | 99/51642 A1 | 10/1999 |
| WO | 00/42072 A2 | 7/2000 |
| WO | 00/61739 A1 | 10/2000 |
| WO | 01/29246 A1 | 4/2001 |
| WO | 01/66126 A1 | 9/2001 |
| WO | 03/011878 A2 | 2/2003 |
| WO | 03/084570 A1 | 10/2003 |
| WO | 03/085119 A1 | 10/2003 |
| WO | 2004/056312 A2 | 7/2004 |
| WO | 2005/035586 A1 | 4/2005 |
| WO | 2005/035778 A1 | 4/2005 |
| WO | 2005/053742 A1 | 6/2005 |
| WO | 2005/116088 A2 | 12/2005 |
| WO | 2007/056525 A2 | 5/2007 |
| WO | 2008/077546 A1 | 7/2008 |

OTHER PUBLICATIONS

Armour et al., "Recombinant Human IgG Molecules Lacking FcGamma Receptor I Binding and Monocyte Triggering Activities", European Journal of Immunology, vol. 29, 1999, pp. 2613-2624.

Barnes et al., "Methods for Growth of Cultured Cells in Serum-Free Medium", Analytical Biochemistry, vol. 102, 1980, pp. 255-270.

Bass et al., "Hormone Phage: an Enrichment Method for Variant Proteins with Altered Binding Properties", Proteins, vol. 8, 1990, pp. 309-314.

Boerner et al., "Production of Antigen-specific Human Monoclonal Antibodies from in Vitro-primed Human Splenocytes", The Journal of Immunology, vol. 147, No. 1, Jul. 1, 1991, pp. 86-95.

Bothmann et al., "The Periplasmic *Escherichia coli* Peptidylprolyl cis,trans-Isomerase FkpA", The Journal of Biological Chemistry, vol. 275, No. 22, 2000, pp. 17100-17105.

Brennan et al., "Preparation of Bispecific Antibodies by Chemical Recombination of Monoclonal Immunoglobulin G1 Fragments", Science, vol. 229, 1985, pp. 81-83.

Brodeur et al., "Mouse-Human Myeloma Partners for the Production of Heterohybridomas", Chapter 4, Monoclonal Antibody Production Techniques and Applications, 1987, pp. 51-63.

Bruggermann et al., "Designer Mice: the Production of Human Antibody Repertoires in Transgenic Animals", The Year in Immunology, vol. 7, 1993, pp. 33-40.

Brunner et al., "Quantitative Assay of the Lytic Action of Immune Lymphoid Cells on 51Cr-Labelled Allogeneic Target Cells in Vitro; Inhibition by Isoantibody and by Drugs", Immunology, vol. 14, 1968, pp. 181-196.

Carter et al., "High Level *Escherichia coli* Expression and Production of a Bivalent Humanized Antibody Fragment", Biotechnology, vol. 10, Feb. 1992, pp. 163-167.

Carter et al., "Humanization of an Anti-p185HER2 Antibody for Human Cancer Therapy", Proceedings of the National Academy of Sciences, vol. 89, May 1992, pp. 4285-4289.

Chen et al., "Chaperone Activity of DsbC*", The Journal of Biological Chemistry, vol. 274, No. 28, 1999, pp. 19601-19605.

Chen et al., "Selection and Analysis of an Optimized Anti-VEGF Antibody: Crystal Structure of an Affinity-matured Fab in Complex with Antigen", Journal of Molecular Biology, vol. 293, 1999, pp. 865-881.

Chothia et al., "Canonical Structures for the Hypervariable Regions of Immunoglobulins", Journal of Molecular Biology, vol. 196, Issue 4, Aug. 20, 1987, pp. 901-917.

Clynes et al., "Fc Receptors are Required in Passive and Active Immunity to Melanoma", Proceedings of the National Academy of Sciences, vol. 95, Jan. 1998, pp. 652-656.

Cunningham et al., "High-Resolution Epitope Mapping of hGH-receptor Interactions by Alanine-Scanning Mutagenesis", Science, vol. 244, Jun. 2, 1989, pp. 1081-1085.

Duncan et al., "Localization of the Binding Site for the Human High-affinity Fc Receptor on IgG", Nature, vol. 332, 1988, pp. 563-564.

Eswar et al., "Comparative Protein Structure Modeling Using Modeller", Current Protocols in Bioinformatics, Unit—5.6, Oct. 2006, pp. 1-47.

Ferrara et al., "Modulation of Therapeutic Antibody Effector Functions by Glycosylation Engineering: Influence of Golgi Enzyme Localization Domain and Co-Expression of Heterologous β1, 4-N-acetylglucosaminyltransferase III and Golgi α-Mannosidase II", Biotechnology and Bioengineering, vol. 93, Issue No. 5, Apr. 5, 2006, pp. 851-861.

Ghetie et al., "Increasing the Serum Persistence of an Igg Fragment by Random Mutagenesis", Nat Biotech, vol. 15, 1997, pp. 637-640.

Goodman et al., "Immunoglobulin Proteins", Chapter 6, Basic and Clinical Immunology, 1994, pp. 66-79.

Graham et al., "Characteristics of a Human Cell Line Transformed by DNA from Human Adenovirus Type 5", Journal of General Virology, vol. 36, 1977, pp. 59-72.

Guhl et al., "Long-Term Cultured Human Skin Mast Cells Are Suitable for Pharmacological Studies of Anti-Allergic Drugs Due to High Responsiveness to FceRI Cross-Linking", Bioscience, Biotechnology, and Biochemistry, vol. 75, No. 2, 2011, pp. 382-384.

Gunten et al., "Intravenous Immunoglobulin Preparations Contain Anti-Siglec-8 Autoantibodies", Journal of Allergy and Clinical Immunology, vol. 119, No. 4, 2007, pp. 1005-1011.

Guss et al., "Structure of the IgG-binding Regions of Streptococcal Protein G", The EMBO Journal, vol. 5, No. 7, 1986, pp. 1567-1575.

Guyer et al., "Immunoglobulin Binding by Mouse Intestinal Epithelial Cell Receptors", The Journal of Immunology, vol. 117, No. 2, Aug. 1, 1976, pp. 587-593.

Ham et al., "Media and Growth Requirements", Methods in Enzymology, vol. 58, 1979, pp. 44-93.

Hamers-Casterman et al., "Naturally Occurring Antibodies Devoid of Light Chains", Nature, vol. 363, Jun. 3, 1993, pp. 446-448.

Hara et al., "Overproduction of Penicillin-Binding Protein 7 Suppresses Thermosensitive Growth Defect at Low Osmolarity due to an spr Mutation of *Escherichia coli*", Microbial Drug Resistance, vol. 2, No. 1, 1996, pp. 63-72.

(56) References Cited

OTHER PUBLICATIONS

Harris, W. J., "Production of Humanized Monoclonal Antibodies for in Vivo Imaging and Therapy", Biochemical Society Transactions, vol. 23, No. 4, Nov. 1, 1995, pp. 1035-1038.

Hudson et al., "Developmental, Malignancy-Related, and Cross-Species Analysis of Eosinophil, Mast Cell, and Basophil Siglec-8 Expression", Journal of Clinical Immunology, vol. 31, No. 6, Dec. 2011, pp. 1045-1053.

Hudson et al., "Engineered Antibodies", Nature Medicine, vol. 9, 2003, pp. 129-134.

Hurle et al., "Protein Engineering Techniques for Antibody Humanization", Current Opinion in Biotechnology, vol. 5, Issue 4, Aug. 1994, pp. 428-433.

Hutchins et al., "Improved Biodistribution, Tumor Targeting, and reduced Immunogenicity in Mice with a Gamma 4 Variant of Campath-IH", Proceedings of the National Academy of Sciences, vol. 92, Dec. 1995, pp. 11980-11984.

Idusogie et al., "Engineered Antibodies with Increased Activity to Recruit Complement", The Journal of Immunology, vol. 166, 2001, pp. 2571-2575.

Idusogie et al., "Mapping of the C1q Binding Site on Rituxan, a Chimeric Antibody with a Human IgG1 Fc", The Journal of Immunology, vol. 164, 2000, pp. 4178-4184.

Jakobovits et al., "Analysis of Homozygous Mutant Chimeric Mice: Deletion of the Immunoglobulin Heavy-chain Joining Region Blocks B-cell Development and Antibody Production", PNAS, Proceedings of the National Academy of Sciences, vol. 90, Mar. 1993, pp. 2551-2555.

Jakobovits et al., "Germ-line Transmission and Expression of a Human-derived Yeast Artificial Chromosome", Nature, vol. 362, Mar. 18, 1993, pp. 255-258.

Jefferis et al., "Human Immunoglobulin Allotypes", MABS, vol. 1, No. 4, Jul./Aug. 2009, pp. 1-7.

Jefferis et al., "Interaction Sites on Human IgG-Fc for FcγR: Current Models", Immunology Letters, vol. 82, Issues 1-2, Jun. 3, 2002, pp. 57-65.

Jefferis et al., "Modulation of Fc(gamma)r and Human Complement Activation by Igg3-core Oligosaccharide Interactions", Immunology Letters, vol. 54, Issues 2-3, Dec. 2, 1996, pp. 101-104.

Jefferis et al., "Recognition Sites on Human Igg for Fcγ Receptors: The Role of Glycosylation", Immunology Letters, vol. 44, Issues 2-3, Jan. 2, 1995, pp. 111-117.

Johnson et al., "The Kabat Database and a Bioinformatics Example", Antibody Engineering Methods in Molecular Biology™, vol. 248, 2004, pp. 11-25.

Jones et al., "Replacing the Complementarity-determining Regions in a Human Antibody with those from a Mouse", Nature, vol. 321, May 29, 1986, pp. 522-525.

Kikly et al., "Identification of Saf-2, a Novel Siglec Expressed on Eosinophils, Mast Cells, and Basophils", The Journal of Allergy and Clinical Immunology, vol. 105, Issue 6, Part 1, 2000, pp. 1093-1100.

Kim et al., "Localization of the Site of the Murine IgG1 Molecule that is Involved in Binding to the Murine Intestinal Fc Receptor", European Journal of Immunology, vol. 24, 1994, pp. 2429-2434.

Kiwamoto et al., "Siglec-8 as a Drugable Target to Treat Eosinophil and Mast Cell Associated Conditions", Pharmacology & Therapeutics, vol. 135, Issue No. 3, Sep. 2012, 22 pages.

Kozbor et al., "A Human Hybrid Myeloma for Production of Human Monoclonal Antibodies", The Journal of Immunology, vol. 133, No. 6, Dec. 1, 1984, pp. 3001-3005.

Lazar et al., "Engineered Antibody Fc Variants with Enhanced Effector Function", PNAS, vol. 103, No. 11, Mar. 14, 2006, pp. 4005-4010.

Lefranc, Marie-Paule, "IMGT, The International ImMunoGeneTics Database ®", Nucleic Acids Research, vol. 31, No. 1, 2003, pp. 307-310.

Lichtenfels et al., "CARE-LASS (calcein-release-assay), an Improved Fluorescence-based Test System to Measure Cytotoxic T Lymphocyte Activity", Journal of Immunological Methods, vol. 172, Issue 2, Jun. 24, 1994, pp. 227-239.

Lindmark et al., "Binding of Immunoglobulins to Protein A and Immunoglobulin Levels in Mammalian Sera", Journal of Immunological Methods, vol. 62, 1983, pp. 1-13.

Lund et al., "Human Fc Gamma Ri and Fc Gamma Rii Interact With Distinct but Overlapping Sites on Human Igg.", The Journal of Immunology, vol. 147, No. 8, Oct. 15, 1991, pp. 2657-2662.

Lund et al., "Multiple Binding Sites on the Ch2 Domain of Igg for Mouse Fcγr11", Molecular Immunology, vol. 29, Issue 1, Jan. 1992, pp. 53-59.

Lund et al., "Multiple Interactions of Igg with its Core Oligosaccharide can Modulate Recognition by Complement and Human Fc Gamma Receptor I and Influence the Synthesis of its Oligosaccharide Chains.", The Journal of Immunology, vol. 157, No. 11, Dec. 1, 1996, pp. 4963-4969.

Lund et al., "Oligosaccharide-Protein Interactions in IgG can Modulate Recognition by FcGamma Receptors", FASEB, vol. 9, Jan. 1995, pp. 115-119.

Mather et al., "Culture of Testicular Cells in Hormone-Supplemented Serum-Free Medium", Annals of the New York Academy of Sciences, Testicular Cell Culture, 1982, pp. 44-68.

Mather, Jennie P., "Establishment and Characterization of Two Distinct Mouse Testicular Epithelial Cell Lines", Biology of Reproduction, vol. 23, 1980, pp. 243-252.

Milstein et al., "Hybrid Hybridomas and Their Use in Immunohistochemistry", Nature, vol. 305, Oct. 6, 1983, pp. 537-540.

Morimoto et al., "Single-step Purification of F(ab')2 Fragments of Mouse Monoclonal Antibodies (immunoglobulins G1) by Hydrophobic Interaction High Performance Liquid Chromatography Using Tskgel Phenyl-5pw", Journal of Biochemical and Biophysical Methods, vol. 24, Issues 1-2, 1992, pp. 107-117.

Morrison et al., "Chimeric Human Antibody Molecules: Mouse Antigen-binding Domains with Human Constant Region Domains", PNAS, vol. 81, Nov. 1984, pp. 6851-6855.

Munson et al., "Ligand: A Versatile Computerized Approach for Characterization of Ligand-binding Systems", Analytical Biochemistry, vol. 107, Issue 1, Sep. 1, 1980, pp. 220-239.

Nutku et al., "Ligation of Siglec-8: A Selective Mechanism for Inductionof Human Eosinophil Apoptosis", Blood, vol. 101, No. 12, Jun. 15, 2003, pp. 5014-5020.

O'Reilly et al., "Siglecs as Targets for Therapy in Immune Cell Mediated Disease", Trends in Pharmacological Sciences, vol. 30, No. 5, May 2009, pp. 240-248.

Okazaki et al., "Fucose Depletion from Human IgG1 Oligosaccharide Enhances Binding Enthalpy and Association Rate Between IgG1 and FcgammaRIIIa", Journal of Molecular Biology, vol. 336, 2004, pp. 1239-1249.

Patel et al., "An Improved Assay for Antibody Dependent Cellular Cytotoxicity Based on Time Resolved Fluorometry", Journal of Immunological Methods, vol. 184, Issue 1, Jul. 17, 1995, pp. 29-38.

Pillai et al., "Siglecs and Immune Regulation", Annual Review of Immunology, vol. 30, 2012, pp. 357-392.

Plückthun, A., "Antibodies from *Escherichia coli*", Chapter 11, The Pharmacology of Monoclonal Antibodies, 1994, pp. 269-315.

Presta et al., "Engineering Therapeutic Antibodies for Improved Function", Biochemical Society Transactions, vol. 30, No. 4, 2002, pp. 487-490.

Presta et al., "Humanization of an Antibody Directed against IgE", The Journal of Immunology, vol. 151, No. 5, Sep. 1, 1993, pp. 2623-2632.

Presta, Leonard G., "Antibody Engineering", Current Opinion in Structural Biology, vol. 2, 1992, pp. 593-596.

Proba et al., "Functional Antibody Single-chain Fragments From the Cytoplasm of *Escherichia coli*: Influence of Thioredoxin Reductase (trxb)", Gene, vol. 159, Issue 2, 1995, pp. 203-207.

Ramm et al., "The Periplasmic *Escherichia coli* Peptidylprolyl cis,Trans-Isomerase FkpA", The Journal of Biological Chemistry, vol. 275, No. 22, 2000, pp. 17106-17113.

Ravetch et al., "Fc Receptors", Annual Review of Immunology, vol. 9, 1991, pp. 457-492.

(56) References Cited

OTHER PUBLICATIONS

Reddy et al., "Elimination of Fc Receptor-Dependent Effector Functions of a Modified IgG4 Monoclonal Antibody to Human CD4", The Journal of Immunology, vol. 164, 2000, pp. 1925-1933.
Reyes et al., "Expression of Human β-Interferon cDNA Under the Control of a Thymidine Kinase Promoter from Herpes Simplex Virus", Nature, vol. 297, Jun. 17, 1982, pp. 598-601.
Riechmann et al., "Reshaping Human Antibodies for Therapy", Nature, vol. 332, Mar. 24, 1988, pp. 323-327.
Ripka et al., "Two Chinese Hamster Ovary Glycosylation Mutants Affected in the Conversion of Gdp-mannose to Gdp-fucose.", Archives of Biochemistry and Biophysics, vol. 249, No. 2, 1986, pp. 533-545.
Scatchard et al., "The Attractions of Proteins for Small Molecules and Ions", Annals of the New York Academy of Sciences, 1949, pp. 660-672.
Settipane, Guy A., "Epidemiology of Nasal Polyps", Allergy and Asthma Proceedings, vol. 17, No. 5, Sep.-Oct. 1996, pp. 231-236.
Sheriff et al., "Redefining the Minimal Antigen-binding Fragment", Nature Structural & Molecular Biology, vol. 3, 1996, pp. 733-736.
Shi et al., "Characterizing T-Cell Phenotypes in Nasal Polyposis in Chinese Patients", Journal of Investigational Allergology and Clinical Immunology, vol. 19, No. 4, 2009, pp. 276-282.
Shields et al., "High resolution Mapping of the binding site on Human IgG1 for Fc Gamma RI, Fc gamma RII, Fc gamma RIII, and FcRn and design of IgG1 variants with improved binding to the Fc gamma R.", The Journal of Biological Chemistry, vol. 276, No. 9, 2001, pp. 6591-6604.
Siebenlist et al., "*E. coli* RNA Polymerase Interacts Homologously with Two Different Promoters", Cell, vol. 20, Isuue 2, Jun. 1980, pp. 269-281.
Simmons et al., "Expression of Full-length Immunoglobulins in *Escherichia coli*: Rapid and Efficient Production of Aglycosylated Antibodies", Journal of Immunological Methods, vol. 263, Issues 1-2, May 1, 2002, pp. 133-147.
Sims et al., "A Humanized Cd18 Antibody Can Block Function Without Cell Destruction", The Journal of Immunology, vol. 151, No. 4, Aug. 15, 1993, pp. 2296-2308.
Suresh et al., "Bispecific Monoclonal Antibodies from Hybrid Hybridomas", Methods in Enzymology, vol. 121, 1986, pp. 210-228.
Tanaka et al., "Development of Mature and Functional Human Myeloid subsets in HSC Engrafted NOD/SCID/IL2rγyKO Mice", Search Results the Journal of Immunology, vol. 188, No. 12, Jun. 2012, pp. 6145-6155.

Traunecker et al., "Bispecific Single Chain Molecules (Janusins) Target Cytotoxic Lymphocytes on HIV Infected Cells", The EMBO Journal, vol. 10, No. 12, 1991, pp. 3655-3659.
Urlaub et al., "Isolation of Chinese Hamster Cell Mutants Deficient in Dihydrofolate Reductase Activity", Proceedings of the National Academy of Sciences, vol. 77, No. 7, Jul. 1980, pp. 4216-4220.
Vaswani et al., "Humanized Antibodies as Potential Therapeutic Drugs", Annals of Allergy, Asthma & Immunology, vol. 81, Issue 2, Aug. 1998, pp. 105-116.
Verhoeyen et al., "Reshaping Human Antibodies: Grafting an Antilysozyme Activity", Science, vol. 239, 1988, pp. 1534-1536.
Wechsler et al., "Novel Targeted Therapies for Eosinophilic Disorders", Journal of Allergy and Clinical Immunology, vol. 130, No. 3, Sep. 2012, pp. 563-571.
Xu et al., "Diversity in the CDR3 Region of VH Is Sufficient for Most Antibody Specificities", Immunity, vol. 13, Jul. 2000, pp. 37-45.
Xu et al., "In Vitro Characterization of Five Humanized OKT3 Effector Function Variant Antibodies", Cellular Immunology, vol. 200, Issue 1, Feb. 25, 2000, pp. 16-26.
Yamane-Ohnuki et al., "Establishment of FUT8 Knockout Chinese Hamster Ovary Cells: An Ideal Host Cell Line for Producing Completely Defucosylated Antibodies with Enhanced Antibody-Dependent Cellular Cytotoxicity", Biotechnology and Bioengineering, vol. 87, Issue No. 5, Sep. 5, 2004, pp. 614-622.
Yaniv, Moshe, "Enhancing Elements for Activation of Eukaryotic Promoters", Nature, vol. 297, May 6, 1982, pp. 17-18.
Yokoi et al., "Inhibition of Fceri-Dependent Mediator Release and Calcium Flux from Human Mast Cells by Sialic Acid-Binding Immunoglobulin-Like Lectin 8 Engagement", Journal of Allergy and Clinical Immunology, vol. 121, No. 2, Feb. 2008, pp. 499-505.
Zapata et al., "Engineering Linear F(ab')2 Fragments for Efficient Production in *Escherichia coli* and Enhanced Antiproliferative Activity", Protein Engineering, vol. 8, No. 10, 1995, pp. 1057-1062.
Bachmann, Barbara J., "Derivations and Genotypes of Some Mutant Derivatives of *Escherichia coli* K-12", Cellular and Molecular Biology, vol. 2, 1987, pp. 1190-1219.
Yansura et al., "Nucleotide Sequence Selection for Increased Expression of Heterologous Genes in *Escherichia coli*", Methods: A Companion to Methods in Enzymol, 1992, pp. 151-158.
Duncan et al., "The binding site for Clq on igG", Nature, vol. 332, 1988, pp. 738-740.
Mroz et al., "Siglec-8 in Induced Sputum of COPD Patients", Advances in Experimental Medicine and Biology, vol. 788, 2013, pp. 19-23.
Steinke et al., "Prominent Role of IFN-γ in Patients with Aspirin-Exacerbated Respiratory Disease", Journal of Allergy and Clinical Immunology, vol. 132, Issue 4, Oct. 2013, pp. 856-865.

* cited by examiner

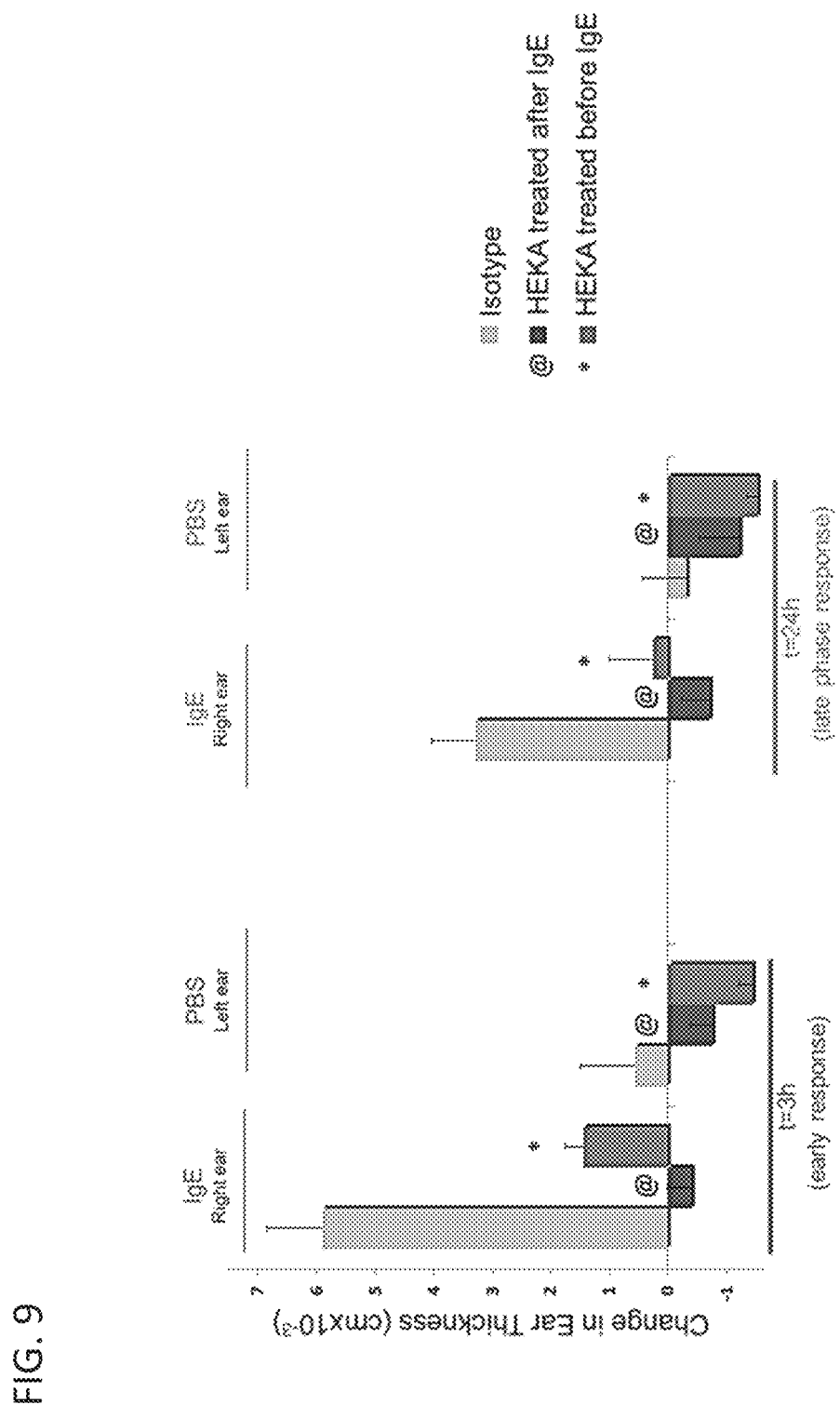

ANTI-SIGLEC-8 ANTIBODIES AND METHODS OF USE THEREOF

CROSS-REFERENCE TO RELATED APPLICATIONS

This application claims priority to U.S. Provisional Patent Application No. 61/913,891, filed Dec. 9, 2013, which are incorporated by reference herein in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 701712000100SeqList.txt, date recorded: Dec. 9, 2014, size: 115 KB).

FIELD OF THE INVENTION

This invention relates to anti-human Siglec-8 antibodies and methods of treating or preventing a disease mediated by cells expressing Siglec-8.

BACKGROUND OF THE INVENTION

Siglecs (sialic acid-binding immunoglobulin-like lectins) are single-pass transmembrane cell surface proteins found predominantly on leukocytes and that are characterized by their specificity for sialic acids attached to cell-surface glycoconjugates. The Siglec family contains at least 15 members that are found in mammals (Pillai et al., *Annu Rev Immunol.*, 2012, 30:357-392). These members include sialoadhesion (Siglec-1), CD22 (Siglec-2), CD33 (Siglec-3), myelin associated glycoprotein (Siglec-4), Siglec-5, OBBP1 (Siglec-6), AIRM1 (Siglec-7), SAF-2 (Siglec-8), and CD329 (Siglec-9). Siglec-8, a member that is expressed in humans but not in mouse, was first discovered as part of efforts to identify novel human eosinophil proteins. In addition to expression by eosinophils, it is also expressed by mast cells and basophils. Siglec-8 recognizes a sulfated glycan, i.e., 6'-sulfo-sialyl Lewis X or 6'-sulfo-sialyl-N-acetyl-S-lactosamine, and contains an intracellular immunoreceptor tyrosine-based inhibitory motif (ITIM) domain shown to inhibit mast cell function.

Along with mast cells, eosinophils can promote an inflammatory response that plays a beneficial functional role such as controlling an infection at a specific tissue site. During an inflammatory response, apoptosis of eosinophils can be inhibited through the activity of survival-promoting cytokines such as IL-3 and GM-CSF. However, an increase of activated eosinophils that are not rapidly removed by apoptosis can result in the release of eosinophil granule proteins at already inflamed sites which can damage tissue and cause inflammation to be further exacerbated. Several diseases have been shown to be linked to eosinophil activation such as Churg Strauss syndrome, rheumatoid arthritis, and allergic asthma (Wechsler et al., *J Allergy Clin Immunol.*, 2012, 130(3):563-71). There is currently a need for therapies that can control the activity of immune cells involved in inflammation, such as the activity of eosinophils and mast cells.

Previous studies have demonstrated that eosinophils undergo apoptosis when Siglec-8 is crosslinked with specific murine antibodies raised against the extracellular portion of Siglec-8 (Nutku et al., *Blood*, 2003, 336:918-24). These antibodies are described in U.S. Pat. No. 8,207,305, U.S. Pat. No. 8,197,811, U.S. Pat. No. 7,871,612, and U.S. Pat. No. 7,557,191. However, there remains a need for developing humanized anti-Siglec-8 antibodies that recognize human Siglec-8 with high affinity and specificity. Discovery of such anti-Siglec-8 antibodies may allow for the development of treatment for diseases mediated by the activity of eosinophils and/or mast cells.

All references cited herein, including patent applications, patent publications, and scientific literature, are herein incorporated by reference in their entirety, as if each individual reference were specifically and individually indicated to be incorporated by reference.

SUMMARY OF THE INVENTION

Provided herein are anti-Siglec-8 antibodies (including humanized anti-Siglec-8 antibodies), compositions comprising thereof, and methods of using the same.

In one aspect, provided herein is a humanized antibody that specifically binds to a human Siglec-8, wherein the binding affinity and/or binding avidity of the humanized antibody to a human Siglec-8 are higher than the binding affinity and/or binding avidity of antibody 2E2 and/or antibody 2C4 to the human Siglec-8. In some embodiments, the human Siglec-8 is a dimer. In some embodiments, the human Siglec-8 comprises an extracellular domain human Siglec-8 fused to a Fc region of an immunoglobulin. In some embodiments, the Fc region is a human IgG1 Fc region. In some embodiments, the Fc region is a human IgG4 Fc region. In some embodiments, the human Siglec-8 comprises the amino acid sequence of SEQ ID NO:74.

In some embodiments, the humanized antibody comprises a heavy chain variable region and a light chain variable region, wherein the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence of SEQ ID NO:63; and/or wherein the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:66. In some embodiments, the antibody comprises a heavy chain variable region comprising the amino acid sequence of SEQ ID NO:6; and/or a light chain variable region comprising the amino acid sequence selected from SEQ ID NOs:16 or 21. In any of the embodiments herein, the antibody may comprise a heavy chain Fc region comprising a human IgG Fc region. In further embodiments, the human IgG Fc region comprises a human IgG1 or IgG4. In some embodiments, the human IgG1 comprises the amino acid sequence of SEQ ID NO:78. In some embodiments, the human IgG4 comprises the amino acid sequence of SEQ ID NO:79. In any of the embodiments herein, the antibody may comprise a heavy chain comprising the amino acid sequence of SEQ ID NO:75; and/or a light chain comprising the amino acid sequence selected from SEQ ID NOs:76 or 77. In some embodiments, the human IgG4 comprises the amino acid substitution S228P, wherein the amino acid residues are numbered according to the EU index as in Kabat. In any of the embodiments herein, the antibody may comprise a heavy chain comprising the amino acid sequence of SEQ ID NO:87; and/or a light chain comprising the amino acid sequence of SEQ ID NO:76. In some embodiments, the antibody has been engineered to improve antibody-dependent cell-mediated cytotoxicity (ADCC) activity. In some embodiments, the antibody comprises two heavy chains and wherein at least one of the two or both heavy chains of the antibody is non-fucosylated.

In another aspect, provided herein is a humanized antibody that specifically binds to a human Siglec-8, wherein the antibody has a Tm of at least about 70° C. to at least about 72° C. in a thermal shift assay. In some embodiments, the antibody has a Tm at about 70° C., at about 71° C., or at about 72° C. in a thermal shift assay. In some embodiments, the antibody has the same or higher Tm as compared to a chimeric 2C4 antibody. In some embodiments, the antibody has the same or higher Tm as compared to an antibody having a heavy chain comprising the amino acid sequence of SEQ ID NO:84 and a light chain comprising the amino acid sequence of SEQ ID NO:85.

In some embodiments, the antibody comprises a heavy chain variable region and a light chain variable region, wherein the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence of SEQ ID NO:63; and/or wherein the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:66. In some embodiments, the antibody comprises a heavy chain variable region comprising the amino acid sequence of SEQ ID NO:6; and/or a light chain variable region comprising the amino acid sequence selected from SEQ ID NOs:16 or 21. In any of the embodiments herein, the antibody may comprise a heavy chain Fc region comprising a human IgG Fc region. In further embodiments, the human IgG Fc region comprises a human IgG1 or IgG4. In some embodiments, the human IgG1 comprises the amino acid sequence of SEQ ID NO:78. In some embodiments, the human IgG4 comprises the amino acid sequence of SEQ ID NO:79. In any of the embodiments herein, the antibody may comprise a heavy chain comprising the amino acid sequence of SEQ ID NO:75; and/or a light chain comprising the amino acid sequence selected from SEQ ID NOs:76 or 77. In some embodiments, the human IgG4 comprises the amino acid substitution S228P, wherein the amino acid residues are numbered according to the EU index as in Kabat. In any of the embodiments herein, the antibody may comprise a heavy chain comprising the amino acid sequence of SEQ ID NO:87; and/or a light chain comprising the amino acid sequence of SEQ ID NO:76. In some embodiments, the antibody has been engineered to improve antibody-dependent cell-mediated cytotoxicity (ADCC) activity. In some embodiments, at least one or two of the heavy chains of the antibody is non-fucosylated.

In yet another aspect, provided herein is a humanized antibody that specifically binds to a human Siglec-8, wherein the antibody comprises a heavy chain variable region and a light chain variable region, wherein the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence selected from SEQ ID NOs:63 and 67-70; and/or wherein the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:66 or 71. In some embodiments, the antibody comprises a heavy chain variable region comprising the amino acid sequence selected from SEQ ID NOs:11-14; and/or a light chain variable region comprising the amino acid sequence selected from SEQ ID NOs:23-24. In some embodiments, the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence selected from SEQ ID NO:63; and/or the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:66. In some embodiments, the antibody comprises a heavy chain variable region comprising the amino acid sequence selected from SEQ ID NO:6; and/or a light chain variable region comprising the amino acid sequence selected from SEQ ID NO:16 or 21. In any of the embodiments herein, the antibody may comprise a heavy chain Fc region comprising a human IgG Fc region. In further embodiments, the human IgG Fc region comprises a human IgG1 or IgG4. In some embodiments, the human IgG1 comprises the amino acid sequence of SEQ ID NO:78. In some embodiments, the human IgG4 comprises the amino acid sequence of SEQ ID NO:79. In some embodiments, the human IgG4 comprises the amino acid substitution S228P, wherein the amino acid residues are numbered according to the EU index as in Kabat. In some embodiments, the antibody has been engineered to improve antibody-dependent cell-mediated cytotoxicity (ADCC) activity. In some embodiments, at least one or two of the heavy chains of the antibody is non-fucosylated.

In yet another aspect, provided herein is a humanized antibody that specifically binds to human Siglec-8, wherein the antibody comprises a heavy chain variable region comprising the amino acid sequence selected from SEQ ID NOs:2-14; and/or a light chain variable region comprising the amino acid sequence selected from SEQ ID NOs:16-24. In some embodiments, the antibody has been engineered to improve antibody-dependent cell-mediated cytotoxicity (ADCC) activity. In some embodiments, at least one or two of the heavy chains of the antibody is non-fucosylated.

In yet another aspect, provided herein is a humanized antibody that specifically binds to human Siglec-8, wherein the antibody comprises a heavy chain variable region comprising the amino acid sequence selected from SEQ ID NOs:2-10; and/or a light chain variable region comprising the amino acid sequence selected from SEQ ID NOs:16-22. In some embodiments, the antibody has been engineered to improve antibody-dependent cell-mediated cytotoxicity (ADCC) activity. In some embodiments, at least one or two of the heavy chains of the antibody is non-fucosylated.

In another aspect, provided herein is a humanized antibody that specifically binds to a human Siglec-8, wherein the antibody comprises a heavy chain variable region and a light chain variable region, wherein (a) the heavy chain variable region comprises: (1) an HC-FR1 comprising the amino acid sequence selected from SEQ ID NOs:26-29; (2) an HVR-H1 comprising the amino acid sequence of SEQ ID NO:61; (3) an HC-FR2 comprising the amino acid sequence selected from SEQ ID NOs:31-36; (4) an HVR-H2 comprising the amino acid sequence of SEQ ID NO:62; (5) an HC-FR3 comprising the amino acid sequence selected from SEQ ID NOs:38-43; (6) an HVR-H3 comprising the amino acid sequence of SEQ ID NO:63; and (7) an HC-FR4 comprising the amino acid sequence selected from SEQ ID NOs:45-46, and/or (b) the light chain variable region comprises: (1) an HC-FR1 comprising the amino acid sequence selected from SEQ ID NOs:48-49; (2) an HVR-H1 comprising the amino acid sequence of SEQ ID NO:64; (3) an HC-FR2 comprising the amino acid sequence selected from SEQ ID NOs:51-53; (4) an HVR-H2 comprising the amino acid sequence of SEQ ID NO:65; (5) an HC-FR3 comprising the amino acid sequence selected from SEQ ID NOs:55-58; (6) an HVR-H3 comprising the amino acid sequence of SEQ ID NO:66; and (7) an HC-FR4 comprising the amino acid sequence of SEQ ID NO:60. In some embodiments, the antibody has been engineered to improve antibody-dependent cell-mediated cytotoxicity (ADCC) activity. In some embodiments, at least one or two of the heavy chains of the antibody is non-fucosylated.

In yet another aspect, provided herein is an isolated antibody that binds a human Siglec-8 and kills mast cells expressing Siglec-8 by ADCC activity. In some embodiments, the antibody kills mast cells expressing Siglec-8 in vitro (e.g., measured in a cell culture assay as described in Example 2). In some embodiments, the antibody depletes mast cells expressing Siglec-8 in a subject when a therapeutically effective amount is administered. In a further embodiment, the antibody depletes at least about 20% (e.g., at least of the mast cells expressing Siglec-8 in a sample obtained from the subject as compared to a baseline level before treatment. In any of the embodiments herein, the sample can be a tissue sample or a biological fluid sample. In some embodiments, the tissue sample is one or more selected from the group consisting of: skin, lung, bone marrow, and nasal polyps. In some embodiments, the biological fluid sample is one or more selected from the group consisting of: blood, bronchoalveolar lavage, and nasal lavage. In any of the embodiments herein, the antibody can be engineered to improve antibody-dependent cell-mediated cytotoxicity (ADCC) activity. In some embodiments, at least one or two of the heavy chains of the antibody is non-fucosylated. In further embodiments, the antibody may be produced in a cell line having a alpha1,6-fucosyltransferase (Fut8) knockout. In some further embodiments, the antibody may be produced in a cell line overexpressing β1,4-N-acetylglycosminyltransferase III (GnT-III). In further embodiments, the cell line additionally overexpresses Golgi μ-mannosidase II (ManII). In any of the embodiments herein, the antibody may comprise at least one amino acid substitution in the Fc region that improves ADCC activity. In any of the embodiments herein, the antibody may be a humanized antibody, a chimeric antibody or a human antibody. In some embodiments, the antibody is a human IgG1 antibody. In some embodiments, the antibody is a murine antibody. In any of the embodiments herein, the antibody may comprise a heavy chain variable region comprising (i) HVR-H1 comprising the amino acid sequence of SEQ ID NO:88, (ii) HVR-H2 comprising the amino acid sequence of SEQ ID NO:91, and (iii) HVR-H3 comprising the amino acid sequence of SEQ ID NO:94; and/or a light chain variable region comprising (i) HVR-L1 comprising the amino acid sequence of SEQ ID NO:97, (ii) HVR-L2 comprising the amino acid sequence of SEQ ID NO:100, and (iii) HVR-L3 comprising the amino acid sequence of SEQ ID NO:103. In a further embodiment, the antibody comprises a heavy chain variable region comprising the amino acid sequence of SEQ ID NO:106; and/or a light chain variable region comprising the amino acid sequence of SEQ ID NO:109. In any of the embodiments herein, the antibody may comprise a heavy chain variable region comprising a heavy chain variable region comprising (i) HVR-H1 comprising the amino acid sequence of SEQ ID NO:89, (ii) HVR-H2 comprising the amino acid sequence of SEQ ID NO:92, and (iii) HVR-H3 comprising the amino acid sequence of SEQ ID NO:95; and/or a light chain variable region comprising (i) HVR-L1 comprising the amino acid sequence of SEQ ID NO:98, (ii) HVR-L2 comprising the amino acid sequence of SEQ ID NO:101, and (iii) HVR-L3 comprising the amino acid sequence of SEQ ID NO:104. In a further embodiment, the antibody comprises a heavy chain variable region comprising the amino acid sequence of SEQ ID NO:107; and/or a light chain variable region comprising the amino acid sequence of SEQ ID NO:110. In any of the embodiments herein, the antibody may comprise a heavy chain variable region comprising a heavy chain variable region comprising a heavy chain variable region comprising (i) HVR-H1 comprising the amino acid sequence of SEQ ID NO:90, (ii) HVR-H2 comprising the amino acid sequence of SEQ ID NO:93, and (iii) HVR-H3 comprising the amino acid sequence of SEQ ID NO:96; and/or a light chain variable region comprising (i) HVR-L1 comprising the amino acid sequence of SEQ ID NO:99, (ii) HVR-L2 comprising the amino acid sequence of SEQ ID NO:102, and (iii) HVR-L3 comprising the amino acid sequence of SEQ ID NO:105. In a further embodiment, the antibody comprises a heavy chain variable region comprising the amino acid sequence of SEQ ID NO:108; and/or a light chain variable region comprising the amino acid sequence of SEQ ID NO:111. In any of the embodiments herein, the antibody may comprise a heavy chain variable region and a light chain variable region, wherein the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence of SEQ ID NO:63; and/or wherein the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:66. In any of the embodiments herein, the antibody may comprise a heavy chain variable region and a light chain variable region, wherein the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence selected from SEQ ID NOs:67-70; and/or wherein the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:71. In any of the embodiments herein, the subject can be a human.

In still another aspect, provided herein is an antibody that binds to a human Siglec-8 and a non-human primate Siglec-8. In any of the embodiments herein, the antibody may comprise a heavy chain variable region comprising a heavy chain variable region comprising (i) HVR-H1 comprising the amino acid sequence of SEQ ID NO:89, (ii) HVR-H2 comprising the amino acid sequence of SEQ ID NO:92, and (iii) HVR-H3 comprising the amino acid sequence of SEQ ID NO:95; and/or a light chain variable region comprising (i) HVR-L1 comprising the amino acid sequence of SEQ ID NO:98, (ii) HVR-L2 comprising the amino acid sequence of SEQ ID NO:101, and (iii) HVR-L3 comprising the amino acid sequence of SEQ ID NO:104. In a further embodiment, the antibody comprises a heavy chain variable region comprising the amino acid sequence of SEQ ID NO:107; and/or a light chain variable region comprising the amino acid sequence of SEQ ID NO:110. In any of the embodiments herein, the antibody may comprise a heavy chain variable region comprising a heavy chain variable region comprising a heavy chain variable region comprising (i) HVR-H1 comprising the amino acid sequence of SEQ ID NO:90, (ii) HVR-H2 comprising the amino acid sequence of SEQ ID NO:93, and (iii) HVR-H3 comprising the amino acid sequence of SEQ ID NO:96; and/or a light chain variable region comprising (i) HVR-L1 comprising the amino acid sequence of SEQ ID NO:99, (ii) HVR-L2 comprising the amino acid sequence of SEQ ID NO:102, and (iii) HVR-L3 comprising the amino acid sequence of SEQ ID NO:105. In a further embodiment, the antibody comprises a heavy chain variable region comprising the amino acid sequence of SEQ ID NO:108; and/or a light chain variable region comprising the amino acid sequence of SEQ ID NO:111. In any of the embodiments herein, the antibody may bind to an epitope in Domain 1 of human Siglec-8 (e.g., Domain 1 that comprises the amino acid sequence of SEQ ID NO:112). In any of the embodiments herein, the antibody may bind to an epitope in Domain 3 of human Siglec-8 (e.g., Domain 3 that comprises the amino acid sequence of SEQ ID NO:114). In any of the embodiments herein, the antibody may bind to an epitope in Domain 2 of human Siglec-8 (e.g., Domain 2 that comprises the amino acid sequence of SEQ ID NO:113). In any of the embodiments herein, the antibody may be a humanized antibody, a chimeric antibody or a human antibody. In some embodiments, the antibody is a murine antibody. In some embodiments, the antibody is an IgG1 or IgG4 antibody (e.g., human IgG1 or IgG4).

In another aspect, provided herein is an anti-human Siglec 8 antibody that binds to a fusion protein comprising the amino acid of SEQ ID NO:116 but not to a fusion protein comprising the amino acid of SEQ ID NO:115. In some embodiments, the antibody described herein binds to a fusion protein comprising the amino acid of SEQ ID NO:117 but not to a fusion protein comprising the amino acid of SEQ ID NO:115. In some embodiments, the antibody described herein binds to a fusion protein comprising the amino acid of SEQ ID NO:117 but not to a fusion protein comprising the amino acid of SEQ ID NO:116. In some embodiments herein, the antibody may comprise a heavy chain variable region comprising (i) HVR-H1 comprising the amino acid sequence of SEQ ID NO:88, (ii) HVR-H2 comprising the amino acid sequence of SEQ ID NO:91, and (iii) HVR-H3 comprising the amino acid sequence of SEQ ID NO:94; and/or a light chain variable region comprising (i) HVR-L1 comprising the amino acid sequence of SEQ ID NO:97, (ii) HVR-L2 comprising the amino acid sequence of SEQ ID NO:100, and (iii) HVR-L3 comprising the amino acid sequence of SEQ ID NO:103. In a further embodiment, the antibody comprises a heavy chain variable region comprising the amino acid sequence of SEQ ID NO:106; and/or a light chain variable region comprising the amino acid sequence of SEQ ID NO:109. In some embodiments herein, the antibody may comprise a heavy chain variable region comprising a heavy chain variable region comprising (i) HVR-H1 comprising the amino acid sequence of SEQ ID NO:89, (ii) HVR-H2 comprising the amino acid sequence of SEQ ID NO:92, and (iii) HVR-H3 comprising the amino acid sequence of SEQ ID NO:95; and/or a light chain variable region comprising (i) HVR-L1 comprising the amino acid sequence of SEQ ID NO:98, (ii) HVR-L2 comprising the amino acid sequence of SEQ ID NO:101, and (iii) HVR-L3 comprising the amino acid sequence of SEQ ID NO:104. In a further embodiment, the antibody comprises a heavy chain variable region comprising the amino acid sequence of SEQ ID NO:107; and/or a light chain variable region comprising the amino acid sequence of SEQ ID NO:110. In some embodiments herein, the antibody may comprise a heavy chain variable region comprising a heavy chain variable region comprising (i) HVR-H1 comprising the amino acid sequence of SEQ ID NO:90, (ii) HVR-H2 comprising the amino acid sequence of SEQ ID NO:93, and (iii) HVR-H3 comprising the amino acid sequence of SEQ ID NO:96; and/or a light chain variable region comprising (i) HVR-L1 comprising the amino acid sequence of SEQ ID NO:99, (ii) HVR-L2 comprising the amino acid sequence of SEQ ID NO:102, and (iii) HVR-L3 comprising the amino acid sequence of SEQ ID NO:105. In a further embodiment, the antibody comprises a heavy chain variable region comprising the amino acid sequence of SEQ ID NO:108; and/or a light chain variable region comprising the amino acid sequence of SEQ ID NO:111.

In another aspect, provided herein is a humanized antibody that binds to a human Siglec-8, wherein the $EC_{50}$ in depleting activated human eosinophils is less than the $EC_{50}$ of antibody 2E2 or 2C4 to the human Siglec-8. In some embodiments, the $EC_{50}$ of the humanized antibody is about 85% or less than the $EC_{50}$ of antibody 2E2 or 2C4 to the human Siglec-8. In some embodiments, the $EC_{50}$ of the humanized antibody is about 85%, about 80%, about 70%, about 65%, about 60%, about 55%, about 50%, about 45%, about 40%, about 35%, about 30%, about 25%, about 20%, about 15%, about 10% or about 5% or less than the $EC_{50}$ of antibody 2E2 or 2C4 to the human Siglec-8. In any of the embodiments herein, the humanized antibody may comprise a heavy chain variable region and a light chain variable region, wherein the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence of SEQ ID NO:63; and/or wherein the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:66. In any of the embodiments herein, the humanized antibody may comprise a heavy chain variable region comprising the amino acid sequence of SEQ ID NO:6; and/or a light chain variable region comprising the amino acid sequence selected from SEQ ID NOs:16 or 21. In some embodiments, the humanized antibody comprises a heavy chain variable region and a light chain variable region, wherein the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence selected from SEQ ID NOs:67-70; and/or wherein the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:71. In any of the embodiments herein, the humanized antibody may comprise a heavy chain variable region comprising the amino acid sequence selected from SEQ ID NOs:2-14; and/or a light chain variable region comprising the amino acid sequence selected from SEQ ID NOs:16-24. In any of the embodiments herein, the antibody may comprise a heavy chain variable region comprising (i) HVR-H1 comprising the amino acid sequence of SEQ ID NO:88, (ii) HVR-H2 comprising the amino acid sequence of SEQ ID NO:91, and (iii) HVR-H3 comprising the amino acid sequence of SEQ ID NO:94; and/or a light chain variable region comprising (i) HVR-L1 comprising the amino acid sequence of SEQ ID NO:97, (ii) HVR-L2 comprising the amino acid sequence of SEQ ID NO:100, and (iii) HVR-L3 comprising the amino acid sequence of SEQ ID NO:103. In any of the embodiments herein, the antibody may comprise a heavy chain variable region comprising a heavy chain variable region comprising (i) HVR-H1 comprising the amino acid sequence of SEQ ID NO:89, (ii) HVR-H2 comprising the amino acid sequence of SEQ ID NO:92, and (iii) HVR-H3 comprising the amino acid sequence of SEQ ID NO:95; and/or a light chain variable region comprising (i) HVR-L1 comprising the amino acid sequence of SEQ ID NO:98, (ii) HVR-L2 comprising the amino acid sequence of SEQ ID NO:101, and (iii) HVR-L3 comprising the amino acid sequence of SEQ ID NO:104. In any of the embodiments herein, the antibody may comprise a heavy chain variable region comprising a heavy chain variable region comprising a heavy chain variable region comprising (i) HVR-H1 comprising the amino acid sequence of SEQ ID NO:90, (ii) HVR-H2 comprising the amino acid sequence of SEQ ID NO:93, and (iii) HVR-H3 comprising the amino acid sequence of SEQ ID NO:96; and/or a light chain variable region comprising (i) HVR-L1 comprising the amino acid sequence of SEQ ID NO:99, (ii) HVR-L2 comprising the amino acid sequence of SEQ ID NO:102, and (iii) HVR-L3 comprising the amino acid sequence of SEQ ID NO:105. In any of the embodiments herein, the antibody may comprise a heavy chain Fc region comprising a human IgG Fc region. In further embodiments, the human IgG Fc region comprises a human IgG1 or IgG4. In some embodiments, the human IgG1 comprises the amino acid sequence of SEQ ID NO:78. In some embodiments, the human IgG4 comprises the amino acid sequence of SEQ ID NO:79. In any of the embodiments herein, the antibody may comprise a heavy chain comprising the amino acid sequence of SEQ ID NO:75; and/or a light chain comprising the amino acid sequence selected from SEQ ID NOs:76 or 77. In some embodiments, the human IgG4 comprises the amino acid substitution S228P, wherein the amino acid residues are numbered according to the EU index as in Kabat. In any of the embodiments herein, the antibody may comprise a heavy chain comprising the amino acid sequence of SEQ ID NO:87; and/or a light chain comprising the amino acid sequence of SEQ ID NO:76.

In another aspect, provided herein is a nucleic acid encoding any antibody described above and herein. In yet another aspect, provided herein is a vector comprising a nucleic acid described herein. In one embodiment, the vector is an expression vector. In yet another aspect, provided herein is a host cell comprising a nucleic acid described herein. In some embodiments, the host cell expresses and produces the antibody.

In another aspect, provided herein is a method of producing an antibody comprising culturing a host cell comprising one or more nucleic acids encoding an antibody described herein under a condition that produces the antibody. In some embodiments, the method further comprises recovering the antibody produced by the host cell. Also provided herein is an anti-Siglec-8 antibody produced by the method. Also provided herein is an antigen-binding fragment of an anti-Siglec-8 antibody described herein.

In another aspect, provided herein is a pharmaceutical composition comprising an antibody described above and herein or an antigen-binding fragment thereof and a pharmaceutically acceptable carrier.

In another aspect, provided herein is a composition comprising an antibody or fragment thereof that specifically binds to human Siglec-8, wherein the antibody comprises a Fc region and N-glycoside-linked carbohydrate chains linked to the Fc region, wherein less than 50% of the N-glycoside-linked carbohydrate chains in the composition contain a fucose residue. In some embodiments, substantially none of the N-glycoside-linked carbohydrate chains contain a fucose residue. In some embodiments, the antibody is a humanized antibody, a chimeric antibody or a human antibody. In some embodiments, the antibody comprises a heavy chain variable region and a light chain variable region, wherein the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence of SEQ ID NO:63; and/or wherein the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:66. In some embodiments, the antibody comprises a heavy chain variable region comprising the amino acid sequence of SEQ ID NOs:2-10; and/or a light chain variable region comprising the amino acid sequence of SEQ ID NOs:16-22. In some embodiments, the antibody comprises a heavy chain variable region and a light chain variable region, wherein the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence selected from SEQ ID NOs:67-70; and/or wherein the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:71. In some embodiments, the antibody comprises a heavy chain variable region comprising the amino acid sequence selected from SEQ ID NOs:11-14; and/or a light chain variable region comprising the amino acid sequence selected from SEQ ID NOs:23-24. In some embodiments, the antibody comprises a heavy chain variable region comprising the amino acid sequence selected from SEQ ID NOs:2-14; and/or a light chain variable region comprising the amino acid sequence selected from SEQ ID NOs:16-24. In any of the embodiments herein, the composition may further comprise a pharmaceutically acceptable carrier. In any of the embodiments herein, the binding affinity and/or binding avidity of the antibody to a human Siglec-8 can be higher than the binding affinity and/or binding avidity of antibody 2E2 or 2C4 to the human Siglec-8. In any of the embodiments herein, the antibody may have a Tm of at least about 70° C. to at least about 72° C. in a thermal shift assay. In some embodiments, the antibody has a Tm of about 70° C., about 71° C., or about 72° C. In some embodiments, the antibody has the same or higher Tm as compared to a chimeric 2C4 antibody. In some embodiments, the antibody has the same or higher Tm as compared to an antibody having a heavy chain comprising the amino acid sequence of SEQ ID NO:84 and a light chain comprising the amino acid sequence of SEQ ID NO:85.

In another aspect, provided herein is a method of treating or preventing a disease mediated by cells expressing Siglec-8 in a subject, the method comprising administering to the subject an effective amount of an antibody described herein or an antigen-binding fragment thereof or a composition described herein. In some embodiments, the disease is an eosinophil mediated-disease. In some embodiments, the disease is a mast cell mediated-disease. In some embodiments, the disease is selected from the group consisting of asthma, allergic rhinitis, nasal polyposis, atopic dermatitis, chronic urticaria, mastocytosis, eosinophilic leukemia, and hypereosinophilic syndrome. In some embodiments, the disease is selected from the group consisting of pauci granulocytic asthma, acute or chronic airway hypersensitivity, eosinophilic esophagitis, Churg-Strauss syndrome, inflammation associated with a cytokine, inflammation associated with cells expressing Siglec-8, malignancy associated with cells expressing Siglec-8, physical urticaria, cold urticaria, pressure-urticaria, bullous pemphigoid, food allergy, and allergic bronchopulmonary aspergillosis (ABPA). In some embodiments, the antibody inhibits one or more symptoms of an allergic reaction. In some embodiments, the allergic reaction is a Type I hypersensitivity reaction. In any of the embodiments herein, the subject may be suffering from asthma that is not adequately controlled by an inhaled corticosteroid, a short acting β2 agonist, a long acting β2 agonist, or a combination thereof.

In another aspect, provided herein is a method of depleting mast cells expressing Siglec-8 in a subject comprising administering to the subject an effective amount of an antibody that binds to human Siglec-8, wherein the antibody kills mast cells expressing Siglec-8 by ADCC activity. In some embodiments, the antibody kills mast cells expressing Siglec-8 in vitro (e.g., measured in a cell culture assay as described in Example 2). In some embodiments, the antibody depletes at least about 20% of the mast cells expressing Siglec-8 in a sample obtained from the subject as compared to a baseline level before treatment. In any of the embodiments herein, the sample can be a tissue sample or a biological fluid sample. In some embodiments, the tissue sample is one or more selected from the group consisting of: skin, lung, bone marrow, and nasal polyps. In some embodiments, the biological fluid sample is one or more selected from the group consisting of: blood, bronchoalveolar lavage, and nasal lavage. In any of the embodiments herein, the antibody can be engineered to improve antibody-dependent cell-mediated cytotoxicity (ADCC) activity. In any of the embodiments herein, the antibody may comprise two heavy chains and wherein at least one of the two or both heavy chains of the antibody is non-fucosylated. In further embodiments, the antibody may be produced in a cell line having a alpha1,6-fucosyltransferase (Fut8) knockout. In some further embodiments, the antibody may be produced in a cell line overexpressing β1,4-N-acetylglycosminyltransferase III (GnT-III). In further embodiments, the cell line additionally overexpresses Golgi μ-mannosidase II (ManII). In any of the embodiments herein, the antibody may comprise at least one amino acid substitution in the Fc region that improves ADCC activity. In any of the embodiments herein, the antibody may be a humanized antibody, a chimeric antibody or a human antibody. In some embodiments, the antibody is a human IgG1 antibody. In any of the embodiments herein, the antibody may comprise a heavy chain variable region comprising (i) HVR-H1 comprising the amino acid sequence of SEQ ID NO:88, (ii) HVR-H2 comprising the amino acid sequence of SEQ ID NO:91, and (iii) HVR-H3 comprising the amino acid sequence of SEQ ID NO:94; and/or a light chain variable region comprising (i) HVR-L1 comprising the amino acid sequence of SEQ ID NO:97, (ii) HVR-L2 comprising the amino acid sequence of SEQ ID NO:100, and (iii) HVR-L3 comprising the amino acid sequence of SEQ ID NO:103. In a further embodiment, the antibody comprises a heavy chain variable region comprising the amino acid sequence of SEQ ID NO:106; and/or a light chain variable region comprising the amino acid sequence of SEQ ID NO:109. In any of the embodiments herein, the antibody may comprise a heavy chain variable region comprising a heavy chain variable region comprising (i) HVR-H1 comprising the amino acid sequence of SEQ ID NO:89, (ii) HVR-H2 comprising the amino acid sequence of SEQ ID NO:92, and (iii) HVR-H3 comprising the amino acid sequence of SEQ ID NO:95; and/or a light chain variable region comprising (i) HVR-L1 comprising the amino acid sequence of SEQ ID NO:98, (ii) HVR-L2 comprising the amino acid sequence of SEQ ID NO:101, and (iii) HVR-L3 comprising the amino acid sequence of SEQ ID NO:104. In a further embodiment, the antibody comprises a heavy chain variable region comprising the amino acid sequence of SEQ ID NO:107; and/or a light chain variable region comprising the amino acid sequence of SEQ ID NO:110. In any of the embodiments herein, the antibody may comprise a heavy chain variable region comprising a heavy chain variable region comprising a heavy chain variable region comprising (i) HVR-H1 comprising the amino acid sequence of SEQ ID NO:90, (ii) HVR-H2 comprising the amino acid sequence of SEQ ID NO:93, and (iii) HVR-H3 comprising the amino acid sequence of SEQ ID NO:96; and/or a light chain variable region comprising (i) HVR-L1 comprising the amino acid sequence of SEQ ID NO:99, (ii) HVR-L2 comprising the amino acid sequence of SEQ ID NO:102, and (iii) HVR-L3 comprising the amino acid sequence of SEQ ID NO:105. In a further embodiment, the antibody comprises a heavy chain variable region comprising the amino acid sequence of SEQ ID NO:108; and/or a light chain variable region comprising the amino acid sequence of SEQ ID NO:111. In any of the embodiments herein, the antibody may comprise a heavy chain variable region and a light chain variable region, wherein the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence of SEQ ID NO:63; and/or wherein the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:66. In any of the embodiments herein, the antibody may comprise a heavy chain variable region and a light chain variable region, wherein the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence selected from SEQ ID NOs:67-70; and/or wherein the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:71. In any of the embodiments herein, the subject has a disease mediated by cells expressing Siglec-8. In some embodiments, the disease is selected from the group consisting of asthma, allergic rhinitis, nasal polyposis, atopic dermatitis, chronic urticaria, mastocytosis, eosinophilic leukemia, and hypereosinophilic syndrome. In some embodiments, the disease is selected from the group consisting of pauci granulocytic asthma, acute or chronic airway hypersensitivity, eosinophilic esophagitis, Churg-Strauss syndrome, inflammation associated with a cytokine, inflammation associated with cells expressing Siglec-8, malignancy associated with cells expressing Siglec-8, physical urticaria, cold urticaria, pressure-urticaria, bullous pemphigoid, food allergy, and allergic bronchopulmonary aspergillosis (ABPA). In some embodiments, the antibody inhibits one or more symptoms of an allergic reaction. In some embodiments, the allergic reaction is a Type I hypersensitivity reaction. In any of the embodiments herein, the subject may be suffering from asthma that is not adequately controlled by an inhaled corticosteroid, a short acting β2 agonist, a long acting β2 agonist, or a combination thereof. In any of the embodiments herein, the subject can be a human.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

BRIEF DESCRIPTION OF THE DRAWINGS

FIG. 1 is a sequence alignment showing the comparison of heavy chain sequences of humanized antibodies. Framework residues within 4 Å of the CDRs in the molecular model of mouse 2E2 antibody are represented by a *; residues within 4 Å of the CDRs and VCI residues that were different in the acceptor human framework are highlighted in ˆ, back-mutations of these residues in the acceptor human framework to mouse are indicated by @; Somatic mutations from human germline are indicated by °; if those residues were different from the AF471521 FW and mou2E2 (i.e., mouse 2E2) or different from the AF471521 framework and identical to the mou2E2 (i.e., mouse 2E2) the corresponding residues in the acceptor human framework were back-mutated to human germline and are indicated by +. Sequences highlighted in version 2 of the heavy chain represent a straight graft of mou2E2 (i.e., mouse 2E2) CDRs into the closest human germline family (i.e., closest germline sequence). m2E2 VH corresponds to SEQ ID NO:1; Human FW AF471521 corresponds to SEQ ID NO:120; Germline X92218 VH366 corresponds to SEQ ID NO:121; 2E2 RHA corresponds to SEQ ID NO:2; 2E2 RHB corresponds to SEQ ID NO:3; 2E2 RHC corresponds to SEQ ID NO:4; 2E2 RHD corresponds to SEQ ID NO:5; 2E2 RHE corresponds to SEQ ID NO:6; 2E2 RHF corresponds to SEQ ID NO:7; 2E2 RHG corresponds to SEQ ID NO:8; IGHV4-59 FW corresponds to SEQ ID NO:122; 2E2 RHA2 corresponds to SEQ ID NO:9; and 2E2 RHB2 corresponds to SEQ ID NO:10.

FIG. 2 is a sequence alignment showing the comparison of light chain sequences of humanized antibodies. Framework residues within 4 Å of the CDRs in the molecular model of mouse 2E2 antibody are represented by a *; residues within 4 Å of the CDRs and VCI residues that are different in the acceptor human framework are indicated by +; back-mutations of these residues in the human FW to mouse are indicated by @; back-mutation to human germline of residues which in the X93721 framework are different from the mouse are indicated by #. m2E2 VK corresponds to SEQ ID NO:15; X93721 corresponds to SEQ ID NO:123; Germline X01668 corresponds to SEQ ID NO:124; m2E2 RKA corresponds to SEQ ID NO:16; m2E2 RKB corresponds to SEQ ID NO:17; m2E2 RKC corresponds to SEQ ID NO:18; m2E2 RKD corresponds to SEQ ID NO:19; m2E2 RKE corresponds to SEQ ID NO:20; m2E2 RKF corresponds to SEQ ID NO:21; and m2E2 RKG corresponds to SEQ ID NO:22.

FIG. 3 is a sequence alignment showing the comparison of CDR sequences that were mutated in both light and heavy chains of humanized antibodies. CDR residues that were mutated in the variant to be closer to the germline sequence are indicated by #. 2E2 RKA corresponds to SEQ ID NO:16; 2E2 RKF corresponds to SEQ ID NO:21; 2E2 RKA F-Y mut corresponds to SEQ ID NO:23; 2E2 RKF F-Y mut corresponds to SEQ ID NO:24; 2E2 RHA corresponds to SEQ ID NO:2; 2E2 RHE corresponds to SEQ ID NO:6; 2E2 RHE S-G mut corresponds to SEQ ID NO:11; 2E2 RHE E-D mut corresponds to SEQ ID NO:12; 2E2 RHE Y-V mut corresponds to SEQ ID NO:13; and 2E2 RHE E-D triple mut corresponds to SEQ ID NO:14.

FIG. 8A. NK-cell mediated antibody-dependent cell-mediated cytotoxicity (ADCC) activity of HEKA IgG4 antibody, non-fucosylated HEKA IgG1 antibody and low fucose chimeric 1H10 IgG1 antibodies on primary human mast cells from peritoneal lavage of NSGS mice engrafted with human hematopoietic stem cells as demonstrated by LDH release at 48 hours. Control indicates a fucosylated human IgG1 isotype antibody that does not bind to Siglec-8.

FIG. 9 is a graph showing inhibition of a Type I hypersensitivity reaction in humanized mice by a humanized anti-Siglec-8 IgG4 antibody. Passive cutaneous anaphylaxis response was induced in the ears of engrafted NSGS mice by sensitization with anti-NP-IgE (delivered to the right ear) or PBS control (delivered to the left ear) and NP-BSA administered 24 hours later sensitization. Mice were treated with HEKA IgG4 or a human IgG4 isotype control antibody that does not bind to Siglec-8 either 24 hours pre-sensitization as indicated by * or 2 hours post-sensitization as indicated by @. Mean change in ear thickness and standard errors at 3 hours or 24 hours post-challenge are shown. n=5 mice per group for HEKA IgG4 antibody treated mice and n=4 mice per group for isotype control antibody treated mice.

DETAILED DESCRIPTION

I. Definitions

Figure 4:
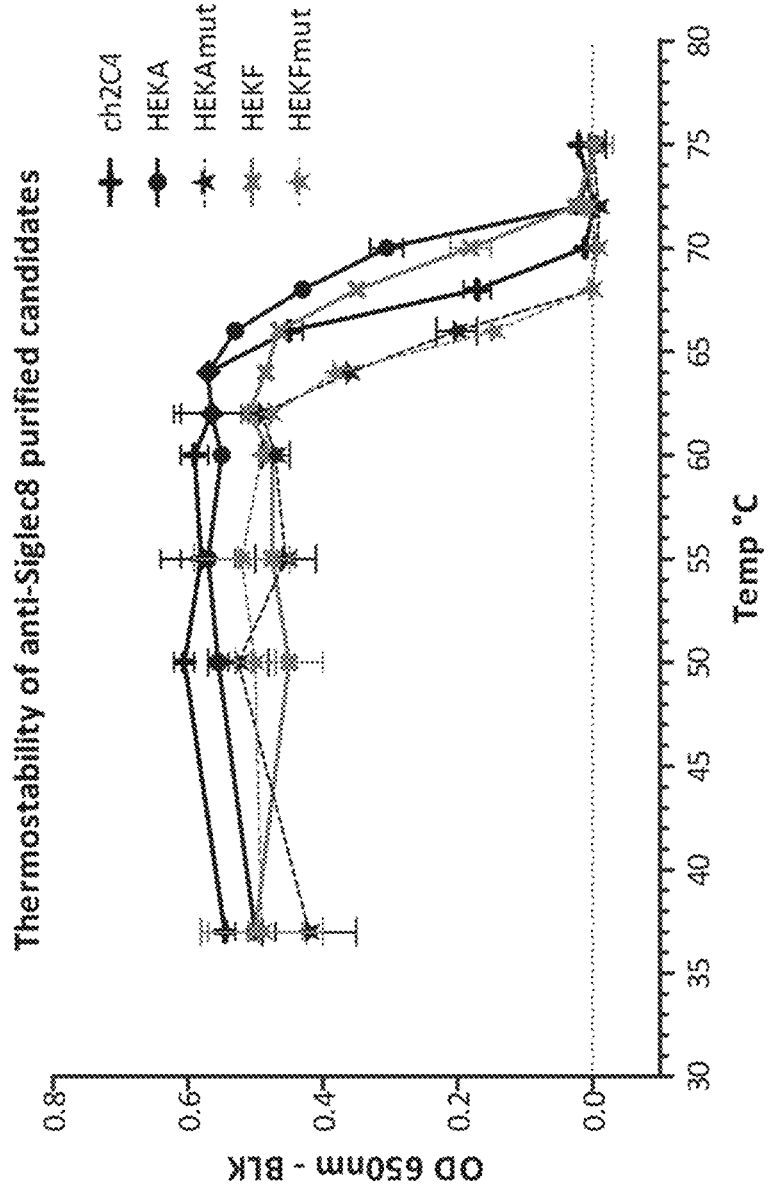
FIG. 4 is a graph showing a comparison of Siglec-8 antigen binding by purified candidate antibodies encoded by chimeric 2C4 or combinations of 2E2 RHE with 2E2 RKA, 2E2 RKF, 2E2 RKA CDR3 mutant, or 2E2 RKF CDR3 mutant, heated for 10 min at the indicated temperature, then cooled to 4° C. before performing the Siglec-8 binding ELISA.

Before describing the invention in detail, it is to be understood that this invention is not limited to particular compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the invention described herein include "comprising," "consisting," and "consisting essentially of" aspects and embodiments.

The term "antibody" includes polyclonal antibodies, monoclonal antibodies (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, F(ab')$_2$, and Fv). The term "immunoglobulin" (Ig) is used interchangeably with "antibody" herein.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., *Basic and Clinical Immunology*, 8th Edition, Daniel P. Sties, Abba I. Terr and Tristram G. Parsolw (eds), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated α, β, ε, γ and μ, respectively. The γ and α classes are further divided into subclasses on the basis of relatively minor differences in the CH sequence and function, e.g., humans express the following subclasses: IgG1, IgG2, IgG3, IgG4, IgA1 and IgA2. IgG1 antibodies can exist in multiple polymorphic variants termed allotypes (reviewed in Jefferis and Lefranc 2009. mAbs Vol 1 Issue 4 1-7) any of which are suitable for use in the invention. Common allotypic variants in human populations are those designated by the letters a,f,n,z.

An "isolated" antibody is one that has been identified, separated and/or recovered from a component of its production environment (e.g., naturally or recombinantly). In some embodiments, the isolated polypeptide is free of association with all other components from its production environment. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In some embodiments, the polypeptide is purified: (1) to greater than 95% by weight of antibody as determined by, for example, the Lowry method, and in some embodiments, to greater than 99% by weight; (1) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or silver stain. Isolated antibody includes the antibody in situ within recombinant cells since at least one component of the antibody's natural environment will not be present. Ordinarily, however, an isolated polypeptide or antibody is prepared by at least one purification step.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. In some embodiments, monoclonal antibodies have a C-terminal cleavage at the heavy chain and/or light chain. For example, 1, 2, 3, 4, or 5 amino acid residues are cleaved at the C-terminus of heavy chain and/or light chain. In some embodiments, the C-terminal cleavage removes a C-terminal lysine from the heavy chain. In some embodiments, monoclonal antibodies have an N-terminal cleavage at the heavy chain and/or light chain. For example, 1, 2, 3, 4, or 5 amino acid residues are cleaved at the N-terminus of heavy chain and/or light chain. In some embodiments truncated forms of monoclonal antibodies can be made by recombinant techniques. In some embodiments, monoclonal antibodies are highly specific, being directed against a single antigenic site. In some embodiments, monoclonal antibodies are highly specific, being directed against multiple antigenic sites (such as a bispecific antibody or a multispecific antibody). The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method, recombinant DNA methods, phage-display technologies, and technologies for producing human or human-like antibodies in animals that have parts or all of the human immunoglobulin loci or genes encoding human immunoglobulin sequences.

The term "naked antibody" refers to an antibody that is not conjugated to a cytotoxic moiety or radiolabel.

The terms "full-length antibody," "intact antibody" or "whole antibody" are used interchangeably to refer to an antibody in its substantially intact form, as opposed to an antibody fragment. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., Protein Eng. 8(10): 1057-1062 [1995]); single-chain antibody molecules and multispecific antibodies formed from antibody fragments.

Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. In some embodiments, the sFv polypeptide further comprises a polypeptide linker between the $V_H$ and $V_L$ domains which enables the sFv to form the desired structure for antigen binding. For a review of the sFv, see Pluckthun in The Pharmacology of Monoclonal Antibodies, vol. 113, Rosenburg and Moore eds., Springer-Verlag, New York, pp. 269-315 (1994).

"Functional fragments" of the antibodies of the invention comprise a portion of an intact antibody, generally including the antigen binding or variable region of the intact antibody or the Fv region of an antibody which retains or has modified FcR binding capability. Examples of antibody fragments include linear antibody, single-chain antibody molecules and multispecific antibodies formed from antibody fragments.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is (are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851-6855 (1984)). Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used as a subset of "chimeric antibodies."

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from an HVR of the recipient are replaced by residues from an HVR of a non-human species (donor antibody) such as mouse, rat, rabbit or non-human primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. In some embodiments, the number of these amino acid substitutions in the FR are no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., Nature 321:522-525 (1986); Riechmann et al., Nature 332: 323-329 (1988); and Presta, Curr. Op. Struct. Biol. 2:593-596 (1992). See also, for example, Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S.

Pat. Nos. 6,982,321 and 7,087,409. In some embodiments, humanized antibodies are directed against a single antigenic site. In some embodiments, humanized antibodies are directed against multiple antigenic sites. An alternative humanization method is described in U.S. Pat. No. 7,981,843 and U.S. Patent Application Publication No. 2006/0134098.

The "variable region" or "variable domain" of an antibody refers to the amino-terminal domains of the heavy or light chain of the antibody. The variable domains of the heavy chain and light chain may be referred to as "VH" and "VL", respectively. These domains are generally the most variable parts of the antibody (relative to other antibodies of the same class) and contain the antigen binding sites.

The term "hypervariable region," "HVR," or "HV," when used herein refers to the regions of an antibody-variable domain that are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al. *Immunity* 13:37-45 (2000); Johnson and Wu in *Methods in Molecular Biology* 248:1-25 (Lo, ed., Human Press, Totowa, N.J., 2003)). Indeed, naturally occurring camelid antibodies consisting of a heavy chain only are functional and stable in the absence of light chain. See, e.g., Hamers-Casterman et al., *Nature* 363:446-448 (1993) and Sheriff et al., *Nature Struct. Biol.* 3:733-736 (1996).

A number of HVR delineations are in use and are encompassed herein. The HVRs that are Kabat complementarity-determining regions (CDRs) are based on sequence variability and are the most commonly used (Kabat et al., *Sequences of Proteins of Immunological Interest*, 5$^{th}$ Ed. Public Health Service, National Institute of Health, Bethesda, Md. (1991)). Chothia HVRs refer instead to the location of the structural loops (Chothia and Lesk *J. Mol. Biol.* 196:901-917 (1987)). The "contact" HVRs are based on an analysis of the available complex crystal structures. The residues from each of these HVRs are noted below.

| Loop | Kabat | Chothia | Contact | |
|------|-------|---------|---------|---|
| L1 | L24-L34 | L26-L34 | L30-L36 | |
| L2 | L50-L56 | L50-L56 | L46-L55 | |
| L3 | L89-L97 | L91-L96 | L89-L96 | |
| H1 | H31-H35B | H26-H32 | H30-H35B | (Kabat Numbering) |
| H1 | H31-H35 | H26-H32 | H30-H35 | (Chothia Numbering) |
| H2 | H50-H65 | H53-H56 | H47-H58 | |
| H3 | H95-H102 | H95-H102 | H93-H101 | |

Unless otherwise indicated, the variable-domain residues (HVR residues and framework region residues) are numbered according to Kabat et al., supra.

"Framework" or "FR" residues are those variable-domain residues other than the HVR residues as herein defined.

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

An "acceptor human framework" for the purposes herein is a framework comprising the amino acid sequence of a VL or VH framework derived from a human immunoglobulin framework or a human consensus framework. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For example, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

An antibody that "binds to", "specifically binds to" or is "specific for" a particular a polypeptide or an epitope on a particular polypeptide is one that binds to that particular polypeptide or epitope on a particular polypeptide without substantially binding to any other polypeptide or polypeptide epitope. In some embodiments, binding of an anti-Siglec-8 antibody described herein to an unrelated, non-Siglec-8 polypeptide is less than about 10% of the antibody binding to Siglec-8 as measured by methods known in the art (e.g., enzyme-linked immunosorbent assay (ELISA)). In some embodiments, the antibody that binds to a Siglec-8 (e.g., Siglec-8 Fc fusion protein in dimer form (SEQ ID NO:74)) has a dissociation constant (Kd) of ≤1 μM, ≤100 nM, ≤10 nM, ≤2 nM, ≤1 nM, ≤0.7 nM, ≤0.6 nM, ≤0.5 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M).

The term "Siglec-8" as used herein refers to a human Siglec-8 protein. The term also includes naturally occurring variants of Siglec-8, including splice variants or allelic variants. The amino acid sequence of an exemplary human Siglec-8 is shown in SEQ ID NO:72. The amino acid sequence of another exemplary human Siglec-8 is shown in SEQ ID NO:73. In some embodiments, a human Siglec-8 protein comprises the human Siglec-8 extracellular domain fused to an immunoglobulin Fc region. The amino acid sequence of an exemplary human Siglec-8 extracellular domain fused to an immunoglobulin Fc region is shown in SEQ ID NO:74. The amino acid sequence underlined in SEQ ID NO:74 indicates the Fc region of the Siglec-8 Fc fusion protein amino acid sequence.

```
Human Siglec-8 Amino Acid Sequence
                                                        (SEQ ID NO: 72)
GYLLQVQELVTVQEGLCVHVPCSFSYPQDGWTDSDPVHGYWFRAGDRPYQDAPVATN

NPDREVQAETQGRFQLLGDIWSNDCSLSIRDARKRDKGSYFFRLERGSMKWSYKSQLN

YKTKQLSVFVTALTHRPDILILGTLESGHSRNLTCSVPWACKQGTPPMISWIGASVSSPGP

TTARSSVLTLTPKPQDHGTSLTCQVTLPGTGVTTTSTVRLDVSYPPWNLTMTVFQGDAT

ASTALGNGSSLSVLEGQSLRLVCAVNSNPPARLSWTRGSLTLCPSRSSNPGLLELPRVHV

RDEGEFTCRAQNAQGSQHISLSLSLQNEGTGTSRPVSQVTLAAVGGAGATALAFLSFCII

FIIVRSCRKKSARPAAGVGDTGMEDAKAIRGSASQGPLTESWKDGNPLKKPPPAVAPSS

GEEGELHYATLSFHKVKPQDPQGQEATDSEYSEIKIHKRETAETQACLRNHNPSSKEVRG

Human Siglec-8 Amino Acid Sequence
                                                        (SEQ ID NO: 73)
GYLLQVQELVTVQEGLCVHVPCSFSYPQDGWTDSDPVHGYWFRAGDRPYQDAPVATN

NPDREVQAETQGRFQLLGDIWSNDCSLSIRDARKRDKGSYFFRLERGSMKWSYKSQLN

YKTKQLSVFVTALTHRPDILILGTLESGHPRNLTCSVPWACKQGTPPMISWIGASVSSPGP

TTARSSVLTLTPKPQDHGTSLTCQVTLPGTGVTTTSTVRLDVSYPPWNLTMTVFQGDAT

ASTALGNGSSLSVLEGQSLRLVCAVNSNPPARLSWTRGSLTLCPSRSSNPGLLELPRVHV

RDEGEFTCRAQNAQGSQHISLSLSLQNEGTGTSRPVSQVTLAAVGGAGATALAFLSFCII

FIIVRSCRKKSARPAAGVGDTGMEDAKAIRGSASQGPLTESWKDGNPLKKPPPAVAPSS

GEEGELHYATLSFHKVKPQDPQGQEATDSEYSEIKIHKRETAETQACLRNHNPSSKEVRG

Siglec-8 Fc Fusion Protein Amino Acid Sequence
                                                        (SEQ ID NO: 74)
GYLLQVQELVTVQEGLCVHVPCSFSYPQDGWTDSDPVHGYWFRAGDRPYQDAPVATN

NPDREVQAETQGRFQLLGDIWSNDCSLSIRDARKRDKGSYFFRLERGSMKWSYKSQLN

YKTKQLSVFVTALTHRPDILILGTLESGHSRNLTCSVPWACKQGTPPMISWIGASVSSPGP

TTARSSVLTLTPKPQDHGTSLTCQVTLPGTGVTTTSTVRLDVSYPPWNLTMTVFQGDAT

ASTALGNGSSLSVLEGQSLRLVCAVNSNPPARLSWTRGSLTLCPSRSSNPGLLELPRVHV

RDEGEFTCRAQNAQGSQHISLSLSLQNEGTGTSRPVSQVTLAAVGGIEGRSDKTHTCPPC

PAPELLGGPSVFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPVLDSDGSFFL

YSKLTVDKSRWQQGNVFSCSVMHEALHNHYTQKSLSLSPGK
```

Antibodies that "induce apoptosis" or are "apoptotic" are those that induce programmed cell death as determined by standard apoptosis assays, such as binding of annexin V, fragmentation of DNA, cell shrinkage, dilation of endoplasmic reticulum, cell fragmentation, and/or formation of membrane vesicles (called apoptotic bodies). For example, the apoptotic activity of the anti-Siglec-8 antibodies of the present invention can be showed by staining cells with annexin V.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptors); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express FcγRIII only, whereas monocytes express FcγRI, FcγRII and FcγRIII Fc expression on hematopoietic cells is summarized in Table 3 on page 464 of Ravetch and Kinet, *Annu. Rev. Immunol.* 9: 457-92 (1991). In some embodiments, an anti-Siglec-8 antibody described herein enhances ADCC. To assess ADCC activity of a molecule of interest, an in vitro ADCC assay, such as that described in U.S. Pat. No. 5,500,362 or U.S. Pat. No. 5,821,337 may be performed. Useful effector cells for such assays include peripheral blood mononuclear cells (PBMC) and natural killer (NK) cells. Alternatively, or additionally, ADCC activity of the molecule of interest may be assessed in vivo, e.g., in an animal model such as that disclosed in Clynes et al., *PNAS USA* 95:652-656 (1998). Other Fc variants that alter ADCC activity and other antibody properties include those disclosed by Ghetie et al., Nat Biotech. 15:637-40, 1997; Duncan et al, Nature 332:563-564, 1988; Lund et al., J. Immunol 147:2657-2662, 1991; Lund et al, Mol Immunol 29:53-59, 1992; Alegre et al, Transplantation 57:1537-1543, 1994; Hutchins et al., Proc Natl. Acad Sci USA 92:11980-11984, 1995; Jefferis et al, Immunol Lett. 44:111-117, 1995; Lund et al., FASEB J9:115-119, 1995; Jefferis et al, Immunol Lett 54:101-104, 1996; Lund et al, J Immunol 157:4963-4969, 1996; Armour et al., Eur J Immunol 29:2613-2624, 1999; Idusogie et al, J Immunol 164: 4178-4184, 200; Reddy et al, J Immunol 164:1925-1933, 2000; Xu et al., Cell Immunol 200:16-26, 2000; Idusogie et al, J Immunol 166:2571-2575, 2001; Shields et al., J Biol Chem 276:6591-6604, 2001; Jefferis et al, Immunol Lett 82:57-65, 2002; Presta et al., Biochem Soc Trans 30:487-490, 2002; Lazar et al., Proc. Natl. Acad. Sci. USA 103: 4005-4010, 2006; U.S. Pat. Nos. 5,624,821; 5,885,573; 5,677,425; 6,165,745; 6,277,375; 5,869,046; 6,121,022; 5,624,821; 5,648,260; 6,194,551; 6,737,056; 6,821,505; 6,277,375; 7,335,742; and 7,317,091.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. Suitable native-sequence Fc regions for use in the antibodies of the invention include human IgG1, IgG2, IgG3 and IgG4. A single amino acid substitution (S228P according to Kabat numbering; designated IgG4Pro) may be introduced to abolish the heterogeneity observed in recombinant IgG4 antibody. See Angal, S. et al. (1993) Mol Immunol 30, 105-108.

"Non-fucosylated" or "fucose-deficient" antibody refers to a glycosylation antibody variant comprising an Fc region wherein a carbohydrate structure attached to the Fc region has reduced fucose or lacks fucose. In some embodiments, an antibody with reduced fucose or lacking fucose has improved ADCC function. Non-fucosylated or fucose-deficient antibodies have reduced fucose relative to the amount of fucose on the same antibody produced in a cell line. A non-fucosylated or fucose-deficient antibody composition contemplated herein is a composition wherein less than about 50% of the N-linked glycans attached to the Fc region of the antibodies in the composition comprise fucose.

The terms "fucosylation" or "fucosylated" refers to the presence of fucose residues within the oligosaccharides attached to the peptide backbone of an antibody. Specifically, a fucosylated antibody comprises α (1,6)-linked fucose at the innermost N-acetylglucosamine (GlcNAc) residue in one or both of the N-linked oligosaccharides attached to the antibody Fc region, e.g. at position Asn 297 of the human IgG1 Fc domain (EU numbering of Fc region residues). Asn297 may also be located about +3 amino acids upstream or downstream of position 297, i.e. between positions 294 and 300, due to minor sequence variations in immunoglobulins.

The "degree of fucosylation" is the percentage of fucosylated oligosaccharides relative to all oligosaccharides identified by methods known in the art e.g., in an N-glycosidase F treated antibody composition assessed by matrix-assisted laser desorption-ionization time-of-flight mass spectrometry (MALDI TOF MS). In a composition of a "fully fucosylated antibody" essentially all oligosaccharides comprise fucose residues, i.e. are fucosylated. In some embodiments, a composition of a fully fucosylated antibody has a degree of fucosylation of at least about 90%. Accordingly, an individual antibody in such a composition typically comprises fucose residues in each of the two N-linked oligosaccharides in the Fc region. Conversely, in a composition of a "fully non-fucosylated" antibody essentially none of the oligosaccharides are fucosylated, and an individual antibody in such a composition does not contain fucose residues in either of the two N-linked oligosaccharides in the Fc region. In some embodiments, a composition of a fully non-fucosylated antibody has a degree of fucosylation of less than about 10%. In a composition of a "partially fucosylated antibody" only part of the oligosaccharides comprise fucose. An individual antibody in such a composition can comprise fucose residues in none, one or both of the N-linked oligosaccharides in the Fc region, provided that the composition does not comprise essentially all individual antibodies that lack fucose residues in the N-linked oligosaccharides in the Fc region, nor essentially all individual antibodies that contain fucose residues in both of the N-linked oligosaccharides in the Fe region. In one embodiment, a composition of a partially fucosylated antibody has a degree of fucosylation of about 10% to about 80% (e.g., about 50% to about 80%, about 60% to about 80%, or about 70% to about 80%).

"Binding affinity" as used herein refers to the strength of the non-covalent interactions between a single binding site of a molecule (e.g., an antibody) and its binding partner (e.g., an antigen). In some embodiments, the affinity of an antibody for a Siglec-8 (which may be a dimer, such as the Siglec-8-Fc fusion protein described herein) can generally be represented by a dissociation constant (Kd). Affinity can be measured by common methods known in the art, including those described herein.

"Binding avidity" as used herein refers to the binding strength of multiple binding sites of a molecule (e.g., an antibody) and its binding partner (e.g., an antigen).

An "isolated" nucleic acid molecule encoding the antibodies herein is a nucleic acid molecule that is identified and separated from at least one contaminant nucleic acid molecule with which it is ordinarily associated in the environment in which it was produced. In some embodiments, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "pharmaceutical formulation" refers to a preparation that is in such form as to permit the biological activity of the active ingredient to be effective, and that contains no additional components that are unacceptably toxic to a subject to which the formulation would be administered. Such formulations are sterile.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. An individual is successfully "treated", for example, if one or more symptoms associated with a disorder (e.g., an eosinophil-mediated disease) are mitigated or eliminated. For example, an individual is successfully "treated" if treatment results in increasing the quality of life of those suffering from a disease, decreasing the dose of other medications required for treating the disease, reducing the frequency of recurrence of the disease, lessening severity of the disease, delaying the development or progression of the disease, and/or prolonging survival of individuals.

As used herein, "in conjunction with" refers to administration of one treatment modality in addition to another treatment modality. As such, "in conjunction with" refers to administration of one treatment modality before, during or after administration of the other treatment modality to the individual.

As used herein, the term "prevention" includes providing prophylaxis with respect to occurrence or recurrence of a disease in an individual. An individual may be predisposed to, susceptible to a disorder, or at risk of developing a disorder, but has not yet been diagnosed with the disorder. In some embodiments, anti-Siglec-8 antibodies described herein are used to delay development of a disorder.

As used herein, an individual "at risk" of developing a disorder may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of the eosinophil-mediated disorder and/or mast cell mediated, as known in the art. An individual having one or more of these risk factors has a higher probability of developing the disorder than an individual without one or more of these risk factors.

An "effective amount" refers to at least an amount effective, at dosages and for periods of time necessary, to achieve the desired or indicated effect, including a therapeutic or prophylactic result. An effective amount can be provided in one or more administrations. A "therapeutically effective amount" is at least the minimum concentration required to effect a measurable improvement of a particular disorder. A therapeutically effective amount herein may vary according to factors such as the disease state, age, sex, and weight of the patient, and the ability of the antibody to elicit a desired response in the individual. A therapeutically effective amount may also be one in which any toxic or detrimental effects of the antibody are outweighed by the therapeutically beneficial effects. A "prophylactically effective amount" refers to an amount effective, at the dosages and for periods of time necessary, to achieve the desired prophylactic result. Typically but not necessarily, since a prophylactic dose is used in subjects prior to or at the earlier stage of disease, the prophylactically effective amount can be less than the therapeutically effective amount.

"Chronic" administration refers to administration of the medicament(s) in a continuous as opposed to acute mode, so as to main the initial therapeutic effect (activity) for an extended period of time. "Intermittent" administration is treatment that is not consecutively done without interruption, but rather is cyclic in nature.

As used herein, an "individual" or a "subject" is a mammal. A "mammal" for purposes of treatment includes humans, domestic and farm animals, and zoo, sports, or pet animals, such as dogs, horses, rabbits, cattle, pigs, hamsters, gerbils, mice, ferrets, rats, cats, etc. In some embodiments, the individual or subject is human.

II. Anti-Siglec-8 Antibodies and Compositions

In one aspect, the invention provides isolated antibodies that bind to a human Siglec-8. In some embodiments, an anti-Siglec-8 antibody described herein has one or more of the following characteristics: (1) binds a human Siglec-8; (2) binds to an extracellular domain of a human Siglec-8; (3) binds a human Siglec-8 with a higher affinity than mouse antibody 2E2 and/or mouse antibody 2C4; (4) binds a human Siglec-8 with a higher avidity than mouse antibody 2E2 and/or mouse antibody 2C4; (5) has a $T_m$ of about 70° C.-72° C. or higher in a thermal shift assay; (6) with a reduced degree of fucosylation or is non-fucosylated; (7) binds a human Siglec-8 expressed on eosinophils and induces apoptosis of eosinophils; (8) binds a human Siglec-8 expressed on mast cells and depletes mast cells; (9) binds a human Siglec-8 expressed on mast cells and inhibits FcεRI-dependent activities of mast cells (e.g., histamine release, $PGD_2$ release, $Ca^{2+}$ flux, and/or β-hexosaminidase release, etc.); (10) has been engineered to improve ADCC activity; (11) binds a human Siglec-8 expressed on mast cells and kills mast cells by ADCC activity (in vitro, and/or in vivo); (12) binds to Siglec-8 of a human and a non-human primate; (13) binds to Domain 1, Domain 2, and/or Domain 3 of human Siglec-8, or binds a Siglec-8 polypeptide comprising Domain 1, Domain 2, and/or Domain 3 of human Siglec-8 (e.g., fusion proteins described herein); and (14) depletes activated eosinophils with an $EC_{50}$ less than the $EC_{50}$ of mouse antibody 2E2 or 2C4.

In one aspect, the invention provides antibodies that bind to a human Siglec-8. In some embodiments, the human Siglec-8 comprises an amino acid sequence of SEQ ID NO:72. In some embodiments, the human Siglec-8 comprises an amino acid sequence of SEQ ID NO:73. In some embodiments, the antibody described herein binds to an epitope in Domain 1 of human Siglec-8, wherein Domain 1 comprises the amino acid sequence of SEQ ID NO: 112. In some embodiments, the antibody described herein binds to an epitope in Domain 2 of human Siglec-8, wherein Domain 2 comprises the amino acid sequence of SEQ ID NO: 113. In some embodiments, the antibody described herein binds to an epitope in Domain 3 of human Siglec-8, wherein Domain 3 comprises the amino acid sequence of SEQ ID NO: 114. In some embodiments, the antibody described herein binds to a fusion protein comprising the amino acid of SEQ ID NO:116 but not to a fusion protein comprising the amino acid of SEQ ID NO:115. In some embodiments, the antibody described herein binds to a fusion protein comprising the amino acid of SEQ ID NO:117 but not to a fusion protein comprising the amino acid of SEQ ID NO:115. In some embodiments, the antibody described herein binds to a fusion protein comprising the amino acid of SEQ ID NO:117 but not to a fusion protein comprising the amino acid of SEQ ID NO:116. In some embodiments, the antibody described herein binds to a linear epitope in the extracellular domain of human Siglec-8. In some embodiments, the antibody described herein binds to a conformational epitope in the extracellular domain of human Siglec-8. In some embodiments, an antibody described herein binds to a human Siglec-8 expressed on eosinophils and induces apoptosis of eosinophils. In some embodiments, an antibody described herein binds to a human Siglec-8 expressed on mast cells and depletes mast cells. In some embodiments, an antibody described herein binds to a human Siglec-8 expressed on mast cells and inhibits mast cell-mediated activity. In some embodiments, an antibody described herein binds to a human Siglec-8 expressed on mast cells and kills mast cells by ADCC activity. In some embodiments, an antibody described herein depletes mast cells and inhibits mast cell activation. In some embodiments, an antibody herein depletes activated eosinophils and inhibits mast cell activation.

Provided herein is an isolated anti-Siglec-8 antibody that binds to human Siglec-8 and non-human primate Siglec-8. Identification of antibodies with primate cross-reactivity would be useful for preclinical testing of anti-Siglec-8 antibodies in non-human primates. In one aspect, the invention provides antibodies that bind to a non-human primate Siglec-8. In one aspect, the invention provides antibodies that bind to a human Siglec-8 and a non-human primate Siglec-8. In some embodiments, the non-human primate Siglec-8 comprises an amino acid sequence of SEQ ID NO:118 or a portion thereof. In some embodiments, the non-human primate Siglec-8 comprises an amino acid sequence of SEQ ID NO:119 or a portion thereof. In some embodiments, the non-human primate is a baboon (e.g., *Papio Anubis*). In some embodiments, the antibody that binds to a human Siglec-8 and a non-human primate Siglec-8, binds to an epitope in Domain 1 of human Siglec-8. In a further embodiment, Domain 1 of human Siglec-8 comprises the amino acid sequence of SEQ ID NO:112. In some embodiments, the antibody that binds to a human Siglec-8 and a non-human primate Siglec-8, binds to an epitope in Domain 3 of human Siglec-8. In a further embodiment, Domain 3 of human Siglec-8 comprises the amino acid sequence of SEQ ID NO:114. In some embodiments, the antibody that binds to a human Siglec-8 and a non-human primate Siglec-8 is a humanized antibody, a chimeric antibody, or a human antibody. In some embodiments, the antibody that binds to a human Siglec-8 and a non-human primate Siglec-8 is a murine antibody. In some embodiments, the antibody that binds to a human Siglec-8 and a non-human primate Siglec-8 is a human IgG1 antibody.

In one aspect, an anti-Siglec-8 antibody described herein is a monoclonal antibody. In one aspect, an anti-Siglec-8 antibody described herein is an antibody fragment (including antigen-binding fragment), e.g., a Fab, Fab'-SH, Fv, scFv, or (Fab')$_2$ fragment. In one aspect, an anti-Siglec-8 antibody described herein is a chimeric, humanized, or human antibody. In one aspect, any of the anti-Siglec-8 antibodies described herein are purified.

In one aspect, anti-Siglec-8 antibodies that compete with murine 2E2 antibody and murine 2C4 antibody binding to Siglec-8 are provided. Anti-Siglec-8 antibodies that bind to the same epitope as murine 2E2 antibody and murine 2C4 antibody are also provided. In one aspect, anti-Siglec-8 antibodies that compete with any anti-Siglec-8 antibody described herein (e.g., HEKA, HEKF, 1C3, 1H10, 4F11) for binding to Siglec-8 are provided. Anti-Siglec-8 antibodies that bind to the same epitope as any anti-Siglec-8 antibody described herein (e.g., HEKA, HEKF, 1C3, 1H10, 4F11) are also provided.

In one aspect of the invention, polynucleotides encoding anti-Siglec-8 antibodies are provided. In certain embodiments, vectors comprising polynucleotides encoding anti-Siglec-8 antibodies are provided. In certain embodiments, host cells comprising such vectors are provided. In another aspect of the invention, compositions comprising anti-Siglec-8 antibodies or polynucleotides encoding anti-Siglec-8 antibodies are provided. In certain embodiments, a composition of the invention is a pharmaceutical formulation for the treatment of an eosinophil-mediated disorder and/or mast cell-mediated disorder, such as those enumerated herein.

In one aspect, provided herein is an anti-Siglec-8 antibody comprising 1, 2, 3, 4, 5, or 6 of the HVR sequences of the murine antibody 2C4. In one aspect, provided herein is an anti-Siglec-8 antibody comprising 1, 2, 3, 4, 5, or 6 of the HVR sequences of the murine antibody 2E2. In some embodiments, the HVR is a Kabat CDR or a Chothia CDR.

In one aspect, provided herein is an anti-Siglec-8 antibody comprising 1, 2, 3, 4, 5, or 6 of the HVR sequences of the murine antibody 1C3. In one aspect, provided herein is an anti-Siglec-8 antibody comprising 1, 2, 3, 4, 5, or 6 of the HVR sequences of the murine antibody 4F11. In one aspect, provided herein is an anti-Siglec-8 antibody comprising 1, 2, 3, 4, 5, or 6 of the HVR sequences of the murine antibody 1H10. In some embodiments, the HVR is a Kabat CDR or a Chothia CDR.

In some embodiments, the antibody described herein binds to an epitope in Domain 1 of human Siglec-8, wherein Domain 1 comprises the amino acid sequence of SEQ ID NO:112. In some embodiments, the antibody described herein binds to an epitope in Domain 2 of human Siglec-8, wherein Domain 2 comprises the amino acid sequence of SEQ ID NO:113. In some embodiments, the antibody described herein binds to an epitope in Domain 3 of human Siglec-8, wherein Domain 3 comprises the amino acid sequence of SEQ ID NO:114.

In some embodiments, the antibody described herein binds to a fusion protein comprising the amino acid of SEQ ID NO:116 but not to a fusion protein comprising the amino acid of SEQ ID NO:115. In some embodiments, the antibody described herein binds to a fusion protein comprising the amino acid of SEQ ID NO:117 but not to a fusion protein comprising the amino acid of SEQ ID NO:115. In some embodiments, the antibody described herein binds to a fusion protein comprising the amino acid of SEQ ID NO:117 but not to a fusion protein comprising the amino acid of SEQ ID NO:116.

In one aspect, provided herein is an anti-Siglec-8 antibody comprising a heavy chain variable region and a light chain variable region, wherein the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence of SEQ ID NO:63; and/or wherein the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:66.

In one aspect, provided herein is an anti-Siglec-8 antibody comprising a heavy chain variable region and a light chain variable region, wherein the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence selected from SEQ ID NOs:67-70; and/or wherein the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:66.

In one aspect, provided herein is an anti-Siglec-8 antibody comprising a heavy chain variable region and a light chain variable region, wherein the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence of SEQ ID NO:63; and/or wherein the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:71.

In another aspect, provided herein is an anti-Siglec-8 antibody comprising a heavy chain variable region and a light chain variable region, wherein the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence selected from SEQ ID NOs:67-70; and/or wherein the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:71.

In another aspect, provided herein is an anti-Siglec-8 antibody comprising a heavy chain variable region and a light chain variable region, wherein the heavy chain variable region comprises (i) HVR-H1 comprising the amino acid sequence of SEQ ID NO:88, (ii) HVR-H2 comprising the amino acid sequence of SEQ ID NO:91, and (iii) HVR-H3 comprising the amino acid sequence of SEQ ID NO:94; and/or a light chain variable region comprising (i) HVR-L1 comprising the amino acid sequence of SEQ ID NO:97, (ii) HVR-L2 comprising the amino acid sequence of SEQ ID NO:100, and (iii) HVR-L3 comprising the amino acid sequence of SEQ ID NO:103. In some embodiments, the antibody described herein binds to an epitope in Domain 2 of human Siglec-8, wherein Domain 2 comprises the amino acid sequence of SEQ ID NO: 113.

In another aspect, provided herein is an anti-Siglec-8 antibody comprising a heavy chain variable region and a light chain variable region, wherein the heavy chain variable region comprises (i) HVR-H1 comprising the amino acid sequence of SEQ ID NO:89, (ii) HVR-H2 comprising the amino acid sequence of SEQ ID NO:92, and (iii) HVR-H3 comprising the amino acid sequence of SEQ ID NO:95; and/or a light chain variable region comprising (i) HVR-L1 comprising the amino acid sequence of SEQ ID NO:98, (ii) HVR-L2 comprising the amino acid sequence of SEQ ID NO:101, and (iii) HVR-L3 comprising the amino acid sequence of SEQ ID NO:104. In some embodiments, the antibody described herein binds to an epitope in Domain 3 of human Siglec-8, wherein Domain 3 comprises the amino acid sequence of SEQ ID NO: 114. In some embodiments, the antibody described herein binds to human Siglec-8 and non-human primate Siglec-8.

In another aspect, provided herein is an anti-Siglec-8 antibody comprising a heavy chain variable region and a light chain variable region, wherein the heavy chain variable region comprises (i) HVR-H1 comprising the amino acid sequence of SEQ ID NO:90, (ii) HVR-H2 comprising the amino acid sequence of SEQ ID NO:93, and (iii) HVR-H3 comprising the amino acid sequence of SEQ ID NO:96; and/or a light chain variable region comprising (i) HVR-L1 comprising the amino acid sequence of SEQ ID NO:99, (ii) HVR-L2 comprising the amino acid sequence of SEQ ID NO:102, and (iii) HVR-L3 comprising the amino acid sequence of SEQ ID NO:105. In some embodiments, the antibody described herein binds to an epitope in Domain 1 of human Siglec-8, wherein Domain 1 comprises the amino acid sequence of SEQ ID NO: 112. In some embodiments, the antibody described herein binds to human Siglec-8 and non-human primate Siglec-8.

An anti-Siglec-8 antibody described herein may comprise any suitable framework variable domain sequence, provided that the antibody retains the ability to bind human Siglec-8. As used herein, heavy chain framework regions are designated "HC-FR1-FR4," and light chain framework regions are designated "LC-FR1-FR4." In some embodiments, the anti-Siglec-8 antibody comprises a heavy chain variable domain framework sequence of SEQ ID NO:26, 34, 38, and 45 (HC-FR1, HC-FR2, HC-FR3, and HC-FR4, respectively). In some embodiments, the anti-Siglec-8 antibody comprises a light chain variable domain framework sequence of SEQ ID NO:48, 51, 55, and 60 (LC-FR1, LC-FR2, LC-FR3, and LC-FR4, respectively). In some embodiments, the anti-Siglec-8 antibody comprises a light chain variable domain framework sequence of SEQ ID NO:48, 51, 58, and 60 (LC-FR1, LC-FR2, LC-FR3, and LC-FR4, respectively).

In one embodiment, an anti-Siglec-8 antibody comprises a heavy chain variable domain comprising a framework sequence and hypervariable regions, wherein the framework sequence comprises the HC-FR1-HC-FR4 sequences SEQ ID NOs:26-29 (HC-FR1), SEQ ID NOs:31-36 (HC-FR2), SEQ ID NOs:38-43 (HC-FR3), and SEQ ID NOs:45 or 46 (HC-FR4), respectively; the HVR-H1 comprises the amino acid sequence of SEQ ID NO:61; the HVR-H2 comprises the amino acid sequence of SEQ ID NO:62; and the HVR-H3 comprises an amino acid sequence of SEQ ID NO:63. In one embodiment, an anti-Siglec-8 antibody comprises a heavy chain variable domain comprising a framework sequence and hypervariable regions, wherein the framework sequence comprises the HC-FR1-HC-FR4 sequences SEQ ID NOs:26-29 (HC-FR1), SEQ ID NOs:31-36 (HC-FR2), SEQ ID NOs:38-43 (HC-FR3), and SEQ ID NOs:45 or 46 (HC-FR4), respectively; the HVR-H1 comprises the amino acid sequence of SEQ ID NO:61; the HVR-H2 comprises the amino acid sequence of SEQ ID NO:62; and the HVR-H3 comprises an amino acid sequence selected from SEQ ID NOs:67-70. In one embodiment, an anti-Siglec-8 antibody comprises a light chain variable domain comprising a framework sequence and hypervariable regions, wherein the framework sequence comprises the LC-FR1-LC-FR4 sequences SEQ ID NOs:48 or 49 (LC-FR1), SEQ ID NOs: 51-53 (LC-FR2), SEQ ID NOs:55-58 (LC-FR3), and SEQ ID NO:60 (LC-FR4), respectively; the HVR-L1 comprises the amino acid sequence of SEQ ID NO:64; the HVR-L2 comprises the amino acid sequence of SEQ ID NO:65; and the HVR-L3 comprises an amino acid sequence of SEQ ID NO:66. In one embodiment, an anti-Siglec-8 antibody comprises a light chain variable domain comprising a framework sequence and hypervariable regions, wherein the framework sequence comprises the LC-FR1-LC-FR4 sequences SEQ ID NOs:48 or 49 (LC-FR1), SEQ ID NOs:51-53 (LC-FR2), SEQ ID NOs:55-58 (LC-FR3), and SEQ ID NO:60 (LC-FR4), respectively; the HVR-L1 comprises the amino acid sequence of SEQ ID NO:64; the HVR-L2 comprises the amino acid sequence of SEQ ID NO:65; and the HVR-L3 comprises an amino acid sequence of SEQ ID NO:71. In one embodiment of these antibodies, the heavy chain variable domain comprises an amino acid sequence selected from SEQ ID NOs:2-10 and the light chain variable domain comprises and amino acid sequence selected from SEQ ID NOs:16-22. In one embodiment of these antibodies, the heavy chain variable domain comprises an amino acid sequence selected from SEQ ID NOs:2-10 and the light chain variable domain comprises and amino acid sequence selected from SEQ ID NOs:23 or 24. In one embodiment of these antibodies, the heavy chain variable domain comprises an amino acid sequence selected from SEQ ID NOs:11-14 and the light chain variable domain comprises and amino acid sequence selected from SEQ ID NOs:16-22. In one embodiment of these antibodies, the heavy chain variable domain comprises an amino acid sequence selected from SEQ ID NOs:11-14 and the light chain variable domain comprises and amino acid sequence selected from SEQ ID NOs:23 or 24. In one embodiment of these antibodies, the heavy chain variable domain comprises an amino acid sequence of SEQ ID NO:6 and the light chain variable domain comprises and amino acid sequence of SEQ ID NO:16. In one embodiment of these antibodies, the heavy chain variable domain comprises an amino acid sequence of SEQ ID NO:6 and the light chain variable domain comprises and amino acid sequence of SEQ ID NO:21.

In some embodiments, the heavy chain HVR sequences comprise the following:

a) HVR-H1 (IYGAH (SEQ ID NO: 61));

b) HVR-H2 (VIWAGGSTNYNSALMS (SEQ ID NO: 62)); and c) HVR-H3 (DGSSPYYYSMEY (SEQ ID NO: 63);

DGSSPYYYGMEY (SEQ ID NO: 67); DGSSPYYYSMDY (SEQ ID NO: 68); DGSSPYYYSMEV (SEQ ID NO: 69); or

GSSPYYYGMDV (SEQ ID NO: 70)).

In some embodiments, the heavy chain HVR sequences comprise the following:

a) HVR-H1 (SYAMS (SEQ ID NO: 88); DYYMY (SEQ ID NO: 89); or SSWMN (SEQ ID NO: 90));

b) HVR-H2 (IISSGGSYTYYSDSVKG (SEQ ID NO: 91);

RIAPEDGDTEYAPKFQG (SEQ ID NO: 92);
or

QIYPGDDYTNYNGKFKG (SEQ ID NO: 93));
and c) HVR-H3 (HETAQAAWFAY (SEQ ID NO: 94);

EGNYYGSSILDY (SEQ ID NO: 95);
or

LGPYGPFAD (SEQ ID NO: 96)).

In some embodiments, the heavy chain FR sequences comprise the following:

a) HC-FR1 (EVQLVESGGGLVQPGGSLRLSCAASGFSLT (SEQ ID NO: 26); EVQLVESGGGLVQPGGSLRLSCAVSGFSLT (SEQ ID NO: 27); QVQLQESGPGLVKPSETLSLTCTVSGGSIS (SEQ ID NO: 28);
or

QVQLQESGPGLVKPSETLSLTCTVSGFSLT (SEQ ID NO: 29));

b) HC-FR2 (WVRQAPGKGLEWVS (SEQ ID NO: 31);

WVRQAPGKGLEWLG (SEQ ID NO: 32); WVRQAPGKGLEWLS (SEQ ID NO: 33); WVRQAPGKGLEWVG (SEQ ID NO: 34);

WIRQPPGKGLEWIG (SEQ ID NO: 35);
or

WVRQPPGKGLEWLG (SEQ ID NO: 36));

c) HC-FR3 (RFTISKDNSKNTVYLQMNSLRAEDTAVYYCAR (SEQ ID NO: 38); RLSISKDNSKNTVYLQMNSLRAEDTAVYYCAR (SEQ ID NO: 39); RLTISKDNSKNTVYLQMNSLRAEDTAVYYCAR (SEQ ID NO: 40); RFSISKDNSKNTVYLQMNSLRAEDTAVYYCAR (SEQ ID NO: 41); RVTISVDTSKNQFSLKLSSVTAADTAVYYCAR (SEQ ID NO: 42);
or

RLSISKDNSKNQVSLKLSSVTAADTAVYYCAR (SEQ ID NO: 43));
and d) HC-FR4 (WGQGTTVTVSS (SEQ ID NO: 45);
or

WGQGTLVTVSS (SEQ ID NO: 46)).

In some embodiments, the light chain HVR sequences comprise the following:

a) HVR-L1 (SATSSVSYMH (SEQ ID NO: 64));

b) HVR-L2 (STSNLAS (SEQ ID NO: 65));
and c) HVR-L3 (QQRSSYPFT (SEQ ID NO: 66);

or

QQRSSYPYT (SEQ ID NO: 71)).

In some embodiments, the light chain HVR sequences comprise the following:

a) HVR-L1 (SASSSVSYMH (SEQ ID NO: 97);

RASQDITNYLN (SEQ ID NO: 98);
or

SASSSVSYMY (SEQ ID NO: 99));

b) HVR-L2 (DTSKLAY (SEQ ID NO: 100);

FTSRLHS (SEQ ID NO: 101);
or

DTSSLAS (SEQ ID NO: 102));
and c) HVR-L3 (QQWSSNPPT (SEQ ID NO: 103);

QQGNTLPWT (SEQ ID NO: 104);
or

QQWNSDPYT (SEQ ID NO: 105)).

In some embodiments, the light chain FR sequences comprise the following:

a) LC-FR1 (EIVLTQSPATLSLSPGERATLSC (SEQ ID NO: 48);
or

EIILTQSPATLSLSPGERATLSC (SEQ ID NO: 49));

b) LC-FR2 (WFQQKPGQAPRLLIY (SEQ ID NO: 51);

WFQQKPGQAPRLWIY (SEQ ID NO: 52);
or

WYQQKPGQAPRLLIY (SEQ ID NO: 53));

c) LC-FR3 (GIPARFSGSGSGTDFTLTISSLEPEDFAVYYC (SEQ ID NO: 55); GVPARFSGSGSGTDYTLTISSLEPEDFAVYYC (SEQ ID NO: 56); GVPARFSGSGSGTDFTLTISSLEPEDFAVYYC (SEQ ID NO: 57);
or

GIPARFSGSGSGTDYTLTISSLEPEDFAVYYC (SEQ ID NO: 58));
and d) LC-FR4 (FGPGTKLDIK (SEQ ID NO: 60)).

In some embodiments, provided herein is an anti-Siglec-8 antibody (e.g., a humanized anti-Siglec-8) antibody that specifically binds to human Siglec-8, wherein the antibody comprises a heavy chain variable region and a light chain variable region, wherein the antibody comprises:

(a) heavy chain variable domain comprising:
(1) an HC-FR1 comprising the amino acid sequence selected from SEQ ID NOs:26-29;
(2) an HVR-H1 comprising the amino acid sequence of SEQ ID NO:61;
(3) an HC-FR2 comprising the amino acid sequence selected from SEQ ID NOs:31-36;
(4) an HVR-H2 comprising the amino acid sequence of SEQ ID NO:62;
(5) an HC-FR3 comprising the amino acid sequence selected from SEQ ID NOs:38-43;
(6) an HVR-H3 comprising the amino acid sequence of SEQ ID NO:63; and
(7) an HC-FR4 comprising the amino acid sequence selected from SEQ NOs:45-46,
and/or
(b) a light chain variable domain comprising:
(1) an LC-FR1 comprising the amino acid sequence selected from SEQ ID NOs:48-49;
(2) an HVR-L1 comprising the amino acid sequence of SEQ ID NO:64;
(3) an LC-FR2 comprising the amino acid sequence selected from SEQ ID NOs:51-53;
(4) an HVR-L2 comprising the amino acid sequence of SEQ ID NO:65;
(5) an LC-FR3 comprising the amino acid sequence selected from SEQ ID NOs:55-58;
(6) an HVR-L3 comprising the amino acid sequence of SEQ ID NO:66; and
(7) an LC-FR4 comprising the amino acid sequence of SEQ ID NO:60.

In one aspect, provided herein is an anti-Siglec-8 antibody comprising a heavy chain variable domain selected from SEQ ID NOs:2-10 and/or comprising a light chain variable domain selected from SEQ ID NOs:16-22. In one aspect, provided herein is an anti-Siglec-8 antibody comprising a heavy chain variable domain selected from SEQ ID NOs: 2-10 and/or comprising a light chain variable domain selected from SEQ ID NO:23 or 24. In one aspect, provided herein is an anti-Siglec-8 antibody comprising a heavy chain variable domain selected from SEQ ID NOs:11-14 and/or comprising a light chain variable domain selected from SEQ ID NOs:16-22. In one aspect, provided herein is an anti-Siglec-8 antibody comprising a heavy chain variable domain selected from SEQ ID NOs:11-14 and/or comprising a light chain variable domain selected from SEQ ID NO:23 or 24. In one aspect, provided herein is an anti-Siglec-8 antibody comprising a heavy chain variable domain of SEQ ID NO:6 and/or comprising a light chain variable domain selected from SEQ ID NO:16 or 21.

In one aspect, provided herein is an anti-Siglec-8 antibody comprising a heavy chain variable domain selected from SEQ ID NOs:106-108 and/or comprising a light chain variable domain selected from SEQ ID NOs:109-111. In one aspect, provided herein is an anti-Siglec-8 antibody comprising a heavy chain variable domain of SEQ ID NO:106 and/or comprising a light chain variable domain of SEQ ID NO:109. In one aspect, provided herein is an anti-Siglec-8 antibody comprising a heavy chain variable domain of SEQ ID NO:107 and/or comprising a light chain variable domain of SEQ ID NO:110. In one aspect, provided herein is an anti-Siglec-8 antibody comprising a heavy chain variable domain of SEQ ID NO:108 and/or comprising a light chain variable domain of SEQ ID NO:111.

In some embodiments, provided herein is an anti-Siglec-8 antibody comprising a heavy chain variable domain comprising an amino acid sequence having at least 90%, 91%, 92%, 93%, 94%, 95%, 96%, 97%, 98%, or 99% sequence identity to an amino acid sequence selected from SEQ ID NOs:2-14. In some embodiments, provided herein is an anti-Siglec-8 antibody comprising a heavy chain variable domain comprising an amino acid sequence having at least 90%, 91%, 92%, 93%, 94%, 95%, 96%, 97%, 98%, or 99% sequence identity to an amino acid sequence selected from SEQ ID NOs:106-108. In some embodiments, an amino acid sequence having at least 90%, 91%, 92%, 93%, 94%, 95%, 96%, 97%, 98%, or 99% sequence identity contains substitutions, insertions, or deletions relative to the reference sequence, but an antibody comprising that amino acid sequence retains the ability to bind to human Siglec-8. In some embodiments, the substitutions, insertions, or deletions (e.g., 1, 2, 3, 4, or 5 amino acids) occur in regions outside the HVRs (i.e., in the FRs). In some embodiments, an anti-Siglec-8 antibody comprises a heavy chain variable domain comprising an amino acid sequence of SEQ ID NO:6. In some embodiments, an anti-Siglec-8 antibody comprises a heavy chain variable domain comprising an amino acid sequence selected from SEQ ID NOs:106-108.

In some embodiments, provided herein is an anti-Siglec-8 antibody comprising a light chain variable domain comprising an amino acid sequence having at least 90%, 91%, 92%, 93%, 94%, 95%, 96%, 97%, 98%, or 99% sequence identity to an amino acid sequence selected from SEQ ID NOs:16-24. In some embodiments, provided herein is an anti-Siglec-8 antibody comprising a light chain variable domain comprising an amino acid sequence having at least 90%, 91%, 92%, 93%, 94%, 95%, 96%, 97%, 98%, or 99% sequence identity to an amino acid sequence selected from SEQ ID NOs:109-111. In some embodiments, an amino acid sequence having at least 90%, 91%, 92%, 93%, 94%, 95%, 96%, 97%, 98%, or 99% sequence identity contains substitutions, insertions, or deletions relative to the reference sequence, but an antibody comprising that amino acid sequence retains the ability to bind to human Siglec-8. In some embodiments, the substitutions, insertions, or deletions (e.g., 1, 2, 3, 4, or 5 amino acids) occur in regions outside the HVRs (i.e., in the FRs). In some embodiments, an anti-Siglec-8 antibody comprises a light chain variable domain comprising an amino acid sequence of SEQ ID NO:16 or 21. In some embodiments, an anti-Siglec-8 antibody comprises a heavy chain variable domain comprising an amino acid sequence selected from SEQ ID NOs:109-111.

Figure 1:
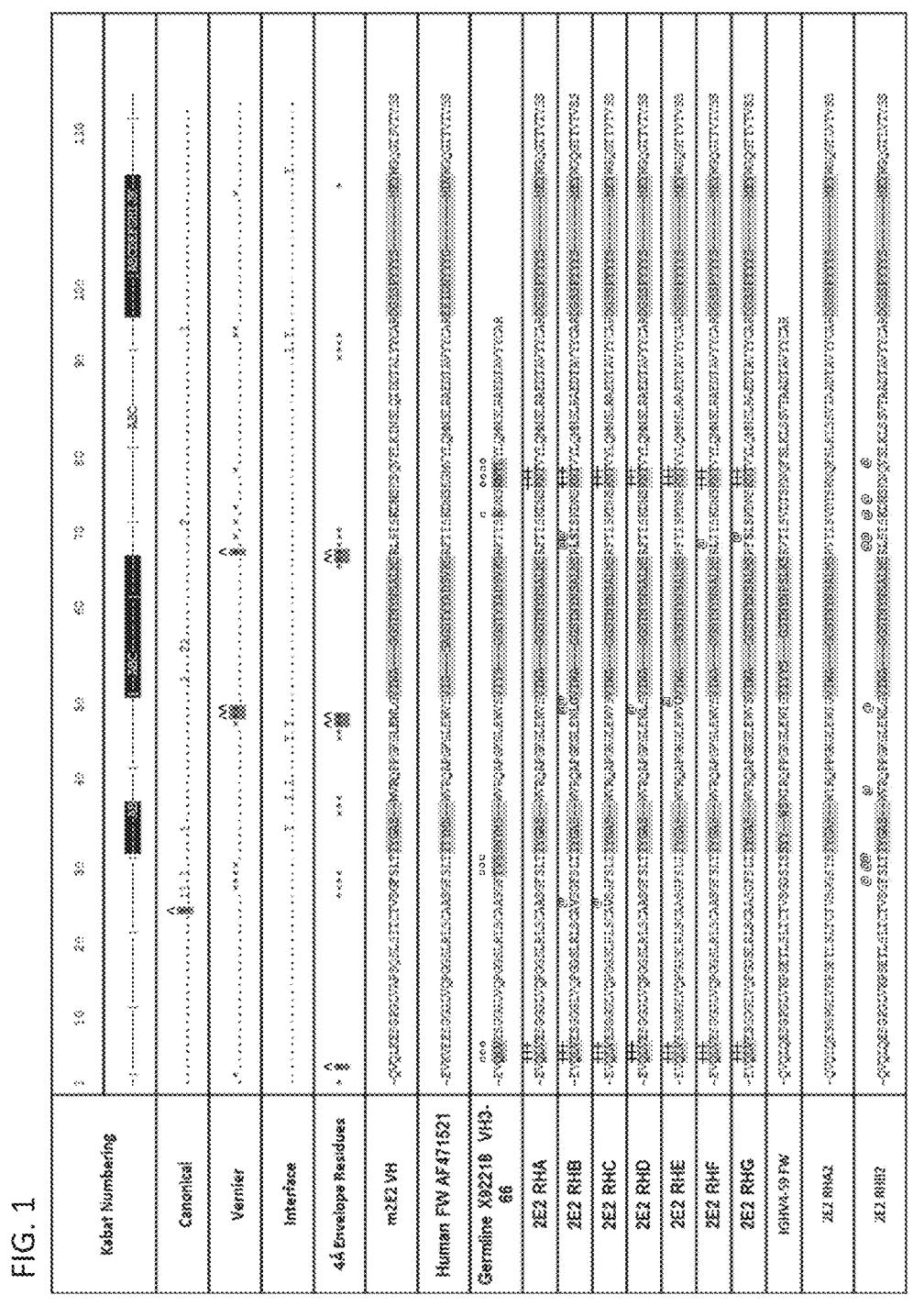
Figure 3:
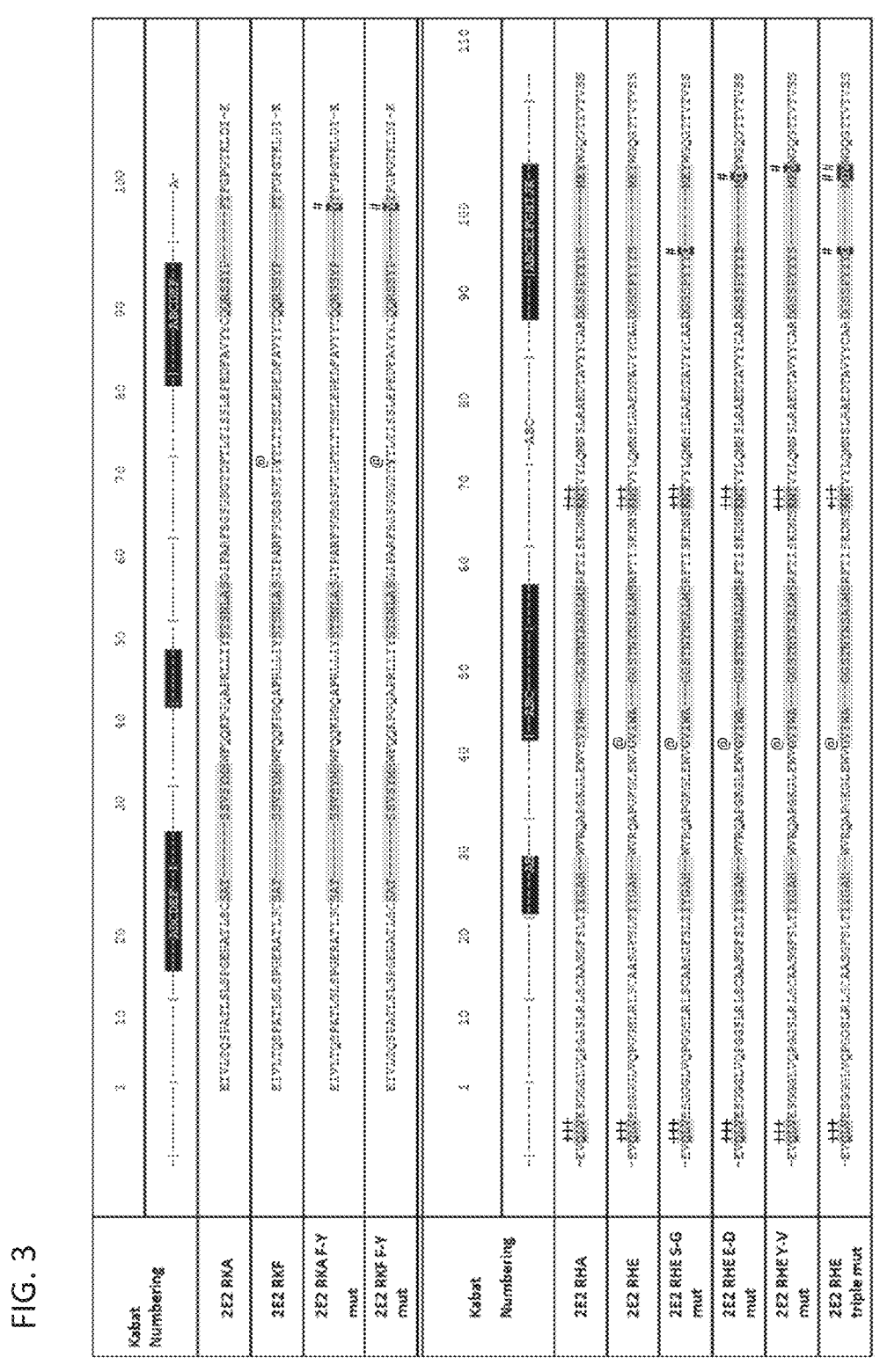

In some embodiments, provided herein is an anti-Siglec-8 antibody comprises a heavy chain variable domain as depicted in FIG. 1 or FIG. 3.

Figure 2:
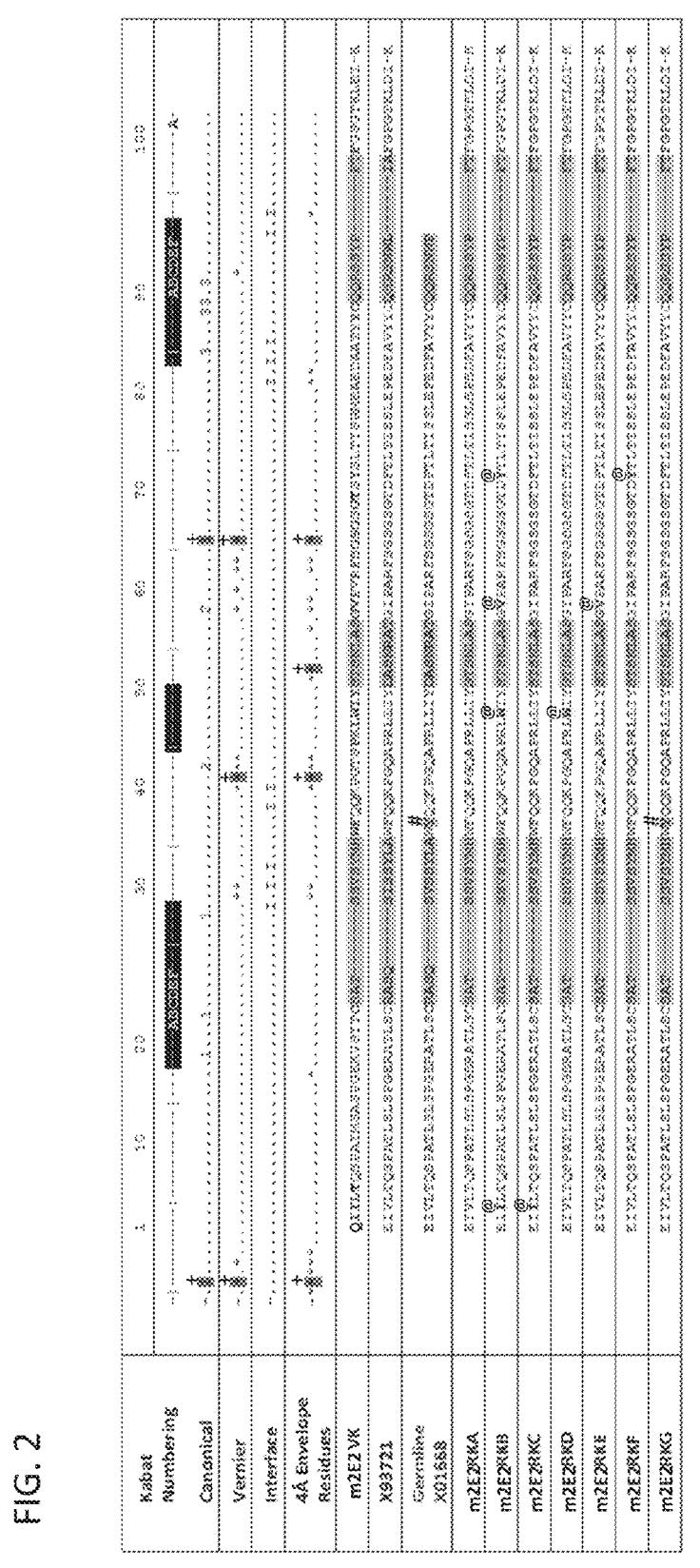

In some embodiments, provided herein is an anti-Siglec-8 antibody comprises a light chain variable domain as depicted in FIG. 2 or FIG. 3.

In one aspect, the invention provides an anti-Siglec-8 antibody comprising (a) one, two, or three VH HVRs selected from those shown in FIG. 1 or FIGS. 3 and/or (b) one, two, or three VL HVRs selected from those in FIG. 2 or FIG. 3. In one aspect, the invention provides an anti-Siglec-8 antibody comprising a heavy chain variable domain selected from those shown in FIG. 1 or FIG. 3 and a light chain variable domain selected from those shown in FIG. 2 or FIG. 3.

In some embodiments, provided herein is an anti-Siglec-8 antibody comprising a heavy chain variable domain and/or a light chain variable domain of an antibody shown in Table 3, for example, HAKA antibody, HAKB antibody, HAKC antibody, etc.

There are five classes of immunoglobulins: IgA, IgD, IgE, IgG and IgM, having heavy chains designated α, β, ε, γ and μ, respectively. The γ and α classes are further divided into subclasses e.g., humans express the following subclasses: IgG1, IgG2, IgG3, IgG4, IgA1 and IgA2. IgG1 antibodies can exist in multiple polymorphic variants termed allotypes (reviewed in Jefferis and Lefranc 2009. mAbs Vol 1 Issue 4 1-7) any of which are suitable for use in some of the embodiments herein. Common allotypic variants in human populations are those designated by the letters a,f,n,z or combinations thereof. In any of the embodiments herein, the antibody may comprise a heavy chain Fc region comprising a human IgG Fc region. In further embodiments, the human IgG Fc region comprises a human IgG1 or IgG4. In some embodiments, the human IgG4 comprises the amino acid substitution S228P, wherein the amino acid residues are numbered according to the EU index as in Kabat. In some embodiments, the human IgG1 comprises the amino acid sequence of SEQ ID NO:78. In some embodiments, the human IgG4 comprises the amino acid sequence of SEQ ID NO:79.

In some embodiments, provided herein is an anti-Siglec-8 antibody comprising a heavy chain comprising the amino acid sequence of SEQ ID NO:75; and/or a light chain comprising the amino acid sequence selected from SEQ ID NOs:76 or 77. In some embodiments, the antibody may comprise a heavy chain comprising the amino acid sequence of SEQ ID NO:87; and/or a light chain comprising the amino acid sequence of SEQ ID NO:76. In some embodiments, the anti-Siglec-8 antibody depletes mast cells and inhibits mast cell activation. In some embodiments, the anti-Siglec-8 antibody depletes activated eosinophils and inhibits mast cell activation.

1. Antibody Affinity

In some aspects, an anti-Siglec-8 antibody described herein binds to human Siglec-8 with about the same or higher affinity and/or higher avidity as compared mouse antibody 2E2 and/or mouse antibody 2C4. In certain embodiments, an anti-Siglec-8 antibody provided herein has a dissociation constant (Kd) of ≤≤150 nM, ≤100 nM, ≤50 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M). In some embodiments, an anti-Siglec-8 antibody described herein binds to human Siglec-8 at about 1.5-fold, about 2-fold, about 3-fold, about 4-fold, about 5-fold, about 6-fold, about 7-fold, about 8-fold, about 9-fold or about 10-fold higher affinity than mouse antibody 2E2 and/or mouse antibody 2C4. In some embodiments herein, the anti-Siglec-8 antibody comprises a heavy chain variable region comprising the amino acid sequence of SEQ ID NO:6; and/or a light chain variable region comprising the amino acid sequence selected from SEQ ID NOs:16 or 21.

In one embodiment, the binding affinity of the anti-Siglec-8 antibody can be determined by a surface plasmon resonance assay. For example, the Kd or Kd value can be measured by using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore® Inc.) are activated with N-ethyl-N'-(3-dimethylaminopropyl)-carbodiimide hydrochloride (EDC) and N-hydroxysuccinimide (NHS) according to the supplier's instructions. Capture antibodies (e.g., anti-human-Fc) are diluted with 10 mM sodium acetate, pH 4.8, before injection at a flow rate of 30 μl/minute and further immobilized with an anti-Siglec-8 antibody. For kinetics measurements, two-fold serial dilutions of dimeric Siglec-8 are injected in PBS with 0.05% Tween 20 (PBST) at 25° C. at a flow rate of approximately 25 μl/min. Association rates (kon) and dissociation rates (koff) are calculated using a simple one-to-one Langmuir binding model (BIAcore® Evaluation Software version 3.2) by simultaneously fitting the association and dissociation sensorgrams. The equilibrium dissociation constant (Kd) is calculated as the ratio koff/kon. See, e.g., Chen, Y., et al., (1999) J. Mol. Biol. 293:865-881.

In another embodiment, biolayer interferometry may be used to determine the affinity of anti-Siglec-8 antibodies against Siglec-8. In an exemplary assay, Siglec-8-Fc tagged protein is immobilized onto anti-human capture sensors, and incubated with increasing concentrations of mouse, chimeric, or humanized anti-Siglec-8 Fab fragments to obtain affinity measurements using an instrument such as, for example, the Octet Red 384 System (ForteBio).

The binding affinity of the anti-Siglec-8 antibody can, for example, also be determined by the Scatchard analysis described in Munson et al., Anal. Biochem., 107:220 (1980) using standard techniques well known in the relevant art. See also Scatchard, G., Ann. N.Y. Acad. Sci. 51:660 (1947).

2. Antibody Avidity

In one embodiment, the binding avidity of the anti-Siglec-8 antibody can be determined by a surface plasmon resonance assay. For example, the Kd or Kd value can be measured by using a BIAcore T100. Capture antibodies (e.g., goat-anti-human-Fc and goat-anti-mouse-Fc) are immobilized on a CMS chip. Flow-cells can be immobilized with anti-human or with anti-mouse antibodies. The assay is conducted at a certain temperature and flow rate, for example, at 25° C. at a flow rate of 30 µl/min. Dimeric Siglec-8 is diluted in assay buffer at various concentrations, for example, at a concentration ranging from 15 nM to 1.88 pM. Antibodies are captured and high performance injections are conducted, followed by dissociations. Flow cells are regenerated with a buffer, for example, 50 mM glycine pH 1.5. Results are blanked with an empty reference cell and multiple assay buffer injections, and analyzed with 1:1 global fit parameters.

3. Competition Assays

Competition assays can be used to determine whether two antibodies bind the same epitope by recognizing identical or sterically overlapping epitopes or one antibody competitively inhibits binding of another antibody to the antigen. These assays are known in the art. Typically, antigen or antigen expressing cells is immobilized on a multi-well plate and the ability of unlabeled antibodies to block the binding of labeled antibodies is measured. Common labels for such competition assays are radioactive labels or enzyme labels. In some embodiments, an anti-Siglec-8 antibody described herein competes with a 2E2 antibody described herein, for binding to the epitope present on the cell surface of a cell (e.g., an eosinophil). In some embodiments, an anti-Siglec-8 antibody described herein competes with an antibody comprising a heavy chain variable domain comprising the amino acid sequence of SEQ ID NO:1, and a light chain variable region comprising the amino acid sequence of SEQ ID NO:15, for binding to the epitope present on the cell surface of a cell (e.g., an eosinophil). In some embodiments, an anti-Siglec-8 antibody described herein competes with a 2C4 antibody described herein, for binding to the epitope present on the cell surface of a cell (e.g., an eosinophil). In some embodiments, an anti-Siglec-8 antibody described herein competes with an antibody comprising a heavy chain variable domain comprising the amino acid sequence of SEQ ID NO:2 (as found in U.S. Pat. No. 8,207,305), and a light chain variable region comprising the amino acid sequence of SEQ ID NO:4 (as found in U.S. Pat. No. 8,207,305), for binding to the epitope present on the cell surface of a cell (e.g., an eosinophil).

4. Thermal Stability

In some aspects, an anti-Siglec-8 described herein has a melting temperature (Tm) of at least about 70° C., at least about 71° C., or at least about 72° C. in a thermal shift assay. In an exemplary thermal shift assay, samples comprising a humanized anti-Siglec-8 antibody are incubated with a fluorescent dye (Sypro Orange) for 71 cycles with 1° C. increase per cycle in a qPCR thermal cycler to determine the Tm. In some embodiments herein, the anti-Siglec-8 antibody has a similar or higher Tm as compared to mouse 2E2 antibody and/or mouse 2C4 antibody. In some embodiments herein, the anti-Siglec-8 antibody comprises a heavy chain variable region comprising the amino acid sequence of SEQ ID NO:6; and/or a light chain variable region comprising the amino acid sequence selected from SEQ ID NOs:16 or 21. In some embodiments, the anti-Siglec-8 antibody has the same or higher Tm as compared to a chimeric 2C4 antibody. In some embodiments, the anti-Siglec-8 antibody has the same or higher Tm as compared to an antibody having a heavy chain comprising the amino acid sequence of SEQ ID NO:84 and a light chain comprising the amino acid sequence of SEQ ID NO:85.

5. Biological Activity Assays

In some aspects, an anti-Siglec-8 described herein induces apoptosis of eosinophils. In some other aspects, an anti-Siglec-8 described herein depletes mast cells. Assays for assessing apoptosis of cells are well known in the art, for example staining with Annexin V and the TUNNEL assay. In an exemplary cell apoptosis assay, fresh buffy coat from a blood sample is resuspended in media and plated in a 96-well U-bottom plate. A series of serial 5-fold dilutions of anti-Siglec-8 antibody is added to each well and the plate is incubated at 37° C. at 5% $CO_2$ for greater than four hours. The cells are fixed with paraformaldehyde diluted in PBS and stained with conjugated antibodies specific for eosinophils for detection using a microscope. The eosinophil population in the total peripheral blood leukocytes is evaluated when the buffy coat is incubated in the presence of the anti-Siglec-8 antibody as compared to when the buffy coat is not incubated in the presence of the anti-Siglec-8 antibody. In another exemplary assay, eosinophils purified from a blood sample (e.g., Miltenyi Eosinophil Isolation Kit) are resuspended in media and cultured in the presence or absence of IL-5 overnight. The cultured eosinophils are subsequently harvested by centrifugation, resuspended in media, and plated in a 96-well U-bottom plate. A series of serial 5-fold dilutions of anti-Siglec-8 antibody is added to each well and the plate is incubated at 37° C. at 5% $CO_2$ for greater than four hours. The cells are fixed and stained with Annexin-V using standard techniques well known in the art the number of eosinophils is detected using a microscope. The eosinophil population in the sample is evaluated when the purified cells are incubated in the presence of the anti-Siglec-8 antibody as compared to when the purified cells are not incubated in the presence of the anti-Siglec-8 antibody.

In some aspects, an anti-Siglec-8 antibody described herein induces ADCC activity. In some other aspects, an anti-Siglec-8 antibody described herein kills mast cells expressing Siglec-8 by ADCC activity. In some embodiments, a composition comprises non-fucosylated (i.e., afucosylated) anti-Siglec-8 antibodies. In some embodiments, a composition comprising non-fucosylated anti-Siglec-8 antibodies described herein enhances ADCC activity as compared to a composition comprising partially fucosylated anti-Siglec-8 antibodies. Assays for assessing ADCC activity are well known in the art and described herein. In an exemplary assay, to measure ADCC activity, effector cells and target cells are used. Examples of effector cells include natural killer (NK) cells, large granular lymphocytes (LGL), lymphokine-activated killer (LAK) cells and PBMC comprising NK and LGL, or leukocytes having Fc receptors on the cell surfaces, such as neutrophils, eosinophils and macrophages. The target cell is any cell which expresses on the cell surface antigens that antibodies to be evaluated can recognize. An example of such a target cell is an eosinophil which expresses Siglec-8 on the cell surface. Another example of such a target cell is a mast cell which expresses Siglec-8 on the cell surface. Target cells are labeled with a reagent that enables detection of cytolysis. Examples of reagents for labeling include a radio-active substance such as sodium chromate ($Na_2^{51}CrO_4$). See, e.g., Immunology, 14, 181 (1968); J. Immunol. Methods, 172, 227 (1994); and J. Immunol. Methods, 184, 29 (1995).

In some aspects, an anti-Siglec-8 antibody described herein inhibits mast cell-mediated activities. Mast cell tryptase has been used as a biomarker for total mast cell number and activation. For example, total and active tryptase as well as histamine, N-methyl histamine, and 11-beta-prostaglandin F2 can be measured in blood or urine to assess the reduction in mast cells. See, e.g., U.S. Patent Application Publication No. US 20110293631 for an exemplary mast cell activity assay. Assays described in Example 2 herein can also be used to assess ADCC and apoptotic activity of anti-Siglec-8 antibodies on mast cells.

6. Fusion Protein Binding Assays

Binding assays with fusion proteins can be used to determine the epitope recognized by an antibody. Assays using fusion proteins for epitope mapping are known in the art. For example, a fusion protein comprising a portion of a Siglec-8 protein fused to a human Ig-Fc is immobilized on a multi-well plate and the ability of antibodies to bind to the fusion protein is measured. In some embodiments, an anti-Siglec-8 antibody described herein binds to a fusion protein comprising the amino acid sequence of SEQ ID NO:115. In some embodiments, an anti-Siglec-8 antibody described herein binds to a fusion protein comprising the amino acid sequence of SEQ ID NO:116. In some embodiments, an anti-Siglec-8 antibody described herein binds to a fusion protein comprising the amino acid sequence of SEQ ID NO:117. In some embodiments, an anti-Siglec-8 antibody described herein binds to a fusion protein comprising the amino acid sequence of SEQ ID NO:118.

III. Antibody Preparation

The antibody described herein is prepared using techniques available in the art for generating antibodies, exemplary methods of which are described in more detail in the following sections.

1. Antibody Fragments

The present invention encompasses antibody fragments. Antibody fragments may be generated by traditional means, such as enzymatic digestion, or by recombinant techniques. In certain circumstances there are advantages of using antibody fragments, rather than whole antibodies. For a review of certain antibody fragments, see Hudson et al. (2003) Nat. Med. 9:129-134.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the facile production of large amounts of these fragments. Antibody fragments can be isolated from the antibody phage libraries discussed above. Alternatively, Fab'-SH fragments can be directly recovered from E. coli and chemically coupled to form F(ab')$_2$ fragments (Carter et al., Bio/Technology 10: 163-167 (1992)). According to another approach, F(ab')$_2$ fragments can be isolated directly from recombinant host cell culture. Fab and F(ab')$_2$ fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See Antibody Engineering, ed. Borrebaeck, supra. The antibody fragment may also be a "linear antibody", e.g., as described in U.S. Pat. No. 5,641,870, for example. Such linear antibodies may be monospecific or bispecific.

2. Humanized Antibodies

The invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter (Jones et al. (1986) Nature 321:522-525; Riechmann et al. (1988) Nature 332:323-327; Verhoeyen et al. (1988) Science 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies can be important to reduce antigenicity. According to the so-called "best-fit" method, the sequence of the variable domain of a rodent (e.g., mouse) antibody is screened against the entire library of known human variable-domain sequences. The human sequence which is closest to that of the rodent is then accepted as the human framework for the humanized antibody (Sims et al. (1993) J. Immunol. 151: 2296; Chothia et al. (1987) J. Mol. Biol. 196:901. Another method uses a particular framework derived from the consensus sequence of all human antibodies of a particular subgroup of light or heavy chains. The same framework may be used for several different humanized antibodies (Carter et al. (1992) Proc. Natl. Acad. Sci. USA, 89:4285; Presta et al. (1993) J. Immunol., 151:2623.

It is further generally desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those, skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

3. Human Antibodies

Human anti-Siglec-8 antibodies of the invention can be constructed by combining Fv clone variable domain sequence(s) selected from human-derived phage display libraries with known human constant domain sequences(s). Alternatively, human monoclonal anti-Siglec-8 antibodies of the invention can be made by the hybridoma method. Human myeloma and mouse-human heteromyeloma cell lines for the production of human monoclonal antibodies have been described, for example, by Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).

It is possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90: 2551 (1993); Jakobovits et al., Nature, 362: 255 (1993); Bruggermann et al., Year in Immunol., 7: 33 (1993).

Gene shuffling can also be used to derive human antibodies from non-human (e.g., rodent) antibodies, where the human antibody has similar affinities and specificities to the starting non-human antibody. According to this method, which is also called "epitope imprinting", either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e., the epitope governs the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

4. Bispecific Antibodies

Bispecific antibodies are monoclonal antibodies that have binding specificities for at least two different antigens. In certain embodiments, bispecific antibodies are human or humanized antibodies. In certain embodiments, one of the binding specificities is for Siglec-8 and the other is for any other antigen. In certain embodiments, bispecific antibodies may bind to two different epitopes of Siglec-8. Bispecific antibodies may also be used to localize cytotoxic agents to cells which express Siglec-8. Bispecific antibodies can be prepared as full length antibodies or antibody fragments (e.g. F(ab')$_2$ bispecific antibodies).

Methods for making bispecific antibodies are known in the art. See Milstein and Cuello, Nature, 305: 537 (1983), WO 93/08829 published May 13, 1993, and Traunecker et al., EMBO J., 10: 3655 (1991). For further details of generating bispecific antibodies see, for example, Suresh et al., Methods in Enzymology, 121:210 (1986). Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking method. Suitable cross-linking agents are well known in the art, and are disclosed in U.S. Pat. No. 4,676,980, along with a number of cross-linking techniques.

5. Single-Domain Antibodies

In some embodiments, an antibody of the invention is a single-domain antibody. A single-domain antibody is a single polypeptide chain comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1). In one embodiment, a single-domain antibody consists of all or a portion of the heavy chain variable domain of an antibody.

6. Antibody Variants

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as arg, asp, his, lys, and glu) and replaced by a neutral or negatively charged amino acid (e.g., alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme or a polypeptide which increases the serum half-life of the antibody.

In certain embodiments, an antibody of the invention is altered to increase or decrease the extent to which the antibody is glycosylated. Glycosylation of polypeptides is typically either N-linked or O-linked. N-linked refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition or deletion of glycosylation sites to the antibody is conveniently accomplished by altering the amino acid sequence such that one or more of the above-described tripeptide sequences (for N-linked glycosylation sites) is created or removed. The alteration may also be made by the addition, deletion, or substitution of one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody are described in US Pat Appl No US 2003/0157108 (Presta, L.). See also US 2004/0093621 (Kyowa Hakko Kogyo Co., Ltd). Antibodies with a bisecting N-acetylglucosamine (GlcNAc) in the carbohydrate attached to an Fc region of the antibody are referenced in WO 2003/011878, Jean-Mairet et al. and U.S. Pat. No. 6,602,684, Umana et al. Antibodies with at least one galactose residue in the oligosaccharide attached to an Fc region of the antibody are reported in WO 1997/30087, Patel et al. See, also, WO 1998/58964 (Raju, S.) and WO 1999/22764 (Raju, S.) concerning antibodies with altered carbohydrate attached to the Fc region thereof. See also US 2005/0123546 (Umana et al.) on antigen-binding molecules with modified glycosylation.

In certain embodiments, a glycosylation variant comprises an Fc region, wherein a carbohydrate structure attached to the Fc region lacks fucose or has reduced fucose. Such variants have improved ADCC function. Optionally, the Fc region further comprises one or more amino acid substitutions therein which further improve ADCC, for example, substitutions at positions 298, 333, and/or 334 of the Fc region (Eu numbering of residues). Examples of publications related to "defucosylated" or "fucose-deficient" antibodies include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; Okazaki et al. J. Mol. Biol. 336:1239-1249 (2004); Yamane-Ohnuki et al. Biotech. Bioeng. 87: 614 (2004). Examples of cell lines producing defucosylated antibodies include Lec13 CHO cells deficient in protein fucosylation (Ripka et al. Arch. Biochem. Biophys. 249: 533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (Yamane-Ohnuki et al. Biotech. Bioeng. 87: 614 (2004)), and cells overexpressing β1,4-N-acetylglycosminyltransferase III (GnT-III) and Golgi μ-mannosidase II (ManII).

Antibodies are contemplated herein that have reduced fucose relative to the amount of fucose on the same antibody produced in a wild-type CHO cell. For example, the antibody has a lower amount of fucose than it would otherwise have if produced by native CHO cells (e.g., a CHO cell that produce a native glycosylation pattern, such as, a CHO cell containing a native FUT8 gene). In certain embodiments, an anti-Siglec-8 antibody provided herein is one wherein less than about 50%, 40%, 30%, 20%, 10%, 5% or 1% of the N-linked glycans thereon comprise fucose. In certain embodiments, an anti-Siglec-8 antibody provided herein is one wherein none of the N-linked glycans thereon comprise fucose, i.e., wherein the antibody is completely without fucose, or has no fucose or is non-fucosylated or is afucosylated. The amount of fucose can be determined by calculating the average amount of fucose within the sugar chain at Asn297, relative to the sum of all glycostructures attached to Asn297 (e.g., complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. In some embodiments, at least one or two of the heavy chains of the antibody is non-fucosylated.

In one embodiment, the antibody is altered to improve its serum half-life. To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule (US 2003/0190311, U.S. Pat. No. 6,821,505; U.S. Pat. No. 6,165,745; U.S. Pat. No. 5,624,821; U.S. Pat. No. 5,648,260; U.S. Pat. No. 6,165,745; U.S. Pat. No. 5,834,597).

Another type of variant is an amino acid substitution variant. These variants have at least one amino acid residue in the antibody molecule replaced by a different residue. Sites of interest for substitutional mutagenesis include the hypervariable regions, but FR alterations are also contemplated. Conservative substitutions are shown in Table 1 under the heading of "preferred substitutions." If such substitutions result in a desirable change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |

TABLE 1-continued

| Original Residue | Exemplary Substitutions | Preferred Substitutions |
|---|---|---|
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or c) the bulk of the side chain. Amino acids may be grouped according to similarities in the properties of their side chains (in A. L. Lehninger, in Biochemistry, second ed., pp. 73-75, Worth Publishers, New York (1975)):

(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His (H)

Alternatively, naturally occurring residues may be divided into groups based on common side-chain properties:

(1) hydrophobic: Norleucine, Met, Ala, Val, Leu, Ile
(2) neutral hydrophilic: Cys, Ser, Thr, Asn, Gln;
(3) acidic: Asp, Glu;
(4) basic: His, Lys,
(5) residues that influence chain orientation: Gly, Pro;
(6) aromatic: Trp, Tyr, Phe, Non-conservative substitutions will entail exchanging a member of one of these classes for another class. Such substituted residues also may be introduced into the conservative substitution sites or, into the remaining (non-conserved) sites.

One type of substitutional variant involves substituting one or more hypervariable region residues of a parent antibody (e.g., a humanized or human antibody). Generally, the resulting variant(s) selected for further development will have modified (e.g., improved) biological properties relative to the parent antibody from which they are generated. A convenient way for generating such substitutional variants involves affinity maturation using phage display. Briefly, several hypervariable region sites (e.g., 6-7 sites) are mutated to generate all possible amino acid substitutions at each site. The antibodies thus generated are displayed from filamentous phage particles as fusions to at least part of a phage coat protein (e.g., the gene III product of M13) packaged within each particle. The phage-displayed variants are then screened for their biological activity (e.g., binding affinity). In order to identify candidate hypervariable region sites for modification, scanning mutagenesis (e.g., alanine scanning) can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to techniques known in the art, including those elaborated herein. Once such variants are generated, the panel of variants is subjected to screening using techniques known in the art, including those described herein, and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of antibodies of the invention, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine. In some embodiments, the Fc region variant comprises a human IgG4 Fc region. In a further embodiment, the human IgG4 Fc region comprises the amino acid substitution S228P, wherein the amino acid residues are numbered according to the EU index as in Kabat.

In accordance with this description and the teachings of the art, it is contemplated that in some embodiments, an antibody of the invention may comprise one or more alterations as compared to the wild type counterpart antibody, e.g. in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) C1q binding and/or Complement Dependent Cytotoxicity (CDC), e.g., as described in WO99/51642. See also Duncan & Winter Nature 322:738-40 (1988); U.S. Pat. No. 5,648,260; U.S. Pat. No. 5,624,821; and WO94/29351 concerning other examples of Fc region variants. WO00/42072 (Presta) and WO 2004/056312 (Lowman) describe antibody variants with improved or diminished binding to FcRs. The content of these patent publications are specifically incorporated herein by reference. See, also, Shields et al. J. Biol. Chem. 9(2): 6591-6604 (2001). Antibodies with increased half-lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). These antibodies comprise an Fc region with one or more substitutions therein which improve binding of the Fc region to FcRn. Polypeptide variants with altered Fc region amino acid sequences and increased or decreased C1q binding capability are described in U.S. Pat. No. 6,194,551B1, WO99/51642. The contents of those patent publications are specifically incorporated herein by reference. See, also, Idusogie et al. J. Immunol. 164: 4178-4184 (2000).

7. Vectors, Host Cells, and Recombinant Methods

For recombinant production of an antibody of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, host cells are of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

Generating Antibodies Using Prokaryotic Host Cells:

a) Vector Construction

Polynucleotide sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species. pBR322 contains genes-encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM.TM.-11 may be utilized in making a recombinant vector which can be used to transform susceptible host cells such as E. coli LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the E. coli trxB-strains) provide cytoplasm conditions that are favorable for disulfide bond formation, thereby permitting proper folding and assembly of expressed protein subunits. Proba and Pluckthun Gene, 159:203 (1995).

Antibodies of the invention can also be produced by using an expression system in which the quantitative ratio of expressed polypeptide components can be modulated in order to maximize the yield of secreted and properly assembled antibodies of the invention. Such modulation is accomplished at least in part by simultaneously modulating translational strengths for the polypeptide components.

One technique for modulating translational strength is disclosed in Simmons et al., U.S. Pat. No. 5,840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence. In certain embodiments, changes in the nucleotide sequence are silent. Alterations in the TIR can include, for example, alterations in the number or spacing of Shine-Dalgarno sequences, along with alterations in the signal sequence. One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (1992) METHODS: A Companion to Methods in Enzymol. 4:151-158.

In one embodiment, a set of vectors is generated with a range of TIR strengths for each cistron therein. This limited set provides a comparison of expression levels of each chain as well as the yield of the desired antibody products under various TIR strength combinations. TIR strengths can be determined by quantifying the expression level of a reporter gene as described in detail in Simmons et al. U.S. Pat. No. 5,840,523. Based on the translational strength comparison, the desired individual TIRs are selected to be combined in the expression vector constructs of the invention.

Prokaryotic host cells suitable for expressing antibodies of the invention include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium*, *Serratia marcescans*, *Klebsiella*, *Proteus*, *Shigella*, *Rhizobia*, *Vitreoscilla*, or *Paracoccus*. In one embodiment, gram-negative cells are used. In one embodiment, *E. coli* cells are used as hosts for the invention. Examples of *E. coli* strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kanR (U.S. Pat. No. 5,639,635). Other strains and derivatives thereof, such as *E. coli* 294 (ATCC 31,446), *E. coli* B, *E. coli*λ 1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. coli*, *Serratia*, or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

b) Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extra-chromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. In certain embodiments, for *E. coli* growth, growth temperatures range from about 20° C. to about 39° C.; from about 25° C. to about 37° C.; or about 30° C. The pH of the medium may be any pH ranging from about 5 to about 9, depending mainly on the host organism. In certain embodiments, for *E. coli*, the pH is from about 6.8 to about 7.4, or about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. In certain embodiments, the phosphate-limiting medium is the C.R.A.P. medium (see, e.g., Simmons et al., J. Immunol. Methods (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, and in certain embodiments, about 1,000 to 100,000 liters of capacity. These fermentors use agitator impellers to distribute oxygen and nutrients, especially glucose. Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) J. Biol. Chem. 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun (2000) J. Biol. Chem. 275: 17106-17113; Arie et al. (2001) Mol. Microbiol. 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al., Microbial Drug Resistance, 2:63-72 (1996).

In one embodiment, *E. coli* strains deficient for proteolytic enzymes and transformed with plasmids overexpressing one or more chaperone proteins are used as host cells in the expression system of the invention.

c) Antibody Purification

In one embodiment, the antibody protein produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the antibody products of the invention. Protein A is a 41 kD cell wall protein from *Staphylococcus aureus* which binds with a high affinity to the Fc region of antibodies. Lindmark et al (1983) J. Immunol. Meth. 62:1-13. The solid phase to which Protein A is immobilized can be a column comprising a glass or silica surface, or a controlled pore glass column or a silicic acid column. In some applications, the column is coated with a reagent, such as glycerol, to possibly prevent non-specific adherence of contaminants.

As the first step of purification, a preparation derived from the cell culture as described above can be applied onto a Protein A immobilized solid phase to allow specific binding of the antibody of interest to Protein A. The solid phase would then be washed to remove contaminants non-specifically bound to the solid phase. Finally the antibody of interest is recovered from the solid phase by elution.

Generating Antibodies Using Eukaryotic Host Cells:

A vector for use in a eukaryotic host cell generally includes one or more of the following non-limiting components: a signal sequence, an origin of replication, one or more marker genes, an enhancer element, a promoter, and a transcription termination sequence.

a) Signal Sequence Component

A vector for use in a eukaryotic host cell may also contain a signal sequence or other polypeptide having a specific cleavage site at the N-terminus of the mature protein or polypeptide of interest. The heterologous signal sequence selected may be one that is recognized and processed (i.e., cleaved by a signal peptidase) by the host cell. In mammalian cell expression, mammalian signal sequences as well as viral secretory leaders, for example, the herpes simplex gD signal, are available. The DNA for such a precursor region is ligated in reading frame to DNA encoding the antibody.

b) Origin of Replication

Generally, an origin of replication component is not needed for mammalian expression vectors. For example, the SV40 origin may typically be used only because it contains the early promoter.

c) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, primate metallothionein genes, adenosine deaminase, ornithine decarboxylase, etc.

For example, in some embodiments, cells transformed with the DHFR selection gene are first identified by culturing all of the transformants in a culture medium that contains methotrexate (Mtx), a competitive antagonist of DHFR. In some embodiments, an appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199. Host cells may include NS0, CHOK1, CHOK1SV or derivatives, including cell lines deficient in glutamine synthetase (GS). Methods for the use of GS as a selectable marker for mammalian cells are described in U.S. Pat. No. 5,122,464 and U.S. Pat. No. 5,891,693.

d) Promoter Component

Expression and cloning vectors usually contain a promoter that is recognized by the host organism and is operably linked to nucleic acid encoding a polypeptide of interest (e.g., an antibody). Promoter sequences are known for eukaryotes. For example, virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. In certain embodiments, any or all of these sequences may be suitably inserted into eukaryotic expression vectors.

Transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982), describing expression of human β-interferon cDNA in mouse cells under the control of a thymidine kinase promoter from herpes simplex virus. Alternatively, the Rous Sarcoma Virus long terminal repeat can be used as the promoter.

e) Enhancer Element Component

Transcription of DNA encoding an antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the human cytomegalovirus early promoter enhancer, the mouse cytomegalovirus early promoter enhancer, the polyoma enhancer on the late side of the replication origin, and adenovirus enhancers. See also Yaniv, Nature 297:17-18 (1982) describing enhancer elements for activation of eukaryotic promoters. The enhancer may be spliced into the vector at a position 5' or 3' to the antibody polypeptide-encoding sequence, but is generally located at a site 5' from the promoter.

f) Transcription Termination Component

Expression vectors used in eukaryotic host cells may also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

g) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; CHOK1 cells, CHOK1SV cells or derivatives and a human hepatoma line (Hep G2).

Host cells are transformed with the above-described-expression or cloning vectors for antibody production and cultured in conventional nutrient media modified as appropriate for inducing promoters, selecting transformants, or amplifying the genes encoding the desired sequences.

h) Culturing the Host Cells

The host cells used to produce an antibody of this invention may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other supplements may also be included at appropriate concentrations that would be known to those skilled in the art. The culture conditions, such as temperature, pH, and the like, are those previously used with the host cell selected for expression, and will be apparent to the ordinarily skilled artisan.

i) Purification of Antibody

When using recombinant techniques, the antibody can be produced intracellularly, or directly secreted into the medium. If the antibody is produced intracellularly, as a first step, the particulate debris, either host cells or lysed fragments, may be removed, for example, by centrifugation or ultrafiltration. Where the antibody is secreted into the medium, supernatants from such expression systems may be first concentrated using a commercially available protein concentration filter, for example, an Amicon or Millipore Pellicon ultrafiltration unit. A protease inhibitor such as PMSF may be included in any of the foregoing steps to inhibit proteolysis, and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a convenient technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Methods 62:1-13 (1983)). Protein G is recommended for all mouse isotypes and for human γ3 (Guss et al., EMBO J. 5:1567-1575 (1986)). The matrix to which the affinity ligand is attached may be agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to further purification, for example, by low pH hydrophobic interaction chromatography using an elution buffer at a pH between about 2.5-4.5, performed at low salt concentrations (e.g., from about 0-0.25M salt).

In general, various methodologies for preparing antibodies for use in research, testing, and clinical use are well-established in the art, consistent with the above-described methodologies and/or as deemed appropriate by one skilled in the art for a particular antibody of interest.

Production of Non-Fucosylated Antibodies

Provided herein are methods for preparing antibodies with a reduced degree of fucosylation. For example, methods contemplated herein include, but are not limited to, use of cell lines deficient in protein fucosylation (e.g., Lec13 CHO cells, alpha-1,6-fucosyltransferase gene knockout CHO cells, cells overexpressing β1,4-N-acetylglycosminyltransferase III and further overexpressing Golgi μ-mannosidase II, etc.), and addition of a fucose analog(s) in a cell culture medium used for the production of the antibodies. See Ripka et al, Arch. Biochem. Biophys. 249:533-545 (1986): US Pat Appl No US 2003/0157108 A1, Presta, L; WO 2004/056312 A1; Yamane-Ohnuki et al. Biotech. Bioeng. 87: 614 (2004); and U.S. Pat. No. 8,574,907, Additional techniques for reducing the fucose content of antibodies include Glymaxx technology described in U.S. Patent Application Publication No. 2012/0214975. Additional techniques for reducing the fucose content of antibodies also include the addition of one or more glycosidase inhibitors in a cell culture medium used for the production of the antibodies. Glycosidase inhibitors include α-glucosidase I, α-glucosidase II, and α-mannosidase I, In some embodiments, the glycosidase inhibitor is an inhibitor of α-mannosidase I (e.g., kifunensine).

As used herein, "core fucosylation" refers to addition of fucose ("fucosylation") to N-acetylglucosamine ("GlcNAc") at the reducing terminal of an N-linked glycan. Also provided are antibodies produced by such methods and compositions thereof.

In some embodiments, fucosylation of complex N-glycoside-linked sugar chains bound to the Fc region (or domain) is reduced. As used herein, a "complex N-glycoside-linked sugar chain" is typically bound to asparagine 297 (according to the number of Kabat), although a complex N-glycoside linked sugar chain can also be linked to other asparagine residues. A "complex N-glycoside-linked sugar chain" excludes a high mannose type of sugar chain, in which only mannose is incorporated at the non-reducing terminal of the core structure, but includes 1) a complex type, in which the non-reducing terminal side of the core structure has one or more branches of galactose-N-acetylglucosamine (also referred to as "gal-GlcNAc") and the non-reducing terminal side of Gal-GlcNAc optionally has a sialic acid, bisecting N-acetylglucosamine or the like; or 2) a hybrid type, in which the non-reducing terminal side of the core structure has both branches of the high mannose N-glycoside-linked sugar chain and complex N-glycoside-linked sugar chain.

In some embodiments, the "complex N-glycoside-linked sugar chain" includes a complex type in which the non-reducing terminal side of the core structure has zero, one or more branches of galactose-N-acetylglucosamine (also referred to as "gal-GlcNAc") and the non-reducing terminal side of Gal-GlcNAc optionally further has a structure such as a sialic acid, bisecting N-acetylglucosamine or the like.

According to the present methods, typically only a minor amount of fucose is incorporated into the complex N-glycoside-linked sugar chain(s). For example, in various embodiments, less than about 60%, less than about 50%, less than about 40%, less than about 30%, less than about 20%, less than about 15%, less than about 10%, less than about 5%, or less than about 1% of the antibody has core fucosylation by fucose in a composition. In some embodiments, substantially none (i.e., less than about 0.5%) of the antibody has core fucosylation by fucose in a composition. In some embodiments, more than about 40%, more than about 50%, more than about 60%, more than about 70%, more than about 80%, more than about 90%, more than about 91%, more than about 92%, more than about 93%, more than about 94%, more than about 95%, more than about 96%, more than about 97%, more than about 98%, or more than about 99% of the antibody is nonfucosylated in a composition.

In some embodiments, provided herein is an antibody wherein substantially none (i.e., less than about 0.5%) of the N-glycoside-linked carbohydrate chains contain a fucose residue. In some embodiments, provided herein is an antibody wherein at least one or two of the heavy chains of the antibody is non-fucosylated.

As described above, a variety of mammalian host-expression vector systems can be utilized to express an antibody.

In some embodiments, the culture media is not supplemented with fucose. In some embodiments, an effective amount of a fucose analog is added to the culture media. In this context, an "effective amount" refers to an amount of the analog that is sufficient to decrease fucose incorporation into a complex N-glycoside-linked sugar chain of an antibody by at least about 10%, at least about 20%, at least about 30%, at least about 40% or at least about 50%. In some embodiments, antibodies produced by the instant methods comprise at least about 10%, at least about 20%, at least about 30%, at least about 40% or at least about 50% non-core fucosylated protein (e.g., lacking core fucosylation), as compared with antibodies produced from the host cells cultured in the absence of a fucose analog.

The content (e.g., the ratio) of sugar chains in which fucose is not bound to N-acetylglucosamine in the reducing end of the sugar chain versus sugar chains in which fucose is bound to N-acetylglucosamine in the reducing end of the sugar chain can be determined, for example, as described in the Examples. Other methods include hydrazinolysis or enzyme digestion (see, e.g., *Biochemical Experimentation Methods* 23: Method for Studying Glycoprotein Sugar Chain (Japan Scientific Societies Press), edited by Reiko Takahashi (1989)), fluorescence labeling or radioisotope labeling of the released sugar chain and then separating the labeled sugar chain by chromatography. Also, the compositions of the released sugar chains can be determined by analyzing the chains by the HPAEC-PAD method (see, e.g., *J. Liq Chromatogr.* 6:1557 (1983)). (See generally U.S. Patent Application Publication No. 2004/0110282.).

IV. Compositions

In some aspects, also provided herein are compositions (e.g., pharmaceutical composition) comprising any of the anti-Siglec-8 antibodies described herein. In some aspects, provided herein is a composition comprising an anti-Siglec-8 antibody described herein, wherein the antibody comprises a Fc region and N-glycoside-linked carbohydrate chains linked to the Fc region, wherein less than about 50% of the N-glycoside-linked carbohydrate chains contain a fucose residue. In some aspects, provided herein is a composition comprising an anti-Siglec-8 antibody described herein, wherein the antibody comprises a Fc region and N-glycoside-linked carbohydrate chains linked to the Fc region, wherein substantially none of the N-glycoside-linked carbohydrate chains contain a fucose residue.

Therapeutic formulations are prepared for storage by mixing the active ingredient having the desired degree of purity with optional pharmaceutically acceptable carriers, excipients or stabilizers (*Remington: The Science and Practice of Pharmacy,* 20th Ed., Lippincott Williams & Wiklins, Pub., Gennaro Ed., Philadelphia, Pa. 2000). Acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers, stabilizers, metal complexes (e.g. Zn-protein complexes); chelating agents such as EDTA and/or non-ionic surfactants.

Buffers can be used to control the pH in a range which optimizes the therapeutic effectiveness, especially if stability is pH dependent. Buffers can be present at concentrations ranging from about 50 mM to about 250 mM. Suitable buffering agents for use with the present invention include both organic and inorganic acids and salts thereof. For example, citrate, phosphate, succinate, tartrate, fumarate, gluconate, oxalate, lactate, acetate. Additionally, buffers may be comprised of histidine and trimethylamine salts such as Tris.

Preservatives can be added to prevent microbial growth, and are typically present in a range from about 0.2%-1.0% (w/v). Suitable preservatives for use with the present invention include octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" can be present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter and intra-molecular interactions. Tonicity agents can be present in any amount between about 0.1% to about 25% by weight or between about 1 to about 5% by weight, taking into account the relative amounts of the other ingredients. In some embodiments, tonicity agents include polyhydric sugar alcohols, trihydric or higher sugar alcohols, such as glycerin, erythritol, arabitol, xylitol, sorbitol and mannitol.

Additional excipients include agents which can serve as one or more of the following: (1) bulking agents, (2) solubility enhancers, (3) stabilizers and (4) and agents preventing denaturation or adherence to the container wall. Such excipients include: polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, α-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") can be present to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants are present in a range of about 0.05 mg/ml to about 1.0 mg/ml or about 0.07 mg/ml to about 0.2 mg/ml. In some embodiments, non-ionic surfactants are present in a range of about 0.001% to about 0.1% w/v or about 0.01% to about 0.1% w/v or about 0.01% to about 0.025% w/v.

Suitable non-ionic surfactants include polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl celluose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

In order for the formulations to be used for in vivo administration, they must be sterile. The formulation may be rendered sterile by filtration through sterile filtration membranes. The therapeutic compositions herein generally are placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intraarterial, intralesional or intraarticular routes, topical administration, inhalation or by sustained release or extended-release means.

The formulation herein may also contain more than one active compound as necessary for the particular indication being treated, preferably those with complementary activities that do not adversely affect each other. Alternatively, or in addition, the composition may comprise a cytotoxic agent, cytokine or growth inhibitory agent. Such molecules are suitably present in combination in amounts that are effective for the purpose intended.

V. Methods of Treatment

Provided herein are methods for treating or preventing a disease mediated by cells expressing Siglec-8 in a subject comprising administering to the subject an effective amount of an anti-Siglec-8 antibody described herein (e.g., a humanized anti-Siglec-8 antibody) or compositions thereof. In some embodiments, the subject (e.g., a human patient) has been diagnosed with an eosinophil-mediated disorder or is at risk of developing the eosinophil-mediated disorder. In some embodiments, the subject (e.g., a human patient) has been diagnosed with a mast cell-mediated disorder or is at risk of developing the mast cell-mediated disorder. In some embodiments, the subject has an eosinophil-mediated disorder or a mast cell-mediated disorder.

Provided herein are methods of depletion or reduction of eosinophils comprising administering to a subject an effective amount of an anti-Siglec-8 antibody described herein (e.g., a humanized anti-Siglec-8 antibody). In some embodiments, the depletion or reduction of eosinophils is measured by comparing the eosinophil population number in a sample (e.g., a tissue sample) from a subject after treatment with the antibody to the eosinophil population number in a sample from a subject before treatment with the antibody. In some embodiments, the depletion or reduction of eosinophils is measured by comparing the eosinophil population number in a sample (e.g., a tissue sample) from a subject after treatment with the antibody to the eosinophil population number in a sample from another subject without the antibody treatment or average eosinophil population number in samples from subjects without the antibody treatment. In some embodiments, the sample is a tissue sample (e.g., a lung sample, a nasal polyposis sample, etc.). In some embodiments, depletion of reduction of eosinophils is due to apoptosis of activated eosinophils. Eosinophils can be activated or sensitized by cytokines or hormones such as, but not limited to, IL-5, GM-CSF, IL-33, IFN-γ, TNF-α, and leptin. In some embodiments, depletion of reduction of eosinophils is due to apoptosis of resting eosinophils. In some embodiments, depletion of reduction of eosinophils is due to antibody-dependent cell-mediated cytotoxicity (ADCC). In some embodiments, the eosinophil production of inflammatory mediators is prevented or reduced. Exemplary inflammatory mediators include, but are not limited to, reactive oxygen species, granule proteins (e.g., eosinophil cationic protein, major basic protein, eosinophil-derived neurotoxin, eosinophil peroxidase, etc.), lipid mediators (e.g., PAF, PGE1, PGE2, etc.), enzymes (e.g., elastase), growth factors (e.g., VEGF, PDGF, TGF-α, TGF-β, etc.), chemokines (e.g., RANTES, MCP-1, MCP-3, MCP4, eotaxin, etc.) and cytokines (e.g., IL-3, IL-5, IL-10, IL-13, IL-15, IL-33, TNF-α, etc.).

Provided herein are also methods of depletion or reduction of mast cells comprising administering to a subject an effective amount of an anti-Siglec-8 antibody described herein (e.g., a humanized anti-Siglec-8 antibody). In some embodiments, the depletion or reduction of mast cells is measured by comparing the mast cell population number in a sample (e.g., a tissue sample or a biological fluid sample) from a subject after treatment with the antibody to the mast cell population number in a sample from a subject before treatment with the antibody. In some embodiments, the depletion or reduction of mast cells is measured by comparing the mast cell population number in a sample (e.g., a tissue sample or a biological fluid sample) from a subject after treatment with the antibody to the mast cell population number in a sample from another subject without the antibody treatment or average mast cell population number in samples from subjects without the antibody treatment. In some embodiments, the sample is a tissue sample (e.g., a skin sample, a lung sample, a bone marrow sample, a nasal polyposis sample, etc.). In some embodiments, the sample is a biological fluid sample (e.g., a blood sample, a bronchoalveolar lavage sample, and a nasal lavage sample). In some embodiments, depletion of reduction of mast cells is due to antibody-dependent cell-mediated cytotoxicity (ADCC). In some embodiments, depletion or reduction of mast cells is the reduction or prevention of preformed or newly formed inflammatory mediators produced from mast cells. Exemplary inflammatory mediators include, but are not limited to, histamine, N-methyl histamine, enzymes (e.g., tryptase, chymase, cathespin G, carboxypeptidase, etc.), lipid mediators (e.g., prostaglandin D2, prostaglandin E2, leukotriene B4, leukotriene C4, platelet-activating factor, 11-beta-prostaglandin F2, etc.), chemokines (e.g., CCL2, CCL3, CCL4, CCL11 (i.e., eotaxin), CXCL1, CXCL2, CXCL3, CXCL10, etc.), and cytokines (e.g., IL-3, IL-4, IL-5, IL-15, IL-33, GM-CSF, TNF, etc.).

Provided herein are also methods of depleting mast cells expressing Siglec-8 in a subject comprising administering to the subject an effective amount of an anti-Siglec-8 antibody described herein (e.g., a humanized anti-Siglec-8 antibody), wherein the anti-Siglec-8 antibody kills mast cells expressing Siglec-8 by ADCC activity. In some embodiments, the anti-Siglec-8 antibody depletes at least about 20%, about 30%, about 40%, about 50%, about 60%, about 70%, about 80%, about 90% or about 100% of the mast cells expressing Siglec-8 in a sample obtained from the subject as compared to a baseline level before treatment. In some embodiments, the anti-Siglec-8 antibody depletes at least about 20% of the mast cells expressing Siglec-8 in a sample obtained from the subject as compared to a baseline level before treatment. In some embodiments, the depletion or killing of mast cells is measured by comparing the mast cell population number in a sample (e.g., a tissue sample or a biological fluid sample) from a subject after treatment with the antibody to the mast cell population number in a sample from a subject before treatment with the antibody. In some embodiments, the depletion or killing of mast cells is measured by comparing the mast cell population number in a sample (e.g., a tissue sample or a biological fluid sample) from a subject after treatment with the antibody to the mast cell population number in a sample from another subject without the antibody treatment or average mast cell population number in samples from subjects without the antibody treatment. In some embodiments, the sample is a tissue sample (e.g., a skin sample, a lung sample, a bone marrow sample, a nasal polyposis sample, etc.). In some embodiments, the sample is a biological fluid sample (e.g., a blood sample, a bronchoalveolar lavage sample, and a nasal lavage sample). In some embodiments, the anti-Siglec-8 antibody has been engineered to improve ADCC activity. In some embodiments, the anti-Siglec-8 antibody comprises at least one amino acid substitution in the Fc region that improves ADCC activity. In some embodiments, at least one or two of the heavy chains of the antibody is non-fucosylated. In some embodiments, depletion or killing of mast cells is the reduction or prevention of preformed or newly formed inflammatory mediators produced from mast cells. Exemplary inflammatory mediators include, but are not limited to, histamine, N-methyl histamine, enzymes (e.g., tryptase, chymase, cathespin G, carboxypeptidase, etc.), lipid mediators (e.g., prostaglandin D2, prostaglandin E2, leukotriene B4, leukotriene C4, platelet-activating factor, 11-beta-prostaglandin F2, etc.), chemokines (e.g., CCL2, CCL3, CCL4, CCL11 (i.e., eotaxin), CXCL1, CXCL2, CXCL3, CXCL10, etc.), and cytokines (e.g., IL-3, IL-4, IL-5, IL-13, IL-15, IL-33, GM-CSF, TNF, etc.).

Also provided herein are methods of inhibiting mast cell-mediated activity comprising administering to a subject an effective amount of an anti-Siglec-8 antibody described herein (e.g., a humanized anti-Siglec-8 antibody). In some embodiments, the inhibition of mast cell-mediated activity is measured by comparing the mast cell-mediated activity in a sample (e.g., a tissue sample or a blood sample) from a subject after treatment with the antibody to the mast cell-mediated activity in a sample from a subject before treatment with the antibody. In some embodiments, the inhibition of mast cell-mediated activity is measured by comparing the mast cell-mediated activity in a sample (e.g., a tissue sample or a biological sample) from a subject after treatment with the antibody to the mast cell-mediated activity in a sample from another subject without the antibody treatment or average mast cell-mediated activity in samples from subjects without the antibody treatment. In some embodiments, the sample is a tissue sample (e.g., a skin sample, a lung sample, a bone marrow sample, a nasal polyposis sample, etc.). In some embodiments, the sample is a biological fluid sample (e.g., a blood sample, a bronchoalveolar lavage sample, and a nasal lavage sample). In some embodiments, inhibition of mast cell-mediated activity is the inhibition of mast cell degranulation. In some embodiments, inhibition of mast cell-mediated activity is the inhibition of airway smooth muscle contraction. In some embodiments, inhibition of mast cell-mediated activity is the inhibition of calcium flux in mast cells. In some embodiments, inhibition of mast cell-mediated activity is the inhibition of release of preformed or newly formed inflammatory mediators from mast cells. Exemplary inflammatory mediators include, but are not limited to, histamine, N-methyl histamine, enzymes (e.g., tryptase, chymase, cathespin G, carboxypeptidase, etc.), lipid mediators (e.g., prostaglandin D2, prostaglandin E2, leukotriene B4, leukotriene C4, platelet-activating factor, 11-beta-prostaglandin F2, etc.), chemokines (e.g., CCL2, CCL3, CCL4, CCL11 (i.e., eotaxin), CXCL1, CXCL2, CXCL3, CXCL10, etc.), and cytokines (e.g., IL-3, IL-4, IL-5, IL-13, IL-15, IL-33, GM-CSF, TNF, etc.).

For the prevention or treatment of disease, the appropriate dosage of an active agent, will depend on the type of disease to be treated, as defined above, the severity and course of the disease, whether the agent is administered for preventive or therapeutic purposes, previous therapy, the subject's clinical history and response to the agent, and the discretion of the attending physician. The agent is suitably administered to the subject at one time or over a series of treatments. In some embodiments of the methods described herein, an interval between administrations of an anti-Siglec-8 antibody described is about one month or longer. In some embodiments, the interval between administrations is about two months, about three months, about four months, about five months, about six months or longer. As used herein, an interval between administrations refers to the time period between one administration of the antibody and the next administration of the antibody. As used herein, an interval of about one month includes four weeks. Accordingly, in some embodiments, the interval between administrations is about four weeks, about eight weeks, about twelve weeks, about sixteen weeks, about twenty weeks, about twenty four weeks, or longer. In some embodiments, the treatment includes multiple administrations of the antibody, wherein the interval between administrations may vary. For example, the interval between the first administration and the second administration is about one month, and the intervals between the subsequent administrations are about three months. In some embodiments, the interval between the first administration and the second administration is about one month, the interval between the second administration and the third administration is about two months, and the intervals between the subsequent administrations are about three months. In some embodiments, an anti-Siglec-8 antibody described herein is administered at a flat dose, in some embodiments, an anti-Siglec-8 antibody described herein is administered to a subject at a dosage from about 150 to about 450 mg per dose. In some embodiments, the anti-Siglec-8 antibody is administered to a subject at a dosage of about any of 150 mg, 200 mg, 250 mg, 300 mg, 350 mg, 400 mg, and 450 mg per dose. In some embodiments, an anti-Siglec-8 antibody described herein is administered to a subject at a dosage from about 0.1 mg/kg to about 10 mg/kg or about 1.0 mg/kg to about 10 mg/kg. In some embodiments, an anti-Siglec-8 antibody described herein is administered to a subject at a dosage of about any of 0.1 mg/kg, 0.5 mg/kg, 1.0 mg/kg, 1.5 mg/kg, 2.0 mg/kg, 2.5 mg/kg, 3.0 mg/kg, 3.5 mg/kg, 4.0 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, or 10.0 mg/kg. Any of the dosing frequency described above may be used.

A method of treatment contemplated herein is the treatment of eosinophil-mediated disorders and/or mast cell-mediated disorders with an anti-Siglec-8 antibody described herein. Eosinophil-mediated disorders include a disorder or disease associated with eosinophil migration, chemotaxis, generation, or granulation. Similarly, mast cell-mediated disorders include a disorder or disease associated with mast cell migration, chemotaxis, generation, or granulation. Eosinophil-mediated disorders and/or mast cell-mediated disorders that are treatable with the formulations of this present invention include asthma, allergic rhinitis, nasal polyposis, atopic dermatitis, chronic urticaria (e.g., chronic idiopathic urticaria and chronic spontaneous urticaria), mastocytosis, eosinophilic leukemia, and hypereosinophilic syndrome. Eosinophil-mediated disorders and/or mast cell-mediated disorders that are treatable with the formulations of this present invention also include pauci granulocytic asthma, acute or chronic airway hypersensitivity, eosinophilic esophagitis, Churg-Strauss syndrome, inflammation associated with a cytokine, inflammation associated with cells expressing Siglec-8, malignancy associated with cells expressing Siglec-8, physical urticaria, cold urticaria, pressure-urticaria, bullous pemphigoid, food allergy, and allergic bronchopulmonary aspergillosis (ABPA).

In some embodiments of the methods herein, an anti-Siglec-8 antibody provided herein inhibits one or more symptoms of an allergic reaction. In some embodiments, the allergic reaction is a Type I hypersensitivity reaction.

Allergic rhinitis, also known as allergic rhinoconjunctivitis or hay fever, is the most common manifestation of an atopic reaction to inhaled allergens, the severity and duration of which is often correlative with the intensity and length of exposure to the allergen. It is a chronic disease, which may first appear at any age, but the onset is usually during childhood or adolescence. A typical attack consists of profuse watery rhinorrhea, paroxysmal sneezing, nasal obstruction and itching of the nose and palate. Postnasal mucus drainage also causes sore throat, throat clearing and cough. There can also be symptoms of allergic blepharoconjunctivitis, with intense itching of the conjunctivae and eyelids, redness, tearing, and photophobia. Severe attacks are often accompanied by systemic malaise, weakness, fatigue, and sometimes, muscle soreness after intense periods of sneezing.

Asthma, also known as reversible obstructive airway disease, is characterized by hyperresponsiveness of the tracheobronchial tree to respiratory irritants and bronchoconstrictor chemicals, producing attacks of wheezing, dyspnea, chest tightness, and cough that are reversible spontaneously or with treatment. It is a chronic disease involving the entire airway, but varies in severity from occasional mild transient episodes to severe, chronic, life-threatening bronchial obstruction. Physical signs of an asthma attack include tachypnea, audible wheezing, and use of the accessory muscles of respiration. Rapid pulse and elevated blood pressure are also typically present, as are elevated levels of eosinophils in the peripheral blood and nasal secretions. Asthma and atopy may coexist, but only about half of asthmatics are also atopic, and an even smaller percentage of atopic patients also have asthma. However, atopy and asthma are not entirely independent in that asthma occurs more frequently among atopic than amongst nonatopic individuals, especially during childhood. Asthma has further been historically broken down into two subgroups, extrinsic asthma and intrinsic asthma. In addition, asthma involves chronic inflammation of the airways, acute exacerbations varying in frequency between different patients and in response to environmental triggers. In severe cases, chronic remodeling of the airways may occur.

Extrinsic asthma, also known as allergic, atopic or immunologic asthma, is descriptive of patients that generally develop asthma early in life, usually during infancy or childhood. Other manifestations of atopy, including eczema or allergic rhinitis often coexist. Asthmatic attacks can occur during pollen seasons, in the presence of animals, or on exposure to house dust, feather pillows, or other allergens. Skin tests show positive wheal-and-flare reactions to the causative allergens. Interestingly, serum total IgE concentrations are frequently elevated, but are sometimes normal. Intrinsic asthma, also known as nonallergic or idopathic asthma, typically first occurs during adult life, after an apparent respiratory infection. Symptoms include chronic or recurrent bronchial obstruction unrelated to pollen seasons or exposure to other allergens. Skin tests are negative to the usual atopic allergens, serum IgE concentration is normal. Additional symptoms include sputum blood and eosinophilia. For purposes of this patent application, "eosinophil-mediated disorders" includes both allergic and non-allergic asthma. In some embodiments, a subject with an eosinophil-mediated disorder(s) and/or mast cell-mediated disorder(s) is suffering from asthma that is not adequately controlled by an inhaled corticosteroid, a short acting β2 agonist, a long acting β2 agonist, or a combination thereof.

Atopic dermatitis, also known as eczema, neurodermatitis, atopic eczema or Besnier's prurigo, is common chronic skin disorder specific to a subset of patients with the familial and immunologic features of atopy. The essential feature is a pruritic dermal inflammatory response, which induces a characteristic symmetrically distributed skin eruption with predilection for certain sites. While atopic dermatitis is classified as a cutaneous form of atopy because it is associated with allergic rhinitis and asthma and high IgE levels, the severity of the dermatitis, however, does not always correlate with exposure to allergens on skin testing, and desensitization (unlike other allergic diseases) is not effective treatment. While high serum IgE is confirmatory of a diagnosis of allergic asthma, normal levels do not preclude it. Onset of the disease can occur at any age, and lesions begin acutely with erythematous edematous papule or plaque with scaling. Itching leads to weeping and crusting, then to chronic lichenification. On the cellular level, acute lesion is edemous and the dermis is infiltrated with mononuclear cells, CD4 lymphocytes. Neutrophils, eosinophils, plasma cells and basophils are rare, but degranulated mast cells are present. Chronic lesions feature epidermal hyperplasia, hyperkeratosis and parakeratosis, and the dermis is infiltrated with mononuclear cells, Langerhans' cells and mast cells. There may also be focal areas of fibrosis, including involvement of the perineurium of small nerves.

Urticaria and angioedema refers to the physical swelling, erythema and itching resulting from histamine stimulated receptor in superficial cutaneous blood vessels, and is the hallmark cutaneous feature of systemic anaphylaxis. Systemic anaphylaxis is the occurrence of an IgE-mediated reaction simultaneously in multiple organs resulting from drug, insect venom or food. It is caused suddenly by allergen induced, mast cell loaded IgE, resulting in profound and life-threatening alteration in the functioning of various vital organs. Vascular collapse, acute airway obstruction, cutaneous vasodilation and edema, and gastrointestinal and genitourinary muscle spasm occur almost simultaneously, although not always to the same degree. The pathology of anaphylaxis includes angioedema and hyperinflated lungs, with mucous plugging of airways and focal atelectasis. On a cellular level, the lungs appear similarly as during an acute asthma attack, with hypersecretion of bronchial submucosal glands, mucosal and submucosal edema, peribronchial vascular congestion and eosinophilia in the bronchial walls. Pulmonary edema and hemorrhage may be present. Bronchial muscle spasm, hyperinflation, and even rupture of alveoli may also be present. Important features of human anaphylaxis include edema, vascular congestion, and eosinophilia in the lamina propria of the larynx, trachea, epiglottis and hypopharynx. Exposure to the allergen may be through ingestion, injection, inhalation or contact with skin or mucous membrane. The reaction begins within seconds or minutes after exposure to the allergen. There may be an initial fright or sense of impending doom, followed rapidly by symptoms in one or more target organ systems: cardiovascular, respiratory, cutaneous or gastrointestinal. The allergens responsible for anaphylaxis differ from those commonly associated with atopy. Foods, drugs, insect venoms or latex are the common sources. Food allergens includes those found in crustaceans, mollusks (e.g., lobster, shrimp, crab), fish, legumes (e.g., peanuts, peas, beans, licorice), seeds (e.g. sesame, cottonseed, caraway, mustard, flaxseed, sunflower), nuts, berries, egg whites, buckwheat and milk. Drug allergens include those found in heterologous proteins and polypeptides, polysaccharides and haptenic drugs. Insect allergens include Hymenoptera insects, including the honeybee, yellow jacket, hornet, wasp and fire ant. While epinephrine is the typical treatment for anaphylaxis, antihistamine or other histamine blockers are typically prescribed for less severe urticaria or angioedemic reaction.

Nasal polyposis is a chronic inflammatory disease of the upper respiratory tract characterized by an outgrowth of inflamed tissue into the nasal cavity, and although the exact etiology is unknown, it is known to have prevalence between 1 to 5% of adults (Settipane G A: Epidemiology of nasal polyps. *Allergy Asthma Proc*, 1996, 17:231-236). Nasal polyposis typically presents in males 20 years of age or older and causes nasal obstruction, hyposmia, and recurrent infections with a significantly higher impact to quality of life than perennial allergic rhinitis (Li et al., Characterizing T-Cell Phenotypes in Nasal Polyposis in Chinese Patients, *J Investig Allergol Clin Immunol,* 2009; Vol. 19(4):276-282). Up to one third of all patients with nasal polyposis are reported to have asthma however only 7% of asthma patients have nasal polyposis. Predominate cell types implicated in nasal polyposis include eosinophils and mast cells.

VI. Articles of Manufacture or Kits

In another aspect, an article of manufacture or kit is provided which comprises an anti-Siglec-8 antibody described herein. The article of manufacture or kit may further comprise instructions for use of the antibody in the methods of the invention. Thus, in certain embodiments, the article of manufacture or kit comprises instructions for the use of an anti-Siglec-8 antibody in methods for treating or preventing an eosinophil-mediated disorder and/or mast cell-mediated disorder in an individual comprising administering to the individual an effective amount of an anti-Siglec-8 antibody. In certain embodiments, the individual is a human. In some embodiments, the individual has a disease selected from the group consisting of asthma, allergic rhinitis, nasal polyposis, atopic dermatitis, chronic urticaria, mastocytosis, eosinophilic leukemia, and hypereosinophilic syndrome. In certain embodiments, the individual has a disease selected from the group consisting of pauci granulocytic asthma, acute or chronic airway hypersensitivity, eosinophilic esophagitis, Churg-Strauss syndrome, inflammation associated with a cytokine, inflammation associated with cells expressing Siglec-8, malignancy associated with cells expressing Siglec-8, physical urticaria, cold urticaria, pressure-urticaria, bullous pemphigoid, food allergy, and allergic bronchopulmonary aspergillosis (ABPA).

The article of manufacture or kit may further comprise a container. Suitable containers include, for example, bottles, vials (e.g., dual chamber vials), syringes (such as single or dual chamber syringes) and test tubes. The container may be formed from a variety of materials such as glass or plastic. The container holds the formulation.

The article of manufacture or kit may further comprise a label or a package insert, which is on or associated with the container, may indicate directions for reconstitution and/or use of the formulation. The label or package insert may further indicate that the formulation is useful or intended for subcutaneous, intravenous, or other modes of administration for treating or preventing an eosinophil-mediated disorder and/or mast cell-mediated disorder in an individual. The container holding the formulation may be a single-use vial or a multi-use vial, which allows for repeat administrations of the reconstituted formulation. The article of manufacture or kit may further comprise a second container comprising a suitable diluent. The article of manufacture or kit may further include other materials desirable from a commercial, therapeutic, and user standpoint, including other buffers, diluents, filters, needles, syringes, and package inserts with instructions for use.

In a specific embodiment, the present invention provides kits for a single dose-administration unit. Such kits comprise a container of an aqueous formulation of therapeutic antibody, including both single or multi-chambered pre-filled syringes. Exemplary pre-filled syringes are available from Vetter GmbH, Ravensburg, Germany.

The article of manufacture or kit herein optionally further comprises a container comprising a second medicament, wherein the anti-Siglec-8 antibody is a first medicament, and which article or kit further comprises instructions on the label or package insert for treating the subject with the second medicament, in an effective amount. An exemplary second medicament may be an anti-IgE antibody, an antihistamine, a bronchodilator, a glucocorticoid, an NSAID, a decongestant, a cough suppressant, an analgesic, a TNF-antagonist, an integrin antagonist, an immunosuppressive agent, an IL-4 antagonist, an IL-13 antagonist, a dual IL-4/IL-13 antagonist, a DMARD, an antibody that binds to a B-cell surface marker, and/or a BAFF antagonist.

In another embodiment, provided herein is an article of manufacture or kit comprising the formulations described herein for administration in an auto-injector device. An auto-injector can be described as an injection device that upon activation, will deliver its contents without additional necessary action from the patient or administrator. They are particularly suited for self-medication of therapeutic formulations when the delivery rate must be constant and the time of delivery is greater than a few moments.

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Siglecs (sialic acid-binding, immunoglobulin-like lectins) are single-pass transmembrane cell surface proteins found predominantly on leukocytes. Siglec-8, a member of the Siglec family, was first discovered as part of efforts to identify novel human eosinophil proteins. In addition to expression with human eosinophils, it is also expressed by mast cells. Siglec-8 recognizes a sulfated glycan, 6'-sulfo-sialyl Lewis X, and contains an intracellular immunoreceptor tyrosine-based inhibitory motif (ITIM) domain shown to inhibit mast cell function. Murine antibodies to Siglec-8, 2E2 and 2C4 antibody are described in U.S. Pat. No. 8,207,305; U.S. Pat. No. 8,197,811, U.S. Pat. No. 7,871,612, and U.S. Pat. No. 7,557,191. The amino acid sequence of the heavy chain variable domain and light chain variable domain of the mouse anti-Siglec-8 2C4 antibody can be found, for example, in U.S. Pat. No. 8,207,305 as SEQ ID NO:2 and SEQ ID NO:4, respectively.

Example 1

Generation and Characterization of Chimeric Anti-Siglec-8 Antibodies

Chimeric antibodies were generated from the mouse 2E2 antibody and mouse 2C4 antibody, and were subsequently analyzed for binding activity to human Siglec-8.

Methods and Results

Generation of Chimeric 2E2 Antibody (ch2E2) and Chimeric 2C4 Antibody (ch2C4)

For generation of a chimeric 2E2 antibody (ch2E2), snap-frozen mouse hybridoma 2E2 cell lysates were processed using the RNeasy Mini kit (Qiagen) to isolate total RNA according to the manufacturer's protocol. A 3 µg sample of isolated RNA was reverse-transcribed to produce 2E2 cDNA using the 1st strand cDNA synthesis kit (GE Life Sciences) according to the manufacturer's protocol. 2E2 cDNA was subsequently amplified by PCR using Phusion Flash High-Fidelity PCR Master Mix (Thermo Scientific) and the sequences in the PCR reactions were confirmed. The immunoglobulin heavy chain variable region (VH) cDNA and kappa light chain variable region (VL) were PCR-amplified using the Phusion High-Fidelity PCR Master Mix. The result of each PCR reaction was a single amplification product that was purified using the QIAquick PCR Purification kit (Qiagen) according to the manufacturer's protocol and the sequence for each immunoglobulin chain was obtained. The consensus sequence of the kappa light chain variable region was designated 2E2 VK and the consensus sequence of the heavy light chain variable region was designated 2E2 VH. The 2E2 VK protein sequence was identical to that of the mouse 2C4 IgG1 antibody (see Kikly et al., *J. Allergy Clin Immunol.*, 2000; 105:1093-1100) except for the first residue, where Gln was replaced by a Glu while the 2E2 VH protein sequence was completely identical to that of 2C4.

Construction of chimeric expression vectors entailed cloning the amplified variable regions into IgG/kappa constant region vectors using ligase-independent cloning. Briefly, the pCMV vectors were digested with BfuA1 (BsPM1), the digested vector was purified by gel electrophoresis, and compatible overhangs in the vector were generated by incubation with T4 DNA polymerase and 100 mM dATP. For the insert, antibody sequences were amplified by PCR from 2E2 cDNA with primers containing the 3' end of the leader sequence, i.e., forward primer, or the beginning of the constant region (IgG1 or kappa), i.e., reverse primer, followed by the beginning of the variable region (in each direction). The amplified inserts was purified using a PCR purification kit (Qiagen) and complementary overhangs were generated in the insert by incubation with T4 DNA polymerase and 100 mM dTTP. Vector and inserts were incubated at room temperature and used to transform chemically-competent TOP10 bacteria (Invitrogen) that were subsequently plated on culture plates containing kanamycin. Several clones were isolated and colonies were screened by PCR. Clones containing the correct sized PCR products were selected, DNA was isolated using a miniprep kit (Qiagen) and the DNA was sequenced.

For generation of a chimeric 2C4 antibody (ch2C4), the 2C4 heavy chain variable region (VH) and kappa light chain variable region (VK) were synthesized (GeneScript) and the same method used to clone the chimeric 2E2 antibody was applied. Expi293 suspension cells (Human Embryonic Kidney cells) growing in Expi293 transfection medium (Invitrogen) and antibiotics were co-transfected with constructs encoding ch2E2 heavy chain and ch2E2 kappa light chain or constructs encoding ch2C4 heavy chain and ch2C4 kappa light chain (1 µg DNA each) using ExpiFectamine 293 Reagent provided with the Expi293 Expression System kit (Invitrogen) according to the manufacturer's protocol. The cells were grown in 2 ml growth medium in six well plates for 7 days before media was harvested and assayed for recombinant protein expression by ELISA.

Siglec-8 Binding Activity of Chimeric Antibody

Binding of recombinant human Siglec-8 extracellular domain (ECD) by chimeric 2E2 and chimeric 2C4 IgG1K antibodies was measured by ELISA. For the Siglec-8 binding assay, a 384-well SpectraPlate (Perkin Elmer) was prepared by coating with 30 µL per well of 0.4 µg/mL Siglec-8 ECD overnight at 4° C. followed by removal of the coating solution by washing wells in wash buffer (0.1% Tween 20), and blocking with 90 µL 5% BSA/TBS solution for 2 hours at room temperature. Three-fold serial dilutions of a chimeric antibody (ch2E2 or ch2C4) or mouse antibody (m2E2 or m2C4) in 0.2% BSA/TBS (starting concentration was 5000 ng/mL) was added to each coated well. The plate was incubated for 2 hours at room temperature and the wells were subsequently washed before addition of goat-anti-human Fc peroxidase conjugate (1:10000 dilution) or anti-mouse Fc peroxidase conjugate (1:30000 dilution) diluted in 0.2% BSA/TBS solution. The plate was incubated for 45 minutes at room temperature, followed by washing and addition of 30 µL K-blue HRP substrate (SkyBio Ltd) to each well. After incubation at room temperature for 15 minutes, the reaction was stopped by adding 10 µL of Red Stop solution (SkyBio Ltd) to each well. The optical density or the experimental samples was read at 650 nm using the ELISA reader PHERAStar FS (BMG Labtech).

Both chimeric antibodies bound full Siglec-8 ECD with comparable $EC_{50}$ values. Chimeric antibody ch2E2 bound to Siglec-8 ECD with a lower $EC_{50}$ value as compared to mouse antibody m2E2 (Table 2).

TABLE 2

| | Antibody binding to human Siglec-8 ECD. | | | |
|---|---|---|---|---|
| | m2E2 | ch2E2 purified | ch2E2 | ch2C4 |
| EC50 | 0.1003 | 0.05701 | 0.04759 | 0.07411 |

Example 2

Generation and Characterization of Humanized Anti-Siglec-8 Antibodies

The sequence of the chimeric antibody 2E2 and chimeric antibody 2C4 was used to design humanized versions of the mouse 2E2 antibodies.

Methods and Results

Design of Humanized Anti-Siglec-8 Antibodies

The protein sequences of human and mouse immunoglobulins from the International Immunogenetics Database 2009 (Lefranc, M P., *Nucleic Acid Res.*, 2003, 31(1):307-10) and the Kabat Database Release 5 of Sequences of Proteins of Immunological Interest (last update 17 Nov. 1999) (Kabat et al., NIH National Technical Information Service, 1991, 1-3242) were used to compile a database of human immunoglobulin sequences in Kabat alignment. The compiled database contained 10,906 VH and 2,912 VK sequences.

A homology model of mouse antibody 2C4 variable regions had been calculated using the Modeller program (Eswar et al., *Curr. Protoc. Bioinformatics,* 2006, Ch. 5:Unit 5.6) included in the Discovery Studio package (Accelrys, Inc.). The atomic coordinates of 1a7O.pdb, 1dqd.pdb and 1ORS.pdb were the highest framework identity sequence templates for the VH, VL and backbone/interface, respectively, as determined by Basic Local Alignment Search Tool (BLAST) analysis of the antibody pdb structures database (Accelrys, Inc.). These templates were used to generate 30 initial models of the framework and the lowest energy model was used to generate 20 loop models (with all CDR loops included), with its 5 best loop templates, using the Kabat definition to eventually generate a final mouse 2C4 model.

Humanization required the identification of suitable human V regions. The Gibbs sequence analysis program (MRCT) was used to interrogate the human VH and VK databases with 2C4 VH and VK protein sequences using various selection criteria. Using the Discovery Studio program (Accelrys), framework (FW) residues within 4 Å of the CDR residues (Kabat definition) in the final homology model of mouse antibody 2C4 were identified, and designated as the "4 Å CDR envelope". There were no human VH sequences sharing CDR 1, 2 and 3 length identity with 2C4 that possessed a high 4 Å CDR envelope and/or VCI identity to 2C4 VH. AF471521 was the next best candidate with a CDR3 size of 14 residues with the highest identity score of key framework residues (19/24 4 Å envelope and 18/22 VCI), while the other sequences had additional differences, which rendered them at lower priority. However, AF471521 had 11 somatic mutations from its germline VH gene X92218. In order to mitigate the somatic mutations, any framework residue that differed from germline and/or was not conserved in the mouse was back mutated to human germline sequence. Therefore six framework residues were back mutated to germline and the remaining five residues that differed from germline were key framework residues and were identical to the mouse sequence.

Since a suitable acceptor human framework had been identified using a homology model of the 2C4 antibody, the synthetic protein and DNA sequence were designed by grafting the CDRs of the 2E2 antibody onto the acceptor human framework. The initial design of 2E2RHA was the grafting of CDR 1, 2 and 3 from 2E2 VH into the acceptor FW of AF471521. Intercalation of the 2E2 VH CDRs (gray shade) into the FW sequence of AF471521 resulted in the design of 2E2RHA, the initial humanized variant (FIG. 1). Five 4 Å CDR envelope/VCI residues, at Kabat positions 24, 48, 49, 67 and 68 were not conserved in 2E2RHA, and these were back-mutated to the mouse equivalent residue, in the humanized version 2E2RHB or mutated one at a time in the following variants: sequences were assembled in silico and designated 2E2RHA through 2E2RHG (FIG. 1).

In order to humanize the light chain, a human kappa chain was identified in a similar process to that of the heavy chain. AY867246 was the sequence with the highest identity to 2E2 VK in the 4 Å CDR envelope/VCI but had six somatic mutations. AY867246 was discarded in favor of X93721, which contained 21/25 4 Å envelope and 15/17 VCI and only one somatic mutation from the nearest germline VK gene, X01668. The framework from X93721 was used to design the DNA and protein for the humanized constructs. CDR 1, 2 and 3 from 2E2 VK (gray shade) were grafted into the acceptor FW of X93721 to generate 2E2RKA (FIG. 2). There were four unmatched 4 Å CDR envelope residues, 3, 47, 58 and 71 in 2E2RKA that were back-mutated to the equivalent mouse residues in variant 2E2RKB or individually in the following variants: sequences were assembled in silico and designated 2E2RKA through 2E2RKG (FIG. 2).

Generation of Humanized Anti-Siglec-8 Antibodies

The genes for 2E2RHA and 2E2RKA were synthesized (GenScript) and codon optimized for human sequences. The natural human framework sequences AF471521 and X93721, heavy and light chains, respectively, and the natural mouse CDR sequences were assembled in silico and designated 2E2RHA through 2E2RHG and 2E2RKA through 2E2RKG. Using software algorithms (GenScript), the sequences were optimized by silent mutagenesis to use codons preferentially utilized by human cells and synthesized. RHA/B and RKA/B constructs were PCR amplified with specific primers to the expression vector and insert, as described above in Example 1 for PCR amplification of the chimeric antibodies, and inserted into IgG/kappa constant region vectors by ligase-independent cloning reactions and used to transform TOP10 bacteria as described in Example 1 for generation of chimeric antibodies. RKA and RHA were subsequently modified by PCR mutagenesis using the QuickChange Lightning Site-Directed Mutagenesis kit (Stratagene) according to the manufacture's protocol to obtain all the human antibody variants (FIG. 1, FIG. 2, Table 3, Table 4, and Table 5).

TABLE 3

Amino acid sequences of variable regions of chimeric and humanized antibody variants

| Antibody Name | Variable Heavy Chain | Variable Light Chain |
|---|---|---|
| ch2C4 | ch2C4 VH | ch2C4 VK |
| ch2E2 | ch2E2 VH (SEQ ID NO: 1) | ch2E2 VK (SEQ ID NO: 15) |
| cVHKA | ch2E2 VH (SEQ ID NO: 1) | 2E2 RKA (SEQ ID NO: 16) |
| cVHKB | ch2E2 VH (SEQ ID NO: 1) | 2E2 RKB (SEQ ID NO: 17) |
| HAcVK | 2E2 RHA (SEQ ID NO: 2) | ch2E2 VK (SEQ ID NO: 15) |
| HBcVK | 2E2 RHB (SEQ ID NO: 3) | ch2E2 VK (SEQ ID NO: 15) |
| HAKA | 2E2 RHA (SEQ ID NO: 2) | 2E2 RKA (SEQ ID NO: 16) |
| HAKB | 2E2 RHA (SEQ ID NO: 2) | 2E2 RKB (SEQ ID NO: 17) |
| HAKC | 2E2 RHA (SEQ ID NO: 2) | 2E2 RKC (SEQ ID NO: 18) |
| HAKD | 2E2 RHA (SEQ ID NO: 2) | 2E2 RKD (SEQ ID NO: 19) |
| HAKE | 2E2 RHA (SEQ ID NO: 2) | 2E2 RKE (SEQ ID NO: 20) |
| HAKF | 2E2 RHA (SEQ ID NO: 2) | 2E2 RKF (SEQ ID NO: 21) |
| HAKG | 2E2 RHA (SEQ ID NO: 2) | 2E2 RKG (SEQ ID NO: 22) |
| HBKA | 2E2 RHB (SEQ ID NO: 3) | 2E2 RKA (SEQ ID NO: 16) |
| HBKB | 2E2 RHB (SEQ ID NO: 3) | 2E2 RKB (SEQ ID NO: 17) |
| HBKC | 2E2 RHB (SEQ ID NO: 3) | 2E2 RKC (SEQ ID NO: 18) |

TABLE 3-continued

Amino acid sequences of variable regions of chimeric and humanized antibody variants

| Antibody Name | Variable Heavy Chain | Variable Light Chain |
| --- | --- | --- |
| HBKD | 2E2 RHB (SEQ ID NO: 3) | 2E2 RKD (SEQ ID NO: 19) |
| HBKE | 2E2 RHB (SEQ ID NO: 3) | 2E2 RKE (SEQ ID NO: 20) |
| HBKF | 2E2 RHB (SEQ ID NO: 3) | 2E2 RKF (SEQ ID NO: 21) |
| HBKG | 2E2 RHB (SEQ ID NO: 3) | 2E2 RKG (SEQ ID NO: 22) |
| HCKA | 2E2 RHC (SEQ ID NO: 4) | 2E2 RKA (SEQ ID NO: 16) |
| HCKB | 2E2 RHC (SEQ ID NO: 4) | 2E2 RKB (SEQ ID NO: 17) |
| HCKC | 2E2 RHC (SEQ ID NO: 4) | 2E2 RKC (SEQ ID NO: 18) |
| HCKD | 2E2 RHC (SEQ ID NO: 4) | 2E2 RKD (SEQ ID NO: 19) |
| HCKE | 2E2 RHC (SEQ ID NO: 4) | 2E2 RKE (SEQ ID NO: 20) |
| HCKF | 2E2 RHC (SEQ ID NO: 4) | 2E2 RKF (SEQ ID NO: 21) |
| HCKG | 2E2 RHC (SEQ ID NO: 4) | 2E2 RKG (SEQ ID NO: 22) |
| HDKA | 2E2 RHD (SEQ ID NO: 5) | 2E2 RKA (SEQ ID NO: 16) |
| HDKB | 2E2 RHD (SEQ ID NO: 5) | 2E2 RKB (SEQ ID NO: 17) |
| HDKC | 2E2 RHD (SEQ ID NO: 5) | 2E2 RKC (SEQ ID NO: 18) |
| HDKD | 2E2 RHD (SEQ ID NO: 5) | 2E2 RKD (SEQ ID NO: 19) |
| HDKE | 2E2 RHD (SEQ ID NO: 5) | 2E2 RKE (SEQ ID NO: 20) |
| HDKF | 2E2 RHD (SEQ ID NO: 5) | 2E2 RKF (SEQ ID NO: 21) |
| HDKG | 2E2 RHD (SEQ ID NO: 5) | 2E2 RKG (SEQ ID NO: 22) |
| HEKA | 2E2 RHE (SEQ ID NO: 6) | 2E2 RKA (SEQ ID NO: 16) |
| HEKB | 2E2 RHE (SEQ ID NO: 6) | 2E2 RKB (SEQ ID NO: 17) |
| HEKC | 2E2 RHE (SEQ ID NO: 6) | 2E2 RKC (SEQ ID NO: 18) |
| HEKD | 2E2 RHE (SEQ ID NO: 6) | 2E2 RKD (SEQ ID NO: 19) |
| HEKE | 2E2 RHE (SEQ ID NO: 6) | 2E2 RKE (SEQ ID NO: 20) |
| HEKF | 2E2 RHE (SEQ ID NO: 6) | 2E2 RKF (SEQ ID NO: 21) |
| HEKG | 2E2 RHE (SEQ ID NO: 6) | 2E2 RKG (SEQ ID NO: 22) |
| HFKA | 2E2 RHF (SEQ ID NO: 7) | 2E2 RKA (SEQ ID NO: 16) |
| HFKB | 2E2 RHF (SEQ ID NO: 7) | 2E2 RKB (SEQ ID NO: 17) |
| HFKC | 2E2 RHF (SEQ ID NO: 7) | 2E2 RKC (SEQ ID NO: 18) |
| HFKD | 2E2 RHF (SEQ ID NO: 7) | 2E2 RKD (SEQ ID NO: 19) |
| HFKE | 2E2 RHF (SEQ ID NO: 7) | 2E2 RKE (SEQ ID NO: 20) |
| HFKF | 2E2 RHF (SEQ ID NO: 7) | 2E2 RKF (SEQ ID NO: 21) |
| HFKG | 2E2 RHF (SEQ ID NO: 7) | 2E2 RKG (SEQ ID NO: 22) |
| HGKA | 2E2 RHG (SEQ ID NO: 8) | 2E2 RKA (SEQ ID NO: 16) |
| HGKB | 2E2 RHG (SEQ ID NO: 8) | 2E2 RKB (SEQ ID NO: 17) |
| HGKC | 2E2 RHG (SEQ ID NO: 8) | 2E2 RKC (SEQ ID NO: 18) |
| HGKD | 2E2 RHG (SEQ ID NO: 8) | 2E2 RKD (SEQ ID NO: 19) |
| HGKE | 2E2 RHG (SEQ ID NO: 8) | 2E2 RKE (SEQ ID NO: 20) |
| HGKF | 2E2 RHG (SEQ ID NO: 8) | 2E2 RKF (SEQ ID NO: 21) |
| HGHG | 2E2 RHG (SEQ ID NO: 8) | 2E2 RKG (SEQ ID NO: 22) |
| HA2KA | 2E2 RHA2 (SEQ ID NO: 9) | 2E2 RKA (SEQ ID NO: 16) |
| HA2KB | 2E2 RHA2 (SEQ ID NO: 9) | 2E2 RKB (SEQ ID NO: 17) |
| HB2KA | 2E2 RHB2 (SEQ ID NO: 10) | 2E2 RKA (SEQ ID NO: 16) |
| HB2KB | 2E2 RHB2 (SEQ ID NO: 10) | 2E2 RKB (SEQ ID NO: 17) |
| HA2KF | 2E2 RHA2 (SEQ ID NO: 9) | 2E2 RKF (SEQ ID NO: 21) |
| HB2KF | 2E2 RHB2 (SEQ ID NO: 10) | 2E2 RKF (SEQ ID NO: 21) |
| HA2KC | 2E2 RHA2 (SEQ ID NO: 9) | 2E2 RKC (SEQ ID NO: 18) |
| HA2KD | 2E2 RHA2 (SEQ ID NO: 9) | 2E2 RKD (SEQ ID NO: 19) |
| HA2KE | 2E2 RHA2 (SEQ ID NO: 9) | 2E2 RKE (SEQ ID NO: 20) |
| HA2KF | 2E2 RHA2 (SEQ ID NO: 9) | 2E2 RKF (SEQ ID NO: 21) |
| HA2KG | 2E2 RHA2 (SEQ ID NO: 9) | 2E2 RKG (SEQ ID NO: 22) |
| HB2KC | 2E2 RHB2 (SEQ ID NO: 10) | 2E2 RKC (SEQ ID NO: 18) |
| HB2KD | 2E2 RHB2 (SEQ ID NO: 10) | 2E2 RKD (SEQ ID NO: 19) |
| HB2KE | 2E2 RHB2 (SEQ ID NO: 10) | 2E2 RKE (SEQ ID NO: 20) |
| HA2KFmut | 2E2 RHA2 (SEQ ID NO: 9) | 2E2 RKF F-Y mut (SEQ ID NO: 24) |
| HB2KFmut | 2E2 RHB2 (SEQ ID NO: 10) | 2E2 RKF F-Y mut (SEQ ID NO: 24) |
| HEKAmut | 2E2 RHE (SEQ ID NO: 6) | 2E2 RKA F-Y mut (SEQ ID NO: 23) |
| HEKFmut | 2E2 RHE (SEQ ID NO: 6) | 2E2 RKF F-Y mut (SEQ ID NO: 24) |
| HAKFmut | 2E2 RHA (SEQ ID NO: 2) | 2E2 RKF F-Y mut (SEQ ID NO: 24) |
| HBKFmut | 2E2 RHB (SEQ ID NO: 3) | 2E2 RKF F-Y mut (SEQ ID NO: 24) |
| HCKFmut | 2E2 RHC (SEQ ID NO: 4) | 2E2 RKF F-Y mut (SEQ ID NO: 24) |
| HDKFmut | 2E2 RHD (SEQ ID NO: 5) | 2E2 RKF F-Y mut (SEQ ID NO: 24) |
| HFKFmut | 2E2 RHF (SEQ ID NO: 7) | 2E2 RKF F-Y mut (SEQ ID NO: 24) |
| HGKFmut | 2E2 RHG (SEQ ID NO: 8) | 2E2 RKF F-Y mut (SEQ ID NO: 24) |
| RHE Y-VKA | 2E2 RHE Y-V (SEQ ID NO: 13) | 2E2 RKA (SEQ ID NO: 16) |
| RHE Y-VKB | 2E2 RHE Y-V (SEQ ID NO: 13) | 2E2 RKB (SEQ ID NO: 17) |
| RHE Y-VKC | 2E2 RHE Y-V (SEQ ID NO: 13) | 2E2 RKC (SEQ ID NO: 18) |
| RHE Y-VKD | 2E2 RHE Y-V (SEQ ID NO: 13) | 2E2 RKD (SEQ ID NO: 19) |
| RHE Y-VKE | 2E2 RHE Y-V (SEQ ID NO: 13) | 2E2 RKE (SEQ ID NO: 20) |
| RHE Y-VKF | 2E2 RHE Y-V (SEQ ID NO: 13) | 2E2 RKF (SEQ ID NO: 21) |
| RHE Y-VKG | 2E2 RHE Y-V (SEQ ID NO: 13) | 2E2 RKG (SEQ ID NO: 22) |
| RHE E-DKA | 2E2 RHE E-D (SEQ ID NO: 12) | 2E2 RKA (SEQ ID NO: 16) |
| RHE E-DKB | 2E2 RHE E-D (SEQ ID NO: 12) | 2E2 RKB (SEQ ID NO: 17) |
| RHE E-DKC | 2E2 RHE E-D (SEQ ID NO: 12) | 2E2 RKC (SEQ ID NO: 18) |
| RHE E-DKD | 2E2 RHE E-D (SEQ ID NO: 12) | 2E2 RKD (SEQ ID NO: 19) |
| RHE E-DKE | 2E2 RHE E-D (SEQ ID NO: 12) | 2E2 RKE (SEQ ID NO: 20) |
| RHE E-DKF | 2E2 RHE E-D (SEQ ID NO: 12) | 2E2 RKF (SEQ ID NO: 21) |

TABLE 3-continued

Amino acid sequences of variable regions of chimeric and humanized antibody variants

| Antibody Name | Variable Heavy Chain | Variable Light Chain |
|---|---|---|
| RHE E-DKG | 2E2 RHE E-D (SEQ ID NO: 12) | 2E2 RKG (SEQ ID NO: 22) |
| RHE E-DKFmut | 2E2 RHE E-D (SEQ ID NO: 12) | 2E2 RKF F-Y mut (SEQ ID NO: 24) |
| RHE S-GKA | 2E2 RHE S-G (SEQ ID NO: 11) | 2E2 RKA (SEQ ID NO: 16) |
| RHE S-GKB | 2E2 RHE S-G (SEQ ID NO: 11) | 2E2 RKB (SEQ ID NO: 17) |
| RHE S-GKC | 2E2 RHE S-G (SEQ ID NO: 11) | 2E2 RKC (SEQ ID NO: 18) |
| RHE S-GKD | 2E2 RHE S-G (SEQ ID NO: 11) | 2E2 RKD (SEQ ID NO: 19) |
| RHE S-GKE | 2E2 RHE S-G (SEQ ID NO: 11) | 2E2 RKE (SEQ ID NO: 20) |
| RHE S-GKF | 2E2 RHE S-G (SEQ ID NO: 11) | 2E2 RKF (SEQ ID NO: 21) |
| RHE S-GKG | 2E2 RHE S-G (SEQ ID NO: 11) | 2E2 RKG (SEQ ID NO: 22) |
| RHE Triple-KA | 2E2 RHE triple (SEQ ID NO: 14) | 2E2 RKA (SEQ ID NO: 16) |
| RHE Triple-KB | 2E2 RHE triple (SEQ ID NO: 14) | 2E2 RKB (SEQ ID NO: 17) |
| RHE Triple-KC | 2E2 RHE triple (SEQ ID NO: 14) | 2E2 RKC (SEQ ID NO: 18) |
| RHE Triple-KD | 2E2 RHE triple (SEQ ID NO: 14) | 2E2 RKD (SEQ ID NO: 19) |
| RHE Triple-KE | 2E2 RHE triple (SEQ ID NO: 14) | 2E2 RKE (SEQ ID NO: 20) |
| RHE Triple-KF | 2E2 RHE triple (SEQ ID NO: 14) | 2E2 RKF (SEQ ID NO: 21) |
| RHE Triple-KG | 2E2 RHE triple (SEQ ID NO: 14) | 2E2 RKG (SEQ ID NO: 22) |
| RHE Triple-KFmut | 2E2 RHE triple (SEQ ID NO: 14) | 2E2 RKF F-Y mut (SEQ ID NO: 24) |
| RHE Y-VKFmut | 2E2 RHE Y-V (SEQ ID NO: 13) | 2E2 RKF F-Y mut (SEQ ID NO: 24) |
| RHE E-DKFmut | 2E2 RHE E-D (SEQ ID NO: 12) | 2E2 RKF F-Y mut (SEQ ID NO: 24) |

TABLE 4

Amino acid sequences of HVRs from 2E2 and humanized antibody variants

| Antibody Chain | HVR1 | HVR2 | HVR3 |
|---|---|---|---|
| 2E2 antibody | | | |
| Heavy chain | IYGAH<br>SEQ ID NO: 61 | VIWAGGSTNYNSALMS<br>SEQ ID NO: 62 | DGSSPYYYSMEY<br>SEQ ID NO: 63 |
| Light chain | SATSSVSYMH<br>SEQ ID NO: 64 | STSNLAS<br>SEQ ID NO: 65 | QQRSSYPFT<br>SEQ ID NO: 66 |
| Humanized Heavy Chain Variants 2E2 RHA, 2E2 RHB, 2E2 RHC, 2E2 RHD, 2E2 RHE, 2E2 RHF, 2E2 RHG, 2E2 RHA2, and 2E2 RHB2 | | | |
| Heavy chain | IYGAH<br>SEQ ID NO: 61 | VIWAGGSTNYNSALMS<br>SEQ ID NO: 62 | DGSSPYYYSMEY<br>SEQ ID NO: 63 |
| Humanized Light Chain Variants 2E2 RKA, 2E2 RKB, 2E2 RKC, 2E2 RKD, 2E2 RKE, 2E2 RKF, and 2E2 RKG | | | |
| Light chain | SATSSVSYMH<br>SEQ ID NO: 64 | STSNLAS<br>SEQ ID NO: 65 | QQRSSYPFT<br>SEQ ID NO: 66 |
| Humanized Heavy Chain Variants 2E2 RHE S-G, 2E2 RHE E-D, 2E2 RHE Y-V, and 2E2 RHE triple | | | |
| 2E2 RHE S-G | IYGAH<br>SEQ ID NO: 61 | VIWAGGSTNYNSALMS<br>SEQ ID NO: 62 | DGSSPYYYGMEY<br>SEQ ID NO: 67 |
| 2E2 RHE E-D | IYGAH<br>SEQ ID NO: 61 | VIWAGGSTNYNSALMS<br>SEQ ID NO: 62 | DGSSPYYYSMDY<br>SEQ ID NO: 68 |
| 2E2 RHE Y-V | IYGAH<br>SEQ ID NO: 61 | VIWAGGSTNYNSALMS<br>SEQ ID NO: 62 | DGSSPYYYSMEV<br>SEQ ID NO: 69 |
| 2E2 RHE triple | IYGAH<br>SEQ ID NO: 61 | VIWAGGSTNYNSALMS<br>SEQ ID NO: 62 | DGSSPYYYGMDV<br>SEQ ID NO: 70 |
| Humanized Light Chain Variants 2E2 RKA F-Y and 2E2 RKF F-Y | | | |
| 2E2 RKA F-Y | SATSSVSYMH<br>SEQ ID NO: 64 | STSNLAS<br>SEQ ID NO: 65 | QQRSSYPYT<br>SEQ ID NO: 71 |
| 2E2 RKF F-Y | SATSSVSYMH<br>SEQ ID NO: 64 | STSNLAS<br>SEQ ID NO: 65 | QQRSSYPYT<br>SEQ ID NO: 71 |

TABLE 5

Amino acid sequences of FRs from 2E2 and humanized antibody variants

| Heavy Chain | FR1 | FR2 | FR3 | FR4 |
|---|---|---|---|---|
| 2E2 | QVQLKESGPGLVAPSQSLSITCTVSGFSLT (SEQ ID NO: 25) | WVRQPPGKGLEWLG (SEQ ID NO: 30) | RLSISKDNSKSQVFLKINSLQTDDTALYYCAR (SEQ ID NO: 37) | WGQGTSVTVSS (SEQ ID NO: 44) |
| 2E2 RHA | EVQLVESGGGLVQPGGSLRLSCAASGFSLT (SEQ ID NO: 26) | WVRQAPGKGLEWVS (SEQ ID NO: 31) | RFTISKDNSKNTVYLQMNSLRAEDTAVYYCAR (SEQ ID NO: 38) | WGQGTTVTVSS (SEQ ID NO: 45) |
| 2E2 RHB | EVQLVESGGGLVQPGGSLRLSCAVSGFSLT (SEQ ID NO: 27) | WVRQAPGKGLEWLG (SEQ ID NO: 32) | RLSISKDNSKNTVYLQMNSLRAEDTAVYYCAR (SEQ ID NO: 39) | WGQGTTVTVSS (SEQ ID NO: 45) |
| 2E2 RHC | EVQLVESGGGLVQPGGSLRLSCAVSGFSLT (SEQ ID NO: 27) | WVRQAPGKGLEWVS (SEQ ID NO: 31) | RFTISKDNSKNTVYLQMNSLRAEDTAVYYCAR (SEQ ID NO: 38) | WGQGTTVTVSS (SEQ ID NO: 45) |
| 2E2 RHD | EVQLVESGGGLVQPGGSLRLSCAASGFSLT (SEQ ID NO: 26) | WVRQAPGKGLEWLS (SEQ ID NO: 33) | RFTISKDNSKNTVYLQMNSLRAEDTAVYYCAR (SEQ ID NO: 38) | WGQGTTVTVSS (SEQ ID NO: 45) |
| 2E2 RHE | EVQLVESGGGLVQPGGSLRLSCAASGFSLT (SEQ ID NO: 26) | WVRQAPGKGLEWVG (SEQ ID NO: 34) | RFTISKDNSKNTVYLQMNSLRAEDTAVYYCAR (SEQ ID NO: 38) | WGQGTTVTVSS (SEQ ID NO: 45) |
| 2E2 RHF | EVQLVESGGGLVQPGGSLRLSCAASGFSLT (SEQ ID NO: 26) | WVRQAPGKGLEWVG (SEQ ID NO: 31) | RLTISKDNSKNTVYLQMNSLRAEDTAVYYCAR (SEQ ID NO: 40) | WGQGTTVTVSS (SEQ ID NO: 45) |
| 2E2 RHG | EVQLVESGGGLVQPGGSLRLSCAASGFSLT (SEQ ID NO: 26) | WVRQAPGKGLEWVG (SEQ ID NO: 31) | RFSISKDNSKNTVYLQMNSLRAEDTAVYYCAR (SEQ ID NO: 41) | WGQGTTVTVSS (SEQ ID NO: 45) |
| 2E2 RHA2 | QVQLQESGPGLVKPSETLSLTCTVSGGSIS (SEQ ID NO: 28) | WIRQPPGKGLEWIG (SEQ ID NO: 35) | RVTISVDTSKNQFSLKLSSVTAADTAVYYCAR (SEQ ID NO: 42) | WGQGTLVTVSS (SEQ ID NO: 46) |
| 2E2 RHB2 | QVQLQESGPGLVKPSETLSLTCTVSGFSLT (SEQ ID NO: 29) | WVRQPPGKGLEWLG (SEQ ID NO: 36) | RLSISKDNSKNQVSLKLSSVTAADTAVYYCAR (SEQ ID NO: 43) | WGQGTLVTVSS (SEQ ID NO: 46) |
| 2E2 RHE S-G | EVQLVESGGGLVQPGGSLRLSCAASGFSLT (SEQ ID NO: 26) | WVRQAPGKGLEWVG (SEQ ID NO: 34) | RFTISKDNSKNTVYLQMNSLRAEDTAVYYCAR (SEQ ID NO: 38) | WGQGTTVTVSS (SEQ ID NO: 45) |
| 2E2 RHE E-D | EVQLVESGGGLVQPGGSLRLSCAASGFSLT (SEQ ID NO: 26) | WVRQAPGKGLEWVG (SEQ ID NO: 34) | RFTISKDNSKNTVYLQMNSLRAEDTAVYYCAR (SEQ ID NO: 38) | WGQGTTVTVSS (SEQ ID NO: 45) |
| 2E2 RHE Y-V | EVQLVESGGGLVQPGGSLRLSCAASGFSLT (SEQ ID NO: 26) | WVRQAPGKGLEWVG (SEQ ID NO: 34) | RFTISKDNSKNTVYLQMNSLRAEDTAVYYCAR (SEQ ID NO: 38) | WGQGTTVTVSS (SEQ ID NO: 45) |
| 2E2 RHE triple | EVQLVESGGGLVQPGGSLRLSCAASGFSLT (SEQ ID NO: 26) | WVRQAPGKGLEWVG (SEQ ID NO: 34) | RFTISKDNSKNTVYLQMNSLRAEDTAVYYCAR (SEQ ID NO: 38) | WGQGTTVTVSS (SEQ ID NO: 45) |

| Light Chain | FR1 | FR2 | FR3 | FR4 |
|---|---|---|---|---|
| 2E2 | QIILTQSPAIMSASPGEKVSITC (SEQ ID NO: 47) | WFQQKPGTSPKLWIY (SEQ ID NO: 50) | GVPVRFSGSGSGTSYSLTISRMEAEDAATYYC (SEQ ID NO: 54) | FGSGTKLEIK (SEQ ID NO: 59) |

TABLE 5 -continued

Amino acid sequences of FRs from 2E2 and humanized antibody variants

| | | | | |
|---|---|---|---|---|
| RKA | EIVLTQSPATLSLSP GERATLSC (SEQ ID NO: 48) | WFQQKPGQAPRLL IY (SEQ ID NO: 51) | GIPARFSGSGSGTD FTLTISSLEPEDFAV YYC (SEQ ID NO: 55) | FGPGTKLDIK (SEQ ID NO: 60) |
| RKB | EIILTQSPATLSLSP GERATLSC (SEQ ID NO: 49) | WFQQKPGQAPRL WIY (SEQ ID NO: 52) | GVPARFSGSGSGT DYTLTISSLEPEDF AVYYC (SEQ ID NO: 56) | FGPGTKLDIK (SEQ ID NO: 60) |
| RKC | EIILTQSPATLSLSP GERATLSC (SEQ ID NO: 49) | WFQQKPGQAPRLL IY (SEQ ID NO: 51) | GIPARFSGSGSGTD FTLTISSLEPEDFAV YYC (SEQ ID NO: 55) | FGPGTKLDIK (SEQ ID NO: 60) |
| RKD | EIVLTQSPATLSLSP GERATLSC (SEQ ID NO: 48) | WFQQKPGQAPRL WIY (SEQ ID NO: 52) | GIPARFSGSGSGTD FTLTISSLEPEDFAV YYC (SEQ ID NO: 55) | FGPGTKLDIK (SEQ ID NO: 60) |
| RKE | EIVLTQSPATLSLSP GERATLSC (SEQ ID NO: 48) | WFQQKPGQAPRLL IY (SEQ ID NO: 51) | GVPARFSGSGSGT DFTLTISSLEPEDFA VYYC (SEQ ID NO: 57) | FGPGTKLDIK (SEQ ID NO: 60) |
| RKF | EIVLTQSPATLSLSP GERATLSC (SEQ ID NO: 48) | WFQQKPGQAPRLL IY (SEQ ID NO: 51) | GIPARFSGSGSGTD YTLTISSLEPEDFA VYYC (SEQ ID NO: 58) | FPGTKLDIK (SEQ ID NO: 60) |
| RKG | EIVLTQSPATLSLSP GERATLSC (SEQ ID NO: 48) | WYQQKPGQAPRL LIY (SEQ ID NO: 53) | GIPARFSGSGSGTD FTLTISSLEPEDFAV YYC (SEQ ID NO: 55) | FGPGTKLDIK (SEQ ID NO: 60) |
| RKA F-Y | EIVLTQSPATLSLSP GERATLSC (SEQ ID NO: 48) | WFQQKPGQAPRLL IY (SEQ ID NO: 51) | GIPARFSGSGSGTD FTLTISSLEPEDFAV YYC (SEQ ID NO: 55) | FGPGTKLDIK (SEQ ID NO: 60) |
| RKA F-Y | EIVLTQSPATLSLSP GERATLSC (SEQ ID NO: 48) | WFQQKPGQAPRLL IY (SEQ ID NO: 51) | GIPARFSGSGSGTD YTLTISSLEPEDFA VYYC (SEQ ID NO: 55) | FGPGTKLDIK (SEQ ID NO: 60) |

Clones were sequenced and expression plasmid DNA was prepared using the Plasmid Miniprep Kit (Qiagen) or PureYield Plasmid Maxiprep System (Promega) according to the manufacturer's protocol. Expression plasmid preparations encoding humanized or chimeric VH and VK were used to transfect Expi293 cells (Invitrogen) as described above in Example 1. The cells were cultured for 7 days in serum free media, whereupon the conditioned medium from the cells was harvested and assayed by ELISA to confirm production of the antibodies.

Siglec-8 Binding by Antibodies Encoded by Humanized VH and VK Constructs

Basic humanized heavy and light chains were paired with their chimeric counterparts in an attempt to identify any gross problems with the humanization design. Siglec-8 antigen was used to measure antibody binding by ELISA as described in Example 1. 2E2RHB, when paired with the chimeric light chain, appeared to be more potent than the RHA heavy chain, while RKB construct in association with the heavy chain chimeric construct (cVH) bound Siglec-8 antigen with a higher potency then both the paired cVK constructs. These results confirmed that humanization design for both heavy and light chains was approximately correct and all bound Siglec-8 but that further work was required to identify additional humanized antibodies with better binding characteristics.

Siglec-8 Binding by Fully Humanized Antibodies Combined with Chimeric Counterpart The fully humanized antibody heavy and light chains were combined and compared with the chimeric antibody to determine if replacing the 4 Å and canonical framework residues and interface residues was sufficient to successfully humanize 2E2. Expi293 cells were co-transfected with combinations of different humanized light chain vectors in association with different humanized heavy chain vectors. Siglec-8 antigen was used to measure antibody binding by ELISA as described in Example 1. The binding of these antibodies to Siglec8 as compared to the chimeric control showed that HBKA and HBKB appeared to be better combinations than HAKA and HAKB (Table 6).

Siglec-8 Binding by Fully Humanized Antibodies

In order to determine the relative importance of the single amino acid substitutions in the heavy chain, the humanized heavy chains RHC (A24V), RHD (V48L), RHE (S49G), RHF (F67L) and RHG (T68S) were expressed in combination with all light chain variants and compared to RHA and RHB versions and the chimeric antibody control. The results of these antibodies binding to Siglec-8 ECD suggested that all these humanized antibody combinations bound Siglec-8 at the same potency except for families RHA, RHF and RHG (with all light chain variants) (Table 6).

It was next determined if changing the light chain from RKA to RKB, with single amino acid substitutions, would affect antibody binding. Binding of antibodies consisting of combinations of all heavy chain variants with light chains RKC (V3I), RKD (V48L), RKE (L47W) and RKF (E58V), compared to the chimeric antibody and the RKA and RKB versions was assessed. There did not appear to be a light chain variant that significantly affected the pattern of binding (Table 6). In addition, the relevance of the light chain germline residue F71 Y (RKG) was also examined in combination with all heavy chain variants and the results demonstrated that this residue generally caused a great decline in binding.

It appeared that HEKA and HEKF were the best candidate antibodies against Siglec-8. Therefore an ELISA was performed to re-test the antibodies that bound with the highest potency to the antigen compared to both the chimeric antibody and HEKA and HEKF as controls. The results indicated that the different combinations of humanized heavy and humanized light chains bound in a similar way to Siglec-8, apart from combinations with RHA (Table 6). The results highlighted that HEKA and HEKF were very good candidates and compared favorably with the chimeric positive control and had minimal mouse residues in the frameworks.

Generation of 2E2RH Version 2 and CDR Mutated Variants

A subsequent humanized heavy chain was generated based on the closest germline gene. The IGHV4-59 germline sequence, the most similar germline to 2E2VH (FIG. 1), was used to design the graft of the mouse CDRs, synthesized (GenScript) and prepared in the same manner as the other constructs described above, to generate humanized antibodies for comparison with the first version of RHA and RHB chains. In addition, to determine if the antibody could tolerate certain CDR3 residues being changed to germline. Three mutations were introduced in the CDR3 of the RHE variant heavy chain (single and triple mutations) and one mutation in the CDR3 of RKA and RKF light chain (FIG. 3) by site-directed mutagenesis. Antibodies containing RHE mutated or RKA/RKF mutated were expressed and combined with the complete panel of the complementary chain using the same method described above.

The heavy chain CDRs grafted into human germline was compared with the other heavy chain versions. The straight graft (RHA2) completely disrupted binding to the antigen and the germline framework with the 4 Å/VCI residues back mutated to mouse (RHB2) behaved very similarly to the first RHB variant but contained 10 mouse residues as compared to the 5 of RHB. The binding data illustrated the influence of introducing mutations in CDR3 of both chains and suggested that the mutations in the heavy chain had a detrimental effect on binding to Siglec-8 while the light chain mutation on its own also did not provide much improvement, although the best antibodies were the ones containing RHB (all mouse back mutations) and RHE, the heavy chain candidate (Table 6).

TABLE 6

Antibody binding to human Siglec-8 ECD.

Humanized Antibodies

| Antibody | EC50 (nM) | Antibody | EC50 (nM) | Antibody | EC50 (nM) | Antibody | EC50 (nM) |
|---|---|---|---|---|---|---|---|
| HAKA | 0.058 | HCKA | 0.056 | HEKA | 0.112 | HGKA | 0.061 |
| HAKB | 0.071 | HCKB | 0.065 | HEKB | 0.057 | HGKB | 0.134 |
| HAKC | 0.066 | HCKC | 0.058 | HEKC | 0.065 | HGKC | 0.065 |
| HAKD | 0.058 | HCKD | 0.049 | HEKD | 0.070 | HGKD | 0.047 |
| HAKE | 0.052 | HCKE | 0.059 | HEKE | 0.205 | HGKE | 0.116 |
| HAKF | 0.062 | HCKF | 0.050 | HEKF | 0.097 | HGKF | 0.088 |
| HAKG | 0.189 | HCKG | 0.273 | HEKG | 0.302 | HGKG | 0.254 |
| HBKA | 0.070 | HDKA | 0.067 | ch2E2 Purif. | 0.062 | VHVK | 0.043 |
| HBKB | 0.056 | HDKB | 0.055 | | | cVHKA | NA |
| HBKC | 0.033 | HDKC | 0.057 | | | cVHKB | 0.027 |
| HBKD | 0.039 | HDKD | 0.048 | | | HAcVK | 0.067 |
| HBKE | 0.061 | HDKE | 0.065 | | | HBcVK | 0.066 |
| HBKF | 0.051 | HDKF | 0.057 | | | ch2E2 Purif. | 0.062 |
| HBKG | 0.212 | HDKG | 0.113 | | | | |
| ch2E2 Purif. | 0.044 | ch2E2 Purif. | 0.062 | | | | |
| ch2C4 | 0.057 | ch2C4 | 0.079 | ch2C4 T1 | 0.075 | | |
| HFKA | 0.106 | HAKA | 0.085 | HA2KA | NA | | |
| HFKB | 0.099 | HAKF | 0.078 | HA2KB | 124.30 | | |
| HFKC | 0.063 | HBKA | 0.055 | HB2KA | NA | | |
| HFKD | 0.058 | HBKF | 0.066 | HB2KB | 0.051 | | |
| HFKE | 0.104 | HA2KF | 8.719 | ch2C4 | 0.069 | | |
| HFKF | 0.118 | HB2KF | 0.063 | HA2KC | 0.488 | | |
| HFKG | 0.355 | HEKA | 0.068 | HA2KD | NA | | |
| | | HEKB | 0.063 | HA2KE | NA | | |
| | | HEKC | 0.069 | HA2KF | NA | | |
| | | HEKD | 0.059 | HA2KG | NA | | |
| | | HEKE | 0.057 | HB2KC | 0.101 | | |
| | | HEKF | 0.064 | HB2KD | 0.075 | | |
| | | HEKF T2 | 0.064 | HB2KE | 0.087 | | |
| | | mo2C4 | 0.115 | HB2KF | 0.089 | | |
| | | | | HB2KG | 0.227 | | |

TABLE 6-continued

Antibody binding to human Siglec-8 ECD.

CDR Human Antibody Variants

| Antibody | EC50 (nM) | Antibody | EC50 (nM) | Antibody | EC50 (nM) |
|---|---|---|---|---|---|
| ch2C4 | 0.052 | ch2C4 | 0.208 | ch2C4 | 0.057 |
| RHE Y-V KA | 0.088 | RHE S-GKA | 50.620 | HAKFmut | 0.086 |
| RHE Y-V KB | 0.306 | RHE S-GKB | 626.900 | HBKFmut | 0.048 |
| RHE Y-V KC | 0.215 | RHE S-GKC | 173.300 | HCKFmut | 0.078 |
| RHE Y-V KD | 0.283 | RHE S-GKD | 8.647 | HDKFmut | 0.056 |
| RHE Y-V KE | 0.070 | RHE S-GKE | NA | HEKFmut | 0.072 |
| RHE Y-V KF | 0.091 | RHE S-GKF | 3.279 | HFKFmut | 0.057 |
| RHE Y-V KG | 8.808 | RHE S-GKG | 33.540 | HFKFmut | 0.062 |
| RHE E-D KA | 0.388 | RHE Triple-KA | 18.640 | | |
| RHE E-D KB | 0.289 | RHE Triple-KB | NA | | |
| RHE E-D KC | 0.516 | RHE Triple-KC | NA | | |
| RHE E-D KD | 0.316 | RHE Triple-KD | 13.200 | | |
| RHE E-D KE | 0.364 | RHE Triple-KE | 34.060 | | |
| RHE E-D KF | 0.445 | RHE Triple-KF | NA | | |
| RHE E-D KG | NA | RHE Triple-KG | NA | | |
| ch2C4 | 0.075 | ch2C4 | 0.075 | ch2C4 | 0.175 |
| HEKA | 0.054 | HA2KA | NA | RHE S-G KFmut | 207.100 |
| HEKE | 0.042 | HA2KB | 124.300 | RHE Triple KFmut | NA |
| HEKF | 0.074 | HA2KFmut | 31.610 | HEKF | 0.052 |
| RHE Y-V KFmut | 0.398 | HB2KA | 0.051 | HEKA | 0.064 |
| RHE E-D KFmut | 1.399 | HB2KB | 0.069 | | |
| | | HB2KFmut | 0.080 | | |

Note:
Each column represents one experiment; NA indicates not available.

Thermo Stability of Humanized Candidate Antibodies to High Temperatures

The thermo stability of the humanized antibodies was compared. The antibodies were subjected to higher temperatures, varying from −20 to 85° C. for 10 minutes, cooled to room temperature and assessed in an ELISA assay at an EC80 concentration of each candidate. The lead antibody candidates appeared stable (FIG. 4). The HEKA/KF with CDRL3 (i.e., CDR3 of the light chain) mutated antibodies were completely inactive at 68° C., while the chimeric was inactive at 70° C., at which temperature the lead candidates HEKA and HEKF were still 25-50% active, only showing complete inactivity at 75° C.

Determination of Humanized Candidate Antibodies Tm

Figure 5:
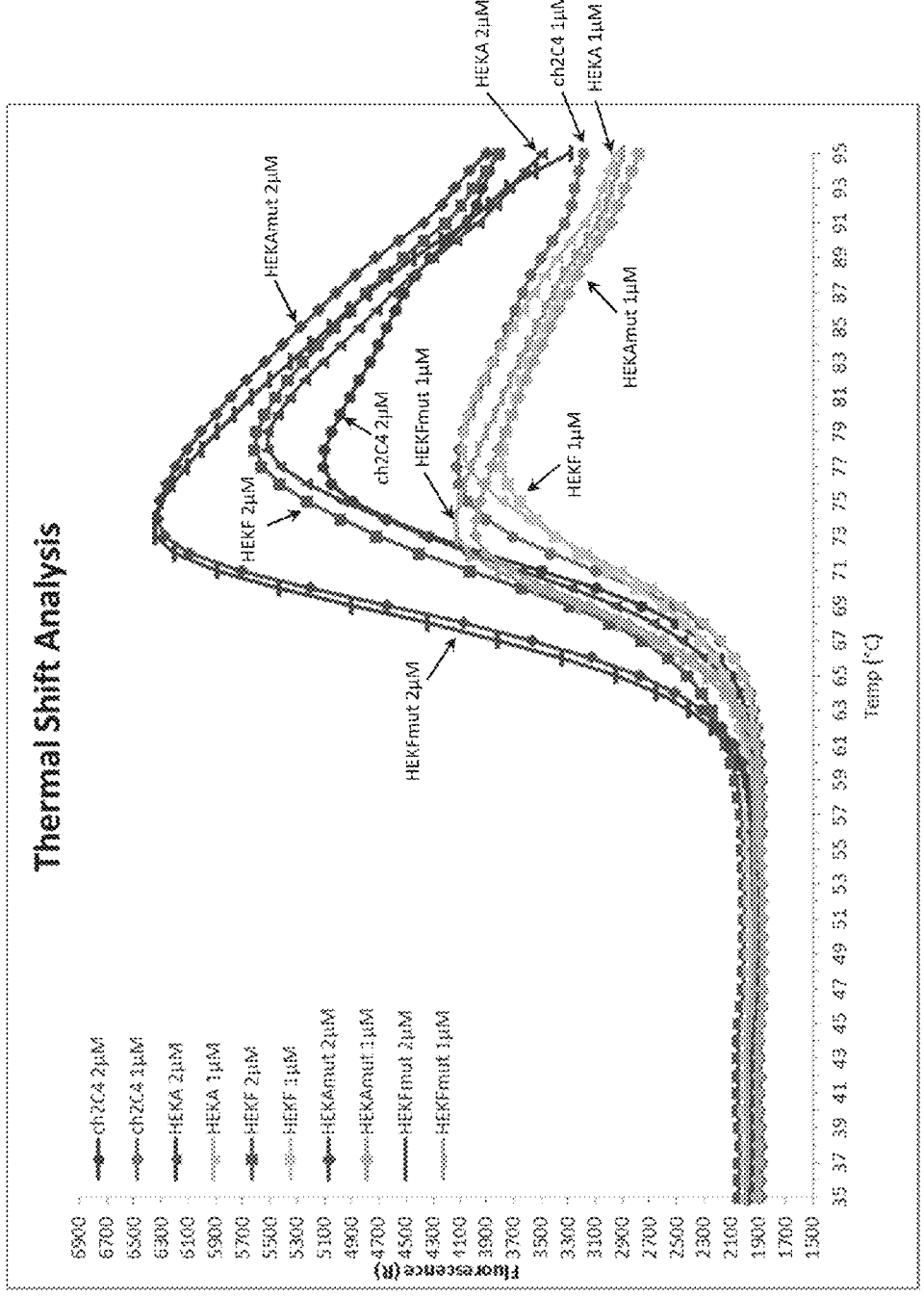
FIG. 5 is a graph showing the Tm of purified 2C4 candidate antibodies as compared to ch2C4 (i.e., chimeric 2C4 antibody).

In order to determine the melting temperature of the lead antibodies, the chimeric, HEKA, HEKF and the same humanized candidates with the CDRL3 (i.e., CDR3 of the light chain) mutation were purified in a 2-step affinity chromatography and gel filtration system and tested in a thermal shift assay. Antibodies were incubated at two different concentrations with a fluorescent dye (Sypro Orange) for 71 cycles with 1° C. increase per cycle in a qPCR thermal cycler. Tm was defined as temperature for 50% maximal fluorescence. Tm for the chimeric and the five humanized antibodies confirmed the results obtained in the thermo stability assay: the most stable antibodies were HEKA and HEKF having a higher Tm than the other humanized antibodies tested. HEKA has a higher Tm than the chimeric antibody (FIG. 5 and Table 7).

TABLE 7

Tm of chimeric and humanized antibodies

| Antibody | TM |
|---|---|
| chVHVK 2 uM | 71° C. |
| chVHVK 1 uM | 71° C. |
| HEKA 2 uM | 72° C. |
| HEKA 1 uM | 72° C. |
| HEKF 2 uM | 70° C. |
| HEKF 1 uM | 70° C. |
| HEKAmut 2 uM | 68° C. |
| HEKAmut 1 uM | 68° C. |
| HEKFmut 2 uM | 67° C. |
| HEKFmut 1 uM | 68° C. |

Affinity and Avidity of Humanized Candidate Antibodies

Antibody avidity determination was carried out by SPR analysis using a Biacore T200. Binding of human Siglec-8 ECD protein to mouse, chimeric and humanized anti-Siglec-8 antibodies was measured on a Biacore T100. The capture antibodies (goat-anti-human-Fc and goat-anti-mouse-Fc from Jackson Immunoresearch) were immobilized on a CMS chip according to manufacturer's protocol (Biacore, GE). Flow-cell 1, 2 and 3 were immobilized with anti-human, and flow cell 4 with anti-mouse antibodies. The assay was conducted at 25° C., at a flow rate of 30 μl/min. Assay buffer was 20 mM Tris-HCl pH 8.3, 150 mM Sodium Chloride, 0.05% Polysorbate 20, 10% glycerol, 0.1% BSA, made in ultrapure water. Dimeric Siglec-8 (impurities of monomeric and oligomeric Siglec-8 were removed by size-exclusion chromatography) was diluted in assay buffer from 15 nM to 1.88 pM with 2× dilutions. Antibodies were captured to a change of approximately 120 RU. Six-minute high performance injections were conducted, followed by 120-minute dissociations. Flow cells were regenerated with 50 mM glycine pH 1.5. Results were double blanked with an empty reference cell and multiple assay buffer injections, and analyzed with 1:1 global fit parameters.

The avidity of murine 2E2 and chimeric 2E2 antibodies was determined to be 28 pM and 16 pM, respectively (Table 8). The avidities for the humanized antibodies were 17 pM for HEKA and 21 pM for HEKF which indicated that the humanization had successfully retained and enhanced the binding activity.

TABLE 8

Avidity determination of mouse, chimeric and humanized antibodies

| Antibody | ka (1/Ms) | kd (1/s) | KD (pM) |
|---|---|---|---|
| mouse 2E2 | 5.56E+05 | 1.54E−05 | 28 |
| chimeric 2E2 | 8.51E+05 | 1.32E−05 | 16 |
| HEKA | 6.38E+05 | 1.11E−05 | 17 |
| HEKF | 6.78E+05 | 1.40E−05 | 21 |

Antibody affinity determination was also carried out by bio-layer interferometry (ForteBio). Binding of mouse, chimeric and humanized anti-Siglec-8 antibody Fab fragments to human Siglec-8 protein was measured on a ForteBio Octet Red 384. The assay was conducted at 25° C., at an RPM of 1000 in assay buffer. HBS buffer with 1× ForteBio Kinetics buffer was made from stock solutions (Biacore BR-10670, ForteBio18-132 respectively) in ultrapure water. Fab fragments (antibodies were digested with Thermo-Pierce immobilized papain per manufacturer's specifications) were diluted in assay buffer from 50 nM to 1.56 nM with 2× dilutions. The Siglec-8-Fc tagged protein was immobilized on Anti-Human-Capture sensors at 100 nM in assay buffer for 3 min to a change in nm of approximately 1.2. Two-minute associations were conducted, followed by 10-minute dissociations. Results were blanked with an empty reference AHC sensor, and analyzed in ForteBio analysis software with 1:1 global fit parameters.

The affinity of murine 2E2 and chimeric 2E2 Fab fragments was determined to be 536 pM and 585 pM, respectively (Table 9). The affinities for the humanized antibodies were 464 pM for HEKA and 592 pM for HEKF which indicated that the humanization had successfully retained the binding activity for these two humanized antibodies. HEKA had a higher monovalent affinity for Siglec-8 than mouse and chimeric 2E2 in this assay. The affinities for the humanized antibody variants, HEKAmut and HEKFmut, also where in the picomolar range with a KD of 902 pM and 1160 pM, respectively.

TABLE 9

Affinity determination of mouse, chimeric and humanized antibodies

| Antibody | kon (1/Ms) | kdis (1/s) | KD (pM) |
|---|---|---|---|
| mouse 2E2 | 1.14E+06 | 6.12E−04 | 536 |
| chimeric 2E2 | 9.51E+05 | 5.56E−04 | 585 |
| HEKA | 1.04E+06 | 4.82E−04 | 464 |
| HEKF | 9.20E+05 | 5.45E−04 | 592 |
| HEKAmut | 7.26E+05 | 6.55E−04 | 902 |
| HEKFmut | 4.45E+05 | 5.16E−04 | 1160 |

Solubility of Humanized Candidate Antibodies

The purified chimeric and candidate antibodies were sequentially concentrated using centrifugal filter devices (Amicon 30K 4 mL, 4000 g 5 min—first concentration; Amicon Ultra 0.5 mL 3K, 14000 g—following concentrations) and the concentration measured at each step. All of the samples were concentrated in total by a factor of up to 21-24 without precipitating and tested by ELISA which showed that none had lost binding potency to Siglec-8. The antibodies were not prone to precipitation at concentrations up to at least 25 mg/mL. Specifically, solubility for ch2E2 was at least 18 mg/mL, for HEKA was at least 25 mg/mL, for HEKF was at least 8 mg/mL, for HEKAmut at least 29 mg/mL, and HEKFmut at least 17 mg/mL.

Aggregation of Humanized Candidate Antibodies

Samples were filtered prior to analysis to remove any salt or protein precipitation and concentrations were re-measured. They were then injected at 0.4 mL/min into a size exclusion column in an HPLC system and analyzed by multi-angle light scattering to determine the absolute molar masses and checked for aggregation. All variants showed no signs of aggregation with an average molecular weight ranging from 134.9-138.2 kDa, which was the expected range for an IgG monomer in this analysis (Table 10).

All samples were monodispersed (Mw/Mn<1.05). However, the distribution analysis plots showed the presence of glycosylation variants (ch2C4, HEKA and HEKFMut). The distribution analysis plots also show the presence of a ~105-120 kDa species in all the samples, which could have been disintegrated antibody or a low glycosylation variant. The mass recoveries were between 82.9-102.8% (calculated mass over injected mass), which indicated good protein recovery and the samples did not seem to stick to the column or contain insoluble aggregates, which would be retained by the guard column. Overall the data indicated there was no significant aggregation in any of the anti-Siglec-8 antibody samples analyzed (Table 10).

TABLE 10

Aggregation analysis of chimeric and humanized variant antibodies

| | MW (kDa) | Uncertainty | Polydispersity (Mw/Mn) | Uncertainty | Calculated mass (μg) | Mass fraction (%) | Mass recovery (%) |
|---|---|---|---|---|---|---|---|
| ch2C4 | 138.7 | 0.80% | 1.01 | 1.10% | 11.02 | 100 | 96.6 |
| ch2C4 | 134.6 | 0.80% | 1.017 | 1.10% | 10.86 | 100 | 95.2 |
| Average | 136.6 | | 1.013 | | 10.94 | 100 | 95.9 |
| % standard deviation | 2.1 | | 0.445 | | 0.11 | 0 | 1 |
| HEKA | 134 | 0.90% | 1.03 | 1.30% | 15 | 100 | 102.8 |
| HEKA | 135.9 | 0.90% | 1.01 | 1.30% | 14.4 | 100 | 98.6 |
| Average | 134.9 | | 1.02 | | 14.7 | 100 | 100.7 |
| % standard deviation | 1 | | 0.014 | | 0.43 | 0 | 2.9 |
| HEKA Mut | 135.4 | 0.80% | 1.013 | 1.10% | 13.61 | 100 | 98.8 |
| HEKA Mut | 137.3 | 0.90% | 1.011 | 1.30% | 13.68 | 100 | 99.3 |

TABLE 10-continued

Aggregation analysis of chimeric and humanized variant antibodies

| | MW (kDa) | Uncertainty | Polydispersity (Mw/Mn) | Uncertainty | Calculated mass (μg) | Mass fraction (%) | Mass recovery (%) |
|---|---|---|---|---|---|---|---|
| Average | 136.3 | | 1.012 | | 13.65 | 100 | 99 |
| % standard deviation | 1.3 | | 0.001 | | 0.05 | 0 | 0.4 |
| HEKF | 291 | 13.90% | 1.742 | 14.40% | 4.83 | 100 | 88.1 |
| HEKF | 138.2 | 0.80% | 1.01 | 1.10% | 4.54 | 100 | 82.9 |
| Average | 214.6 | | 1.376 | | 4.69 | 100 | 85.5 |
| % standard deviation | 50.3 | | 37.622 | | 4.31 | 0 | 4.3 |

Freeze-Thaw Stability of Humanized Candidate Antibodies

Figure 6:
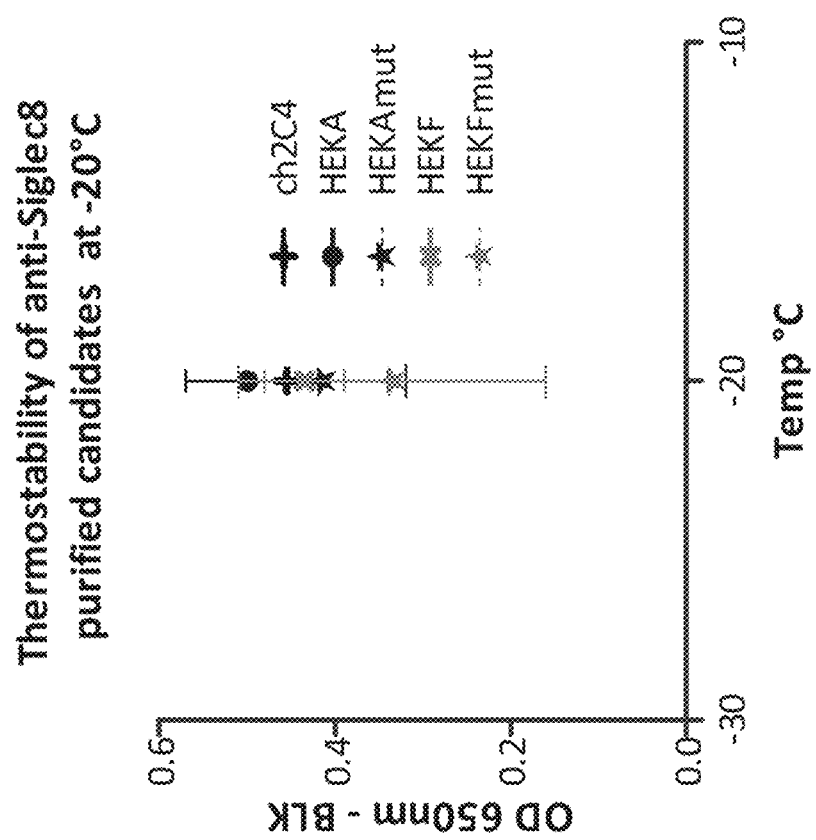
FIG. 6 is a graph showing the stability of chimeric and humanized anti-Siglec-8 antibodies after being frozen at −20° C. for 60 minutes and thawed at room temperature.

Purified chimeric ch2C4 antibody, humanized HEKA and HEKF antibodies, and humanized HEKAmut and HEKFmut antibody variants were subjected to −20° C. for 60 minutes, thawed at room temperature and used in an ELISA assay at the EC80 concentration for each candidate. HEKA showed the highest stability in this assay (FIG. 6).

ADCC Activity of Non-Fucosylated Antibodies

Materials

RBC Lysis Buffer (10×RBC Lysis Buffer): Dilute to 1× as directed by manufacturer (eBioscience, 00-4300-54).

PBS: DPBS without $Ca^{2+}/Mg^{2+}$ (Hyclone, SH30028.02).

Complete RPMI: Sterile Filtered RPMI-1640 (Invitrogen) with 10% FBS.

96-well U-Bottom Plate (Falcon, 353077).

LDH Assay: CytoTox 96 Non-Radioactive Cytotoxicity Assay (Promega, G1780)

FIX Buffer: 1-4% paraformaldehyde in PBS. Prepare from 16% paraformaldehyde (EM grade, methanol-free) by diluting in PBS (Electron Microscopy Diatom, 50-980-488).

Methods

Figure 7:
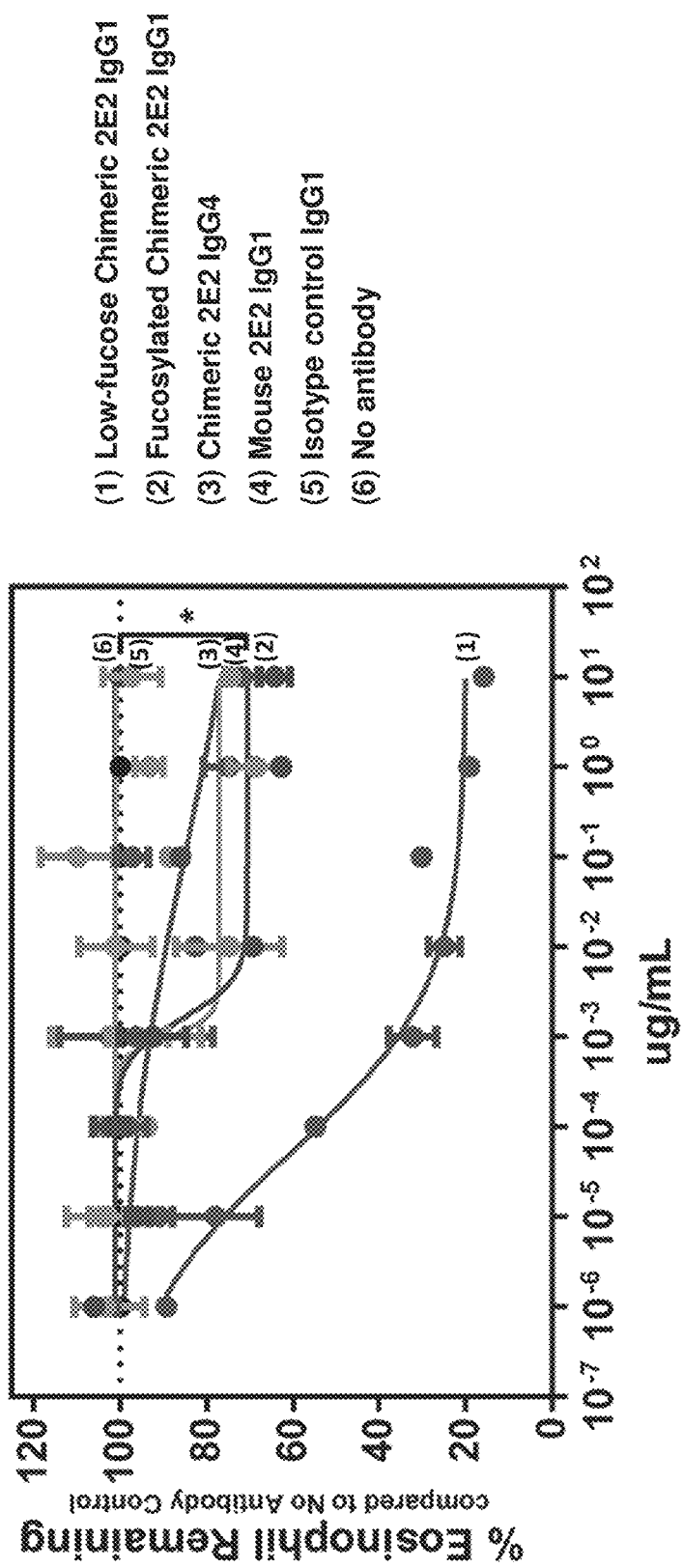
FIG. 7 is a graph showing killing of eosinophils with anti-Siglec-8 antibodies. Total peripheral blood leukocytes were incubated in the presence of the indicated anti-Siglec-8 and control antibodies concentrations for 16 hours. Reduction of eosinophil numbers were monitored by flow cytometry and quantified as a loss of CD16-negative IL5Rα+ cells with high side-scatter ($SSC^{HI}$).

To test ADCC and apoptotic activity of anti-Siglec-8 antibodies on eosinophils, fresh peripheral blood leukocytes (PBLs) were incubated with chimeric and mouse 2E2 antibodies. Low-fucose chimeric 2E2 IgG1 antibody showed the most potent killing of eosinophils and had significantly higher potency than fucosylated chimeric 2E2 IgG1 consistent with higher ADCC activity for the low-fucose form of the antibody (FIG. 7).

For evaluation of anti-Siglec-8 antibody activity in total peripheral blood leukocytes, PBLs are obtained by standard methods from donor blood collected less than 24 hours since harvest and are resuspended in Complete RPMI medium. Cells are counted and adjusted to $10 \times 10^6$/mL in Complete RPMI medium and plated at 100 μL/well in a sterile 96-well U-bottom plate. Anti-Siglec-8 antibody is added at a concentration between 0.0001 ng/mL to 10 μg/mL. Plates are centrifuged at 200 g for 1 minute and incubated in a humidified 37° C. incubator at 5% $CO_2$ for >4 hours. The cell populations are evaluated by flow cytometry to assess depletion of eosinophils and basophils for example using reagents shown in Table 11 and evaluated by flow cytometry. Removal of CCR3-positive, CD16-negative granular cells (high side-scatter) cells can be used to detect depletion of eosinophils. Basophil counts can be determined for example by analysis of CCR3-positive low side-scatter cells.

TABLE 11

Reagents

| Target | Format | Clone | Target Species | Host | Isotype | Vendor | Catalog Number |
|---|---|---|---|---|---|---|---|
| 7AAD | 7AAD | N/A | N/A | N/A | N/A | BD | 559925 |
| Annexin V | PE | N/A | N/A | N/A | N/A | BD | 559763 |
| CD117 | APC | A3C6E2 | Human | Mouse | $IgG_1$ | Miltenyi | 130-091-733 |
| CD16 | FITC | 3G8 | Human | Mouse | $IgG_1$ | BD | 555406 |
| CD193 (CCR3) | Alexa Fluor ® 647 | 5E8 | Human | Mouse | $IgG_{2b}$ | BD | 558208 |
| CDw125 (IL-5Rα) | PE | A14 | Human | Mouse | $IgG_1$ | BD | 555902 |
| Cleaved PARP | Alexa Fluor ® 647 | F21-852 AER-37 | Human | Mouse | $IgG_1$ | BD | 558710 |
| FCeR1α | FITC | CRA1 | Human | Mouse | $IgG_{2b}$ | Miltenyi | 130-095-978 |
| Isotype $IgG_1$ | PE | MOPC-21 | N/A | Mouse | $IgG_1$ | BD | 555749 |
| Isotype $IgG_{2b}$ | FITC | 27-35 | N/A | Mouse | $IgG_{2b}$ | BD | 555742 |
| Isotype $IgG_{2b}$ | APC | eBMG2b | N/A | Mouse | $IgG_{2b}$ | eBioscience | 17-4732 |

For the evaluation of the ability of anti-Siglec-8 antibodies to induce apoptosis in purified eosinophils, fresh buffy coat collected less than 24 hours since harvest from a blood sample or an equivalent blood product is used. Purification of eosinophils is conducted following the manufacturer's instructions (Miltenyi Eosinophil Isolation Kit, 130-092-010). Purified eosinophils are resuspended at $1 \times 10^6$/mL in Complete RPMI medium and cultured in the presence or absence of IL-5 (at a concentration of about 1 ng/mL to about 50 ng/mL) overnight. The following day, cultured eosinophils are harvested by repeated washing of the plate or flask. The cells are centrifuged at 200-400 g for less than 10 minutes and resuspended at $1 \times 10^6$/mL in Complete RPMI medium. Eosinophils are plated at 100 μL/well in a sterile 96-well U-bottom plate. 100 uL of 2× reagents prepared in Complete RPMI medium are added to each well and dilutions are prepared as described above. The plates are centrifuged at 200 g for 1 minute and incubated in a humidified 37° C. incubator at 5% $CO_2$ for ≥4 hours. Annexin-V staining is performed according to manufacturer instructions, and apoptotic and necrotic cells are analyzed by flow cytometry.

For evaluation of ADCC and apoptotic activity of anti-Siglec-8 antibodies on isolated mast cells, human mast cells are isolated from human tissues according to published protocols (Guhl et al., Biosci. Biotechnol. Biochem., 2011, 75:382-384; Kulka et al., In Current Protocols in Immunology, 2001, (John Wiley & Sons, Inc.)) or differentiated from human hematopoietic stem cells, for example as described by Yokoi et al., J Allergy Clin Immunol., 2008, 121:499-505. Purified mast cells are resuspended at $1\times10^6$/mL in Complete RPMI medium in a sterile 96-well U-bottom plate and incubated in the presence or absence of anti-Siglec-8 antibodies for 30 minutes at concentrations ranging between 0.0001 ng/ml and 10 µg/ml. Samples are incubated for a further 4 to 16 hours with and without purified natural killer (NK) cells or fresh PBL to induce ADCC. Cell-killing by apoptosis or ADCC is analyzed by flow cytometry using fluorescent conjugated antibodies to detect mast cells (CD117 and FcεR1) and Annexin-V and 7AAD to discriminate live and dead or dying cells. Annexin-V and 7AAD staining are performed according to manufacturer's instructions.

Evaluation of Eosinophil-Depleting Activity of Humanized Antibodies In Vitro

Humanized antibodies were evaluated for their ability to induce Siglec-8 mediated depletion of eosinophils from normal human blood in vitro in comparison with the murine 2E2 antibody.

Peripheral blood leukocytes (PBL) from human donor blood collected less than 24 hours after harvest were resuspended in complete RPMI medium [(RPMI-1640 medium (Invitrogen, Catalog Number A10491-01) supplemented with 10% Fetal Bovine Serum)]. Cells were adjusted to $10^7$ per mL in Complete RPMI medium supplemented with 50 ng/ml recombinant human IL-5 (R&D Systems, Catalog Number 205-IL-025) and plated at 100 µL/well in a sterile 96-well U-bottom plate. Anti-Siglec-8 antibodies were added at concentrations ranging from 0.1 pg/mL and 10 µg/mL (i.e., 1 pg/mL, 10 pg/mL, 0.1 ng/mL, 1 ng/mL, 10 ng/mL, 0.1 µg/mL, 1 µg/mL, and 10 µg/mL) to determine the dose response and concentration providing 50% maximal eosinophil depletion ($EC_{50}$). Plates were centrifuged at 200 g for 1 minute and incubated in a humidified 37° C. incubator at 5% $CO_2$ for 16 hours. Incubation of PBLs with anti-Siglec-8 antibodies for 16 hours in the presence of IL-5 sensitized eosinophils to Siglec-8-mediated apoptosis. The cell populations were evaluated by flow cytometry to assess depletion of eosinophils. Eosinophil depletion was detected by the removal of CCR3-positive granular (high side-scatter) cells.

Each of the tested humanized antibodies, with the exception of the HEKAmut IgG1 antibody, showed equivalent or increased potency (i.e., lower $EC_{50}$) compared with the mouse 2E2 antibody for depletion of human eosinophils (Table 12). The antibody potency for depletion of human eosinophils was not dependent on isotype as the HEKA IgG1 antibody and HEKA IgG4 antibody showed similar potency.

TABLE 12

Potency of humanized anti-Siglec-8 antibodies for depletion of eosinophils in vitro

| Antibody | Isotype | Mean $EC_{50}$ (ng/ml) for eosinophil depletion |
|---|---|---|
| 2E2 | IgG1 | 6.8 |
| HEKA | IgG1 | 4.3 |
| HEKA | IgG4 | 3.9 |
| HEKAmut | IgG1 | 43.3 |
| HEKF | IgG1 | 6.7 |
| HEKFmut | IgG1 | 6.9 |

Mean EC50 indicates mean half-maximal antibody concentrations required for eosinophil depletion from 2 independent assays.

Anti-Siglec-8 Antibodies with an Active Isotype are Capable of Inducing ADCC-Mediated Killing of Human Mast Cells In Vitro and In Vivo.

To generate a humanized anti-Siglec-8 antibody with potent Fc-receptor mediated ADCC activity, the HEKA IgG1 antibody was expressed from a CHO cell line deficient in fucosyl transferase-8 (Lonza, Potelligent CHOK1SV cells) to generate an antibody with carbohydrates lacking α1,6 fucose (i.e., non-fucosylated antibody). A murine monoclonal anti-Siglec-8 antibody with a murine IgG2a isotype (i.e., 1C3 antibody) that recognizes a different extracellular region of Siglec-8 than the HEKA IgG1 antibody was generated as described in Example 3. The chimeric 1H10 antibody contains the V-regions of mouse monoclonal antibody 1H10 and human IgG1 kappa constant regions. Chimeric 1H10 antibody was expressed from the human 293TS cell line cultured in the presence of 10 µM Kifunensine to generate low fucose antibody and purified by Protein A affinity chromatography.

Figure 8A:
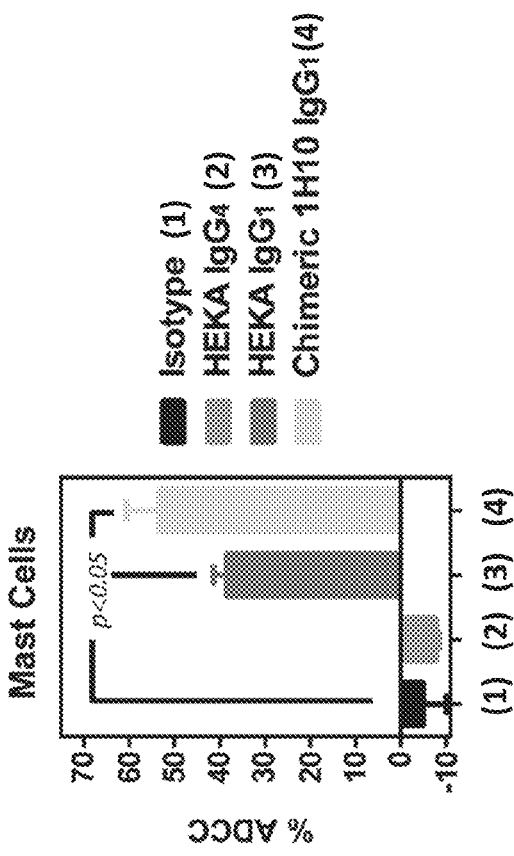
FIGS. 8A and B is a series of graphs showing in vitro apoptosis and in vivo depletion of human mast cells by anti-Siglec-8 antibodies.

The ability of non-fucosylated HEKA IgG1 and chimeric 1H10 low-fucose antibody to induce NK-cell-mediated ADCC activity against human mast cells was evaluated in vitro. Primary human mast cells were isolated by lavage of the peritoneal cavity of immunodeficient NSGS mice engrafted with human hematopoietic stem cells. Mast cells were incubated for 48 hours with 10 µg/ml of non-fucosylated HEKA IgG1 antibody, chimeric 1H10 low-fucose antibody, HEKA IgG4 antibody or isotype control human IgG1 antibody, and with purified human $CD56^+CD16^+$ NK effector cells at an effector to target cell (E:T) ratio of 10.75:1. ADCC activity was determined by LDH release using a CytoTox 96 Cytotoxicity Assay kit (Promega, Catalog Number G1780). Non-fucosylated HEKA IgG1 antibody and chimeric 1H10 low-fucose antibody induced marked ADCC-mediated killing of human mast cells after 48 hours (FIG. 8A). LDH release induced by non-fucosylated or low fucose anti-Siglec-8 antibody was 38-53% of the maximum LDH release induced using lysis solution (Promega, Catalog Number G1821).

Figure 8B:
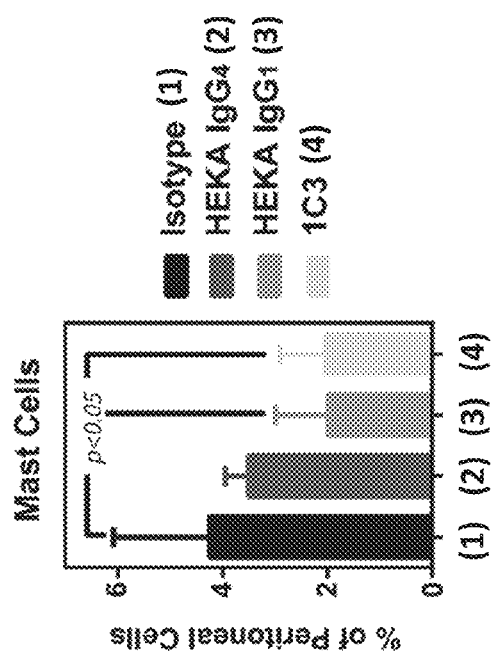
FIG. 8B Depletion of Siglec-8 positive mast cells in vivo. Siglec-8 transgenic mice selectively expressing Siglec-8 on the surface of mast cells at levels comparable to those on human mast cells were treated intraperotineally with HEKA IgG4 antibody, non-fucosylated HEKA IgG1 antibody, murine 1C3 antibody, or a human IgG4 isotype control antibody that does not bind to Siglec-8. n=4 mice per group.

The ability of anti-Siglec-8 antibodies to deplete Siglec-8-positive mast cells in vivo was evaluated in a transgenic mouse model in which human Siglec-8 is selectively expressed on the surface of mast cells, eosinophils and basophils. Mice were treated twice by intra-peritoneal injection with 100 µg of HEKA IgG4 antibody, HEKA IgG1 non-fucosylated humanized antibody, murine 1C3 antibody (murine IgG2a isotype) or human IgG1 isotype control antibody. The two intra-peritoneal injections were administered 48 hours apart and peritoneal mast cells were isolated by lavage of the peritoneum 48 hours after the second injection. Non-fucosylated HEKA IgG1 antibody and murine 1C3 antibody administration led to significant depletion of peritoneal mast cells. In contrast, HEKA IgG4 antibody did not show significant mast cell depletion, indicating that an active isotype is required for in vivo depletion of mast cells (FIG. 8B). These results demonstrate that two different anti-Siglec-8 antibodies with an active isotype, murine IgG2a isotype or human IgG1 non-fucosylated isotype, directed against different regions of the extracellular domain of Siglec-8, can deplete Siglec-8-positive mast cells in vivo.

These results were unexpected since Siglec-8 has been described to be rapidly internalized and therefore not suitable for inducing ADCC activity. See O'Reilly et al., *Trends Pharmacol Sci.*, 2009, 30(5):240-248.

Humanized Anti-Siglec-8 Inhibits an IgE-Induced Passive Cutaneous Anaphylaxis Reaction Mediated by Human Mast Cells In Vivo Immunodeficient mice capable of generating abundant human mast cells after engraftment with human hematopoietic stem cells (HSC) have been described (Tanaka et al., J Immunol., 2012, 188(12):6145-55). The mouse strain designated NSGS (The Jackson Laboratory) is a derivative of the nonobese diabetic/severe combined immunodeficiency (NOD SCID) mouse with a deletion of the IL-2 receptor gamma-chain gene (NSG mouse). NSGS mice are additionally transgenic for 3 human cytokines (stem cell factor [SCF], IL-3, and GM-CSF) to facilitate engraftment with human hematopoietic stem cells. Upon engraftment of NSGS mice, human CD34$^+$ cells generate human eosinophils and enhanced numbers of human mast cells. Both cell types in engrafted NSGS mice express Siglec-8 at levels comparable to the levels on the corresponding cell types isolated from human peripheral blood and tissues. Thus, these mice provide an attractive model for evaluation of activity of anti-Siglec-8 antibodies on human cells in vivo.

In order to evaluate the effect of anti-Siglec-8 antibodies on mast cell activity in vivo, an IgE-mediated ear swelling model was established in humanized NSGS mice. In this model, passive cutaneous anaphylaxis (PCA), a Type I hypersensitivity reaction, was induced by injection of specific monoclonal anti-hapten IgE (anti-NP IgE) into one ear 24 hours prior to systemic injection of hapten-conjugated bovine serum albumin (NP-BSA). Chimeric anti-NP IgE with a human epsilon constant region was used to ensure human mast-cell specific responses to hapten were generated, and the immediate and late-phase edematous responses were measured by changes in ear thickness.

NSGS mice were engrafted with human CD34$^+$ HSC eight to twelve weeks prior to the assay. Chimeric monoclonal anti-NP IgE with a human constant region was intradermally injected in a mouse at a dose of 100 ng into the right ear to sensitize human but not mouse skin mast cells and PBS was intradermally injected into the left ear. Twenty four hours later, PCA was induced by intravenous injection of 0.5 mg NP-BSA. The mice were dosed by intravenous injection with 0.1 mg anti-Siglec-8 antibody (i.e., HEKA IgG4 antibody) or human IgG4 isotype control antibody 24 hours pre-sensitization or 2 hours post-sensitization with anti-NP IgE. Ear thickness was measured at time points up to four hours post-induction and at 24 hours post-induction to determine the early-phase and late-phase ear swelling response, respectively.

HEKA IgG4 antibody prevented or inhibited both early and late-phase cutaneous allergic reactions in this PCA in vivo model (FIG. 9). In this model, the early-phase reaction is dependent on mast-cell degranulation and histamine release while the late-phase reaction is dependent on mast cell secretion of de novo synthesized mediators, including cytokines, as well as eosinophil and basophil infiltration. HEKA IgG4 antibody also prevented or inhibited the PCA response in humanized NSGS mice when dosed either 24 hours pre-sensitization or 2 hours post-sensitization with anti-NP IgE (FIG. 9). No adverse effects of antibody treatment were observed during the course of these experiments.

Example 3

Generation and Characterization of Murine Anti-Siglec-8 Antibodies

The extracellular region of Siglec-8 is composed of three immunoglobulin-like domains: a unique N-terminal V-set domain (Domain 1) that binds ligands, followed by two C-set domains (Domains 2 and 3). Antibody 1C3 is a murine monoclonal antibody with an IgG2a heavy chain and kappa light chain raised against a recombinant extracellular domain of human Siglec-8 (SEQ ID NO:74). Monoclonal antibodies 1H10 and 4F11 are murine IgG1 heavy chain and kappa light chain antibodies raised against a recombinant extracellular domain of human Siglec-8 (SEQ ID NO:74). See Table 13. These antibodies were identified from a hybridoma screen for antibodies that bound to recombinant Siglec-8 sequences from human (SEQ ID NO:74) and non-human primates (SEQ ID NO:118).

TABLE 13

Amino acid sequences of HVRs from murine 1C3, 1H10, and 4F11 antibodies

| Antibody | Chain | HVR1 | HVR2 | HVR3 |
|---|---|---|---|---|
| 1C3 | Heavy Chain | SYAMS<br>SEQ ID NO: 88 | IISSGGSYTYYSDSVKG<br>SEQ ID NO: 91 | HETAQAAWFAY<br>SEQ ID NO: 94 |
| 1H10 | Heavy Chain | DYYMY<br>SEQ ID NO: 89 | RIAPEDGDTEYAPKFQG<br>SEQ ID NO: 92 | EGNYYGSSILDY<br>SEQ ID NO: 95 |
| 4F11 | Heavy Chain | SSWMN<br>SEQ ID NO: 90 | QIYPGDDYTNYNGKFKG<br>SEQ ID NO: 93 | LGPYGPFAD<br>SEQ ID NO: 96 |
| 1C3 | Light Chain | SASSSVSYMH<br>SEQ ID NO: 97 | DTSKLAY<br>SEQ ID NO: 100 | QQWSSNPPT<br>SEQ ID NO: 103 |
| 1H10 | Light Chain | RASQDITNYLN<br>SEQ ID NO: 98 | FTSRLHS<br>SEQ ID NO: 101 | QQGNTLPWT<br>SEQ ID NO: 104 |

TABLE 13 -continued

Amino acid sequences of HVRs from murine 1C3, 1H10, and 4F11 antibodies

| Antibody | Chain | HVR1 | HVR2 | HVR3 |
|---|---|---|---|---|
| 4F11 | Light Chain | SASSSVSYMY SEQ ID NO: 99 | DTSSLAS SEQ ID NO: 102 | QQWNSDPYT SEQ ID NO: 105 |

To identify the region comprising the epitope for anti-Siglec-8 antibodies, fusion proteins containing each of the Siglec-8 extracellular domains fused to human Ig-Fc were expressed and purified from CHO cells. Fusion proteins containing human Domain 1 (SEQ ID NO:115), Domains 1 and 2 (SEQ ID NO:116); or Domains 1, 2, and 3 (SEQ ID NO:117) were used in ELISA assays for determination of antibody binding. In some experiments, specificity of antibodies for human Siglec-8 was evaluated in comparison with a fusion protein containing the extracellular Domains 1, 2, and 3 of Siglec-8 (SEQ ID NO:118) from the olive baboon (*Papio anubis*) (National Center for Biotechnology Information reference sequence XP_009193370.1).

For the antibody binding assays, ELISA plates (MaxiSorp; Nunc) were coated overnight at 4° C. with fusion protein at 0.2 µg/ml and blocked for 1 hour at room temperature with 2% BSA in PBS. Antibodies at 1 µg/ml were added and the plates were incubated for 2 hours at room temperature. After washing the plates, horseradish peroxidase conjugated secondary antibody was added and the plates were incubated for 1 hour. Secondary antibodies were anti-human H+L HRP (Jackson ImmunoResearch, Catalog Number 709-035-149) for humanized antibodies or anti-mouse H+L HRP (Jackson ImmunoResearch, Catalog Number 715-035-151) for mouse antibodies. The plates were developed with TMB Substrate (Sigma, Catalog Number T0440-1L).

The murine 2E2 antibody and the HEKA IgG1 antibody bound to the Domain 1 fusion protein, indicating that the epitope for these two antibodies resides in the N-terminal ligand-binding domain (Table 14). In contrast, murine 1C3 antibody bound to the Domain 1 and Domain 2 fusion protein but did not demonstrate detectable binding to the Domain 1 fusion protein, indicating that the epitope for this antibody is in Domain 2 (Table 14).

TABLE 14

Binding of anti-Siglec-8 antibodies to epitopes in human Siglec-8

| Antibody | Domain 1-Fc (SEQ ID NO: 115) | Domain 1 + 2-Fc (SEQ ID NO: 116) | Domain 1 + 2 + 3-Fc (SEQ ID NO: 117) | Epitope domain |
|---|---|---|---|---|
| 2E2 | + | + | + | 1 |
| HEKA | + | + | + | 1 |
| 1C3 | − | + | + | 2 |

The murine 4F11 and 1H10 antibodies bound to human Siglec-8 and the predicted Siglec-8 protein sequence from the olive baboon (*Papio anubis*) (National Center for Biotechnology Information reference sequence XP_009193370.1). In ELISA screens of domain fusion proteins and on Western blots of reduced SDS-PAGE gels, 4F11 recognized a linear epitope in human Siglec-8 Domain 1 and 1H10 recognized a linear epitope that included sequences in human Siglec-8 Domain 3. 1C3 did not recognize denatured sequences in human Siglec-8 Domain 2 indicating it recognized a conformational epitope. Antibodies 4F11 and 1H10 show potent depletion of eosinophils from human peripheral blood leukocytes in the presence of 50 ng/ml IL-5, with an $EC_{50}$ of 5.9 and 41 ng/ml, respectively (Table 15). Murine 1C3 antibody and murine 2E2 antibody specific for human Siglec-8 did not cross-react with baboon Siglec-8.

TABLE 15

Binding of anti-Siglec-8 antibodies to epitopes in human or baboon Siglec-8 and depleting activity of the antibodies for human eosinophils

| Antibody | Epitope in human Siglec-8 domain | Linear epitope (reduced SDS-PAGE) | Baboon cross-reactivity (ELISA) | Mean $EC_{50}$ (ng/ml) for eosinophil killing (2 donors) |
|---|---|---|---|---|
| 4F11 | 1 | + | + | 5.9 |
| 1H10 | 3 | + | + | 41 |
| 1C3 | 2 | − | − | 7.7 |
| 2E2 | 1 | + | − | 6.9 |

Mean EC50 indicates mean half-maximal antibody concentrations required for eosinophil depletion from 2 independent assays.

Figure 10:
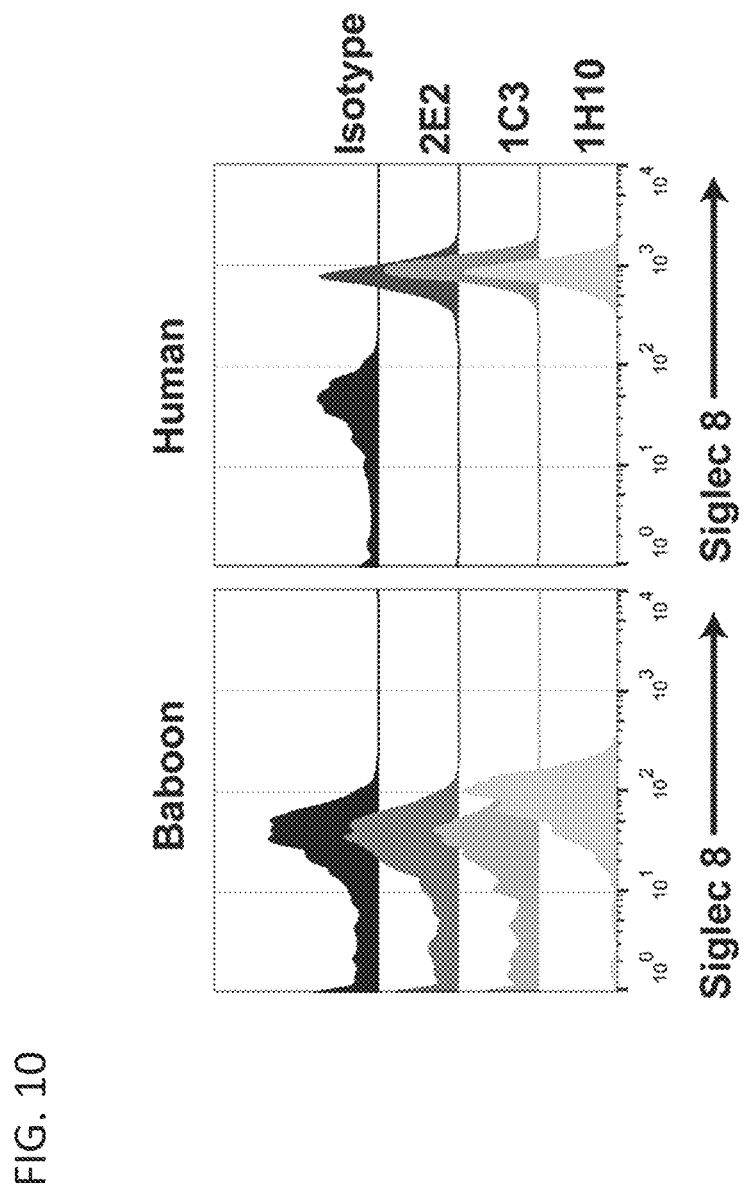
FIG. 10 is a series of histograms showing binding of murine anti-Siglec-8 monoclonal antibodies 2E2, 1C3, and 1H10 to baboon and human eosinophils (CD49+ CD16− SSC$^{high}$ cells) as demonstrated by flow cytometry. Histograms show number of baboon or human blood eosinophils plotted against fluorescence intensity for each antibody in comparison to a mouse IgG1 isotype control antibody that does not bind to Siglec-8.

Binding of antibodies to human and baboon eosinophils was determined by flow cytometry. Human or baboon peripheral blood leukocyte preparations were labeled with saturating amounts of anti-Siglec-8 monoclonal antibodies 2E2, 1C3, and 1H10 or mouse IgG1 isotype control antibody. Anti-Siglec-8 antibodies were visualized by a secondary anti-mouse IgG H+L AlexaFluor 647. Eosinophils were identified using primate cross-reactive monoclonal antibodies to CD49d and CD16 along with high granularity scatter. Murine 1H10 antibody bound to baboon and human eosinophils while mouse 2E2 and 1C3 antibodies bound to human eosinophils but did not cross-react with baboon eosinophils (FIG. 10). These results were unexpected since other monoclonal mouse anti-Siglec-8 antibodies that bind to human Siglec-8 have been shown to not recognize non-human primate Siglec-8. See Hudson et al., *J. Clin. Immunol.*, 2011, 31(6):1045-53.

SEQUENCES

Amino acid sequence of mouse 2E2 heavy chain variable domain
QVQLKESGPGLVAPSQSLSITCTVSGFSLTIYGAHWVRQPPGKGLEWLGVIWAGGSTNY
NSALMSRLSISKDNSKSQVFLKINSLQTDDTALYYCARDGSSPYYYSMEYWGQGTSVTV
SS (SEQ ID NO: 1)

SEQUENCES

Amino acid sequence of 2E2 RHA heavy chain variable domain
EVQLVESGGGLVQPGGSLRLSCAASGFSLTIYGAHWVRQAPGKGLEWVSVIWAGGSTN
YNSALMSRFTISKDNSKNTVYLQMNSLRAEDTAVYYCARDGSSPYYYSMEYWGQGTT
VTVSS (SEQ ID NO: 2)

Amino acid sequence of 2E2 RHB heavy chain variable domain
EVQLVESGGGLVQPGGSLRLSCAVSGFSLTIYGAHWVRQAPGKGLEWLGVIWAGGSTN
YNSALMSRLSISKDNSKNTVYLQMNSLRAEDTAVYYCARDGSSPYYYSMEYWGQGTT
VTVSS (SEQ ID NO: 3)

Amino acid sequence of 2E2 RHC heavy chain variable domain
EVQLVESGGGLVQPGGSLRLSCAVSGFSLTIYGAHWVRQAPGKGLEWVSVIWAGGSTN
YNSALMSRFTISKDNSKNTVYLQMNSLRAEDTAVYYCARDGSSPYYYSMEYWGQGTT
VTVSS (SEQ ID NO: 4)

Amino acid sequence of 2E2 RHD heavy chain variable domain
EVQLVESGGGLVQPGGSLRLSCAASGFSLTIYGAHWVRQAPGKGLEWLSVIWAGGSTN
YNSALMSRFTISKDNSKNTVYLQMNSLRAEDTAVYYCARDGSSPYYYSMEYWGQGTT
VTVSS (SEQ ID NO: 5)

Amino acid sequence of 2E2 RHE heavy chain variable domain
EVQLVESGGGLVQPGGSLRLSCAASGFSLTIYGAHWVRQAPGKGLEWVGVIWAGGSTN
YNSALMSRFTISKDNSKNTVYLQMNSLRAEDTAVYYCARDGSSPYYYSMEYWGQGTT
VTVSS (SEQ ID NO: 6)

Amino acid sequence of 2E2 RHF heavy chain variable domain
EVQLVESGGGLVQPGGSLRLSCAASGFSLTIYGAHWVRQAPGKGLEWVSVIWAGGSTN
YNSALMSRLTISKDNSKNTVYLQMNSLRAEDTAVYYCARDGSSPYYYSMEYWGQGTT
VTVSS (SEQ ID NO: 7)

Amino acid sequence of 2E2 RHG heavy chain variable domain
EVQLVESGGGLVQPGGSLRLSCAASGFSLTIYGAHWVRQAPGKGLEWVSVIWAGGSTN
YNSALMSRFSISKDNSKNTVYLQMNSLRAEDTAVYYCARDGSSPYYYSMEYWGQGTT
VTVSS (SEQ ID NO: 8)

Amino acid sequence of 2E2 RHA2 heavy chain variable domain
QVQLQESGPGLVKPSETLSLTCTVSGGSISIYGAHWIRQPPGKGLEWIGVIWAGGSTNYN
SALMSRVTISVDTSKNQFSLKLSSVTAADTAVYYCARDGSSPYYYSMEYWGQGTLVTV
SS (SEQ ID NO: 9)

Amino acid sequence of 2E2 RHB2 heavy chain variable domain
QVQLQESGPGLVKPSETLSLTCTVSGFSLTIYGAHWVRQPPGKGLEWLGVIWAGGSTNY
NSALMSRLSISKDNSKNQVSLKLSSVTAADTAVYYCARDGSSPYYYSMEYWGQGTLVT
VSS (SEQ ID NO: 10)

Amino acid sequence of 2E2 RHE S-G mutant heavy chain variable domain
EVQLVESGGGLVQPGGSLRLSCAASGFSLTIYGAHWVRQAPGKGLEWVGVIWAGGSTN
YNSALMSRFTISKDNSKNTVYLQMNSLRAEDTAVYYCARDGSSPYYYGMEYWGQGTT
VTVSS (SEQ ID NO: 11)

Amino acid sequence of 2E2 RHE E-D heavy chain variable domain
EVQLVESGGGLVQPGGSLRLSCAASGFSLTIYGAHWVRQAPGKGLEWVGVIWAGGSTN
YNSALMSRFTISKDNSKNTVYLQMNSLRAEDTAVYYCARDGSSPYYYSMDYWGQGTT
VTVSS (SEQ ID NO: 12)

Amino acid sequence of 2E2 RHE Y-V heavy chain variable domain
EVQLVESGGGLVQPGGSLRLSCAASGFSLTIYGAHWVRQAPGKGLEWVGVIWAGGSTN
YNSALMSRFTISKDNSKNTVYLQMNSLRAEDTAVYYCARDGSSPYYYSMEVWGQGTT
VTVSS (SEQ ID NO: 13)

Amino acid sequence of 2E2 RHE triple mutant heavy chain variable domain
EVQLVESGGGLVQPGGSLRLSCAASGFSLTIYGAHWVRQAPGKGLEWVGVIWAGGSTN
YNSALMSRFTISKDNSKNTVYLQMNSLRAEDTAVYYCARDGSSPYYYGMDVWGQGTT
VTVSS (SEQ ID NO: 14)

Amino acid sequence of mouse 2E2 light chain variable domain
QIILTQSPAIMSASPGEKVSITCSATSSVSYMHWFQQKPGTSPKLWIYSTSNLASGVPVRF
SGSGSGTSYSLTISRMEAEDAATYYCQQRSSYPFTFGSGTKLEIK (SEQ ID NO: 15)

Amino acid sequence of 2E2 RKA light chain variable domain
EIVLTQSPATLSLSPGERATLSCSATSSVSYMHWFQQKPGQAPRLLIYSTSNLASGIPARF
SGSGSGTDFTLTISSLEPEDFAVYYCQQRSSYPFTFGPGTKLDIK (SEQ ID NO: 16)

Amino acid sequence of 2E2 RKB light chain variable domain
EIILTQSPATLSLSPGERATLSCSATSSVSYMHWFQQKPGQAPRLWIYSTSNLASGVPARF
SGSGSGTDYTLTISSLEPEDFAVYYCQQRSSYPFTFGPGTKLDIK (SEQ ID NO: 17)

-continued

SEQUENCES

Amino acid sequence of 2E2 RKC light chain variable domain
EIILTQSPATLSLSPGERATLSCSATSSVSYMHWFQQKPGQAPRLLIYSTSNLASGIPARFS
GSGSGTDFTLTISSLEPEDFAVYYCQQRSSYPFTFGPGTKLDIK (SEQ ID NO: 18)

Amino acid sequence of 2E2 RKD light chain variable domain
EIVLTQSPATLSLSPGERATLSCSATSSVSYMHWFQQKPGQAPRLWIYSTSNLASGIPARF
SGSGSGTDFTLTISSLEPEDFAVYYCQQRSSYPFTFGPGTKLDIK (SEQ ID NO: 19)

Amino acid sequence of 2E2 RKE light chain variable domain
EIVLTQSPATLSLSPGERATLSCSATSSVSYMHWFQQKPGQAPRLLIYSTSNLASGVPARF
SGSGSGTDFTLTISSLEPEDFAVYYCQQRSSYPFTFGPGTKLDIK (SEQ ID NO: 20)

Amino acid sequence of 2E2 RKF light chain variable domain
EIVLTQSPATLSLSPGERATLSCSATSSVSYMHWFQQKPGQAPRLLIYSTSNLASGIPARF
SGSGSGTDYTLTISSLEPEDFAVYYCQQRSSYPFTFGPGTKLDIK (SEQ ID NO: 21)

Amino acid sequence of 2E2 RKG light chain variable domain
EIVLTQSPATLSLSPGERATLSCSATSSVSYMHWYQQKPGQAPRLLIYSTSNLASGIPARF
SGSGSGTDFTLTISSLEPEDFAVYYCQQRSSYPFTFGPGTKLDIK (SEQ ID NO: 22)

Amino acid sequence of 2E2 RKA F-Y mutant light chain variable domain
EIVLTQSPATLSLSPGERATLSCSATSSVSYMHWFQQKPGQAPRLLIYSTSNLASGIPARF
SGSGSGTDFTLTISSLEPEDFAVYYCQQRSSYPYTFGPGTKLDIK (SEQ ID NO: 23)

Amino acid sequence of 2E2 RKF F-Y mutant light chain variable domain
EIVLTQSPATLSLSPGERATLSCSATSSVSYMHWFQQKPGQAPRLLIYSTSNLASGIPARF
SGSGSGTDYTLTISSLEPEDFAVYYCQQRSSYPYTFGPGTKLDIK (SEQ ID NO: 24)

Amino acid sequence of HEKA IgG1 heavy chain and HEKF IgG1 heavy chain
EVQLVESGGGLVQPGGSLRLSCAASGFSLTIYGAHWVRQAPGKGLEWVGVIWAGGSTN
YNSALMSRFTISKDNSKNTVYLQMNSLRAEDTAVYYCARDGSSPYYYSMEYWGQGTT
VTVSSASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKRVEPKSCDKTHTCPPCPAP
ELLGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQVY
TLPPSREEMTKNQVSLTCLVKGFYPSDIAVEWESNGQPENNYKTTPPVLDSDGSFFLYSK
LTVDKSRWQQGNVFSCSVMHEALHNHYTQKSLSLSPG (SEQ ID NO: 75)

Amino acid sequence of HEKA kappa light chain
EIVLTQSPATLSLSPGERATLSCSATSSVSYMHWFQQKPGQAPRLLIYSTSNLASGIPARF
SGSGSGTDFTLTISSLEPEDFAVYYCQQRSSYPFTFGPGTKLDIKRTVAAPSVFIFPPSDEQ
LKSGTASVVCLLNNFYPREAKVQWKVDNALQSGNSQESVTEQDSKDSTYSLSSTLTLSK
ADYEKHKVYACEVTHQGLSSPVTKSFNRGEC (SEQ ID NO: 76)

Amino acid sequence of HEKF kappa light chain
EIVLTQSPATLSLSPGERATLSCSATSSVSYMHWFQQKPGQAPRLLIYSTSNLASGIPARF
SGSGSGTDYTLTISSLEPEDFAVYYCQQRSSYPFTFGPGTKLDIKRTVAAPSVFIFPPSDEQ
LKSGTASVVCLLNNFYPREAKVQWKVDNALQSGNSQESVTEQDSKDSTYSLSSTLTLSK
ADYEKHKVYACEVTHQGLSSPVTKSFNRGEC (SEQ ID NO: 77)

Amino acid sequence of IgG1 heavy chain constant region
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGG
PSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSR
EEMTKNQVSLTCLVKGFYPSDIAVEWESNGQPENNYKTTPPVLDSDGSFFLYSKLTVDK
SRWQQGNVFSCSVMHEALHNHYTQKSLSLSPG (SEQ ID NO: 78)

Amino acid sequence of IgG4 heavy chain constant region
(IgG4 contains a S228P mutation)
ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCPPCPAPEFLGGPSV
FLFPPKPKDTLMISRTPEVTCVVVDVSQEDPEVQFNWYVDGVEVHNAKTKPREEQFNST
YRVVSVLTVLHQDWLNGKEYKCKVSNKGLPSSIEKTISKAKGQPREPQVYTLPPSQEEM
TKNQVSLTCLVKGFYPSDIAVEWESNGQPENNYKTTPPVLDSDGSFFLYSRLTVDKSRW
QEGNVFSCSVMHEALHNHYTQKSLSLSLG (SEQ ID NO: 79)

Amino acid sequence of Ig kappa light chain constant region
RTVAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC (SEQ ID NO: 80)

Amino acid sequence of murine 2C4 and 2E2 IgG1 heavy chain
QVQLKRASGPGLVAPSQSLSITCTVSGFSLTIYGAHWVRQPPGKGLEWLGVIWAGGSTN
YNSALMSRLSISKDNSKSQVFLKINSLQTDDTALYYCARDGSSPYYYSMEYWGQGTSVT
VSSAKTTPPSVYPLAPGSAAQTNSMVTLGCLVKGYFPEPVTVTWNSGSLSSGVHTFPAV
LESDLYTLSSSVTVPSSPRPSETVTCNVAHPASSTKVDKKIVPRDCGCKPCICTVPEVSSV
FIFPPKPKDVLTITLTPKVTCVVVDISKDDPEVQFSWFVDDVEVHTAQTQPREEQFNSTF

```
RSVSELPIMHQDWLNGKEFKCRVNSAAFPAPIEKTISKTKGRPKAPQVYTIPPPKEQMAK
DKVSLTCMITDFFPEDITVEWQWNGQPAENYKNTQPIMNTNGSYFVYSKLNVQKSNWE
AGNTFTCSVLHEGLHNHHTEKSLSHSPG (SEQ ID NO: 81)

Amino acid sequence of murine 2C4 kappa light chain
EIILTQSPAIMSASPGEKVSITCSATSSVSYMHWFQQKPGTSPKLWIYSTSNLASGVPVRF
SGSGSGTSYSLTISRMEAEDAATYYCQQRSSYPFTFGSGTKLEIKADAAPTVSIFPPSSEQ
LTSGGASVVCFLNNFYPKDINVKWKIDGSERQNGVLNSWTDQDSKDSTYSMSSTLTLT
KDEYERHNSYTCEATHKTSTSPIVKSFNRNEC (SEQ ID NO: 82)

Amino acid sequence of murine 2E2 kappa light chain
QIILTQSPAIMSASPGEKVSITCSATSSVSYMHWFQQKPGTSPKLWIYSTSNLASGVPVRF
SGSGSGTSYSLTISRMEAEDAATYYCQQRSSYPFTFGSGTKLEIKADAAPTVSIFPPSSEQ
LTSGGASVVCFLNNFYPKDINVKWKIDGSERQNGVLNSWTDQDSKDSTYSMSSTLTLT
KDEYERHNSYTCEATHKTSTSPIVKSFNRNEC (SEQ ID NO: 83)

Amino acid sequence of chimeric 2C4 and 2E2 IgG1 heavy chain
QVQLKRASGPGLVAPSQSLSITCTVSGFSLTIYGAHWVRQPPGKGLEWLGVIWAGGSTN
YNSALMSRLSISKDNSKSQVFLKINSLQTDDTALYYCARDGSSPYYYSMEYWGQGTSVT
VSSASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKRVEPKSCDKTHTCPPCPAPEL
LGGPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLP
PSREEMTKNQVSLTCLVKGFYPSDIAVEWESNGQPENNYKTTPPVLDSDGSFFLYSKLT
VDKSRWQQGNVFSCSVMHEALHNHYTQKSLSLSPG (SEQ ID NO: 84)

Amino acid sequence of chimeric 2C4 kappa light chain
EIILTQSPAIMSASPGEKVSITCSATSSVSYMHWFQQKPGTSPKLWIYSTSNLASGVPVRF
SGSGSGTSYSLTISRMEAEDAATYYCQQRSSYPFTFGSGTKLEIKRTVAAPSVFIFPPSDE
QLKSGTASVVCLLNNFYPREAKVQWKVDNALQSGNSQESVTEQDSKDSTYSLSSTLTLS
KADYEKHKVYACEVTHQGLSSPVTKSFNRGEC (SEQ ID NO: 85)

Amino acid sequence of chimeric 2E2 kappa light chain
QIILTQSPAIMSASPGEKVSITCSATSSVSYMHWFQQKPGTSPKLWIYSTSNLASGVPVRF
SGSGSGTSYSLTISRMEAEDAATYYCQQRSSYPFTFGSGTKLEIKRTVAAPSVFIFPPSDE
QLKSGTASVVCLLNNFYPREAKVQWKVDNALQSGNSQESVTEQDSKDSTYSLSSTLTLS
KADYEKHKVYACEVTHQGLSSPVTKSFNRGEC (SEQ ID NO: 86)

Amino acid sequence of HEKA IgG4 heavy chain
(IgG4 contains a S228P mutation)
EVQLVESGGGLVQPGGSLRLSCAASGFSLTIYGAHWVRQAPGKGLEWVGVIWAGGSTN
YNSALMSRFTISKDNSKNTVYLQMNSLRAEDTAVYYCARDGSSPYYYSMEYWGQGTT
VTVSSASTKGPSVFPLAPCSRSTSESTAALGCLVKDYFPEPVTVSWNSGALTSGVHTFPA
VLQSSGLYSLSSVVTVPSSSLGTKTYTCNVDHKPSNTKVDKRVESKYGPPCPPCPAPEFL
GGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPP
SQEEMTKNQVSLTCLVKGFYPSDIAVEWESNGQPENNYKTTPPVLDSDGSFFLYSRLTV
DKSRWQEGNVFSCSVMHEALHNHYTQKSLSLSLG (SEQ ID NO: 87)

Amino acid sequence of mouse 1C3 heavy chain variable domain
(underlined residues comprise CDRs H1 and H2 according to Chothia
numbering)
EVQVVESGGDLV KSGGSLKLSCAASGFPFSSYAMSWVRQTPDKRLEWVAIISSGGSYTY
YSDSVKGRFTISRDNAKNTLYLQM SSLKSEDTAMYYCARHETAQAAWFAYWGQTLV
TVSA (SEQ ID NO: 106)

Amino acid sequence of mouse 1H10 heavy chain variable domain
(underlined residues comprise CDRs H1 and H2 according to Chothia
numbering)
EVQLQQSGAELVRPGASVKLSCTASGFNIKDYYMYWVKQRPEQGLEWIGRIAPEDGDT
EYAPKFQGKATVTADTSSNTAYLHLSSLTSEDTAVYYCTTEGNYYGSSILDYWGQGTTL
TVSS (SEQ ID NO: 107)

Amino acid sequence of mouse 4F11 heavy chain variable domain
(underlined residues comprise CDRs H1 and H2 according to Chothia
numbering)
QVQLQQSGAELVKPGASVKISCKASGYAFRSSWMNWVKQRPGKGLEWIGQIYPGDDY
TNYNGKFKGKVTLTADRSSSTAYMQLSSLTSEDSAVYFCARLGPYGPFADWGQGTLVT
VSA (SEQ ID NO: 108)

Amino acid sequence of mouse 1C3 light chain variable domain
QIVLTQSPAIMSASPGEKVTMTCSASSSVSYMHWYQQKSGTSPKRWIYDTSKLAYGVPA
RFSGSGSGTSYSLTISSMEAEDAATYYCQQWSSNPPTFGGGTKLEIK (SEQ ID NO: 109)

Amino acid sequence of mouse 1H10 light chain variable domain
DIQMTQTTSSLSASLGDRVTISCRASQDITNYLNWYQQKPDGTVKLLIYFTSRLHSGVPS
RFSGSGSGTDYSLTISNLEQEDIATYFCQQGNTLPWTFGGGTKLEIK (SEQ ID NO: 110)
```

-continued

SEQUENCES

Amino acid sequence of mouse 4F11 light chain variable domain
QIVLTQSPAIVSASPGEKVTMTCSASSSVSYMYWYQQRPGSSPRLLIYDTSSLASGVPVR
FSGSGSGTSYSLTISRIESEDAANYYCQQWNSDPYTFGGGTKLEIK (SEQ ID NO: 111)

Amino acid sequence of human Siglec-8 Domain 1
MEGDRQYGDGYLLQVQELVTVQEGLCVHVPCSFSYPQDGWTDSDPVHGYWFRAGDR
PYQDAPVATNNPDREVQAETQGRFQLLGDIWSNDCSLSIRDARKRDKGSYFFRLERGSM
KWSYKSQLNYKTKQLSVFVTALTHRP (SEQ ID NO: 112)

Amino acid sequence of human Siglec-8 Domain 2
DILILGTLESGHSRNLTCSVPWACKQGTPPMISWIGASVSSPGPTTARSSVLTLTPKPQDH
GTSLTCQVTLPGTGVTTTSTVRLDVS (SEQ ID NO: 113)

Amino acid sequence of human Siglec-8 Domain 3
YPPWNLTMTVFQGDATASTALGNGSSLSVLEGQSLRLVCAVNSNPPARLSWTRGSLTL
CPSRSSNPGLLELPRVHVRDEGEFTCRAQNAQGSQHISLSLSLQNEGTGTSRPVSQVTLA
AVGG (SEQ ID NO: 114)

Amino acid sequence of human Siglec-8 Domain 1 Fusion Protein
MEGDRQYGDGYLLQVQELVTVQEGLCVHVPCSFSYPQDGWTDSDPVHGYWFRAGDR
PYQDAPVATNNPDREVQAETQGRFQLLGDIWSNDCSLSIRDARKRDKGSYFFRLERGSM
KWSYKSQLNYKTKQLSVFVTALTHRPIEGRSDKTHTCPPCPAPELLGGPSVFLFPPKPKD
TLMISRTPEVTCVVVDVSHEDPEVKFNWYVDGVEVHNAKTKPREEQYNSTYRVVSVLT
VLHQDWLNGKEYKCKVSNKALPAPIEKTISKAKGQPREPQVYTLPPSREEMTKNQVSLT
CLVKGFYPSDIAVEWESNGQPENNYKTTPPVLDSDGSFFLYSKLTVDKSRWQQGNVFSC
SVMHEALHNHYTQKSLSLSPGK (SEQ ID NO: 115)

Amino acid sequence of human Siglec-8 Domains 1 and 2 Fusion Protein
MEGDRQYGDGYLLQVQELVTVQEGLCVHVPCSFSYPQDGWTDSDPVHGYWFRAGDR
PYQDAPVATNNPDREVQAETQGRFQLLGDIWSNDCSLSIRDARKRDKGSYFFRLERGSM
KWSYKSQLNYKTKQLSVFVTALTHRPDILILGTLESGHSRNLTCSVPWACKQGTPPMIS
WIGASVSSPGPTTARSSVLTLTPKPQDHGTSLTCQVTLPGTGVTTTSTVRLDVSIEGRSDK
THTCPPCPAPELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAPIEKTISKA
KGQPREPQVYTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPGK (SEQ ID NO: 116)

Amino acid sequence of human Siglec-8 Domains 1, 2, and 3 Fusion Protein
MEGDRQYGDGYLLQVQELVTVQEGLCVHVPCSFSYPQDGWTDSDPVHGYWFRAGDR
PYQDAPVATNNPDREVQAETQGRFQLLGDIWSNDCSLSIRDARKRDKGSYFFRLERGSM
KWSYKSQLNYKTKQLSVFVTALTHRPDILILGTLESGHSRNLTCSVPWACKQGTPPMIS
WIGASVSSPGPTTARSSVLTLTPKPQDHGTSLTCQVTLPGTGVTTTSTVRLDVSYPPWNL
TMTVFQGDATASTALGNGSSLSVLEGQSLRLVCAVNSNPPARLSWTRGSLTLCPSRSSN
PGLLELPRVHVRDEGEFTCRAQNAQGSQHISLSLSLQNEGTGTSRPVSQVTLAAVGGIEG
RSDKTHTCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALPAPIEKTI
SKAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPGK (SEQ ID NO: 117)

Amino acid sequence of baboon Siglec-8 Domains 1, 2, and 3 Fusion Protein
MEGDRKYGDGYLLQVQELVTVQEGLCVHVPCSFSYPKDDWTYSDPVHGYWFRAGDR
PYQEAPVATNNPDTEVQAETQGRFQLLGDRWSNDCSLSINDARKGDEGSYFFRLERGR
MKWSYKSQLNYKAKQLSVFVTALTQRPDILIQGTLESGHPRNLTCSVPWACEQRMPPMI
SWIGTSVSSLGPITARFSVLTLIPKPQDHGTSLTCQVTLPGTGVTTTRTVQLDVSYPPWNL
TVTVFQGDDTASTALGNGSSLSVLEGQSLRLVCAVDSNPPARLSWTRGSLTLCPSQPWN
PGLLELLRVHVKDEGEFTCQAENPRGSQHISLSLSLQNEGTGTARPVSEVTLAAVGGIEG
RSDKTHTCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESNGQPENNYKTTP
PVLDSDGSFFLYSKLTVDKSRWQQGNVFSCSVMHEALHNHYTQKSLSLSPGK (SEQ ID NO: 118)

Amino acid sequence of baboon Siglec-8 Domains 1, 2, and 3
MEGDRKYGDGYLLQVQELVTVQEGLCVHVPCSFSYPKDDWTYSDPVHGYWFRAGDR
PYQEAPVATNNPDTEVQAETQGRFQLLGDRWSNDCSLSINDARKGDEGSYFFRLERGR
MKWSYKSQLNYKAKQLSVFVTALTQRPDILIQGTLESGHPRNLTCSVPWACEQRMPPMI
SWIGTSVSSLGPITARFSVLTLIPKPQDHGTSLTCQVTLPGTGVTTTRTVQLDVSYPPWNL
TVTVFQGDDTASTALGNGSSLSVLEGQSLRLVCAVDSNPPARLSWTRGSLTLCPSQPWN
PGLLELLRVHVKDEGEFTCQAENPRGSQHISLSLSLQNEGTGTARPVSEVTLAAVGG
(SEQ ID NO: 119)

What is claimed is:

1. An antibody that binds to a human Siglec-8, wherein the antibody comprises a heavy chain variable region and a light chain variable region, wherein the heavy chain variable region comprises the amino acid sequence of SEQ ID NO:6 or the light chain variable region comprises the amino acid sequence of SEQ ID NOs:16 or 21.

2. The antibody of claim 1, wherein the antibody comprises a heavy chain Fc region comprising a human IgG Fc region.

3. The antibody of claim 2, wherein the human IgG Fc region comprises a human IgG1 or a human IgG4.

4. The antibody of claim 3, wherein the human IgG4 comprises the amino acid substitution S228P, and wherein the amino acid residues are numbered according to the EU index as in Kabat.

5. The antibody of claim 1, wherein the heavy chain comprises the amino acid sequence of SEQ ID NO:75 and the light chain comprises the amino acid sequence of SEQ ID NO:76.

6. The antibody of claim 1, wherein the heavy chain comprises the amino acid sequence of SEQ ID NO:87 and the light chain comprises the amino acid sequence of SEQ ID NO:76.

7. The antibody of claim 1, wherein the antibody has been engineered to improve antibody-dependent cell-mediated cytotoxicity (ADCC) activity.

8. The antibody of claim 1, wherein one or two of the heavy chains of the antibody is non-fucosylated.

9. A nucleic acid encoding the antibody of claim 1.

10. A vector comprising the nucleic acid of claim 9.

11. The vector of claim 10, which is an expression vector.

12. An isolated host cell comprising the nucleic acid of claim 9.

13. A method of producing an antibody comprising culturing the host cell of claim 12 under a condition that produces the antibody.

14. The method of claim 13, further comprising recovering the antibody produced by the host cell.

15. An anti-Siglec-8 antibody produced by a method comprising culturing a host cell comprising the nucleic acid of claim 9 under a condition that produces the antibody, wherein the host cell is mammalian cell.

16. The antibody of claim 1, wherein the heavy chain variable region comprises the amino acid sequence of SEQ ID NO:6 and the light chain variable region comprises the amino acid sequence of SEQ ID NO:16.

17. The antibody of claim 1, wherein the heavy chain variable region comprises the amino acid sequence of SEQ ID NO:6 and the light chain variable region comprises the amino acid sequence of SEQ ID NO:21.

18. A composition comprising the antibody of claim 16 or 17, wherein the antibody comprises a Fc region and N-glycoside-linked carbohydrate chains linked to the Fc region, wherein less than 50% of the N-glycoside-linked carbohydrate chains contain a fucose residue.

19. The composition of claim 18, wherein substantially none of the N-glycoside-linked carbohydrate chains contain a fucose residue.

20. The composition of claim 18, further comprising a pharmaceutically acceptable carrier.

21. The antibody of claim 16 or 17, wherein the antibody kills mast cells expressing Siglec-8 by ADCC activity.

22. The antibody of claim 21, wherein the antibody depletes mast cells expressing Siglec-8 in a subject when a therapeutically effective amount is administered.

23. The antibody of claim 22, wherein the antibody depletes at least about 20% of the mast cells expressing Siglec-8 in a sample obtained from the subject as compared to a baseline level before treatment.

24. The antibody of claim 23, wherein the sample is a tissue sample or a biological fluid sample.

25. The antibody of claim 24, wherein the tissue sample is one or more selected from the group consisting of: skin, lung, bone marrow, and nasal polyps.

26. The antibody of claim 24, wherein the biological fluid sample is one or more selected from the group consisting of: blood, bronchoalveolar lavage, and nasal lavage.

27. The antibody of claim 21, wherein the antibody has been engineered to improve antibody-dependent cell-mediated cytotoxicity (ADCC) activity.

28. The antibody of claim 27, wherein the antibody comprises at least one amino acid substitution in the Fc region that improves ADCC activity.

29. The antibody of claim 21, wherein one or two of the heavy chains of the antibody is non-fucosylated.

30. The antibody of claim 29, wherein the antibody is produced in a cell line having a alpha1,6-fucosyltransferase (Fut8) knockout.

31. The antibody of claim 29, wherein the antibody is produced in a cell line overexpressing β1,4-N-acetylglycosminyltransferase III (GnT-III).

32. The antibody of claim 31, wherein the cell line additionally overexpresses Golgi µ-mannosidase II (ManII).

33. The antibody of claim 21, wherein the antibody is a human IgG1 antibody.

34. A pharmaceutical composition comprising the antibody of claim 21 and a pharmaceutically acceptable carrier.

35. A method of depleting mast cells expressing Siglec-8 in a subject comprising administering to the subject an effective amount of the antibody of claim 16 or 17, wherein the antibody kills mast cells expressing Siglec-8 by ADCC activity.

36. The method of claim 35, wherein the antibody depletes at least about 20% of the mast cells expressing Siglec-8 in a sample obtained from the subject as compared to a baseline level before treatment.

37. The method of claim 36, wherein the sample is a tissue sample or a biological fluid sample.

38. The method of claim 37, wherein the tissue sample is one or more selected from the group consisting of: skin, lung, bone marrow, and nasal polyps.

39. The method of claim 37, wherein the biological fluid sample is one or more selected from the group consisting of: blood, bronchoalveolar lavage, and nasal lavage.

40. The method of claim 35, wherein the antibody has been engineered to improve antibody-dependent cell-mediated cytotoxicity (ADCC) activity.

41. The method of claim 40, wherein the antibody comprises at least one amino acid substitution in the Fc region that improves ADCC activity.

42. The method of claim 35, wherein one or two of the heavy chains of the antibody is non-fucosylated.

43. The method of claim 42, wherein the antibody is produced in a cell line having a alpha1,6-fucosyltransferase (Fut8) knockout.

44. The method of claim 42, wherein the antibody is produced in a cell line overexpressing β1,4-N-acetylglycosminyltransferase III (GnT-III).

45. The method of claim 44, wherein the cell line additionally overexpresses Golgi μ-mannosidase II (ManII).

46. The method of claim 35, wherein the antibody is a human IgG1 antibody.

47. The method of claim 35, wherein the subject has a disease mediated by cells expressing Siglec-8.

48. The method of claim 47, wherein the disease is selected from the group consisting of: asthma, allergic rhinitis, nasal polyposis, atopic dermatitis, chronic urticaria, mastocytosis, eosinophilic leukemia, and hypereosinophilic syndrome.

49. The method of claim 47, wherein the disease is selected from the group consisting of: pauci granulocytic asthma, acute or chronic airway hypersensitivity, eosinophilic esophagitis, Churg-Strauss syndrome, inflammation associated with a cytokine, inflammation associated with cells expressing Siglec-8, malignancy associated with cells expressing Siglec-8, physical urticaria, cold urticaria, pressure-urticaria, bullous pemphigoid, food allergy, and allergic bronchopulmonary aspergillosis (ABPA).

50. The method of claim 47, wherein the subject is suffering from asthma that is not adequately controlled by an inhaled corticosteroid, a short acting β2 agonist, a long acting β2 agonist, or a combination thereof.

51. The method of claim 35, wherein the antibody inhibits one or more symptoms of an allergic reaction.

52. The method of claim 51, wherein the allergic reaction is a Type I hypersensitivity reaction.

53. The antibody of claim 1, wherein the heavy chain comprises the amino acid sequence of SEQ ID NO:75 and the light chain comprises the amino acid sequence of SEQ ID NO:77.

54. The antibody of claim 1, wherein the heavy chain comprises the amino acid sequence of SEQ ID NO:87 and the light chain comprises the amino acid sequence of SEQ ID NO:77.

55. A pharmaceutical composition comprising the antibody of claim 1, 16 or 17 and a pharmaceutically acceptable carrier.

56. A method of treating a disease characterized by an increase of activated eosinophils or increased activity of mast cells expressing Siglec-8 in a subject, the method comprising administering to the subject an effective amount of the antibody of claim 1, 16 or 17.

57. The method of claim 56, wherein the antibody inhibits one or more symptoms of an allergic reaction.

58. The method of claim 57, wherein the allergic reaction is a Type I hypersensitivity reaction.

59. The method of claim 56, wherein the disease is selected from the group consisting of: asthma, allergic rhinitis, nasal polyposis, atopic dermatitis, chronic urticaria, mastocytosis, eosinophilic leukemia, and hypereosinophilic syndrome.

60. The method of claim 59, wherein the subject is suffering from asthma that is not adequately controlled by an inhaled corticosteroid, a short acting β2 agonist, a long acting β2 agonist, or a combination thereof.

61. The method of claim 56, wherein the disease is selected from the group consisting of: pauci granulocytic asthma, acute or chronic airway hypersensitivity, eosinophilic esophagitis, Churg-Strauss syndrome, inflammation associated with a cytokine, inflammation associated with cells expressing Siglec-8, malignancy associated with cells expressing Siglec-8, physical urticaria, cold urticaria, pressure-urticaria, bullous pemphigoid, food allergy, and allergic bronchopulmonary aspergillosis (ABPA).

62. A kit comprising the antibody of claim 1, 16 or 17.

63. An antibody that binds to a human Siglec-8, wherein the antibody comprises:
(a) a heavy chain variable region comprising:
(1) an HC-FR1 comprising the amino acid sequence of SEQ ID NO:26;
(2) an HVR-H1 comprising the amino acid sequence of SEQ ID NO:61;
(3) an HC-FR2 comprising the amino acid sequence of SEQ ID NO:34;
(4) an HVR-H2 comprising the amino acid sequence of SEQ ID NO:62;
(5) an HC-FR3 comprising the amino acid sequence of SEQ ID NO:38;
(6) an HVR-H3 comprising the amino acid sequence of SEQ ID NO:63; and
(7) an HC-FR4 comprising the amino acid sequence of SEQ ID NOs:45;
and
(b) a light chain variable region comprising:
(1) an LC-FR1 comprising the amino acid sequence of SEQ ID NO:48;
(2) an HVR-L1 comprising the amino acid sequence of SEQ ID NO:64;
(3) an LC-FR2 comprising the amino acid sequence of SEQ ID NO:51;
(4) an HVR-L2 comprising the amino acid sequence of SEQ ID NO:65;
(5) an LC-FR3 comprising the amino acid sequence of SEQ ID NO:55;
(6) an HVR-L3 comprising the amino acid sequence of SEQ ID NO:66; and
(7) an LC-FR4 comprising the amino acid sequence of SEQ ID NO:60.

64. The antibody of claim 63, wherein the antibody has been engineered to improve antibody-dependent cell-mediated cytotoxicity (ADCC) activity.

65. The antibody of claim 63, wherein one or two of the heavy chains of the antibody is non-fucosylated.

66. An antibody that binds to a human Siglec-8, wherein the antibody comprises:
(a) a heavy chain variable region comprising:
(1) an HC-FR1 comprising the amino acid sequence of SEQ ID NO:26;
(2) an HVR-H1 comprising the amino acid sequence of SEQ ID NO:61;
(3) an HC-FR2 comprising the amino acid sequence of SEQ ID NO:34;
(4) an HVR-H2 comprising the amino acid sequence of SEQ ID NO:62;

(5) an HC-FR3 comprising the amino acid sequence of SEQ ID NO:38;
(6) an HVR-H3 comprising the amino acid sequence of SEQ ID NO:63; and
(7) an HC-FR4 comprising the amino acid sequence of SEQ ID NOs:45;
and
(b) a light chain variable region comprising:
(1) an LC-FR1 comprising the amino acid sequence of SEQ ID NO:48;
(2) an HVR-L1 comprising the amino acid sequence of SEQ ID NO:64;
(3) an LC-FR2 comprising the amino acid sequence of SEQ ID NO:51;
(4) an HVR-L2 comprising the amino acid sequence of SEQ ID NO:65;
(5) an LC-FR3 comprising the amino acid sequence of SEQ ID NO:58;
(6) an HVR-L3 comprising the amino acid sequence of SEQ ID NO:66; and
(7) an LC-FR4 comprising the amino acid sequence of SEQ ID NO:60.

67. A pharmaceutical composition comprising an antibody and a pharmaceutically acceptable carrier, wherein the antibody comprises a heavy chain variable region comprising the amino acid sequence of SEQ ID NO:6 and a light chain variable region comprising the amino acid sequence of SEQ ID NO:16.

68. A pharmaceutical composition comprising an antibody and a pharmaceutically acceptable carrier, wherein the antibody comprises a heavy chain variable region comprising the amino acid sequence of SEQ ID NO:6 and a light chain variable region comprising the amino acid sequence of SEQ ID NO:21.

* * * * *

SEQUENCE LISTING

<160> NUMBER OF SEQ ID NOS: 124

<210> SEQ ID NO 1
<211> LENGTH: 120
<212> TYPE: PRT
<213> ORGANISM: Mus musculus

<400> SEQUENCE: 1

Gln Val Gln Leu Lys Glu Ser Gly Pro Gly Leu Val Ala Pro Ser Gln
 1               5                  10                  15

Ser Leu Ser Ile Thr Cys Thr Val Ser Gly Phe Ser Leu Thr Ile Tyr
             20                  25                  30

Gly Ala His Trp Val Arg Gln Pro Pro Gly Lys Gly Leu Glu Trp Leu
         35                  40                  45

Gly Val Ile Trp Ala Gly Gly Ser Thr Asn Tyr Asn Ser Ala Leu Met
     50                  55                  60

Ser Arg Leu Ser Ile Ser Lys Asp Asn Ser Lys Ser Gln Val Phe Leu
 65                  70                  75                  80

Lys Ile Asn Ser Leu Gln Thr Asp Asp Thr Ala Leu Tyr Tyr Cys Ala
                 85                  90                  95

Arg Asp Gly Ser Ser Pro Tyr Tyr Tyr Ser Met Glu Tyr Trp Gly Gln
            100                 105                 110

Gly Thr Ser Val Thr Val Ser Ser
        115                 120

<210> SEQ ID NO 2
<211> LENGTH: 120
<212> TYPE: PRT
<213> ORGANISM: Artificial Sequence
<220> FEATURE:
<223> OTHER INFORMATION: Synthetic Construct

<400> SEQUENCE: 2

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Leu Thr Ile Tyr
             20                  25                  30

Gly Ala His Trp Val Arg Gln Ala Pro Gly Lys Gly Leu Glu Trp Val
         35                  40                  45

Ser Val Ile Trp Ala Gly Gly Ser Thr Asn Tyr Asn Ser Ala Leu Met
     50                  55                  60

Ser Arg Phe Thr Ile Ser Lys Asp Asn Ser Lys Asn Thr Val Tyr Leu
 65                  70                  75                  80

Gln Met Asn Ser Leu Arg Ala Glu Asp Thr Ala Val Tyr Tyr Cys Ala
                 85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser
        115                 120

<210> SEQ ID NO 3
<211> LENGTH: 120
<212> TYPE: PRT
<213> ORGANISM: Artificial Sequence
<220> FEATURE:
<223> OTHER INFORMATION: Synthetic Construct

<400> SEQUENCE: 3

Glu Val Gln Leu Val Glu Ser Gly Gly Gly Leu Val Gln Pro Gly Gly

```
                1               5                   10                  15
Ser Leu Arg Leu Ser Cys Ala Val Ser Gly Phe Ser Leu Thr Ile Tyr
            20                  25                  30

Gly Ala His Trp Val Arg Gln Ala Pro Gly Lys Gly Leu Glu Trp Leu
            35                  40                  45

Gly Val Ile Trp Ala Gly Gly Ser Thr Asn Tyr Asn Ser Ala Leu Met
            50                  55                  60

Ser Arg Leu Ser Ile Ser Lys Asp Asn Ser Lys Asn Thr Val Tyr Leu
 65                 70                  75                  80

Gln Met Asn Ser Leu Arg Ala Glu Asp Thr Ala Val Tyr Tyr Cys Ala
            85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser
            115                 120

<210> SEQ ID NO 4
<211> LENGTH: 120
<212> TYPE: PRT
<213> ORGANISM: Artificial Sequence
<220> FEATURE:
<223> OTHER INFORMATION: Synthetic Construct

<400> SEQUENCE: 4

Glu Val Gln Leu Val Glu Ser Gly Gly Gly Leu Val Gln Pro Gly Gly
 1               5                  10                  15

Ser Leu Arg Leu Ser Cys Ala Val Ser Gly Phe Ser Leu Thr Ile Tyr
            20                  25                  30

Gly Ala His Trp Val Arg Gln Ala Pro Gly Lys Gly Leu Glu Trp Val
            35                  40                  45

Ser Val Ile Trp Ala Gly Gly Ser Thr Asn Tyr Asn Ser Ala Leu Met
            50                  55                  60

Ser Arg Phe Thr Ile Ser Lys Asp Asn Ser Lys Asn Thr Val Tyr Leu
 65                 70                  75                  80

Gln Met Asn Ser Leu Arg Ala Glu Asp Thr Ala Val Tyr Tyr Cys Ala
            85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser
            115                 120

<210> SEQ ID NO 5
<211> LENGTH: 120
<212> TYPE: PRT
<213> ORGANISM: Artificial Sequence
<220> FEATURE:
<223> OTHER INFORMATION: Synthetic Construct

<400> SEQUENCE: 5

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Leu
            35                  40                  45

Ser Val Ile Trp Ala Gly Gly Ser Thr Asn Tyr Asn Ser Ala Leu Met
            50                  55                  60
```

```
Ser Arg Phe Thr Ile Ser Lys Asp Asn Ser Lys Asn Thr Val Tyr Leu
 65                  70                  75                  80

Gln Met Asn Ser Leu Arg Ala Glu Asp Thr Ala Val Tyr Tyr Cys Ala
                 85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser
        115                 120

<210> SEQ ID NO 6
<211> LENGTH: 120
<212> TYPE: PRT
<213> ORGANISM: Artificial Sequence
<220> FEATURE:
<223> OTHER INFORMATION: Synthetic Construct

<400> SEQUENCE: 6

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Ser Leu Thr Ile Tyr
             20                  25                  30

Gly Ala His Trp Val Arg Gln Ala Pro Gly Lys Gly Leu Glu Trp Val
         35                  40                  45

Gly Val Ile Trp Ala Gly Gly Ser Thr Asn Tyr Asn Ser Ala Leu Met
     50                  55                  60

Ser Arg Phe Thr Ile Ser Lys Asp Asn Ser Lys Asn Thr Val Tyr Leu
 65                  70                  75                  80

Gln Met Asn Ser Leu Arg Ala Glu Asp Thr Ala Val Tyr Tyr Cys Ala
                 85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser
        115                 120

<210> SEQ ID NO 7
<211> LENGTH: 120
<212> TYPE: PRT
<213> ORGANISM: Artificial Sequence
<220> FEATURE:
<223> OTHER INFORMATION: Synthetic Construct

<400> SEQUENCE: 7

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Ser Leu Thr Ile Tyr
             20                  25                  30

Gly Ala His Trp Val Arg Gln Ala Pro Gly Lys Gly Leu Glu Trp Val
         35                  40                  45

Ser Val Ile Trp Ala Gly Gly Ser Thr Asn Tyr Asn Ser Ala Leu Met
     50                  55                  60

Ser Arg Leu Thr Ile Ser Lys Asp Asn Ser Lys Asn Thr Val Tyr Leu
 65                  70                  75                  80

Gln Met Asn Ser Leu Arg Ala Glu Asp Thr Ala Val Tyr Tyr Cys Ala
                 85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser
        115                 120
```

<210> SEQ ID NO 8
<211> LENGTH: 120
<212> TYPE: PRT
<213> ORGANISM: Artificial Sequence
<220> FEATURE:
<223> OTHER INFORMATION: Synthetic Construct

<400> SEQUENCE: 8

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
        35                  40                  45

Ser Val Ile Trp Ala Gly Gly Ser Thr Asn Tyr Asn Ser Ala Leu Met
    50                  55                  60

Ser Arg Phe Ser Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser
        115                 120
```

<210> SEQ ID NO 9
<211> LENGTH: 120
<212> TYPE: PRT
<213> ORGANISM: Artificial Sequence
<220> FEATURE:
<223> OTHER INFORMATION: Synthetic Construct

<400> SEQUENCE: 9

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ile Tyr
            20                  25                  30

Gly Ala His Trp Ile Arg Gln Pro Pro Gly Lys Gly Leu Glu Trp Ile
        35                  40                  45

Gly Val Ile Trp Ala Gly Gly Ser Thr Asn Tyr Asn Ser Ala Leu Met
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110

Gly Thr Leu Val Thr Val Ser Ser
        115                 120
```

<210> SEQ ID NO 10
<211> LENGTH: 120
<212> TYPE: PRT
<213> ORGANISM: Artificial Sequence
<220> FEATURE:
<223> OTHER INFORMATION: Synthetic Construct

<400> SEQUENCE: 10

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ile Tyr
            20                  25                  30

Gly Ala His Trp Val Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110

Gly Thr Leu Val Thr Val Ser Ser
        115                 120

<210> SEQ ID NO 11
<211> LENGTH: 120
<212> TYPE: PRT
<213> ORGANISM: Artificial Sequence
<220> FEATURE:
<223> OTHER INFORMATION: Synthetic Construct

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
        35                  40                  45

Gly Val Ile Trp Ala Gly Gly Ser Thr Asn Tyr Asn Ser Ala Leu Met
    50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Gly Met Glu Tyr Trp Gly Gln
            100                 105                 110

Gly Thr Thr Val Thr Val Ser Ser
        115                 120

<210> SEQ ID NO 12
<211> LENGTH: 120
<212> TYPE: PRT
<213> ORGANISM: Artificial Sequence
<220> FEATURE:
<223> OTHER INFORMATION: Synthetic Construct

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
        35                  40                  45

Gly Val Ile Trp Ala Gly Gly Ser Thr Asn Tyr Asn Ser Ala Leu Met
    50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Asp Tyr Trp Gly Gln
            100                 105                 110

Gly Thr Thr Val Thr Val Ser Ser
        115                 120

<210> SEQ ID NO 13
<211> LENGTH: 120
<212> TYPE: PRT
<213> ORGANISM: Artificial Sequence
<220> FEATURE:
<223> OTHER INFORMATION: Synthetic Construct

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
        35                  40                  45

Gly Val Ile Trp Ala Gly Gly Ser Thr Asn Tyr Asn Ser Ala Leu Met
    50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Glu Val Trp Gly Gln
            100                 105                 110

Gly Thr Thr Val Thr Val Ser Ser
        115                 120

<210> SEQ ID NO 14
<211> LENGTH: 120
<212> TYPE: PRT
<213> ORGANISM: Artificial Sequence
<220> FEATURE:
<223> OTHER INFORMATION: Synthetic Construct

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
        35                  40                  45

Gly Val Ile Trp Ala Gly Gly Ser Thr Asn Tyr Asn Ser Ala Leu Met
    50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Gly Met Asp Val Trp Gly Gln
            100                 105                 110

Gly Thr Thr Val Thr Val Ser Ser

<210> SEQ ID NO 15
<211> LENGTH: 106
<212> TYPE: PRT
<213> ORGANISM: Artificial Sequence
<220> FEATURE:
<223> OTHER INFORMATION: Synthetic Construct

<400> SEQUENCE: 15

Gln Ile Ile Leu Thr Gln Ser Pro Ala Ile Met Ser Ala Ser Pro Gly
1               5                   10                  15

Glu Lys Val Ser Ile Thr Cys Ser Ala Thr Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95

Phe Gly Ser Gly Thr Lys Leu Glu Ile Lys
            100                 105

<210> SEQ ID NO 16
<211> LENGTH: 106
<212> TYPE: PRT
<213> ORGANISM: Artificial Sequence
<220> FEATURE:
<223> OTHER INFORMATION: Synthetic Construct

<400> SEQUENCE: 16

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Leu Ile Tyr
        35                  40                  45

Ser Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
            100                 105

<210> SEQ ID NO 17
<211> LENGTH: 106
<212> TYPE: PRT
<213> ORGANISM: Artificial Sequence
<220> FEATURE:
<223> OTHER INFORMATION: Synthetic Construct

<400> SEQUENCE: 17

Glu Ile Ile Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Trp Ile Tyr
            35                  40                  45

Ser Thr Ser Asn Leu Ala Ser Gly Val Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
            100                 105

<210> SEQ ID NO 18
<211> LENGTH: 106
<212> TYPE: PRT
<213> ORGANISM: Artificial Sequence
<220> FEATURE:
<223> OTHER INFORMATION: Synthetic Construct

<400> SEQUENCE: 18

Glu Ile Ile Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Leu Ile Tyr
            35                  40                  45

Ser Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
            100                 105

<210> SEQ ID NO 19
<211> LENGTH: 106
<212> TYPE: PRT
<213> ORGANISM: Artificial Sequence
<220> FEATURE:
<223> OTHER INFORMATION: Synthetic Construct

<400> SEQUENCE: 19

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Trp Ile Tyr
            35                  40                  45

Ser Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
            100                 105

```
<210> SEQ ID NO 20
<211> LENGTH: 106
<212> TYPE: PRT
<213> ORGANISM: Artificial Sequence
<220> FEATURE:
<223> OTHER INFORMATION: Synthetic Construct

<400> SEQUENCE: 20

Glu Ile Val Leu Thr Gln Ser Pro Ala Thr Leu Ser Leu Ser Pro Gly
 1               5                  10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Leu Ile Tyr
        35                  40                  45

Ser Thr Ser Asn Leu Ala Ser Gly Val Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
            100                 105

<210> SEQ ID NO 21
<211> LENGTH: 106
<212> TYPE: PRT
<213> ORGANISM: Artificial Sequence
<220> FEATURE:
<223> OTHER INFORMATION: Synthetic Construct

<400> SEQUENCE: 21

Glu Ile Val Leu Thr Gln Ser Pro Ala Thr Leu Ser Leu Ser Pro Gly
 1               5                  10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Leu Ile Tyr
        35                  40                  45

Ser Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
            100                 105

<210> SEQ ID NO 22
<211> LENGTH: 106
<212> TYPE: PRT
<213> ORGANISM: Artificial Sequence
<220> FEATURE:
<223> OTHER INFORMATION: Synthetic Construct

<400> SEQUENCE: 22

Glu Ile Val Leu Thr Gln Ser Pro Ala Thr Leu Ser Leu Ser Pro Gly
 1               5                  10                  15

Glu Arg Ala Thr Leu Ser Cys Ser Ala Thr Ser Ser Val Ser Tyr Met
            20                  25                  30

His Trp Tyr Gln Gln Lys Pro Gly Gln Ala Pro Arg Leu Leu Ile Tyr
        35                  40                  45
```

Ser Thr Ser Asn Leu Ala Ser Gly Ile Pro Ala Arg Phe Ser Gly Ser
            50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys Gln Gln Arg Ser Ser Tyr Pro Phe Thr
                 85                  90                  95

Phe Gly Pro Gly Thr Lys Leu Asp Ile Lys
            100                 105

<210> SEQ ID NO 23
<211> LENGTH: 106
<212> TYPE: PRT
<213> ORGANISM: Artificial Sequence
<220> FEATURE:
<223> OTHER INFORMATION: Synthetic Construct

<400> SEQUENCE: 23

Glu Ile Val Leu Thr Gln Ser Pro Ala Thr Leu Ser Leu Ser Pro Gly
  1               5                  10                  15

Glu Arg Ala Thr Leu Ser Cys Ser Ala Thr Ser Ser Val Ser Tyr Met
                 20                  25                  30

His Trp Phe Gln Gln Lys Pro Gly Gln Ala Pro Arg Leu Leu Ile Tyr
             35                  40                  45

Ser Thr Ser Asn Leu Ala Ser Gly Ile Pro Ala Arg Phe Ser Gly Ser
            50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys Gln Gln Arg Ser Ser Tyr Pro Tyr Thr
                 85                  90                  95

Phe Gly Pro Gly Thr Lys Leu Asp Ile Lys
            100                 105

<210> SEQ ID NO 24
<211> LENGTH: 106
<212> TYPE: PRT
<213> ORGANISM: Artificial Sequence
<220> FEATURE:
<223> OTHER INFORMATION: Synthetic Construct

<400> SEQUENCE: 24

Glu Ile Val Leu Thr Gln Ser Pro Ala Thr Leu Ser Leu Ser Pro Gly
  1               5                  10                  15

Glu Arg Ala Thr Leu Ser Cys Ser Ala Thr Ser Ser Val Ser Tyr Met
                 20                  25                  30

His Trp Phe Gln Gln Lys Pro Gly Gln Ala Pro Arg Leu Leu Ile Tyr
             35                  40                  45

Ser Thr Ser Asn Leu Ala Ser Gly Ile Pro Ala Arg Phe Ser Gly Ser
            50                  55                  60

Gly Ser Gly Thr Asp Tyr Thr Leu Thr Ile Ser Ser Leu Glu Pro Glu
 65                  70                  75                  80

Asp Phe Ala Val Tyr Tyr Cys Gln Gln Arg Ser Ser Tyr Pro Tyr Thr
                 85                  90                  95

Phe Gly Pro Gly Thr Lys Leu Asp Ile Lys
            100                 105

<210> SEQ ID NO 25
<211> LENGTH: 30
<212> TYPE: PRT

```
<213> ORGANISM: Homo sapiens

<400> SEQUENCE: 25

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr
            20                  25                  30

<210> SEQ ID NO 26
<211> LENGTH: 30
<212> TYPE: PRT
<213> ORGANISM: Homo sapiens

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr
            20                  25                  30

<210> SEQ ID NO 27
<211> LENGTH: 30
<212> TYPE: PRT
<213> ORGANISM: Homo sapiens

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr
            20                  25                  30

<210> SEQ ID NO 28
<211> LENGTH: 30
<212> TYPE: PRT
<213> ORGANISM: Homo sapiens

<400> SEQUENCE: 28

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser
            20                  25                  30

<210> SEQ ID NO 29
<211> LENGTH: 30
<212> TYPE: PRT
<213> ORGANISM: Homo sapiens

<400> SEQUENCE: 29

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr
            20                  25                  30

<210> SEQ ID NO 30
<211> LENGTH: 14
<212> TYPE: PRT
<213> ORGANISM: Homo sapiens

<400> SEQUENCE: 30

Trp Val Arg Gln Pro Pro Gly Lys Gly Leu Glu Trp Leu Gly
1               5                   10

<210> SEQ ID NO 31
```

```
<211> LENGTH: 14
<212> TYPE: PRT
<213> ORGANISM: Homo sapiens

<400> SEQUENCE: 31

Trp Val Arg Gln Ala Pro Gly Lys Gly Leu Glu Trp Val Ser
 1               5                  10

<210> SEQ ID NO 32
<211> LENGTH: 14
<212> TYPE: PRT
<213> ORGANISM: Homo sapiens

<400> SEQUENCE: 32

Trp Val Arg Gln Ala Pro Gly Lys Gly Leu Glu Trp Leu Gly
 1               5                  10

<210> SEQ ID NO 33
<211> LENGTH: 14
<212> TYPE: PRT
<213> ORGANISM: Homo sapiens

<400> SEQUENCE: 33

Trp Val Arg Gln Ala Pro Gly Lys Gly Leu Glu Trp Leu Ser
 1               5                  10

<210> SEQ ID NO 34
<211> LENGTH: 14
<212> TYPE: PRT
<213> ORGANISM: Homo sapiens

<400> SEQUENCE: 34

Trp Val Arg Gln Ala Pro Gly Lys Gly Leu Glu Trp Val Gly
 1               5                  10

<210> SEQ ID NO 35
<211> LENGTH: 14
<212> TYPE: PRT
<213> ORGANISM: Homo sapiens

<400> SEQUENCE: 35

Trp Ile Arg Gln Pro Pro Gly Lys Gly Leu Glu Trp Ile Gly
 1               5                  10

<210> SEQ ID NO 36
<211> LENGTH: 14
<212> TYPE: PRT
<213> ORGANISM: Homo sapiens

<400> SEQUENCE: 36

Trp Val Arg Gln Pro Pro Gly Lys Gly Leu Glu Trp Leu Gly
 1               5                  10

<210> SEQ ID NO 37
<211> LENGTH: 32
<212> TYPE: PRT
<213> ORGANISM: Homo sapiens

<400> SEQUENCE: 37

Arg Leu Ser Ile Ser Lys Asp Asn Ser Lys Ser Gln Val Phe Leu Lys
 1               5                  10                  15

Ile Asn Ser Leu Gln Thr Asp Asp Thr Ala Leu Tyr Tyr Cys Ala Arg
            20                  25                  30
```

```
<210> SEQ ID NO 38
<211> LENGTH: 32
<212> TYPE: PRT
<213> ORGANISM: Homo sapiens

<400> SEQUENCE: 38

Arg Phe Thr Ile Ser Lys Asp Asn Ser Lys Asn Thr Val Tyr Leu Gln
 1               5                  10                  15

Met Asn Ser Leu Arg Ala Glu Asp Thr Ala Val Tyr Tyr Cys Ala Arg
            20                  25                  30

<210> SEQ ID NO 39
<211> LENGTH: 32
<212> TYPE: PRT
<213> ORGANISM: Homo sapiens

<400> SEQUENCE: 39

Arg Leu Ser Ile Ser Lys Asp Asn Ser Lys Asn Thr Val Tyr Leu Gln
 1               5                  10                  15

Met Asn Ser Leu Arg Ala Glu Asp Thr Ala Val Tyr Tyr Cys Ala Arg
            20                  25                  30

<210> SEQ ID NO 40
<211> LENGTH: 32
<212> TYPE: PRT
<213> ORGANISM: Homo sapiens

<400> SEQUENCE: 40

Arg Leu Thr Ile Ser Lys Asp Asn Ser Lys Asn Thr Val Tyr Leu Gln
 1               5                  10                  15

Met Asn Ser Leu Arg Ala Glu Asp Thr Ala Val Tyr Tyr Cys Ala Arg
            20                  25                  30

<210> SEQ ID NO 41
<211> LENGTH: 32
<212> TYPE: PRT
<213> ORGANISM: Homo sapiens

<400> SEQUENCE: 41

Arg Phe Ser Ile Ser Lys Asp Asn Ser Lys Asn Thr Val Tyr Leu Gln
 1               5                  10                  15

Met Asn Ser Leu Arg Ala Glu Asp Thr Ala Val Tyr Tyr Cys Ala Arg
            20                  25                  30

<210> SEQ ID NO 42
<211> LENGTH: 32
<212> TYPE: PRT
<213> ORGANISM: Homo sapiens

<400> SEQUENCE: 42

Arg Val Thr Ile Ser Val Asp Thr Ser Lys Asn Gln Phe Ser Leu Lys
 1               5                  10                  15

Leu Ser Ser Val Thr Ala Ala Asp Thr Ala Val Tyr Tyr Cys Ala Arg
            20                  25                  30

<210> SEQ ID NO 43
<211> LENGTH: 32
<212> TYPE: PRT
<213> ORGANISM: Homo sapiens

<400> SEQUENCE: 43

Arg Leu Ser Ile Ser Lys Asp Asn Ser Lys Asn Gln Val Ser Leu Lys
 1               5                  10                  15
```

Leu Ser Ser Val Thr Ala Ala Asp Thr Ala Val Tyr Tyr Cys Ala Arg
            20                  25                  30

<210> SEQ ID NO 44
<211> LENGTH: 11
<212> TYPE: PRT
<213> ORGANISM: Homo sapiens

<400> SEQUENCE: 44

Trp Gly Gln Gly Thr Ser Val Thr Val Ser Ser
1               5                   10

<210> SEQ ID NO 45
<211> LENGTH: 11
<212> TYPE: PRT
<213> ORGANISM: Homo sapiens

<400> SEQUENCE: 45

Trp Gly Gln Gly Thr Thr Val Thr Val Ser Ser
1               5                   10

<210> SEQ ID NO 46
<211> LENGTH: 11
<212> TYPE: PRT
<213> ORGANISM: Homo sapiens

<400> SEQUENCE: 46

Trp Gly Gln Gly Thr Leu Val Thr Val Ser Ser
1               5                   10

<210> SEQ ID NO 47
<211> LENGTH: 23
<212> TYPE: PRT
<213> ORGANISM: Homo sapiens

<400> SEQUENCE: 47

Gln Ile Ile Leu Thr Gln Ser Pro Ala Ile Met Ser Ala Ser Pro Gly
1               5                   10                  15

Glu Lys Val Ser Ile Thr Cys
            20

<210> SEQ ID NO 48
<211> LENGTH: 23
<212> TYPE: PRT
<213> ORGANISM: Homo sapiens

<400> SEQUENCE: 48

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 49
<211> LENGTH: 23
<212> TYPE: PRT
<213> ORGANISM: Homo sapiens

<400> SEQUENCE: 49

Glu Ile Ile Leu Thr Gln Ser Pro Ala Thr Leu Ser Leu Ser Pro Gly
1               5                   10                  15

Glu Arg Ala Thr Leu Ser Cys
            20

<210> SEQ ID NO 50
<211> LENGTH: 15
<212> TYPE: PRT
<213> ORGANISM: Homo sapiens

<400> SEQUENCE: 50

Trp Phe Gln Gln Lys Pro Gly Thr Ser Pro Lys Leu Trp Ile Tyr
1               5                   10                  15

<210> SEQ ID NO 51
<211> LENGTH: 15
<212> TYPE: PRT
<213> ORGANISM: Homo sapiens

<400> SEQUENCE: 51

Trp Phe Gln Gln Lys Pro Gly Gln Ala Pro Arg Leu Leu Ile Tyr
1               5                   10                  15

<210> SEQ ID NO 52
<211> LENGTH: 15
<212> TYPE: PRT
<213> ORGANISM: Homo sapiens

<400> SEQUENCE: 52

Trp Phe Gln Gln Lys Pro Gly Gln Ala Pro Arg Leu Trp Ile Tyr
1               5                   10                  15

<210> SEQ ID NO 53
<211> LENGTH: 15
<212> TYPE: PRT
<213> ORGANISM: Homo sapiens

<400> SEQUENCE: 53

Trp Tyr Gln Gln Lys Pro Gly Gln Ala Pro Arg Leu Leu Ile Tyr
1               5                   10                  15

<210> SEQ ID NO 54
<211> LENGTH: 32
<212> TYPE: PRT
<213> ORGANISM: Homo sapiens

<400> SEQUENCE: 54

Gly Val Pro Val Arg Phe Ser Gly Ser Gly Ser Gly Thr Ser Tyr Ser
1               5                   10                  15

Leu Thr Ile Ser Arg Met Glu Ala Glu Asp Ala Ala Thr Tyr Tyr Cys
                20                  25                  30

<210> SEQ ID NO 55
<211> LENGTH: 32
<212> TYPE: PRT
<213> ORGANISM: Homo sapiens

<400> SEQUENCE: 55

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
                20                  25                  30

<210> SEQ ID NO 56
<211> LENGTH: 32
<212> TYPE: PRT
<213> ORGANISM: Homo sapiens

<400> SEQUENCE: 56

```
Gly Val Pro Ala Arg Phe Ser Gly Ser Gly Ser Gly Thr Asp Tyr Thr
1               5                   10                  15

Leu Thr Ile Ser Ser Leu Glu Pro Glu Asp Phe Ala Val Tyr Tyr Cys
            20                  25                  30
```

<210> SEQ ID NO 57
<211> LENGTH: 32
<212> TYPE: PRT
<213> ORGANISM: Homo sapiens

<400> SEQUENCE: 57

```
Gly Val Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30
```

<210> SEQ ID NO 58
<211> LENGTH: 32
<212> TYPE: PRT
<213> ORGANISM: Homo sapiens

<400> SEQUENCE: 58

```
Gly Ile Pro Ala Arg Phe Ser Gly Ser Gly Ser Gly Thr Asp Tyr Thr
1               5                   10                  15

Leu Thr Ile Ser Ser Leu Glu Pro Glu Asp Phe Ala Val Tyr Tyr Cys
            20                  25                  30
```

<210> SEQ ID NO 59
<211> LENGTH: 10
<212> TYPE: PRT
<213> ORGANISM: Homo sapiens

<400> SEQUENCE: 59

```
Phe Gly Ser Gly Thr Lys Leu Glu Ile Lys
1               5                   10
```

<210> SEQ ID NO 60
<211> LENGTH: 10
<212> TYPE: PRT
<213> ORGANISM: Homo sapiens

<400> SEQUENCE: 60

```
Phe Gly Pro Gly Thr Lys Leu Asp Ile Lys
1               5                   10
```

<210> SEQ ID NO 61
<211> LENGTH: 5
<212> TYPE: PRT
<213> ORGANISM: Homo sapiens

<400> SEQUENCE: 61

```
Ile Tyr Gly Ala His
1               5
```

<210> SEQ ID NO 62
<211> LENGTH: 16
<212> TYPE: PRT
<213> ORGANISM: Homo sapiens

<400> SEQUENCE: 62

```
Val Ile Trp Ala Gly Gly Ser Thr Asn Tyr Asn Ser Ala Leu Met Ser
1               5                   10                  15
```

<210> SEQ ID NO 63
<211> LENGTH: 12
<212> TYPE: PRT
<213> ORGANISM: Homo sapiens

<400> SEQUENCE: 63

Asp Gly Ser Ser Pro Tyr Tyr Tyr Ser Met Glu Tyr
1               5                   10

<210> SEQ ID NO 64
<211> LENGTH: 10
<212> TYPE: PRT
<213> ORGANISM: Homo sapiens

<400> SEQUENCE: 64

Ser Ala Thr Ser Ser Val Ser Tyr Met His
1               5                   10

<210> SEQ ID NO 65
<211> LENGTH: 7
<212> TYPE: PRT
<213> ORGANISM: Homo sapiens

<400> SEQUENCE: 65

Ser Thr Ser Asn Leu Ala Ser
1               5

<210> SEQ ID NO 66
<211> LENGTH: 9
<212> TYPE: PRT
<213> ORGANISM: Homo sapiens

<400> SEQUENCE: 66

Gln Gln Arg Ser Ser Tyr Pro Phe Thr
1               5

<210> SEQ ID NO 67
<211> LENGTH: 12
<212> TYPE: PRT
<213> ORGANISM: Homo sapiens

<400> SEQUENCE: 67

Asp Gly Ser Ser Pro Tyr Tyr Tyr Gly Met Glu Tyr
1               5                   10

<210> SEQ ID NO 68
<211> LENGTH: 12
<212> TYPE: PRT
<213> ORGANISM: Homo sapiens

<400> SEQUENCE: 68

Asp Gly Ser Ser Pro Tyr Tyr Tyr Ser Met Asp Tyr
1               5                   10

<210> SEQ ID NO 69
<211> LENGTH: 12
<212> TYPE: PRT
<213> ORGANISM: Homo sapiens

<400> SEQUENCE: 69

Asp Gly Ser Ser Pro Tyr Tyr Tyr Ser Met Glu Val
1               5                   10

<210> SEQ ID NO 70

```
<211> LENGTH: 12
<212> TYPE: PRT
<213> ORGANISM: Homo sapiens

<400> SEQUENCE: 70

Asp Gly Ser Ser Pro Tyr Tyr Tyr Gly Met Asp Val
1               5                   10

<210> SEQ ID NO 71
<211> LENGTH: 9
<212> TYPE: PRT
<213> ORGANISM: Homo sapiens

<400> SEQUENCE: 71

Gln Gln Arg Ser Ser Tyr Pro Tyr Thr
1               5

<210> SEQ ID NO 72
<211> LENGTH: 474
<212> TYPE: PRT
<213> ORGANISM: Homo sapiens

<400> SEQUENCE: 72

Gly Tyr Leu Leu Gln Val Gln Glu Leu Val Thr Val Gln Glu Gly Leu
1               5                   10                  15

Cys Val His Val Pro Cys Ser Phe Ser Tyr Pro Gln Asp Gly Trp Thr
            20                  25                  30

Asp Ser Asp Pro Val His Gly Tyr Trp Phe Arg Ala Gly Asp Arg Pro
        35                  40                  45

Tyr Gln Asp Ala Pro Val Ala Thr Asn Asn Pro Asp Arg Glu Val Gln
    50                  55                  60

Ala Glu Thr Gln Gly Arg Phe Gln Leu Leu Gly Asp Ile Trp Ser Asn
65                  70                  75                  80

Asp Cys Ser Leu Ser Ile Arg Asp Ala Arg Lys Arg Asp Lys Gly Ser
                85                  90                  95

Tyr Phe Phe Arg Leu Glu Arg Gly Ser Met Lys Trp Ser Tyr Lys Ser
            100                 105                 110

Gln Leu Asn Tyr Lys Thr Lys Gln Leu Ser Val Phe Val Thr Ala Leu
        115                 120                 125

Thr His Arg Pro Asp Ile Leu Ile Leu Gly Thr Leu Glu Ser Gly His
    130                 135                 140

Ser Arg Asn Leu Thr Cys Ser Val Pro Trp Ala Cys Lys Gln Gly Thr
145                 150                 155                 160

Pro Pro Met Ile Ser Trp Ile Gly Ala Ser Val Ser Pro Gly Pro
                165                 170                 175

Thr Thr Ala Arg Ser Ser Val Leu Thr Leu Thr Pro Lys Pro Gln Asp
            180                 185                 190

His Gly Thr Ser Leu Thr Cys Gln Val Thr Leu Pro Gly Thr Gly Val
        195                 200                 205

Thr Thr Thr Ser Thr Val Arg Leu Asp Val Ser Tyr Pro Pro Trp Asn
    210                 215                 220

Leu Thr Met Thr Val Phe Gln Gly Asp Ala Thr Ala Ser Thr Ala Leu
225                 230                 235                 240

Gly Asn Gly Ser Ser Leu Ser Val Leu Glu Gly Gln Ser Leu Arg Leu
                245                 250                 255

Val Cys Ala Val Asn Ser Asn Pro Pro Ala Arg Leu Ser Trp Thr Arg
            260                 265                 270
```

```
Gly Ser Leu Thr Leu Cys Pro Ser Arg Ser Ser Asn Pro Gly Leu Leu
            275                 280                 285

Glu Leu Pro Arg Val His Val Arg Asp Glu Gly Glu Phe Thr Cys Arg
290                 295                 300

Ala Gln Asn Ala Gln Gly Ser Gln His Ile Ser Leu Ser Leu Ser Leu
305                 310                 315                 320

Gln Asn Glu Gly Thr Gly Thr Ser Arg Pro Val Ser Gln Val Thr Leu
                325                 330                 335

Ala Ala Val Gly Gly Ala Gly Ala Thr Ala Leu Ala Phe Leu Ser Phe
                340                 345                 350

Cys Ile Ile Phe Ile Ile Val Arg Ser Cys Arg Lys Lys Ser Ala Arg
            355                 360                 365

Pro Ala Ala Gly Val Gly Asp Thr Gly Met Glu Asp Ala Lys Ala Ile
370                 375                 380

Arg Gly Ser Ala Ser Gln Gly Pro Leu Thr Glu Ser Trp Lys Asp Gly
385                 390                 395                 400

Asn Pro Leu Lys Lys Pro Pro Ala Val Ala Pro Ser Ser Gly Glu
                405                 410                 415

Glu Gly Glu Leu His Tyr Ala Thr Leu Ser Phe His Lys Val Lys Pro
                420                 425                 430

Gln Asp Pro Gln Gly Gln Glu Ala Thr Asp Ser Glu Tyr Ser Glu Ile
            435                 440                 445

Lys Ile His Lys Arg Glu Thr Ala Glu Thr Gln Ala Cys Leu Arg Asn
            450                 455                 460

His Asn Pro Ser Ser Lys Glu Val Arg Gly
465                 470

<210> SEQ ID NO 73
<211> LENGTH: 474
<212> TYPE: PRT
<213> ORGANISM: Homo sapiens

<400> SEQUENCE: 73

Gly Tyr Leu Leu Gln Val Gln Glu Leu Val Thr Val Gln Glu Gly Leu
1               5                   10                  15

Cys Val His Val Pro Cys Ser Phe Ser Tyr Pro Gln Asp Gly Trp Thr
            20                  25                  30

Asp Ser Asp Pro Val His Gly Tyr Trp Phe Arg Ala Gly Asp Arg Pro
        35                  40                  45

Tyr Gln Asp Ala Pro Val Ala Thr Asn Asn Pro Asp Arg Glu Val Gln
    50                  55                  60

Ala Glu Thr Gln Gly Arg Phe Gln Leu Leu Gly Asp Ile Trp Ser Asn
65                  70                  75                  80

Asp Cys Ser Leu Ser Ile Arg Asp Ala Arg Lys Arg Asp Lys Gly Ser
                85                  90                  95

Tyr Phe Phe Arg Leu Glu Arg Gly Ser Met Lys Trp Ser Tyr Lys Ser
            100                 105                 110

Gln Leu Asn Tyr Lys Thr Lys Gln Leu Ser Val Phe Val Thr Ala Leu
        115                 120                 125

Thr His Arg Pro Asp Ile Leu Ile Leu Gly Thr Leu Glu Ser Gly His
    130                 135                 140

Pro Arg Asn Leu Thr Cys Ser Val Pro Trp Ala Cys Lys Gln Gly Thr
145                 150                 155                 160

Pro Pro Met Ile Ser Trp Ile Gly Ala Ser Val Ser Ser Pro Gly Pro
                165                 170                 175
```

```
Thr Thr Ala Arg Ser Ser Val Leu Thr Leu Thr Pro Lys Pro Gln Asp
            180                 185                 190

His Gly Thr Ser Leu Thr Cys Gln Val Thr Leu Pro Gly Thr Gly Val
        195                 200                 205

Thr Thr Thr Ser Thr Val Arg Leu Asp Val Ser Tyr Pro Pro Trp Asn
        210                 215                 220

Leu Thr Met Thr Val Phe Gln Gly Asp Ala Thr Ala Ser Thr Ala Leu
225                 230                 235                 240

Gly Asn Gly Ser Ser Leu Ser Val Leu Glu Gly Gln Ser Leu Arg Leu
                245                 250                 255

Val Cys Ala Val Asn Ser Asn Pro Pro Ala Arg Leu Ser Trp Thr Arg
            260                 265                 270

Gly Ser Leu Thr Leu Cys Pro Ser Arg Ser Ser Asn Pro Gly Leu Leu
        275                 280                 285

Glu Leu Pro Arg Val His Val Arg Asp Glu Gly Glu Phe Thr Cys Arg
        290                 295                 300

Ala Gln Asn Ala Gln Gly Ser Gln His Ile Ser Leu Ser Leu Ser Leu
305                 310                 315                 320

Gln Asn Glu Gly Thr Gly Thr Ser Arg Pro Val Ser Gln Val Thr Leu
                325                 330                 335

Ala Ala Val Gly Gly Ala Gly Ala Thr Ala Leu Ala Phe Leu Ser Phe
            340                 345                 350

Cys Ile Ile Phe Ile Ile Val Arg Ser Cys Arg Lys Lys Ser Ala Arg
        355                 360                 365

Pro Ala Ala Gly Val Gly Asp Thr Gly Met Glu Asp Ala Lys Ala Ile
        370                 375                 380

Arg Gly Ser Ala Ser Gln Gly Pro Leu Thr Glu Ser Trp Lys Asp Gly
385                 390                 395                 400

Asn Pro Leu Lys Lys Pro Pro Ala Val Ala Pro Ser Ser Gly Glu
                405                 410                 415

Glu Gly Glu Leu His Tyr Ala Thr Leu Ser Phe His Lys Val Lys Pro
            420                 425                 430

Gln Asp Pro Gln Gly Gln Glu Ala Thr Asp Ser Glu Tyr Ser Glu Ile
        435                 440                 445

Lys Ile His Lys Arg Glu Thr Ala Glu Thr Gln Ala Cys Leu Arg Asn
450                 455                 460

His Asn Pro Ser Ser Lys Glu Val Arg Gly
465                 470

<210> SEQ ID NO 74
<211> LENGTH: 573
<212> TYPE: PRT
<213> ORGANISM: Homo sapiens

<400> SEQUENCE: 74

Gly Tyr Leu Leu Gln Val Gln Glu Leu Val Thr Val Gln Glu Gly Leu
1               5                   10                  15

Cys Val His Val Pro Cys Ser Phe Ser Tyr Pro Gln Asp Gly Trp Thr
            20                  25                  30

Asp Ser Asp Pro Val His Gly Tyr Trp Phe Arg Ala Gly Asp Arg Pro
        35                  40                  45

Tyr Gln Asp Ala Pro Val Ala Thr Asn Asn Pro Asp Arg Glu Val Gln
    50                  55                  60

Ala Glu Thr Gln Gly Arg Phe Gln Leu Leu Gly Asp Ile Trp Ser Asn
```

-continued

```
                65                  70                  75                  80
Asp Cys Ser Leu Ser Ile Arg Asp Ala Arg Lys Arg Asp Lys Gly Ser
                    85                  90                  95
Tyr Phe Phe Arg Leu Glu Arg Gly Ser Met Lys Trp Ser Tyr Lys Ser
                    100                 105                 110
Gln Leu Asn Tyr Lys Thr Lys Gln Leu Ser Val Phe Val Thr Ala Leu
                    115                 120                 125
Thr His Arg Pro Asp Ile Leu Ile Leu Gly Thr Leu Glu Ser Gly His
                    130                 135                 140
Ser Arg Asn Leu Thr Cys Ser Val Pro Trp Ala Cys Lys Gln Gly Thr
145                 150                 155                 160
Pro Pro Met Ile Ser Trp Ile Gly Ala Ser Val Ser Ser Pro Gly Pro
                    165                 170                 175
Thr Thr Ala Arg Ser Ser Val Leu Thr Leu Thr Pro Lys Pro Gln Asp
                    180                 185                 190
His Gly Thr Ser Leu Thr Cys Gln Val Thr Leu Pro Gly Thr Gly Val
                    195                 200                 205
Thr Thr Thr Ser Thr Val Arg Leu Asp Val Ser Tyr Pro Pro Trp Asn
                    210                 215                 220
Leu Thr Met Thr Val Phe Gln Gly Asp Ala Thr Ala Ser Thr Ala Leu
225                 230                 235                 240
Gly Asn Gly Ser Ser Leu Ser Val Leu Glu Gly Gln Ser Leu Arg Leu
                    245                 250                 255
Val Cys Ala Val Asn Ser Asn Pro Pro Ala Arg Leu Ser Trp Thr Arg
                    260                 265                 270
Gly Ser Leu Thr Leu Cys Pro Ser Arg Ser Ser Asn Pro Gly Leu Leu
                    275                 280                 285
Glu Leu Pro Arg Val His Val Arg Asp Glu Gly Glu Phe Thr Cys Arg
                    290                 295                 300
Ala Gln Asn Ala Gln Gly Ser Gln His Ile Ser Leu Ser Leu Ser Leu
305                 310                 315                 320
Gln Asn Glu Gly Thr Gly Thr Ser Arg Pro Val Ser Gln Val Thr Leu
                    325                 330                 335
Ala Ala Val Gly Gly Ile Glu Gly Arg Ser Asp Lys Thr His Thr Cys
                    340                 345                 350
Pro Pro Cys Pro Ala Pro Glu Leu Leu Gly Gly Pro Ser Val Phe Leu
                    355                 360                 365
Phe Pro Pro Lys Pro Lys Asp Thr Leu Met Ile Ser Arg Thr Pro Glu
                    370                 375                 380
Val Thr Cys Val Val Val Asp Val Ser His Glu Asp Pro Glu Val Lys
385                 390                 395                 400
Phe Asn Trp Tyr Val Asp Gly Val Glu Val His Asn Ala Lys Thr Lys
                    405                 410                 415
Pro Arg Glu Glu Gln Tyr Asn Ser Thr Tyr Arg Val Val Ser Val Leu
                    420                 425                 430
Thr Val Leu His Gln Asp Trp Leu Asn Gly Lys Glu Tyr Lys Cys Lys
                    435                 440                 445
Val Ser Asn Lys Ala Leu Pro Ala Pro Ile Glu Lys Thr Ile Ser Lys
                    450                 455                 460
Ala Lys Gly Gln Pro Arg Glu Pro Gln Val Tyr Thr Leu Pro Pro Ser
465                 470                 475                 480
Arg Glu Glu Met Thr Lys Asn Gln Val Ser Leu Thr Cys Leu Val Lys
                    485                 490                 495
```

```
Gly Phe Tyr Pro Ser Asp Ile Ala Val Glu Trp Glu Ser Asn Gly Gln
                500                 505                 510

Pro Glu Asn Asn Tyr Lys Thr Thr Pro Pro Val Leu Asp Ser Asp Gly
            515                 520                 525

Ser Phe Phe Leu Tyr Ser Lys Leu Thr Val Asp Lys Ser Arg Trp Gln
    530                 535                 540

Gln Gly Asn Val Phe Ser Cys Ser Val Met His Glu Ala Leu His Asn
545                 550                 555                 560

His Tyr Thr Gln Lys Ser Leu Ser Leu Ser Pro Gly Lys
                565                 570

<210> SEQ ID NO 75
<211> LENGTH: 449
<212> TYPE: PRT
<213> ORGANISM: Artificial Sequence
<220> FEATURE:
<223> OTHER INFORMATION: Synthetic Construct

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
        35                  40                  45

Gly Val Ile Trp Ala Gly Gly Ser Thr Asn Tyr Asn Ser Ala Leu Met
    50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285
```

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445
Gly

<210> SEQ ID NO 76
<211> LENGTH: 213
<212> TYPE: PRT
<213> ORGANISM: Artificial Sequence
<220> FEATURE:
<223> OTHER INFORMATION: Synthetic Construct

<400> SEQUENCE: 76

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Leu Ile Tyr
        35                  40                  45

Ser Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

```
Cys Glu Val Thr His Gln Gly Leu Ser Ser Pro Val Thr Lys Ser Phe
            195                 200                 205

Asn Arg Gly Glu Cys
    210
```

<210> SEQ ID NO 77
<211> LENGTH: 213
<212> TYPE: PRT
<213> ORGANISM: Artificial Sequence
<220> FEATURE:
<223> OTHER INFORMATION: Synthetic Construct

<400> SEQUENCE: 77

```
Glu Ile Val Leu Thr Gln Ser Pro Ala Thr Leu Ser Leu Ser Pro Gly
  1               5                  10                  15

Glu Arg Ala Thr Leu Ser Cys Ser Ala Thr Ser Ser Val Ser Tyr Met
             20                  25                  30

His Trp Phe Gln Gln Lys Pro Gly Gln Ala Pro Arg Leu Leu Ile Tyr
         35                  40                  45

Ser Thr Ser Asn Leu Ala Ser Gly Ile Pro Ala Arg Phe Ser Gly Ser
     50                  55                  60

Gly Ser Gly Thr Asp Tyr Thr Leu Thr Ile Ser Ser Leu Glu Pro Glu
 65                  70                  75                  80

Asp Phe Ala Val Tyr Tyr Cys Gln Gln Arg Ser Ser Tyr Pro Phe Thr
                 85                  90                  95

Phe Gly Pro Gly Thr Lys Leu Asp Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 78
<211> LENGTH: 329
<212> TYPE: PRT
<213> ORGANISM: Homo sapiens

<400> SEQUENCE: 78

```
Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
```

```
                 65                  70                  75                  80
Tyr Ile Cys Asn Val Asn His Lys Pro Ser Asn Thr Lys Val Asp Lys
                    85                  90                  95
Arg Val Glu Pro Lys Ser Cys Asp Lys Thr His Thr Cys Pro Pro Cys
                100                 105                 110
Pro Ala Pro Glu Leu Leu Gly Pro Ser Val Phe Leu Phe Pro Pro
                115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
                180                 185                 190
His Gln Asp Trp Leu Asn Gly Lys Glu Tyr Lys Cys Lys Val Ser Asn
                195                 200                 205
Lys Ala Leu Pro Ala Pro Ile Glu Lys Thr Ile Ser Lys Ala Lys Gly
                210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
                275                 280                 285
Leu Tyr Ser Lys Leu Thr Val Asp Lys Ser Arg Trp Gln Gln Gly Asn
                290                 295                 300
Val Phe Ser Cys Ser Val Met His Glu Ala Leu His Asn His Tyr Thr
305                 310                 315                 320
Gln Lys Ser Leu Ser Leu Ser Pro Gly
                325

<210> SEQ ID NO 79
<211> LENGTH: 326
<212> TYPE: PRT
<213> ORGANISM: Homo sapiens

<400> SEQUENCE: 79

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
                35                  40                  45
Gly Val His Thr Phe Pro Ala Val Leu Gln Ser Ser Gly Leu Tyr Ser
            50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                    85                  90                  95
Arg Val Glu Ser Lys Tyr Gly Pro Pro Cys Pro Pro Cys Pro Ala Pro
                100                 105                 110
```

```
Glu Phe Leu Gly Gly Pro Ser Val Phe Leu Phe Pro Pro Lys Pro Lys
            115                 120                 125
Asp Thr Leu Met Ile Ser Arg Thr Pro Glu Val Thr Cys Val Val Val
130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
290                 295                 300
Cys Ser Val Met His Glu Ala Leu His Asn His Tyr Thr Gln Lys Ser
305                 310                 315                 320
Leu Ser Leu Ser Leu Gly
                325

<210> SEQ ID NO 80
<211> LENGTH: 107
<212> TYPE: PRT
<213> ORGANISM: Homo sapiens

<400> SEQUENCE: 80

Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105

<210> SEQ ID NO 81
<211> LENGTH: 444
<212> TYPE: PRT
<213> ORGANISM: Mus musculus

<400> SEQUENCE: 81
```

```
Gln Val Gln Leu Lys Arg Ala Ser Gly Pro Gly Leu Val Ala Pro Ser
 1               5                  10                  15

Gln Ser Leu Ser Ile Thr Cys Thr Val Ser Gly Phe Ser Leu Thr Ile
            20                  25                  30

Tyr Gly Ala His Trp Val Arg Gln Pro Pro Gly Lys Gly Leu Glu Trp
            35                  40                  45

Leu Gly Val Ile Trp Ala Gly Gly Ser Thr Asn Tyr Asn Ser Ala Leu
 50                  55                  60

Met Ser Arg Leu Ser Ile Ser Lys Asp Asn Ser Lys Ser Gln Val Phe
 65                  70                  75                  80

Leu Lys Ile Asn Ser Leu Gln Thr Asp Asp Thr Ala Leu Tyr Tyr Cys
                 85                  90                  95

Ala Arg Asp Gly Ser Ser Pro Tyr Tyr Tyr Ser Met Glu Tyr Trp Gly
            100                 105                 110

Gln Gly Thr Ser Val Thr Val Ser Ser Ala Lys Thr Thr Pro Pro Ser
            115                 120                 125

Val Tyr Pro Leu Ala Pro Gly Ser Ala Ala Gln Thr Asn Ser Met Val
            130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Glu Ser Asp Leu Tyr Thr Leu Ser Ser Ser Val Thr Val Pro
                180                 185                 190

Ser Ser Pro Arg Pro Ser Glu Thr Val Thr Cys Asn Val Ala His Pro
                195                 200                 205

Ala Ser Ser Thr Lys Val Asp Lys Lys Ile Val Pro Arg Asp Cys Gly
            210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
                260                 265                 270

Phe Ser Trp Phe Val Asp Asp Val Glu Val His Thr Ala Gln Thr Gln
            275                 280                 285

Pro Arg Glu Glu Gln Phe Asn Ser Thr Phe Arg Ser Val Ser Glu Leu
            290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
                340                 345                 350

Lys Glu Gln Met Ala Lys Asp Lys Val Ser Leu Thr Cys Met Ile Thr
            355                 360                 365

Asp Phe Phe Pro Glu Asp Ile Thr Val Glu Trp Gln Trp Asn Gly Gln
            370                 375                 380

Pro Ala Glu Asn Tyr Lys Asn Thr Gln Pro Ile Met Asn Thr Asn Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
```

```
                    420             425             430
His His Thr Glu Lys Ser Leu Ser His Ser Pro Gly
            435                 440

<210> SEQ ID NO 82
<211> LENGTH: 212
<212> TYPE: PRT
<213> ORGANISM: Mus musculus

<400> SEQUENCE: 82

Glu Ile Ile Leu Thr Gln Ser Pro Ala Ile Met Ser Ala Ser Pro Gly
 1               5                  10                  15

Glu Lys Val Ser Ile Thr Cys Ser Ala Thr Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95

Phe Gly Ser Gly Thr Lys Leu Glu Ile Lys Ala Asp Ala Ala Pro Thr
            100                 105                 110

Val Ser Ile Phe Pro Pro Ser Ser Glu Gln Leu Thr Ser Gly Gly Ala
        115                 120                 125

Ser Val Val Cys Phe Leu Asn Asn Phe Tyr Pro Lys Asp Ile Asn Val
    130                 135                 140

Lys Trp Lys Ile Asp Gly Ser Glu Arg Gln Asn Gly Val Leu Asn Ser
145                 150                 155                 160

Trp Thr Asp Gln Asp Ser Lys Asp Ser Thr Tyr Ser Met Ser Ser Thr
                165                 170                 175

Leu Thr Leu Thr Lys Asp Glu Tyr Glu Arg His Asn Ser Tyr Thr Cys
            180                 185                 190

Glu Ala Thr His Lys Thr Ser Thr Ser Pro Ile Val Lys Ser Phe Asn
        195                 200                 205

Arg Asn Glu Cys
    210

<210> SEQ ID NO 83
<211> LENGTH: 212
<212> TYPE: PRT
<213> ORGANISM: Mus musculus

<400> SEQUENCE: 83

Gln Ile Ile Leu Thr Gln Ser Pro Ala Ile Met Ser Ala Ser Pro Gly
 1               5                  10                  15

Glu Lys Val Ser Ile Thr Cys Ser Ala Thr Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
```

```
                85                  90                  95
Phe Gly Ser Gly Thr Lys Leu Glu Ile Lys Ala Asp Ala Ala Pro Thr
               100                 105                 110

Val Ser Ile Phe Pro Pro Ser Ser Glu Gln Leu Thr Ser Gly Gly Ala
           115                 120                 125

Ser Val Val Cys Phe Leu Asn Asn Phe Tyr Pro Lys Asp Ile Asn Val
       130                 135                 140

Lys Trp Lys Ile Asp Gly Ser Glu Arg Gln Asn Gly Val Leu Asn Ser
145                 150                 155                 160

Trp Thr Asp Gln Asp Ser Lys Asp Ser Thr Tyr Ser Met Ser Ser Thr
               165                 170                 175

Leu Thr Leu Thr Lys Asp Glu Tyr Glu Arg His Asn Ser Tyr Thr Cys
           180                 185                 190

Glu Ala Thr His Lys Thr Ser Thr Ser Pro Ile Val Lys Ser Phe Asn
       195                 200                 205

Arg Asn Glu Cys
   210

<210> SEQ ID NO 84
<211> LENGTH: 450
<212> TYPE: PRT
<213> ORGANISM: Artificial Sequence
<220> FEATURE:
<223> OTHER INFORMATION: Synthetic Construct

<400> SEQUENCE: 84

Gln Val Gln Leu Lys Arg Ala Ser Gly Pro Gly Leu Val Ala Pro Ser
  1               5                  10                  15

Gln Ser Leu Ser Ile Thr Cys Thr Val Ser Gly Phe Ser Leu Thr Ile
               20                  25                  30

Tyr Gly Ala His Trp Val Arg Gln Pro Pro Gly Lys Gly Leu Glu Trp
           35                  40                  45

Leu Gly Val Ile Trp Ala Gly Gly Ser Thr Asn Tyr Asn Ser Ala Leu
       50                  55                  60

Met Ser Arg Leu Ser Ile Ser Lys Asp Asn Ser Lys Ser Gln Val Phe
 65                 70                  75                  80

Leu Lys Ile Asn Ser Leu Gln Thr Asp Asp Thr Ala Leu Tyr Tyr Cys
               85                  90                  95

Ala Arg Asp Gly Ser Ser Pro Tyr Tyr Tyr Ser Met Glu Tyr Trp Gly
               100                 105                 110

Gln Gly Thr Ser Val Thr Val Ser Ser Ala Ser Thr Lys Gly Pro Ser
           115                 120                 125

Val Phe Pro Leu Ala Pro Ser Ser Lys Ser Thr Ser Gly Gly Thr Ala
       130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
               165                 170                 175

Val Leu Gln Ser Ser Gly Leu Tyr Ser Leu Ser Ser Val Val Thr Val
           180                 185                 190

Pro Ser Ser Ser Leu Gly Thr Gln Thr Tyr Ile Cys Asn Val Asn His
       195                 200                 205

Lys Pro Ser Asn Thr Lys Val Asp Lys Arg Val Glu Pro Lys Ser Cys
 210                215                 220

Asp Lys Thr His Thr Cys Pro Pro Cys Pro Ala Pro Glu Leu Leu Gly
```

```
                225                 230                 235                 240
Gly Pro Ser Val Phe Leu Phe Pro Pro Lys Pro Lys Asp Thr Leu Met
                    245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly
    450

<210> SEQ ID NO 85
<211> LENGTH: 213
<212> TYPE: PRT
<213> ORGANISM: Artificial Sequence
<220> FEATURE:
<223> OTHER INFORMATION: Synthetic Construct

<400> SEQUENCE: 85

Glu Ile Ile Leu Thr Gln Ser Pro Ala Ile Met Ser Ala Ser Pro Gly
  1               5                  10                  15

Glu Lys Val Ser Ile Thr Cys Ser Ala Thr Ser Ser Val Ser Tyr Met
                 20                  25                  30

His Trp Phe Gln Gln Lys Pro Gly Thr Ser Pro Lys Leu Trp Ile Tyr
             35                  40                  45

Ser Thr Ser Asn Leu Ala Ser Gly Val Pro Val Arg Phe Ser Gly Ser
         50                  55                  60

Gly Ser Gly Thr Ser Tyr Ser Leu Thr Ile Ser Arg Met Glu Ala Glu
 65                  70                  75                  80

Asp Ala Ala Thr Tyr Tyr Cys Gln Gln Arg Ser Ser Tyr Pro Phe Thr
                 85                  90                  95

Phe Gly Ser Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
```

-continued

```
                    130                 135                 140
Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
        210

<210> SEQ ID NO 86
<211> LENGTH: 213
<212> TYPE: PRT
<213> ORGANISM: Artificial Sequence
<220> FEATURE:
<223> OTHER INFORMATION: Synthetic Construct

<400> SEQUENCE: 86

Gln Ile Ile Leu Thr Gln Ser Pro Ala Ile Met Ser Ala Ser Pro Gly
1               5                   10                  15

Glu Lys Val Ser Ile Thr Cys Ser Ala Thr Ser Ser Val Ser Tyr Met
                20                  25                  30

His Trp Phe Gln Gln Lys Pro Gly Thr Ser Pro Lys Leu Trp Ile Tyr
            35                  40                  45

Ser Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95

Phe Gly Ser Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
                115                 120                 125

Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
        210

<210> SEQ ID NO 87
<211> LENGTH: 446
<212> TYPE: PRT
<213> ORGANISM: Artificial Sequence
<220> FEATURE:
<223> OTHER INFORMATION: Synthetic Construct

<400> SEQUENCE: 87
```

-continued

```
Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Ser Leu Thr Ile Tyr
             20                  25                  30
Gly Ala His Trp Val Arg Gln Ala Pro Gly Lys Gly Leu Glu Trp Val
         35                  40                  45
Gly Val Ile Trp Ala Gly Gly Ser Thr Asn Tyr Asn Ser Ala Leu Met
 50                  55                  60
Ser Arg Phe Thr Ile Ser Lys Asp Asn Ser Lys Asn Thr Val Tyr Leu
 65                  70                  75                  80
Gln Met Asn Ser Leu Arg Ala Glu Asp Thr Ala Val Tyr Tyr Cys Ala
             85                  90                  95
Arg Asp Gly Ser Ser Pro Tyr Tyr Ser Met Glu Tyr Trp Gly Gln
            100                 105                 110
Gly Thr Thr Val Thr Val Ser Ser Ala Ser Thr Lys Gly Pro Ser Val
            115                 120                 125
Phe Pro Leu Ala Pro Cys Ser Arg Ser Thr Ser Glu Ser Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
            165                 170                 175
Leu Gln Ser Ser Gly Leu Tyr Ser Leu Ser Ser Val Val Thr Val Pro
        180                 185                 190
Ser Ser Ser Leu Gly Thr Lys Thr Tyr Thr Cys Asn Val Asp His Lys
        195                 200                 205
Pro Ser Asn Thr Lys Val Asp Lys Arg Val Glu Ser Lys Tyr Gly Pro
210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Tyr Arg Val Val Ser
        290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
```

His Asn His Tyr Thr Gln Lys Ser Leu Ser Leu Ser Leu Gly
            435                 440                 445

<210> SEQ ID NO 88
<211> LENGTH: 5
<212> TYPE: PRT
<213> ORGANISM: Mus musculus

<400> SEQUENCE: 88

Ser Tyr Ala Met Ser
1               5

<210> SEQ ID NO 89
<211> LENGTH: 5
<212> TYPE: PRT
<213> ORGANISM: Mus musculus

<400> SEQUENCE: 89

Asp Tyr Tyr Met Tyr
1               5

<210> SEQ ID NO 90
<211> LENGTH: 5
<212> TYPE: PRT
<213> ORGANISM: Mus musculus

<400> SEQUENCE: 90

Ser Ser Trp Met Asn
1               5

<210> SEQ ID NO 91
<211> LENGTH: 17
<212> TYPE: PRT
<213> ORGANISM: Mus musculus

<400> SEQUENCE: 91

Ile Ile Ser Ser Gly Gly Ser Tyr Thr Tyr Tyr Ser Asp Ser Val Lys
1               5                   10                  15

Gly

<210> SEQ ID NO 92
<211> LENGTH: 17
<212> TYPE: PRT
<213> ORGANISM: Mus musculus

<400> SEQUENCE: 92

Arg Ile Ala Pro Glu Asp Gly Asp Thr Glu Tyr Ala Pro Lys Phe Gln
1               5                   10                  15

Gly

<210> SEQ ID NO 93
<211> LENGTH: 17
<212> TYPE: PRT
<213> ORGANISM: Mus musculus

<400> SEQUENCE: 93

Gln Ile Tyr Pro Gly Asp Asp Tyr Thr Asn Tyr Asn Gly Lys Phe Lys
1               5                   10                  15

Gly

<210> SEQ ID NO 94

```
<211> LENGTH: 11
<212> TYPE: PRT
<213> ORGANISM: Mus musculus

<400> SEQUENCE: 94

His Glu Thr Ala Gln Ala Ala Trp Phe Ala Tyr
1               5                   10

<210> SEQ ID NO 95
<211> LENGTH: 12
<212> TYPE: PRT
<213> ORGANISM: Mus musculus

<400> SEQUENCE: 95

Glu Gly Asn Tyr Tyr Gly Ser Ser Ile Leu Asp Tyr
1               5                   10

<210> SEQ ID NO 96
<211> LENGTH: 9
<212> TYPE: PRT
<213> ORGANISM: Mus musculus

<400> SEQUENCE: 96

Leu Gly Pro Tyr Gly Pro Phe Ala Asp
1               5

<210> SEQ ID NO 97
<211> LENGTH: 10
<212> TYPE: PRT
<213> ORGANISM: Mus musculus

<400> SEQUENCE: 97

Ser Ala Ser Ser Ser Val Ser Tyr Met His
1               5                   10

<210> SEQ ID NO 98
<211> LENGTH: 11
<212> TYPE: PRT
<213> ORGANISM: Mus musculus

<400> SEQUENCE: 98

Arg Ala Ser Gln Asp Ile Thr Asn Tyr Leu Asn
1               5                   10

<210> SEQ ID NO 99
<211> LENGTH: 10
<212> TYPE: PRT
<213> ORGANISM: Mus musculus

<400> SEQUENCE: 99

Ser Ala Ser Ser Ser Val Ser Tyr Met Tyr
1               5                   10

<210> SEQ ID NO 100
<211> LENGTH: 7
<212> TYPE: PRT
<213> ORGANISM: Mus musculus

<400> SEQUENCE: 100

Asp Thr Ser Lys Leu Ala Tyr
1               5

<210> SEQ ID NO 101
<211> LENGTH: 7
<212> TYPE: PRT
```

```
<213> ORGANISM: Mus musculus

<400> SEQUENCE: 101

Phe Thr Ser Arg Leu His Ser
 1               5

<210> SEQ ID NO 102
<211> LENGTH: 7
<212> TYPE: PRT
<213> ORGANISM: Mus musculus

<400> SEQUENCE: 102

Asp Thr Ser Ser Leu Ala Ser
 1               5

<210> SEQ ID NO 103
<211> LENGTH: 9
<212> TYPE: PRT
<213> ORGANISM: Mus musculus

<400> SEQUENCE: 103

Gln Gln Trp Ser Ser Asn Pro Pro Thr
 1               5

<210> SEQ ID NO 104
<211> LENGTH: 9
<212> TYPE: PRT
<213> ORGANISM: Mus musculus

<400> SEQUENCE: 104

Gln Gln Gly Asn Thr Leu Pro Trp Thr
 1               5

<210> SEQ ID NO 105
<211> LENGTH: 9
<212> TYPE: PRT
<213> ORGANISM: Mus musculus

<400> SEQUENCE: 105

Gln Gln Trp Asn Ser Asp Pro Tyr Thr
 1               5

<210> SEQ ID NO 106
<211> LENGTH: 120
<212> TYPE: PRT
<213> ORGANISM: Mus musculus

<400> SEQUENCE: 106

Glu Val Gln Val Val Glu Ser Gly Gly Asp Leu Val Lys Ser Gly Gly
 1               5                  10                  15

Ser Leu Lys Leu Ser Cys Ala Ala Ser Gly Phe Pro Phe Ser Ser Tyr
                20                  25                  30

Ala Met Ser Trp Val Arg Gln Thr Pro Asp Lys Arg Leu Glu Trp Val
            35                  40                  45

Ala Ile Ile Ser Ser Gly Gly Ser Tyr Thr Tyr Tyr Ser Asp Ser Val
        50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                85                  90                  95

Ala Arg His Glu Thr Ala Gln Ala Ala Trp Phe Ala Tyr Trp Gly Gln
                100                 105                 110
```

```
Gly Thr Leu Val Thr Val Ser Ala
        115                 120

<210> SEQ ID NO 107
<211> LENGTH: 121
<212> TYPE: PRT
<213> ORGANISM: Mus musculus

<400> SEQUENCE: 107

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Tyr
            20                  25                  30

Tyr Met Tyr Trp Val Lys Gln Arg Pro Glu Gln Gly Leu Glu Trp Ile
        35                  40                  45

Gly Arg Ile Ala Pro Glu Asp Gly Asp Thr Glu Tyr Ala Pro Lys Phe
    50                  55                  60

Gln Gly Lys Ala Thr Val Thr Ala Asp Thr Ser Ser Asn Thr Ala Tyr
65                  70                  75                  80

Leu His Leu Ser Ser Leu Thr Ser Glu Asp Thr Ala Val Tyr Tyr Cys
                85                  90                  95

Thr Thr Glu Gly Asn Tyr Tyr Gly Ser Ser Ile Leu Asp Tyr Trp Gly
            100                 105                 110

Gln Gly Thr Thr Leu Thr Val Ser Ser
        115                 120

<210> SEQ ID NO 108
<211> LENGTH: 118
<212> TYPE: PRT
<213> ORGANISM: Mus musculus

<400> SEQUENCE: 108

Gln Val Gln Leu Gln Gln Ser Gly Ala Glu Leu Val Lys Pro Gly Ala
1               5                   10                  15

Ser Val Lys Ile Ser Cys Lys Ala Ser Gly Tyr Ala Phe Arg Ser Ser
            20                  25                  30

Trp Met Asn Trp Val Lys Gln Arg Pro Gly Lys Gly Leu Glu Trp Ile
        35                  40                  45

Gly Gln Ile Tyr Pro Gly Asp Asp Tyr Thr Asn Tyr Asn Gly Lys Phe
    50                  55                  60

Lys Gly Lys Val Thr Leu Thr Ala Asp Arg Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Leu Gly Pro Tyr Gly Pro Phe Ala Asp Trp Gly Gln Gly Thr
            100                 105                 110

Leu Val Thr Val Ser Ala
        115

<210> SEQ ID NO 109
<211> LENGTH: 106
<212> TYPE: PRT
<213> ORGANISM: Mus musculus

<400> SEQUENCE: 109

Gln Ile Val Leu Thr Gln Ser Pro Ala Ile Met Ser Ala Ser Pro Gly
1               5                   10                  15
```

-continued

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Tyr Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Asn Pro Pro Thr
                85                  90                  95

Phe Gly Gly Gly Thr Lys Leu Glu Ile Lys
            100                 105

<210> SEQ ID NO 110
<211> LENGTH: 107
<212> TYPE: PRT
<213> ORGANISM: Mus musculus

<400> SEQUENCE: 110

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Thr Asn Tyr
            20                  25                  30

Leu Asn Trp Tyr Gln Gln Lys Pro Asp Gly Thr Val Lys Leu Leu Ile
        35                  40                  45

Tyr Phe Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 111
<211> LENGTH: 106
<212> TYPE: PRT
<213> ORGANISM: Mus musculus

<400> SEQUENCE: 111

Gln Ile Val Leu Thr Gln Ser Pro Ala Ile Val Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Arg Pro Gly Ser Ser Pro Arg Leu Leu Ile Tyr
        35                  40                  45

Asp Thr Ser Ser Leu Ala Ser Gly Val Pro Val Arg Phe Ser Gly Ser
    50                  55                  60

Gly Ser Gly Thr Ser Tyr Ser Leu Thr Ile Ser Arg Ile Glu Ser Glu
65                  70                  75                  80

Asp Ala Ala Asn Tyr Tyr Cys Gln Gln Trp Asn Ser Asp Pro Tyr Thr
                85                  90                  95

Phe Gly Gly Gly Thr Lys Leu Glu Ile Lys
            100                 105

<210> SEQ ID NO 112
<211> LENGTH: 141

```
<212> TYPE: PRT
<213> ORGANISM: Homo sapiens

<400> SEQUENCE: 112

Met Glu Gly Asp Arg Gln Tyr Gly Asp Gly Tyr Leu Leu Gln Val Gln
 1               5                  10                  15

Glu Leu Val Thr Val Gln Glu Gly Leu Cys Val His Val Pro Cys Ser
             20                  25                  30

Phe Ser Tyr Pro Gln Asp Gly Trp Thr Asp Ser Asp Pro Val His Gly
         35                  40                  45

Tyr Trp Phe Arg Ala Gly Asp Arg Pro Tyr Gln Asp Ala Pro Val Ala
     50                  55                  60

Thr Asn Asn Pro Asp Arg Glu Val Gln Ala Glu Thr Gln Gly Arg Phe
65                  70                  75                  80

Gln Leu Leu Gly Asp Ile Trp Ser Asn Asp Cys Ser Leu Ser Ile Arg
                 85                  90                  95

Asp Ala Arg Lys Arg Asp Lys Gly Ser Tyr Phe Phe Arg Leu Glu Arg
            100                 105                 110

Gly Ser Met Lys Trp Ser Tyr Lys Ser Gln Leu Asn Tyr Lys Thr Lys
        115                 120                 125

Gln Leu Ser Val Phe Val Thr Ala Leu Thr His Arg Pro
    130                 135                 140

<210> SEQ ID NO 113
<211> LENGTH: 87
<212> TYPE: PRT
<213> ORGANISM: Homo sapiens

<400> SEQUENCE: 113

Asp Ile Leu Ile Leu Gly Thr Leu Glu Ser Gly His Ser Arg Asn Leu
 1               5                  10                  15

Thr Cys Ser Val Pro Trp Ala Cys Lys Gln Gly Thr Pro Pro Met Ile
             20                  25                  30

Ser Trp Ile Gly Ala Ser Val Ser Ser Pro Gly Pro Thr Thr Ala Arg
         35                  40                  45

Ser Ser Val Leu Thr Leu Thr Pro Lys Pro Gln Asp His Gly Thr Ser
     50                  55                  60

Leu Thr Cys Gln Val Thr Leu Pro Gly Thr Gly Val Thr Thr Thr Ser
65                  70                  75                  80

Thr Val Arg Leu Asp Val Ser
                 85

<210> SEQ ID NO 114
<211> LENGTH: 122
<212> TYPE: PRT
<213> ORGANISM: Homo sapiens

<400> SEQUENCE: 114

Tyr Pro Pro Trp Asn Leu Thr Met Thr Val Phe Gln Gly Asp Ala Thr
 1               5                  10                  15

Ala Ser Thr Ala Leu Gly Asn Gly Ser Ser Leu Ser Val Leu Glu Gly
             20                  25                  30

Gln Ser Leu Arg Leu Val Cys Ala Val Asn Ser Asn Pro Pro Ala Arg
         35                  40                  45

Leu Ser Trp Thr Arg Gly Ser Leu Thr Leu Cys Pro Ser Arg Ser Ser
     50                  55                  60

Asn Pro Gly Leu Leu Glu Leu Pro Arg Val His Val Arg Asp Glu Gly
```

```
                65                  70                  75                  80
Glu Phe Thr Cys Arg Ala Gln Asn Ala Gln Gly Ser Gln His Ile Ser
                    85                  90                  95

Leu Ser Leu Ser Leu Gln Asn Glu Gly Thr Gly Thr Ser Arg Pro Val
                100                 105                 110

Ser Gln Val Thr Leu Ala Ala Val Gly Gly
                115                 120

<210> SEQ ID NO 115
<211> LENGTH: 373
<212> TYPE: PRT
<213> ORGANISM: Homo sapiens

<400> SEQUENCE: 115

Met Glu Gly Asp Arg Gln Tyr Gly Asp Gly Tyr Leu Leu Gln Val Gln
  1               5                  10                  15

Glu Leu Val Thr Val Gln Glu Gly Leu Cys Val His Val Pro Cys Ser
                 20                  25                  30

Phe Ser Tyr Pro Gln Asp Gly Trp Thr Asp Ser Asp Pro Val His Gly
             35                  40                  45

Tyr Trp Phe Arg Ala Gly Asp Arg Pro Tyr Gln Asp Ala Pro Val Ala
 50                  55                  60

Thr Asn Asn Pro Asp Arg Glu Val Gln Ala Glu Thr Gln Gly Arg Phe
 65                  70                  75                  80

Gln Leu Leu Gly Asp Ile Trp Ser Asn Asp Cys Ser Leu Ser Ile Arg
                 85                  90                  95

Asp Ala Arg Lys Arg Asp Lys Gly Ser Tyr Phe Phe Arg Leu Glu Arg
                100                 105                 110

Gly Ser Met Lys Trp Ser Tyr Lys Ser Gln Leu Asn Tyr Lys Thr Lys
            115                 120                 125

Gln Leu Ser Val Phe Val Thr Ala Leu Thr His Arg Pro Ile Glu Gly
    130                 135                 140

Arg Ser Asp Lys Thr His Thr Cys Pro Pro Cys Pro Ala Pro Glu Leu
145                 150                 155                 160

Leu Gly Gly Pro Ser Val Phe Leu Phe Pro Pro Lys Pro Lys Asp Thr
                165                 170                 175

Leu Met Ile Ser Arg Thr Pro Glu Val Thr Cys Val Val Val Asp Val
            180                 185                 190

Ser His Glu Asp Pro Glu Val Lys Phe Asn Trp Tyr Val Asp Gly Val
        195                 200                 205

Glu Val His Asn Ala Lys Thr Lys Pro Arg Glu Glu Gln Tyr Asn Ser
    210                 215                 220

Thr Tyr Arg Val Val Ser Val Leu Thr Val Leu His Gln Asp Trp Leu
225                 230                 235                 240

Asn Gly Lys Glu Tyr Lys Cys Lys Val Ser Asn Lys Ala Leu Pro Ala
                245                 250                 255

Pro Ile Glu Lys Thr Ile Ser Lys Ala Lys Gly Gln Pro Arg Glu Pro
            260                 265                 270

Gln Val Tyr Thr Leu Pro Pro Ser Arg Glu Glu Met Thr Lys Asn Gln
        275                 280                 285

Val Ser Leu Thr Cys Leu Val Lys Gly Phe Tyr Pro Ser Asp Ile Ala
    290                 295                 300

Val Glu Trp Glu Ser Asn Gly Gln Pro Glu Asn Asn Tyr Lys Thr Thr
305                 310                 315                 320
```

-continued

```
Pro Pro Val Leu Asp Ser Asp Gly Ser Phe Leu Tyr Ser Lys Leu
            325                 330                 335

Thr Val Asp Lys Ser Arg Trp Gln Gln Gly Asn Val Phe Ser Cys Ser
            340                 345                 350

Val Met His Glu Ala Leu His Asn His Tyr Thr Gln Lys Ser Leu Ser
            355                 360                 365

Leu Ser Pro Gly Lys
        370

<210> SEQ ID NO 116
<211> LENGTH: 460
<212> TYPE: PRT
<213> ORGANISM: Homo sapiens

<400> SEQUENCE: 116

Met Glu Gly Asp Arg Gln Tyr Gly Asp Gly Tyr Leu Leu Gln Val Gln
  1               5                  10                  15

Glu Leu Val Thr Val Gln Glu Gly Leu Cys Val His Val Pro Cys Ser
            20                  25                  30

Phe Ser Tyr Pro Gln Asp Gly Trp Thr Asp Ser Asp Pro Val His Gly
        35                  40                  45

Tyr Trp Phe Arg Ala Gly Asp Arg Pro Tyr Gln Asp Ala Pro Val Ala
    50                  55                  60

Thr Asn Asn Pro Asp Arg Glu Val Gln Ala Glu Thr Gln Gly Arg Phe
65                  70                  75                  80

Gln Leu Leu Gly Asp Ile Trp Ser Asn Asp Cys Ser Leu Ser Ile Arg
                85                  90                  95

Asp Ala Arg Lys Arg Asp Lys Gly Ser Tyr Phe Phe Arg Leu Glu Arg
            100                 105                 110

Gly Ser Met Lys Trp Ser Tyr Lys Ser Gln Leu Asn Tyr Lys Thr Lys
        115                 120                 125

Gln Leu Ser Val Phe Val Thr Ala Leu Thr His Arg Pro Asp Ile Leu
    130                 135                 140

Ile Leu Gly Thr Leu Glu Ser Gly His Ser Arg Asn Leu Thr Cys Ser
145                 150                 155                 160

Val Pro Trp Ala Cys Lys Gln Gly Thr Pro Pro Met Ile Ser Trp Ile
                165                 170                 175

Gly Ala Ser Val Ser Ser Pro Gly Pro Thr Thr Ala Arg Ser Ser Val
            180                 185                 190

Leu Thr Leu Thr Pro Lys Pro Gln Asp His Gly Thr Ser Leu Thr Cys
        195                 200                 205

Gln Val Thr Leu Pro Gly Thr Gly Val Thr Thr Ser Thr Val Arg
    210                 215                 220

Leu Asp Val Ser Ile Glu Gly Arg Ser Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320
```

```
Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
            355                 360                 365

Glu Glu Met Thr Lys Asn Gln Val Ser Leu Thr Cys Leu Val Lys Gly
        370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
            435                 440                 445

Tyr Thr Gln Lys Ser Leu Ser Leu Ser Pro Gly Lys
    450                 455                 460

<210> SEQ ID NO 117
<211> LENGTH: 582
<212> TYPE: PRT
<213> ORGANISM: Homo sapiens

<400> SEQUENCE: 117

Met Glu Gly Asp Arg Gln Tyr Gly Asp Gly Tyr Leu Leu Gln Val Gln
1               5                   10                  15

Glu Leu Val Thr Val Gln Glu Gly Leu Cys Val His Val Pro Cys Ser
            20                  25                  30

Phe Ser Tyr Pro Gln Asp Gly Trp Thr Asp Ser Asp Pro Val His Gly
        35                  40                  45

Tyr Trp Phe Arg Ala Gly Asp Arg Pro Tyr Gln Asp Ala Pro Val Ala
    50                  55                  60

Thr Asn Asn Pro Asp Arg Glu Val Gln Ala Glu Thr Gln Gly Arg Phe
65                  70                  75                  80

Gln Leu Leu Gly Asp Ile Trp Ser Asn Asp Cys Ser Leu Ser Ile Arg
                85                  90                  95

Asp Ala Arg Lys Arg Asp Lys Gly Ser Tyr Phe Phe Arg Leu Glu Arg
            100                 105                 110

Gly Ser Met Lys Trp Ser Tyr Lys Ser Gln Leu Asn Tyr Lys Thr Lys
        115                 120                 125

Gln Leu Ser Val Phe Val Thr Ala Leu Thr His Arg Pro Asp Ile Leu
    130                 135                 140

Ile Leu Gly Thr Leu Glu Ser Gly His Ser Arg Asn Leu Thr Cys Ser
145                 150                 155                 160

Val Pro Trp Ala Cys Lys Gln Gly Thr Pro Pro Met Ile Ser Trp Ile
                165                 170                 175

Gly Ala Ser Val Ser Ser Pro Gly Pro Thr Thr Ala Arg Ser Ser Val
            180                 185                 190

Leu Thr Leu Thr Pro Lys Pro Gln Asp His Gly Thr Ser Leu Thr Cys
        195                 200                 205

Gln Val Thr Leu Pro Gly Thr Gly Val Thr Thr Thr Ser Thr Val Arg
    210                 215                 220

Leu Asp Val Ser Tyr Pro Pro Trp Asn Leu Thr Met Thr Val Phe Gln
```

```
                225                 230                 235                 240
        Gly Asp Ala Thr Ala Ser Thr Ala Leu Gly Asn Gly Ser Ser Leu Ser
                        245                 250                 255
        Val Leu Glu Gly Gln Ser Leu Arg Leu Val Cys Ala Val Asn Ser Asn
                        260                 265                 270
        Pro Pro Ala Arg Leu Ser Trp Thr Arg Gly Ser Leu Thr Leu Cys Pro
                        275                 280                 285
        Ser Arg Ser Ser Asn Pro Gly Leu Leu Glu Leu Pro Arg Val His Val
                        290                 295                 300
        Arg Asp Glu Gly Glu Phe Thr Cys Arg Ala Gln Asn Ala Gln Gly Ser
        305                 310                 315                 320
        Gln His Ile Ser Leu Ser Leu Ser Leu Gln Asn Glu Gly Thr Gly Thr
                        325                 330                 335
        Ser Arg Pro Val Ser Gln Val Thr Leu Ala Ala Val Gly Gly Ile Glu
                        340                 345                 350
        Gly Arg Ser Asp Lys Thr His Thr Cys Pro Pro Cys Pro Ala Pro Glu
                        355                 360                 365
        Leu Leu Gly Gly Pro Ser Val Phe Leu Phe Pro Pro Lys Pro Lys Asp
                        370                 375                 380
        Thr Leu Met Ile Ser Arg Thr Pro Glu Val Thr Cys Val Val Val Asp
        385                 390                 395                 400
        Val Ser His Glu Asp Pro Glu Val Lys Phe Asn Trp Tyr Val Asp Gly
                        405                 410                 415
        Val Glu Val His Asn Ala Lys Thr Lys Pro Arg Glu Glu Gln Tyr Asn
                        420                 425                 430
        Ser Thr Tyr Arg Val Val Ser Val Leu Thr Val Leu His Gln Asp Trp
                        435                 440                 445
        Leu Asn Gly Lys Glu Tyr Lys Cys Lys Val Ser Asn Lys Ala Leu Pro
                        450                 455                 460
        Ala Pro Ile Glu Lys Thr Ile Ser Lys Ala Lys Gly Gln Pro Arg Glu
        465                 470                 475                 480
        Pro Gln Val Tyr Thr Leu Pro Pro Ser Arg Asp Glu Leu Thr Lys Asn
                        485                 490                 495
        Gln Val Ser Leu Thr Cys Leu Val Lys Gly Phe Tyr Pro Ser Asp Ile
                        500                 505                 510
        Ala Val Glu Trp Glu Ser Asn Gly Gln Pro Glu Asn Asn Tyr Lys Thr
                        515                 520                 525
        Thr Pro Pro Val Leu Asp Ser Asp Gly Ser Phe Phe Leu Tyr Ser Lys
        530                 535                 540
        Leu Thr Val Asp Lys Ser Arg Trp Gln Gln Gly Asn Val Phe Ser Cys
        545                 550                 555                 560
        Ser Val Met His Glu Ala Leu His Asn His Tyr Thr Gln Lys Ser Leu
                        565                 570                 575
        Ser Leu Ser Pro Gly Lys
                        580

<210> SEQ ID NO 118
<211> LENGTH: 582
<212> TYPE: PRT
<213> ORGANISM: Papio spp.

<400> SEQUENCE: 118

Met Glu Gly Asp Arg Lys Tyr Gly Asp Gly Tyr Leu Leu Gln Val Gln
1               5                   10                  15
```

-continued

```
Glu Leu Val Thr Val Gln Glu Gly Leu Cys Val His Val Pro Cys Ser
             20                  25                  30
Phe Ser Tyr Pro Lys Asp Asp Trp Thr Tyr Ser Asp Pro Val His Gly
         35                  40                  45
Tyr Trp Phe Arg Ala Gly Asp Arg Pro Tyr Gln Glu Ala Pro Val Ala
     50                  55                  60
Thr Asn Asn Pro Asp Thr Glu Val Gln Ala Glu Thr Gln Gly Arg Phe
 65                  70                  75                  80
Gln Leu Leu Gly Asp Arg Trp Ser Asn Asp Cys Ser Leu Ser Ile Asn
                 85                  90                  95
Asp Ala Arg Lys Gly Asp Glu Gly Ser Tyr Phe Phe Arg Leu Glu Arg
             100                 105                 110
Gly Arg Met Lys Trp Ser Tyr Lys Ser Gln Leu Asn Tyr Lys Ala Lys
         115                 120                 125
Gln Leu Ser Val Phe Val Thr Ala Leu Thr Gln Arg Pro Asp Ile Leu
    130                 135                 140
Ile Gln Gly Thr Leu Glu Ser Gly His Pro Arg Asn Leu Thr Cys Ser
145                 150                 155                 160
Val Pro Trp Ala Cys Glu Gln Arg Met Pro Pro Met Ile Ser Trp Ile
                165                 170                 175
Gly Thr Ser Val Ser Ser Leu Gly Pro Ile Thr Ala Arg Phe Ser Val
            180                 185                 190
Leu Thr Leu Ile Pro Lys Pro Gln Asp His Gly Thr Ser Leu Thr Cys
        195                 200                 205
Gln Val Thr Leu Pro Gly Thr Gly Val Thr Thr Thr Arg Thr Val Gln
    210                 215                 220
Leu Asp Val Ser Tyr Pro Pro Trp Asn Leu Thr Val Thr Val Phe Gln
225                 230                 235                 240
Gly Asp Asp Thr Ala Ser Thr Ala Leu Gly Asn Gly Ser Ser Leu Ser
                245                 250                 255
Val Leu Glu Gly Gln Ser Leu Arg Leu Val Cys Ala Val Asp Ser Asn
            260                 265                 270
Pro Pro Ala Arg Leu Ser Trp Thr Arg Gly Ser Leu Thr Leu Cys Pro
        275                 280                 285
Ser Gln Pro Trp Asn Pro Gly Leu Leu Glu Leu Leu Arg Val His Val
    290                 295                 300
Lys Asp Glu Gly Glu Phe Thr Cys Gln Ala Glu Asn Pro Arg Gly Ser
305                 310                 315                 320
Gln His Ile Ser Leu Ser Leu Ser Leu Gln Asn Glu Gly Thr Gly Thr
                325                 330                 335
Ala Arg Pro Val Ser Glu Val Thr Leu Ala Ala Val Gly Gly Ile Glu
            340                 345                 350
Gly Arg Ser Asp Lys Thr His Thr Cys Pro Pro Cys Pro Ala Pro Glu
        355                 360                 365
Leu Leu Gly Gly Pro Ser Val Phe Leu Phe Pro Pro Lys Pro Lys Asp
    370                 375                 380
Thr Leu Met Ile Ser Arg Thr Pro Glu Val Thr Cys Val Val Val Asp
385                 390                 395                 400
Val Ser His Glu Asp Pro Glu Val Lys Phe Asn Trp Tyr Val Asp Gly
                405                 410                 415
Val Glu Val His Asn Ala Lys Thr Lys Pro Arg Glu Glu Gln Tyr Asn
            420                 425                 430
Ser Thr Tyr Arg Val Val Ser Val Leu Thr Val Leu His Gln Asp Trp
```

```
                435                 440                 445
Leu Asn Gly Lys Glu Tyr Lys Cys Lys Val Ser Asn Lys Ala Leu Pro
450                 455                 460

Ala Pro Ile Glu Lys Thr Ile Ser Lys Ala Lys Gly Gln Pro Arg Glu
465                 470                 475                 480

Pro Gln Val Tyr Thr Leu Pro Pro Ser Arg Glu Glu Met Thr Lys Asn
                485                 490                 495

Gln Val Ser Leu Thr Cys Leu Val Lys Gly Phe Tyr Pro Ser Asp Ile
                500                 505                 510

Ala Val Glu Trp Glu Ser Asn Gly Gln Pro Glu Asn Asn Tyr Lys Thr
                515                 520                 525

Thr Pro Pro Val Leu Asp Ser Asp Gly Ser Phe Phe Leu Tyr Ser Lys
530                 535                 540

Leu Thr Val Asp Lys Ser Arg Trp Gln Gln Gly Asn Val Phe Ser Cys
545                 550                 555                 560

Ser Val Met His Glu Ala Leu His Asn His Tyr Thr Gln Lys Ser Leu
                565                 570                 575

Ser Leu Ser Pro Gly Lys
                580

<210> SEQ ID NO 119
<211> LENGTH: 350
<212> TYPE: PRT
<213> ORGANISM: Papio spp.

<400> SEQUENCE: 119

Met Glu Gly Asp Arg Lys Tyr Gly Asp Gly Tyr Leu Leu Gln Val Gln
1               5                   10                  15

Glu Leu Val Thr Val Gln Glu Gly Leu Cys Val His Val Pro Cys Ser
                20                  25                  30

Phe Ser Tyr Pro Lys Asp Asp Trp Thr Tyr Ser Asp Pro Val His Gly
                35                  40                  45

Tyr Trp Phe Arg Ala Gly Asp Arg Pro Tyr Gln Glu Ala Pro Val Ala
        50                  55                  60

Thr Asn Asn Pro Asp Thr Glu Val Gln Ala Glu Thr Gln Gly Arg Phe
65                  70                  75                  80

Gln Leu Leu Gly Asp Arg Trp Ser Asn Asp Cys Ser Leu Ser Ile Asn
                85                  90                  95

Asp Ala Arg Lys Gly Asp Glu Gly Ser Tyr Phe Phe Arg Leu Glu Arg
                100                 105                 110

Gly Arg Met Lys Trp Ser Tyr Lys Ser Gln Leu Asn Tyr Lys Ala Lys
            115                 120                 125

Gln Leu Ser Val Phe Val Thr Ala Leu Thr Gln Arg Pro Asp Ile Leu
    130                 135                 140

Ile Gln Gly Thr Leu Glu Ser Gly His Pro Arg Asn Leu Thr Cys Ser
145                 150                 155                 160

Val Pro Trp Ala Cys Glu Gln Arg Met Pro Met Ile Ser Trp Ile
                165                 170                 175

Gly Thr Ser Val Ser Ser Leu Gly Pro Ile Thr Ala Arg Phe Ser Val
            180                 185                 190

Leu Thr Leu Ile Pro Lys Pro Gln Asp His Gly Thr Ser Leu Thr Cys
        195                 200                 205

Gln Val Thr Leu Pro Gly Thr Gly Val Thr Thr Thr Arg Thr Val Gln
    210                 215                 220
```

```
Leu Asp Val Ser Tyr Pro Pro Trp Asn Leu Thr Val Thr Val Phe Gln
225                 230                 235                 240

Gly Asp Asp Thr Ala Ser Thr Ala Leu Gly Asn Gly Ser Ser Leu Ser
            245                 250                 255

Val Leu Glu Gly Gln Ser Leu Arg Leu Val Cys Ala Val Asp Ser Asn
        260                 265                 270

Pro Pro Ala Arg Leu Ser Trp Thr Arg Gly Ser Leu Thr Leu Cys Pro
        275                 280                 285

Ser Gln Pro Trp Asn Pro Gly Leu Leu Glu Leu Leu Arg Val His Val
    290                 295                 300

Lys Asp Glu Gly Glu Phe Thr Cys Gln Ala Glu Asn Pro Arg Gly Ser
305                 310                 315                 320

Gln His Ile Ser Leu Ser Leu Ser Leu Gln Asn Glu Gly Thr Gly Thr
                325                 330                 335

Ala Arg Pro Val Ser Glu Val Thr Leu Ala Ala Val Gly Gly
            340                 345                 350

<210> SEQ ID NO 120
<211> LENGTH: 120
<212> TYPE: PRT
<213> ORGANISM: Homo sapiens

<400> SEQUENCE: 120

Glu Val Lys Val Glu Glu Ser Gly Gly Gly Leu Val Gln Pro Gly Gly
1               5                   10                  15

Ser Leu Arg Leu Ser Cys Ala Ala Ser Gly Phe Ser Leu Thr Ile Thr
            20                  25                  30

Tyr Met Asn Trp Val Arg Gln Ala Pro Gly Lys Gly Leu Glu Trp Val
        35                  40                  45

Ser Val Ile Gly Ser Ala Gly Ser Thr Tyr Tyr Ala Asp Ser Val Lys
    50                  55                  60

Gly Arg Phe Thr Ile Ser Lys Asp Asn Ser Glu Gly Met Val Tyr Leu
65                  70                  75                  80

Gln Met Asn Ser Leu Arg Ala Glu Asp Thr Ala Val Tyr Tyr Cys Ala
                85                  90                  95

Arg Glu Glu Ile Asp Asn Tyr Tyr Gly Met Asp Val Trp Gly Gln
            100                 105                 110

Gly Thr Thr Val Thr Val Ser Ser
        115                 120

<210> SEQ ID NO 121
<211> LENGTH: 97
<212> TYPE: PRT
<213> ORGANISM: Homo sapiens

<400> SEQUENCE: 121

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80
```

Gln Met Asn Ser Leu Arg Ala Glu Asp Thr Ala Val Tyr Tyr Cys Ala
                85                  90                  95

Arg

<210> SEQ ID NO 122
<211> LENGTH: 97
<212> TYPE: PRT
<213> ORGANISM: Homo sapiens

<400> SEQUENCE: 122

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 123
<211> LENGTH: 107
<212> TYPE: PRT
<213> ORGANISM: Homo sapiens

<400> SEQUENCE: 123

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Phe Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln His Arg Ser Asn Trp Leu Ile
                85                  90                  95

Ala Phe Gly Pro Gly Thr Lys Leu Asp Ile Lys
                100                 105

<210> SEQ ID NO 124
<211> LENGTH: 95
<212> TYPE: PRT
<213> ORGANISM: Homo sapiens

<400> SEQUENCE: 124

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

-continued

```
Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65              70                  75                  80

Glu Asp Phe Ala Val Tyr Tyr Cys Gln Gln Arg Ser Asn Trp Pro
                85                  90                  95
```